(12) United States Patent
Belef et al.

(10) Patent No.: US 7,846,179 B2
(45) Date of Patent: Dec. 7, 2010

(54) SUTURE-BASED SYSTEMS AND METHODS FOR TREATING SEPTAL DEFECTS

(75) Inventors: W. Martin Belef, San Jose, CA (US); Dean Carson, Mountain View, CA (US); Richard S. Ginn, San Jose, CA (US); Ronald J. Jabba, Redwood City, CA (US)

(73) Assignee: Ovalis, Inc., Mountain View, CA (US)

(*) Notice: Subject to any disclaimer, the term of this patent is extended or adjusted under 35 U.S.C. 154(b) by 391 days.

(21) Appl. No.: 11/218,794

(22) Filed: Sep. 1, 2005

(65) Prior Publication Data

US 2007/0049970 A1 Mar. 1, 2007

(51) Int. Cl.
*A61B 17/06* (2006.01)

(52) U.S. Cl. .................. 606/222; 606/144; 606/151

(58) Field of Classification Search .................. 606/139, 606/151, 222, 223–227; 623/2.11, 2.36
See application file for complete search history.

(56) References Cited

U.S. PATENT DOCUMENTS

| | | | |
|---|---|---|---|
| 2,670,673 | A | 3/1954 | Gordon et al. |
| 3,874,388 | A | 4/1975 | King et al. |
| 3,875,648 | A | 4/1975 | Bone |
| 4,006,747 | A | 2/1977 | Kronenthal et al. |
| 4,007,743 | A | 2/1977 | Blake |
| 4,316,469 | A | 2/1982 | Kapitanov |
| 4,576,162 | A | 3/1986 | McCorkle |
| 4,601,718 | A | 7/1986 | Possis et al. |
| 4,665,906 | A | 5/1987 | Jervis |
| 4,669,473 | A | 6/1987 | Richards et al. |
| 4,696,300 | A | 9/1987 | Anderson |
| 4,702,250 | A | 10/1987 | Ovil et al. |
| 4,705,040 | A | 11/1987 | Mueller et al. |

(Continued)

FOREIGN PATENT DOCUMENTS

EP  0 432 320 A1  6/1991

(Continued)

OTHER PUBLICATIONS

Ruiz, et al., The Puncture Technique: A New Method for Transcatheter Closure of Patent Foramen Ovale, Catheterization and Cardiovascular Interventions 53:369-372 (2001).

(Continued)

*Primary Examiner*—Todd E Manahan
*Assistant Examiner*—Katherine M Dowe
(74) *Attorney, Agent, or Firm*—Orrick Herrington & Sutcliffe LLP

(57) ABSTRACT

A system for treating a septal defect having a suture-like implantable treatment apparatus and devices for delivering the implantable treatment apparatus and methods for treating a septal defect are provided. The suture-like apparatus is preferably implantable through a septal wall or portion thereof. The treatment system can include a flexible elongate body member, a delivery device configured to deliver the suture-like apparatus, a stabilization device configured to stabilize the delivery device and a positioning device configured to position the delivery device in a desired location. The suture-like device can include a suture body coupled with one or more lock devices or anchor devices.

74 Claims, 79 Drawing Sheets

U.S. PATENT DOCUMENTS

| | | | |
|---|---|---|---|
| 4,721,115 | A | 1/1988 | Owens |
| 4,741,336 | A | 5/1988 | Failla et al. |
| 4,779,616 | A | 10/1988 | Johnson |
| 4,800,890 | A | 1/1989 | Cramer |
| 4,802,478 | A | 2/1989 | Powell |
| 4,836,204 | A | 6/1989 | Landymore et al. |
| 4,850,960 | A | 7/1989 | Grayzel |
| 4,861,336 | A | 8/1989 | Helzel |
| 4,878,893 | A | 11/1989 | Chin |
| 4,892,098 | A | 1/1990 | Sauer |
| 4,902,508 | A | 2/1990 | Badylak et al. |
| 4,917,089 | A | 4/1990 | Sideris |
| 4,929,246 | A | 5/1990 | Sinofsky |
| 4,985,014 | A | 1/1991 | Orejola |
| 4,994,069 | A | 2/1991 | Ritchart et al. |
| 5,021,059 | A | 6/1991 | Kensey et al. |
| 5,037,433 | A | 8/1991 | Wilk et al. |
| 5,041,129 | A | 8/1991 | Hayhurst et al. |
| 5,049,153 | A | 9/1991 | Nakao et al. |
| 5,067,957 | A | 11/1991 | Jervis |
| 5,073,166 | A | 12/1991 | Parks et al. |
| 5,108,420 | A | 4/1992 | Marks |
| 5,112,310 | A | 5/1992 | Grobe |
| 5,171,218 | A | 12/1992 | Fonger et al. |
| 5,171,259 | A | 12/1992 | Inoue |
| 5,190,050 | A | 3/1993 | Nitzsche |
| 5,190,528 | A | 3/1993 | Fonger et al. |
| 5,192,301 | A | 3/1993 | Kamiya et al. |
| 5,219,358 | A | 6/1993 | Bendel et al. |
| 5,222,974 | A | 6/1993 | Kensey et al. |
| 5,236,440 | A | 8/1993 | Hlavacek |
| 5,242,427 | A | 9/1993 | Bilweis |
| 5,250,054 | A | 10/1993 | Li |
| 5,250,055 | A | 10/1993 | Moore et al. |
| 5,257,637 | A | 11/1993 | El Gazayerli |
| 5,281,234 | A | 1/1994 | Wilk et al. |
| 5,282,827 | A | 2/1994 | Kensey et al. |
| 5,284,488 | A | 2/1994 | Sideris |
| 5,290,272 | A | 3/1994 | Burstein et al. |
| 5,290,278 | A | 3/1994 | Anderson |
| 5,300,065 | A | 4/1994 | Anderson |
| 5,304,184 | A | 4/1994 | Hathaway et al. |
| 5,304,185 | A | 4/1994 | Taylor |
| 5,312,341 | A | 5/1994 | Turi |
| 5,312,435 | A | 5/1994 | Nash et al. |
| 5,318,525 | A | 6/1994 | West et al. |
| 5,330,488 | A | 7/1994 | Goldrath |
| 5,330,496 | A | 7/1994 | Alferness |
| 5,334,191 | A | 8/1994 | Poppas et al. |
| 5,334,217 | A | 8/1994 | Das |
| 5,357,979 | A | 10/1994 | Imran |
| 5,364,410 | A | 11/1994 | Faille et al. |
| 5,370,679 | A | 12/1994 | Atlee, III |
| 5,383,852 | A | 1/1995 | Stevens-Wright |
| 5,383,905 | A | 1/1995 | Golds et al. |
| 5,387,227 | A | 2/1995 | Grice |
| 5,394,880 | A | 3/1995 | Atlee, III |
| 5,403,329 | A | 4/1995 | Hinchcliffe |
| 5,403,338 | A | 4/1995 | Milo |
| 5,409,469 | A | 4/1995 | Schaerf |
| 5,409,481 | A | 4/1995 | Poppas et al. |
| 5,413,584 | A | 5/1995 | Schulze |
| 5,417,699 | A | 5/1995 | Klein et al. |
| 5,417,713 | A | 5/1995 | Cohen |
| 5,421,338 | A | 6/1995 | Crowley et al. |
| 5,425,744 | A | 6/1995 | Fagan et al. |
| 5,431,696 | A | 7/1995 | Atlee, III |
| 5,433,727 | A | 7/1995 | Sideris |
| 5,441,504 | A | 8/1995 | Pohndorf et al. |
| 5,443,478 | A | 8/1995 | Purdy |
| 5,451,235 | A | 9/1995 | Lock et al. |
| 5,461,235 | A | 10/1995 | Cottrell et al. |
| 5,462,560 | A | 10/1995 | Stevens |
| 5,462,561 | A | 10/1995 | Vode |
| 5,474,573 | A | 12/1995 | Hatcher |
| 5,478,353 | A | 12/1995 | Yoon |
| 5,486,183 | A | 1/1996 | Middleman et al. |
| 5,486,193 | A | 1/1996 | Bourne et al. |
| 5,503,634 | A | 4/1996 | Christy |
| 5,507,744 | A | 4/1996 | Tay et al. |
| 5,507,811 | A | 4/1996 | Koike et al. |
| 5,522,873 | A | 6/1996 | Jackman et al. |
| 5,527,388 | A | 6/1996 | Berke et al. |
| 5,545,138 | A | 8/1996 | Fugoso et al. |
| 5,548,872 | A | 8/1996 | Oetiker |
| 5,554,162 | A | 9/1996 | DeLange |
| 5,570,671 | A | 11/1996 | Hickey |
| 5,573,540 | A * | 11/1996 | Yoon .......................... 606/139 |
| 5,573,542 | A | 11/1996 | Stevens |
| 5,575,772 | A | 11/1996 | Lennox |
| 5,577,299 | A | 11/1996 | Thompson et al. |
| 5,578,045 | A | 11/1996 | Das |
| 5,582,616 | A | 12/1996 | Bolduc et al. |
| 5,584,803 | A | 12/1996 | Stevens et al. |
| 5,601,571 | A | 2/1997 | Moss |
| 5,618,311 | A | 4/1997 | Gryskiewicz |
| 5,620,461 | A | 4/1997 | Muijs Van De Moer et al. |
| 5,626,599 | A | 5/1997 | Bourne et al. |
| 5,634,936 | A | 6/1997 | Linden et al. |
| 5,645,557 | A | 7/1997 | Yoon |
| 5,649,950 | A | 7/1997 | Bourne et al. |
| 5,658,280 | A | 8/1997 | Issa |
| 5,662,643 | A | 9/1997 | Kung et al. |
| 5,682,906 | A | 11/1997 | Sterman et al. |
| 5,702,368 | A | 12/1997 | Stevens et al. |
| 5,702,421 | A | 12/1997 | Schneidt |
| 5,709,224 | A | 1/1998 | Behl et al. |
| 5,709,707 | A | 1/1998 | Lock et al. |
| 5,713,867 | A | 2/1998 | Morris |
| 5,713,911 | A | 2/1998 | Racenet et al. |
| 5,714,297 | A | 2/1998 | Chamberlain et al. |
| 5,716,367 | A | 2/1998 | Koike et al. |
| 5,720,754 | A | 2/1998 | Middleman et al. |
| 5,722,981 | A | 3/1998 | Stevens |
| 5,725,512 | A | 3/1998 | Swartz et al. |
| 5,725,552 | A | 3/1998 | Kotula et al. |
| 5,725,554 | A | 3/1998 | Simon et al. |
| 5,728,151 | A | 3/1998 | Garrison et al. |
| 5,733,294 | A | 3/1998 | Forber et al. |
| 5,735,877 | A | 4/1998 | Pagedas |
| 5,738,652 | A | 4/1998 | Boyd et al. |
| 5,741,429 | A | 4/1998 | Donadio, III et al. |
| 5,759,170 | A | 6/1998 | Peters |
| 5,769,812 | A | 6/1998 | Stevens et al. |
| 5,772,672 | A | 6/1998 | Toy et al. |
| 5,776,162 | A | 7/1998 | Kleshinski |
| 5,782,860 | A | 7/1998 | Epstein et al. |
| 5,792,094 | A | 8/1998 | Stevens et al. |
| 5,797,960 | A | 8/1998 | Stevens et al. |
| 5,807,339 | A | 9/1998 | Bostrom et al. |
| 5,810,882 | A | 9/1998 | Bolduc et al. |
| 5,810,884 | A | 9/1998 | Kiim |
| 5,814,016 | A | 9/1998 | Valley et al. |
| 5,814,068 | A | 9/1998 | Koike et al. |
| 5,814,097 | A | 9/1998 | Sterman et al. |
| 5,823,956 | A | 10/1998 | Roth et al. |
| 5,827,216 | A | 10/1998 | Igo et al. |
| 5,829,447 | A | 11/1998 | Stevens et al. |
| 5,836,311 | A | 11/1998 | Borst et al. |
| 5,853,422 | A | 12/1998 | Huebsch et al. |
| 5,855,614 | A | 1/1999 | Stevens et al. |
| 5,861,003 | A | 1/1999 | Latson et al. |
| 5,865,791 | A | 2/1999 | Whayne et al. |
| 5,868,702 | A | 2/1999 | Stevens et al. |

| Patent | Kind | Date | Inventor |
|---|---|---|---|
| 5,868,733 | A | 2/1999 | Ockuly et al. |
| 5,868,753 | A | 2/1999 | Schatz |
| 5,868,762 | A | 2/1999 | Cragg et al. |
| 5,879,366 | A | 3/1999 | Shaw et al. |
| 5,879,499 | A | 3/1999 | Corvi |
| 5,885,238 | A | 3/1999 | Stevens et al. |
| 5,893,856 | A | 4/1999 | Jacob et al. |
| 5,895,404 | A | 4/1999 | Ruiz |
| 5,902,319 | A | 5/1999 | Daley |
| 5,904,703 | A | 5/1999 | Gilson |
| 5,908,428 | A | 6/1999 | Scirica et al. |
| 5,910,150 | A | 6/1999 | Saadat |
| 5,911,717 | A | 6/1999 | Jacobsen et al. |
| 5,913,810 | A | 6/1999 | Andre |
| 5,913,842 | A | 6/1999 | Boyd et al. |
| 5,919,200 | A | 7/1999 | Stambaugh et al. |
| 5,924,424 | A | 7/1999 | Stevens et al. |
| 5,927,284 | A | 7/1999 | Borst et al. |
| 5,928,181 | A | 7/1999 | Coleman et al. |
| 5,928,250 | A | 7/1999 | Koike et al. |
| 5,931,848 | A | 8/1999 | Saadat |
| 5,941,899 | A | 8/1999 | Granger et al. |
| 5,944,738 | A | 8/1999 | Amplatz et al. |
| 5,947,997 | A | 9/1999 | Pavcnik et al. |
| 5,955,110 | A | 9/1999 | Patel et al. |
| 5,967,977 | A | 10/1999 | Mullis et al. |
| 5,972,013 | A | 10/1999 | Schmidt |
| 5,976,174 | A | 11/1999 | Ruiz |
| 5,980,503 | A | 11/1999 | Chin |
| 5,989,268 | A | 11/1999 | Pugsley, Jr. et al. |
| 5,993,475 | A | 11/1999 | Lin et al. |
| 6,007,563 | A | 12/1999 | Nash et al. |
| 6,010,517 | A | 1/2000 | Baccaro |
| 6,013,052 | A | 1/2000 | Durman et al. |
| 6,015,378 | A | 1/2000 | Borst et al. |
| 6,015,417 | A | 1/2000 | Reynolds, Jr. |
| 6,024,756 | A | 2/2000 | Huebsch et al. |
| 6,027,476 | A | 2/2000 | Sterman et al. |
| 6,030,007 | A | 2/2000 | Bassily et al. |
| 6,036,699 | A | 3/2000 | Andreas et al. |
| 6,036,720 | A | 3/2000 | Abrams et al. |
| 6,056,760 | A | 5/2000 | Koike et al. |
| 6,071,271 | A | 6/2000 | Baker et al. |
| 6,071,292 | A | 6/2000 | Makower et al. |
| 6,077,281 | A | 6/2000 | Das |
| 6,077,291 | A | 6/2000 | Das |
| 6,079,414 | A | 6/2000 | Roth |
| 6,080,182 | A | 6/2000 | Shaw et al. |
| 6,090,084 | A | 7/2000 | Hassett et al. |
| 6,090,096 | A | 7/2000 | St. Goar et al. |
| 6,093,199 | A | 7/2000 | Brown et al. |
| 6,095,997 | A | 8/2000 | French et al. |
| 6,110,145 | A | 8/2000 | Macoviak |
| 6,113,609 | A | 9/2000 | Adams |
| 6,113,610 | A * | 9/2000 | Poncet ................ 606/139 |
| 6,113,611 | A | 9/2000 | Allen et al. |
| 6,117,145 | A | 9/2000 | Wood et al. |
| 6,117,159 | A | 9/2000 | Huebsch et al. |
| 6,126,658 | A | 10/2000 | Baker |
| 6,127,410 | A | 10/2000 | Duhaylongsod |
| 6,132,438 | A | 10/2000 | Fleischman et al. |
| 6,135,981 | A | 10/2000 | Dyke |
| 6,142,975 | A | 11/2000 | Jalisi et al. |
| 6,149,664 | A | 11/2000 | Kurz |
| 6,152,141 | A | 11/2000 | Stevens et al. |
| 6,152,144 | A | 11/2000 | Lesh et al. |
| 6,162,195 | A | 12/2000 | Igo et al. |
| 6,162,202 | A | 12/2000 | Sicurelli et al. |
| 6,165,183 | A | 12/2000 | Kuehn et al. |
| 6,165,204 | A | 12/2000 | Levinson et al. |
| 6,171,329 | B1 | 1/2001 | Shaw et al. |
| 6,171,338 | B1 | 1/2001 | Talja et al. |
| 6,174,322 | B1 | 1/2001 | Schneidt |
| 6,179,809 | B1 | 1/2001 | Khairkhahan et al. |
| 6,187,039 | B1 | 2/2001 | Hiles et al. |
| 6,200,313 | B1 | 3/2001 | Abe et al. |
| 6,206,895 | B1 | 3/2001 | Levinson |
| 6,206,907 | B1 | 3/2001 | Marino et al. |
| 6,214,029 | B1 | 4/2001 | Thill et al. |
| 6,221,092 | B1 | 4/2001 | Koike et al. |
| 6,231,561 | B1 | 5/2001 | Frazier et al. |
| 6,245,080 | B1 | 6/2001 | Levinson |
| 6,254,550 | B1 | 7/2001 | McNamara et al. |
| 6,270,490 | B1 | 8/2001 | Hahnen |
| 6,270,515 | B1 | 8/2001 | Linden et al. |
| 6,275,730 | B1 | 8/2001 | KenKnight et al. |
| 6,277,138 | B1 | 8/2001 | Levinson et al. |
| 6,277,139 | B1 | 8/2001 | Levinson et al. |
| 6,280,432 | B1 | 8/2001 | Turovskiy et al. |
| 6,280,460 | B1 | 8/2001 | Bolduc et al. |
| 6,287,317 | B1 | 9/2001 | Makower et al. |
| 6,290,674 | B1 | 9/2001 | Roue et al. |
| 6,293,920 | B1 | 9/2001 | Sweezer et al. |
| 6,302,903 | B1 | 10/2001 | Mulier et al. |
| 6,305,378 | B1 | 10/2001 | Lesh |
| 6,306,150 | B1 | 10/2001 | Levinson |
| 6,306,424 | B1 | 10/2001 | Vyakarnam et al. |
| 6,308,090 | B1 | 10/2001 | Tu et al. |
| 6,309,415 | B1 | 10/2001 | Pulnev et al. |
| 6,312,446 | B1 | 11/2001 | Huebsch et al. |
| 6,319,263 | B1 | 11/2001 | Levinson |
| 6,322,548 | B1 | 11/2001 | Payne et al. |
| 6,328,727 | B1 | 12/2001 | Frazier et al. |
| 6,336,898 | B1 | 1/2002 | Borst et al. |
| 6,342,064 | B1 | 1/2002 | Koike et al. |
| 6,346,074 | B1 | 2/2002 | Roth |
| 6,346,099 | B1 | 2/2002 | Altman |
| 6,346,112 | B2 | 2/2002 | Adams |
| 6,350,229 | B1 | 2/2002 | Borst et al. |
| 6,352,531 | B1 | 3/2002 | O'Connor et al. |
| 6,352,552 | B1 | 3/2002 | Levinson et al. |
| 6,355,052 | B1 | 3/2002 | Neuss et al. |
| 6,364,826 | B1 | 4/2002 | Borst et al. |
| 6,371,906 | B1 | 4/2002 | Borst et al. |
| 6,375,671 | B1 | 4/2002 | Kobayashi et al. |
| 6,379,368 | B1 | 4/2002 | Corcoran et al. |
| 6,387,104 | B1 | 5/2002 | Pugsley, Jr. et al. |
| 6,394,948 | B1 | 5/2002 | Borst et al. |
| 6,398,796 | B2 | 6/2002 | Levinson |
| 6,401,720 | B1 | 6/2002 | Stevens et al. |
| 6,402,772 | B1 | 6/2002 | Amplatz et al. |
| 6,416,493 | B1 | 7/2002 | Del Giglio |
| 6,419,669 | B1 | 7/2002 | Frazier et al. |
| 6,432,059 | B2 | 8/2002 | Hickey |
| 6,436,088 | B2 | 8/2002 | Frazier et al. |
| 6,440,152 | B1 | 8/2002 | Gainor et al. |
| 6,458,100 | B2 | 10/2002 | Roue et al. |
| 6,464,640 | B1 | 10/2002 | Guracar et al. |
| 6,464,645 | B1 | 10/2002 | Park et al. |
| 6,482,224 | B1 | 11/2002 | Michler et al. |
| 6,482,228 | B1 | 11/2002 | Norred |
| 6,485,504 | B1 | 11/2002 | Johnson et al. |
| 6,488,706 | B1 | 12/2002 | Solymar |
| 6,497,698 | B1 | 12/2002 | Fonger |
| 6,532,388 | B1 | 3/2003 | Hill et al. |
| 6,537,300 | B2 | 3/2003 | Girton |
| 6,551,272 | B2 | 4/2003 | Gobel |
| 6,551,303 | B1 | 4/2003 | Van Tassel et al. |
| 6,551,344 | B2 | 4/2003 | Thill |
| 6,560,489 | B2 | 5/2003 | Hauck |
| 6,562,052 | B2 | 5/2003 | Nobles et al. |
| 6,572,593 | B1 | 6/2003 | Daum |
| 6,579,259 | B2 | 6/2003 | Stevens et al. |
| 6,585,716 | B2 | 7/2003 | Altman |
| 6,592,552 | B1 | 7/2003 | Schmidt |
| 6,592,557 | B2 | 7/2003 | Barbut |

| Patent No. | Date | Name |
|---|---|---|
| 6,596,013 B2 | 7/2003 | Yang et al. |
| 6,606,513 B2 | 8/2003 | Lardo et al. |
| 6,613,062 B1 | 9/2003 | Leckrone et al. |
| 6,623,508 B2 | 9/2003 | Shaw et al. |
| 6,623,518 B2 | 9/2003 | Thompson et al. |
| 6,626,841 B1 | 9/2003 | Atlee, III |
| 6,626,890 B2 | 9/2003 | Nguyen et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,632,223 B1 | 10/2003 | Keane |
| 6,645,225 B1 | 11/2003 | Atkinson |
| 6,650,923 B1 | 11/2003 | Lesh et al. |
| 6,651,672 B2 | 11/2003 | Roth |
| 6,656,206 B2 | 12/2003 | Corcoran et al. |
| 6,659,981 B2 | 12/2003 | Stewart et al. |
| 6,662,045 B2 | 12/2003 | Zheng et al. |
| 6,663,639 B1 | 12/2003 | Laufer et al. |
| 6,666,861 B1 | 12/2003 | Grabek |
| 6,679,268 B2 | 1/2004 | Stevens et al. |
| 6,685,728 B2 | 2/2004 | Sinnott et al. |
| 6,689,062 B1 | 2/2004 | Mesallum |
| 6,692,471 B2 | 2/2004 | Boudreaux |
| 6,692,512 B2 | 2/2004 | Jang |
| 6,695,838 B2 | 2/2004 | Wellman et al. |
| 6,699,231 B1 | 3/2004 | Sterman et al. |
| 6,699,263 B2 | 3/2004 | Cope |
| 6,702,835 B2 | 3/2004 | Ginn |
| 6,706,033 B1 | 3/2004 | Martinez et al. |
| 6,706,047 B2 | 3/2004 | Trout et al. |
| 6,712,804 B2 | 3/2004 | Roue et al. |
| 6,712,836 B1 | 3/2004 | Berg et al. |
| 6,726,662 B2 | 4/2004 | Altman |
| 6,730,061 B1 | 5/2004 | Cuschieri et al. |
| 6,735,471 B2 | 5/2004 | Hill et al. |
| 6,736,828 B1 | 5/2004 | Adams et al. |
| 6,746,404 B2 | 6/2004 | Schwartz |
| 6,746,456 B2 | 6/2004 | Xiao |
| 6,749,617 B1 | 6/2004 | Palasis et al. |
| 6,773,441 B1 | 8/2004 | Laufer et al. |
| 6,776,784 B2 | 8/2004 | Ginn |
| 6,776,797 B1 | 8/2004 | Blom et al. |
| 6,783,499 B2 | 8/2004 | Schwartz |
| 6,790,218 B2 | 9/2004 | Jayaraman |
| 6,802,840 B2 | 10/2004 | Chin et al. |
| 6,821,265 B1 | 11/2004 | Bertolero et al. |
| 6,840,246 B2 | 1/2005 | Downing |
| 6,854,467 B2 | 2/2005 | Boekstegers |
| 6,855,116 B2 | 2/2005 | Atlee, III |
| 6,866,650 B2 | 3/2005 | Stevens et al. |
| 6,878,118 B2 | 4/2005 | Atlee, III |
| 6,882,883 B2 | 4/2005 | Condie et al. |
| 6,889,694 B2 | 5/2005 | Hooven |
| 6,899,704 B2 | 5/2005 | Sterman et al. |
| 6,902,545 B2 | 6/2005 | Bertolero et al. |
| 6,913,600 B2 | 7/2005 | Valley et al. |
| 6,913,607 B2 | 7/2005 | Ainsworth et al. |
| 6,915,149 B2 | 7/2005 | Ben-Haim |
| 6,918,890 B2 | 7/2005 | Schmidt |
| 6,918,908 B2 | 7/2005 | Bonner et al. |
| 6,929,011 B2 | 8/2005 | Knudson et al. |
| 6,932,792 B1 | 8/2005 | St. Goar et al. |
| 6,932,811 B2 | 8/2005 | Hooven et al. |
| 6,934,583 B2 | 8/2005 | Weinberg et al. |
| 6,939,348 B2 | 9/2005 | Malecki et al. |
| 6,939,361 B1 | 9/2005 | Kleshinski |
| 6,952,613 B2 | 10/2005 | Swoyer et al. |
| 6,953,466 B2 | 10/2005 | Palasis et al. |
| 6,955,175 B2 | 10/2005 | Steven et al. |
| 6,960,220 B2 | 11/2005 | Marino et al. |
| 6,971,998 B2 | 12/2005 | Rosenman et al. |
| 6,976,990 B2 | 12/2005 | Mowry |
| 6,991,635 B2 | 1/2006 | Takamoto et al. |
| 6,994,094 B2 | 2/2006 | Schwartz |
| 6,994,713 B2 | 2/2006 | Berg et al. |
| 7,001,415 B2 | 2/2006 | Hooven |
| 7,004,952 B2 | 2/2006 | Nobles et al. |
| 7,018,390 B2 | 3/2006 | Turovskiy et al. |
| 7,020,518 B2 | 3/2006 | Zheng et al. |
| 7,039,467 B2 | 5/2006 | Hauck |
| 7,044,135 B2 | 5/2006 | Lesh |
| 7,048,733 B2 | 5/2006 | Hartley et al. |
| 7,056,331 B2 | 6/2006 | Kaplan et al. |
| 7,083,628 B2 | 8/2006 | Bachman |
| 7,087,072 B2 | 8/2006 | Marino et al. |
| 7,090,683 B2 | 8/2006 | Brock et al. |
| 7,090,686 B2 | 8/2006 | Nobles et al. |
| 7,094,244 B2 | 8/2006 | Schreck |
| 7,097,653 B2 | 8/2006 | Freudenthal et al. |
| 7,101,395 B2 | 9/2006 | Tremulis et al. |
| 7,108,660 B2 | 9/2006 | Stephens et al. |
| 7,112,219 B2 | 9/2006 | Vidlund et al. |
| 7,113,831 B2 | 9/2006 | Hooven |
| 7,115,135 B2 | 10/2006 | Corcoran et al. |
| 7,186,251 B2 | 3/2007 | Malecki et al. |
| 7,320,692 B1 | 1/2008 | Bender et al. |
| 7,507,252 B2 | 3/2009 | Lashinski et al. |
| 2001/0014800 A1 | 8/2001 | Frazier et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0032462 A1 | 3/2002 | Houser et al. |
| 2002/0035361 A1 | 3/2002 | Houser et al. |
| 2002/0035374 A1 | 3/2002 | Borillo et al. |
| 2002/0039048 A1 | 4/2002 | Matsuge |
| 2002/0043307 A1 | 4/2002 | Ishida et al. |
| 2002/0052572 A1 | 5/2002 | Franco et al. |
| 2002/0077555 A1 | 6/2002 | Schwartz |
| 2002/0096183 A1 | 7/2002 | Stevens et al. |
| 2002/0099389 A1 | 7/2002 | Michler et al. |
| 2002/0099437 A1 | 7/2002 | Anson et al. |
| 2002/0107531 A1* | 8/2002 | Schreck et al. ............... 606/142 |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0138095 A1 | 9/2002 | Mazzocchi et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0025421 A1 | 2/2003 | Ebihara et al. |
| 2003/0028213 A1 | 2/2003 | Thill et al. |
| 2003/0033006 A1 | 2/2003 | Phillips et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0059640 A1 | 3/2003 | Marton et al. |
| 2003/0100920 A1 | 5/2003 | Akin et al. |
| 2003/0139819 A1 | 7/2003 | Beer et al. |
| 2003/0144694 A1 | 7/2003 | Chanduszko et al. |
| 2003/0167071 A1* | 9/2003 | Martin et al. ............... 606/232 |
| 2003/0191495 A1 | 10/2003 | Ryan et al. |
| 2003/0195530 A1 | 10/2003 | Thill |
| 2003/0195555 A1 | 10/2003 | Khairkhahan et al. |
| 2003/0204203 A1 | 10/2003 | Khairkhahan et al. |
| 2003/0208232 A1* | 11/2003 | Blaeser et al. ............... 606/213 |

| | | | | | | |
|---|---|---|---|---|---|---|
| 2003/0225421 | A1 | 12/2003 | Peavey et al. | EP | 1352613 A2 | 10/2003 |
| 2004/0044361 | A1 | 3/2004 | Frazier et al. | EP | 1 046 375 B1 | 11/2004 |
| 2004/0073242 | A1 | 4/2004 | Chanduszko | JP | 04-226643 | 8/1992 |
| 2004/0092973 | A1 | 5/2004 | Chanduszko et al. | WO | WO 92/05828 A1 | 4/1992 |
| 2004/0098042 | A1 | 5/2004 | Devellian et al. | WO | WO 92/06733 A1 | 4/1992 |
| 2004/0098121 | A1 | 5/2004 | Opolski | WO | WO 96/25179 A1 | 8/1996 |
| 2004/0133230 | A1 | 7/2004 | Carpenter et al. | WO | WO 96/31157 A1 | 10/1996 |
| 2004/0133236 | A1 | 7/2004 | Chanduszko | WO | WO 97/30639 A1 | 8/1997 |
| 2004/0176799 | A1 | 9/2004 | Chanduszko et al. | WO | WO 97/42878 A1 | 11/1997 |
| 2004/0210301 | A1 | 10/2004 | Obermiller | WO | WO 98/02100 A1 | 1/1998 |
| 2004/0220596 | A1 | 11/2004 | Frazier et al. | WO | WO 98/07375 A1 | 2/1998 |
| 2004/0225183 | A1 | 11/2004 | Michlitsch et al. | WO | WO 99/02100 A1 | 1/1999 |
| 2004/0230185 | A1 | 11/2004 | Malecki et al. | WO | WO 99/18862 A1 | 4/1999 |
| 2004/0243122 | A1 | 12/2004 | Auth et al. | WO | WO 99/18864 A1 | 4/1999 |
| 2004/0267191 | A1 | 12/2004 | Gifford, III et al. | WO | WO 99/18870 A1 | 4/1999 |
| 2004/0267306 | A1 | 12/2004 | Blaeser et al. | WO | WO 99/18871 A1 | 4/1999 |
| 2005/0034735 | A1 | 2/2005 | Deem et al. | WO | WO 00/07506 A2 | 2/2000 |
| 2005/0043759 | A1 | 2/2005 | Chanduszko | WO | WO 00/27292 A1 | 5/2000 |
| 2005/0055050 | A1 | 3/2005 | Alfaro | WO | WO 00/35352 A2 | 6/2000 |
| 2005/0059984 | A1 | 3/2005 | Chanduszko et al. | WO | WO 00/44428 A2 | 8/2000 |
| 2005/0070923 | A1* | 3/2005 | McIntosh ................ 606/139 | WO | WO 01/21247 A1 | 3/2001 |
| 2005/0075653 | A1 | 4/2005 | Saadat et al. | WO | WO 01/49185 A1 | 7/2001 |
| 2005/0080406 | A1 | 4/2005 | Malecki et al. | WO | WO 01/78596 A1 | 10/2001 |
| 2005/0119675 | A1 | 6/2005 | Adams et al. | WO | WO 02/24106 A2 | 3/2002 |
| 2005/0125032 | A1 | 6/2005 | Whisenant et al. | WO | WO 03/059152 A2 | 7/2003 |
| 2005/0131460 | A1 | 6/2005 | Gifford, III et al. | WO | WO 03/063732 A2 | 8/2003 |
| 2005/0149066 | A1* | 7/2005 | Stafford ................ 606/144 | WO | WO 03/077733 A2 | 9/2003 |
| 2005/0149115 | A1 | 7/2005 | Roue et al. | WO | WO 03/094742 A1 | 11/2003 |
| 2005/0187568 | A1 | 8/2005 | Klenk et al. | WO | WO 03/103476 A2 | 12/2003 |
| 2005/0187588 | A1 | 8/2005 | Stahmann et al. | WO | WO 2004/026146 A1 | 4/2004 |
| 2005/0187620 | A1 | 8/2005 | Pai et al. | WO | WO 2004/043266 A2 | 5/2004 |
| 2005/0192626 | A1 | 9/2005 | Widomski et al. | WO | WO 2004/052213 A1 | 6/2004 |
| 2005/0192627 | A1 | 9/2005 | Whisenant et al. | WO | WO 2004/069054 A2 | 8/2004 |
| 2005/0192654 | A1 | 9/2005 | Chanduszko et al. | WO | WO 2004/069055 A2 | 8/2004 |
| 2005/0209636 | A1 | 9/2005 | Widomski et al. | WO | WO 2004/086951 A2 | 10/2004 |
| 2005/0216054 | A1 | 9/2005 | Widomski et al. | WO | WO 2004/087235 A2 | 10/2004 |
| 2005/0228434 | A1 | 10/2005 | Amplatz et al. | WO | WO 2005/006990 A2 | 1/2005 |
| 2005/0234509 | A1 | 10/2005 | Widomski et al. | WO | WO 2005/027752 A1 | 3/2005 |
| 2005/0250988 | A1 | 11/2005 | Ewers et al. | WO | WO 2005/034738 A2 | 4/2005 |
| 2005/0251154 | A1 | 11/2005 | Chanduszko et al. | WO | WO2005/039419 A1 | 5/2005 |
| 2005/0251201 | A1 | 11/2005 | Roue et al. | WO | WO 2005/039419 A1 | 5/2005 |
| 2005/0256532 | A1 | 11/2005 | Nayak et al. | WO | WO 2005/074517 A2 | 8/2005 |
| 2005/0267493 | A1 | 12/2005 | Schreck et al. | WO | WO 2005/074814 A2 | 8/2005 |
| 2005/0267495 | A1 | 12/2005 | Ginn et al. | WO | WO 2005/082255 A1 | 9/2005 |
| 2005/0267523 | A1 | 12/2005 | Devellian et al. | WO | WO 2005/092203 A1 | 10/2005 |
| 2005/0267524 | A1 | 12/2005 | Chanduszko | WO | WO 2005/110240 A1 | 11/2005 |
| 2005/0267525 | A1 | 12/2005 | Chanduszko | WO | WO 2005/112779 A1 | 12/2005 |
| 2005/0267526 | A1 | 12/2005 | Wahr et al. | WO | WO 2006/036837 A2 | 4/2006 |
| 2005/0267529 | A1 | 12/2005 | Crockett et al. | WO | WO 2007/024615 A1 | 3/2007 |
| 2005/0271631 | A1 | 12/2005 | Lee et al. | WO | WO 2008/024489 A2 | 2/2008 |
| 2005/0273119 | A1 | 12/2005 | Widomski et al. | WO | WO 2008/153872 A2 | 12/2008 |
| 2005/0273124 | A1 | 12/2005 | Chanduszko | | | |
| 2005/0273135 | A1 | 12/2005 | Chanduszko et al. | | | |
| 2005/0277982 | A1 | 12/2005 | Marino et al. | | | |
| 2005/0288706 | A1 | 12/2005 | Widomski et al. | | | |
| 2005/0288786 | A1 | 12/2005 | Chanduszko | | | |
| 2006/0009800 | A1 | 1/2006 | Christianson et al. | | | |
| 2006/0015002 | A1 | 1/2006 | Moaddeb et al. | | | |
| 2006/0036282 | A1 | 2/2006 | Wahr et al. | | | |
| 2006/0036284 | A1 | 2/2006 | Blaeser et al. | | | |
| 2006/0052821 | A1 | 3/2006 | Abbott et al. | | | |
| 2006/0069408 | A1 | 3/2006 | Kato | | | |
| 2006/0079870 | A1 | 4/2006 | Barry | | | |
| 2006/0095052 | A1 | 5/2006 | Chambers | | | |
| 2006/0122633 | A1 | 6/2006 | To et al. | | | |
| 2007/0005018 | A1* | 1/2007 | Tekbuchava ............ 604/164.01 | | | |
| 2008/0312646 | A9* | 12/2008 | Auth et al. ................ 606/41 | | | |

FOREIGN PATENT DOCUMENTS

| | | |
|---|---|---|
| EP | 0 553 259 B1 | 3/1995 |
| EP | 1 013 227 A2 | 6/2000 |
| EP | 1 222 897 A2 | 7/2002 |

OTHER PUBLICATIONS

Baim, D., Percutaneous Approach, Including Transseptal and Apical Puncture, Grossman's Cardiac Catheterization, Angiography, and Intervention, 6th Ed., 2000.

Daoud, E., et al. Intracardiac Echocardiography to Guide Transseptal Left Heart Catheterization for Radiofrequency Catheter Ablation, Journal of Cardiovascular Electrophysiology, vol. 10, No. 3, Mar. 1999.

De Ponti, R., et al., Trans-septal catheterization for radiofrequency catheter ablation of cardiac arrhythmias, European Heart Journal, vol. 19, 1998.

Epstein, L., et al., Nonfluoroscopic Transseptal Catheterization: Safety and Efficacy of Intracardiac Echocardiographic Guidance, Journal of Cardiovascular Electrophysiology, vol. 9, No. 6, Jun. 1998.

Hara, H., et al., Patent Foramen Ovale: Current Pathology, Pathophysiology, and Clinical Status, Journal of the American College of Cardiology, vol. 46, No. 9, Nov. 2005:1768-1776.

Hurrell, D., et al., Echocardiography in the Invasive Laboratory: Utility of Two-Dimensional Echocardiography in Performing Transseptal Catheterization, Mayo Clinic Proc., 1998:73:126-131.

Lesh, M., et al., Comparison of the Retrograde and Transseptal Methods for Ablation of Left Free Wall Accessory Pathways, Journal of American College of Cardiology, vol. 22, No. 2, Aug. 1993:542-549.

Lundqvist, C., et al., Transseptal Left Heart Catheterization: A Review of 278 Studies, Clin. Cardiol. 9, Jan. 1986.

Mitchel, J., et al., Intracardiac Ultrasound Imaging During Transseptal Catheterization, CHEST, vol. 108, No. 1, Jul. 1995.

Montenero, A., et al., Catheter Ablation of Left Accessory Atrioventricular Connections: The Transseptal Approach, Journal of Interventional Cardiology, vol. 8, No. 6 (Suppl), 1995.

Peckham, G., et al., Combined Percutaneous Retrograde Aortic and Transseptal Left Heart Catheterization, Brit. Heart Journal, vol. 26, 1964.

Reig, J., et al., Morphologic characteristics of the fossa ovalis as an anatomic basis for transseptal catheterization, Surg. Radiol. Anat. vol. 19, No. 5, 1997.

Roelke, M., et al., The Technique and Safety of Transseptal Left Heart Catheterization: The Massachusetts General Hospital Experience With 1,279 Procedures, Catheterization and Cardiovascular Diagnosis, vol. 32, No. 4, Aug. 1994.

St. Jude Medical, BRK™ Transseptal Needle (Instructions for Use), Nov. 2006.

Szili-Torok, T., Transseptal left heart catherisation guided by intracardiac echocardiography, Heart, vol. 86, e. 11, 2001.

Tucker, K., Transesophageal Echocardiographic Guidance of Transseptal Left Heart Catheterization During Radiofrequency Ablation of Left-Sided Accessory Pathways in Humans, PACE, vol. 19, Mar. 1996.

* cited by examiner

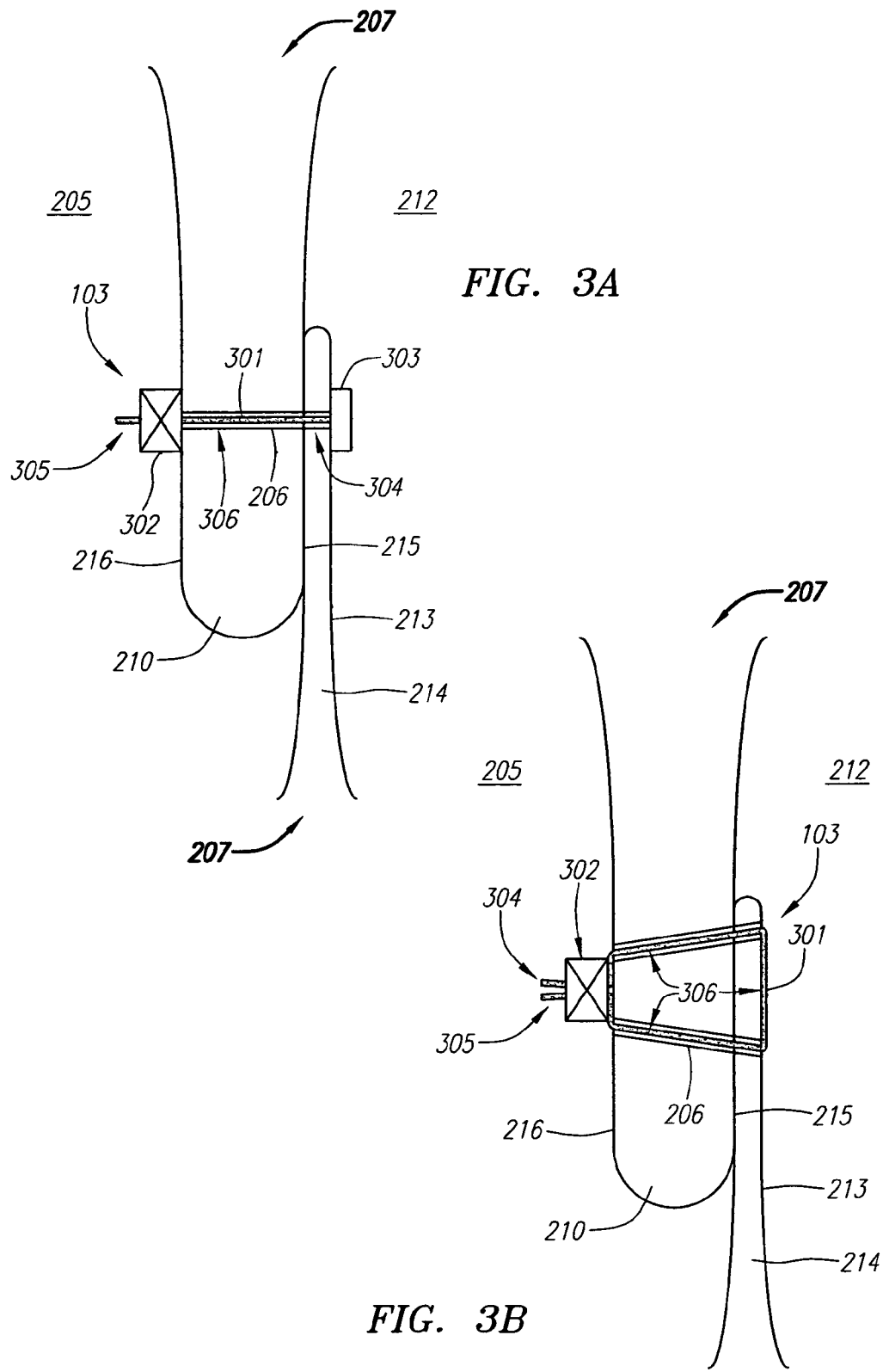

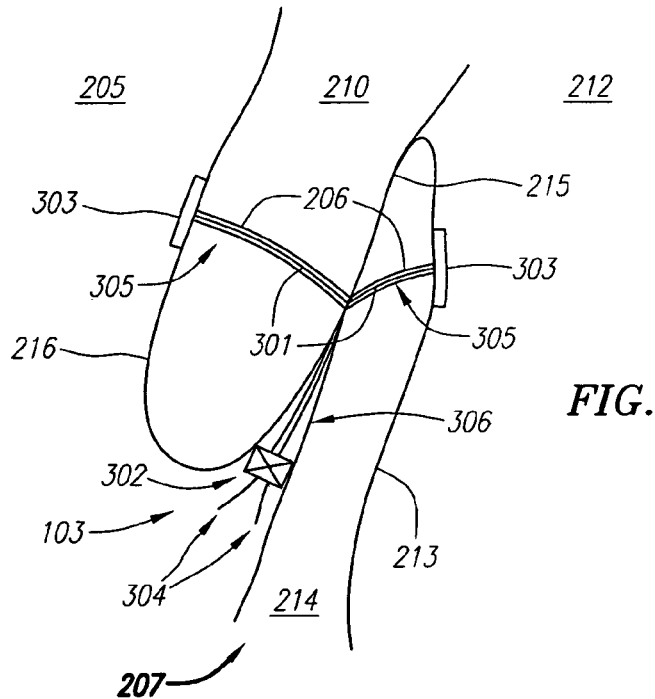
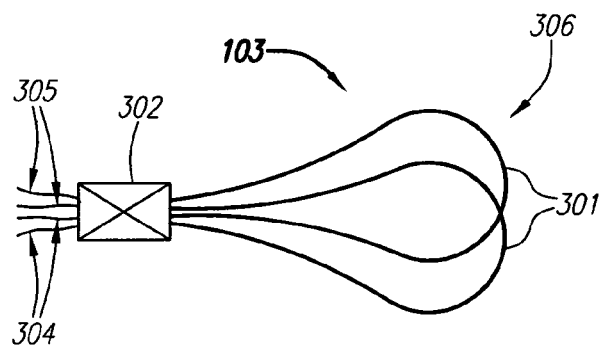
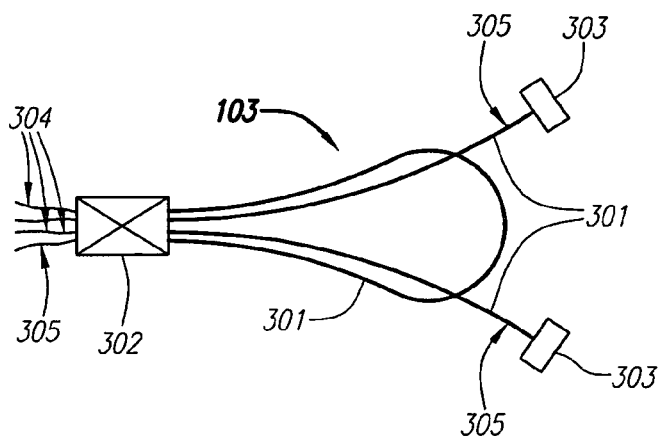

SUTURE-BASED SYSTEMS AND METHODS FOR TREATING SEPTAL DEFECTS

FIELD OF THE INVENTION

The present invention relates generally to systems and methods for closing internal tissue defects, and more particularly to suture-based systems and methods for closing a patent foramen ovale or other septal defect.

BACKGROUND OF THE INVENTION

By nature of their location, the treatment of internal tissue defects is inherently difficult. Access to a defect through invasive surgery introduces a high level of risk that can result in serious complications for the patient. Access to the defect remotely with a catheter or equivalent device is less risky, but treatment of the defect itself is made more difficult given the limited physical abilities of the catheter. The difficulty in accessing and treating tissue defects is compounded when the defect is found in or near a vital organ. For instance, a patent foramen ovale ("PFO") is a serious septal defect that can occur between the left and right atria of the heart and a patent ductus arteriosus ("PDA") is an abnormal shunt between the aorta and pulmonary artery.

During development of a fetus in utero, oxygen is transferred from maternal blood to fetal blood through complex interactions between the developing fetal vasculature and the mother's placenta. During this process, blood is not oxygenated within the fetal lungs. In fact, most of the fetus' circulation is shunted away from the lungs through specialized vessels and foramens that are open during fetal life, but typically will close shortly after birth. Occasionally, however, these foramen fail to close and create hemodynamic problems, which, in extreme cases, can ultimately prove fatal. During fetal life, an opening called the foramen ovale allows blood to pass directly from the right atrium to the left atrium (bypassing the lungs). Thus, blood that is oxygenated via gas exchange with the placenta may travel through the vena cava into the right atrium, through the foramen ovale into the left atrium, and from there into the left ventricle for delivery to the fetal systemic circulation. After birth, with pulmonary circulation established, the increased left atrial blood flow and pressure causes the functional closure of the foramen ovale and, as the heart continues to develop, this closure allows the foramen ovale to grow completely sealed.

In some cases, however, the foramen ovale fails to close entirely. This condition, known as a PFO, can allow blood to continue to shunt between the left and right atria of the heart throughout the adult life of the individual. A PFO can pose serious health risks for the individual, including strokes and migraines. The presence of PFO's have been implicated as a possible contributing factor in the pathogenesis of migraine. Two current hypothesis that link PFO's with migraine include the transit of vasoactive substances or thrombus/emboli from the venous circulation directly into the left atrium without passing through the lungs where they would normally be deactivated or filtered respectively. Other diseases that have been associated with PFO's (and which could benefit from PFO closure) include but are not limited to depression and affective disorders, personality and anxiety disorders, pain, stroke, TIA, dementia, epilepsy, and sleep disorders.

Still other septal defects can occur between the various chambers of the heart, such as atrial-septal defects (ASD's), ventricular-septal defects (VSD's), and the like. To treat these defects as well as PFO's, open heart surgery can be performed to ligate and close the defect. Alternatively, catheter-based procedures have been developed that require introducing umbrella or disc-like devices into the heart. These devices include opposing expandable structures connected by a hub or waist. Generally, in an attempt to close the defect, the device is inserted through the natural opening of the defect and the expandable structures are deployed on either side of the septum to secure the tissue surrounding the defect between the umbrella or disc-like structure.

These devices suffer from numerous shortcomings. For instance, these devices typically involve frame structures that often support membranes, either of which may fail during the life of the patient, thereby introducing the risk that the defect may reopen or that portions of the device could be released within the patient's heart. These devices can fail to form a perfect seal of the septal defect, allowing blood to continue to shunt through the defect. Also, the size and expansive nature of these devices makes safe withdrawal from the patient difficult in instances where withdrawal becomes necessary. The presence of these devices within the heart typically requires the patient to use anti-coagulant drugs for prolonged periods of time, thereby introducing additional health risks to the patient. Furthermore, these devices can come into contact with other portions of the heart tissue and cause undesirable side effects such as an arrhythmia, local tissue damage, and perforation.

Accordingly, improved systems and methods for closing internal tissue defects within the heart are needed.

SUMMARY

Improved suture-based systems and methods for closing internal tissue defects, such as septal defects and the like, are provided in this section by the way of exemplary embodiments. These embodiments are examples only and are not intended to limit the invention.

In one exemplary embodiment, a treatment system for treating a septal defect is provided, the system including an elongate needle-like member having a substantially sharp distal end, the needle-like member being deflectable from a first, substantially straight configuration to a second, curved configuration. The needle is preferably configured to penetrate at least a portion of a septal wall from a first side of the portion of the septal wall to a second side of the portion of the septal wall in the first configuration, and wherein the needle is configured to penetrate the portion of the septal wall from the second side of the portion of the septal wall to the first side of the portion of the septal wall in the second configuration.

The needle-like member is preferably used to create openings in the septal wall for deployment of a suture or other implantable device therein, for the purpose of at least partially closing or otherwise treating a septal defect. The needle-like member can be deflected in numerous ways, including, but not limited to, using a curved stylet or fabricating the needle-like member from a shape memory material so that the curved configuration can be instilled into the needle and a substantially straight stylet or other member can be used to deflect the needle to the substantially straight configuration.

The needle-like member is preferably part of a delivery device configured for off-axis delivery of the implant to the septal wall. In addition to the delivery device with needle-like member, the treatment system can also include a stabilization device for stabilizing the needle-like member and a positioning device for positioning the needle-like member in a desired location with respect to the septal defect.

In additional exemplary embodiments, the needle-like member can be a substantially rigid and straight member, or can be detachable. Furthermore, multiple needles can be used, either straight, deflectable or otherwise, as desired.

In another exemplary embodiment, a method of treating a septal defect is provided, including advancing a flexible outer tubular member having a inner lumen into proximity with a septal defect. The outer tubular member is preferably configured to house a first and a second inner elongate tubular member in a first configuration, each inner elongate tubular member having a substantially sharp distal end. The method can also include advancing the first and second inner elongate tubular members out of the inner lumen of the outer tubular member such that the first and second inner elongate tubular members deflect from the first configuration to a second configuration wherein a distal portion of each inner elongate tubular member is deflected away from the other. The method can also include penetrating at least a portion of the septal wall in different locations with the first and second inner elongate tubular members. In one exemplary embodiment, the first and second inner elongate members are coupled together.

In another exemplary embodiment, the first and second inner elongate members each have a distal portion, a proximal portion and a curved intermediate portion located therebetween. The distal and proximal portions of each inner elongate member can be substantially straight and can have longitudinal axes that are substantially parallel with each other.

The treatment system can be configured to deliver numerous types of suture devices and other implantable devices. Each suture device can be one of at least a looped, non-looped or combination looped and non-looped configuration. Each suture device, depending on the configuration, can include one or more lock devices and/or one or more anchor devices. Each suture device also includes a suture body, which can be relatively rigid or relatively elastic for applying additional closing force. Numerous different embodiments of lock devices, anchor devices and suture bodies are described herein, each of which can be used with one or more embodiments of the others. For instance, each suture body embodiment can be used with multiple lock devices and anchor device embodiments.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention, both as to its structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

FIGS. 3A-C are partial cross-sectional views depicting exemplary embodiments of a suture device.

FIGS. 3D-J are schematic views depicting additional exemplary embodiments of a suture device.

FIGS. 5A-G are partial cross-sectional views depicting additional exemplary embodiments of a delivery device.

FIGS. 14K-J are partial cross-sectional views of this embodiment of the lock device.

DETAILED DESCRIPTION

Improved suture-based systems and methods for treating septal defects are described herein. For ease of discussion, the systems and methods will be described with reference to treatment of a PFO. However, it should be understood that the systems and methods can be used in treatment of any type of septal defect including ASD's, VSD's and the like, as well as PDA's or other structural cardiac, vascular or non-vascular defects.

Figure 1:
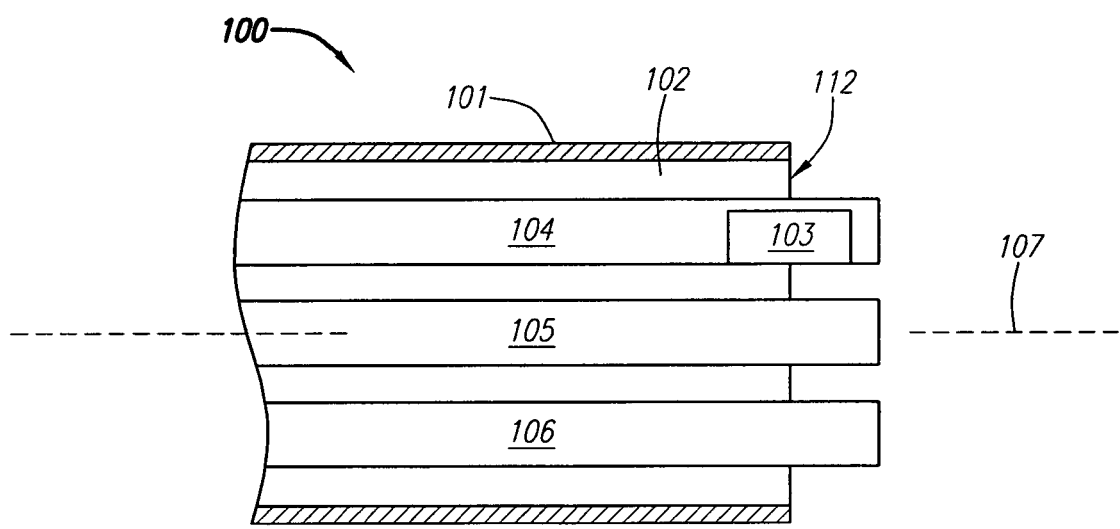
FIG. 1 is a block diagram depicting an exemplary embodiment of a septal defect treatment system.

FIG. 1 is a block diagram depicting a distal portion of an exemplary embodiment of a septal defect treatment system 100 configured to treat and preferably close a PFO. In this embodiment, treatment system 100 includes an elongate body member 101 configured for insertion into the vasculature of a patient (human or animal) having a septal defect. Body member 101 has a longitudinal axis 107, a distal end 112 and can include one or more lumens 102, each of which can be configured for achieving multiple functions. Preferably, treatment system 100 includes an implantable device 103 configured to facilitate closure of or at least partially close a septal defect. Implantable device 103 is preferably configured as a suture and, to facilitate this description, will be referred to herein as suture device 103. Treatment system 100 can include a flexible elongate delivery device 104 configured to house and deliver suture device 103. To minimize the width of body member 101, suture device 103 can be deformable from the configuration desired after implantation to a configuration having a smaller cross-section for storage and housing within delivery device 104 prior to implantation.

Treatment system 100 can also optionally include a stabilization device 105 for stabilization of body member 101 during delivery of suture device 103 and a positioning device 106 for facilitating the positioning or the centering of delivery device 104 for delivery. Although shown here as four separate components, any combination of body member 101, delivery device 104, stabilization device 105 and centering device 106 can be integrated together to reduce the number of components to three, two or one total components in treatment system 100. The use of a similar treatment system 100, also having delivery device 104, stabilization device 105 and centering device 106 is described in detail in co-pending U.S. patent application Ser. No. 11/175,814, filed Jul. 5, 2151 and entitled "Systems and Methods for Treating Septal Defects," which is fully incorporated by reference herein.

Figure 2A:
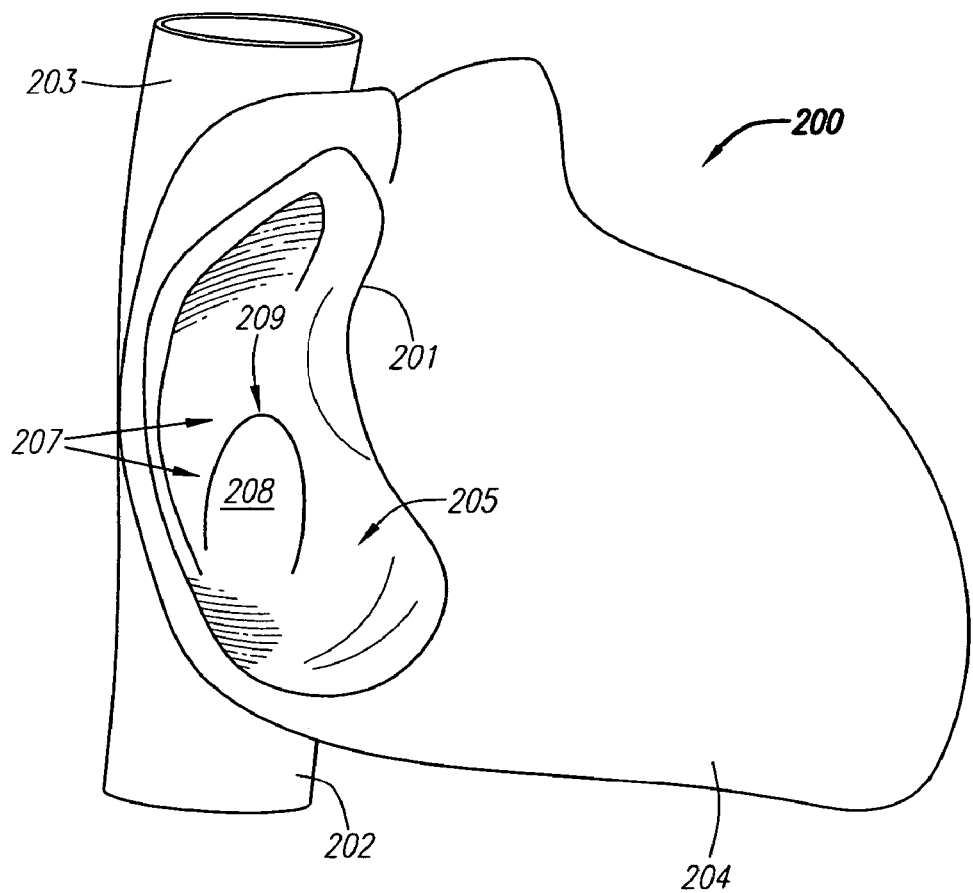
FIG. 2A is an exterior/interior view depicting an example human heart.

To better understand the many alternative embodiments of treatment system 100, the anatomical structure of an example human heart having a PFO will be described in brief. FIG. 2A is an exterior/interior view depicting an example human heart 200 with a portion of the inferior vena cava 202 and the superior vena cava 203 connected thereto. Outer tissue surface 204 of heart 200 is shown along with the interior of right atrium 205 via cutaway portion 201. Depicted within right atrium 205 is septal wall 207, which is placed between right atrium 205 and the left atrium located on the opposite side (not shown). Also depicted is fossa ovalis 208, which is a region of septal wall 207 where the tissue is relatively thinner than the surrounding tissue. PFO region 209 is located near the upper portion beyond the fossa ovalis 208.

Figure 2B:
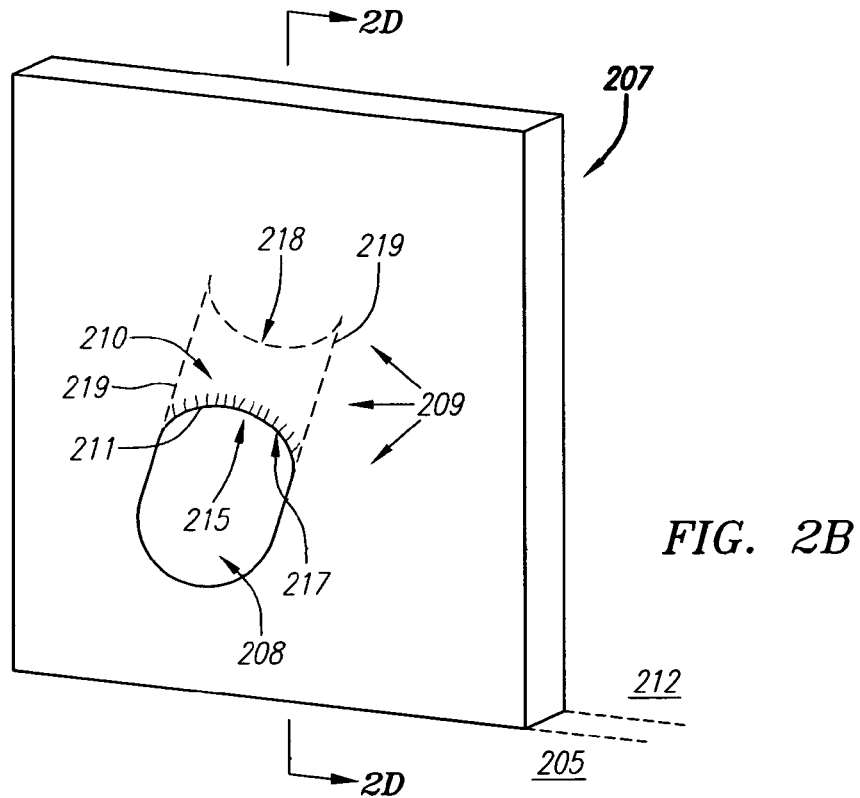
FIGS. 2B-C are enlarged views depicting a septal wall with a PFO region.
Figure 2C:
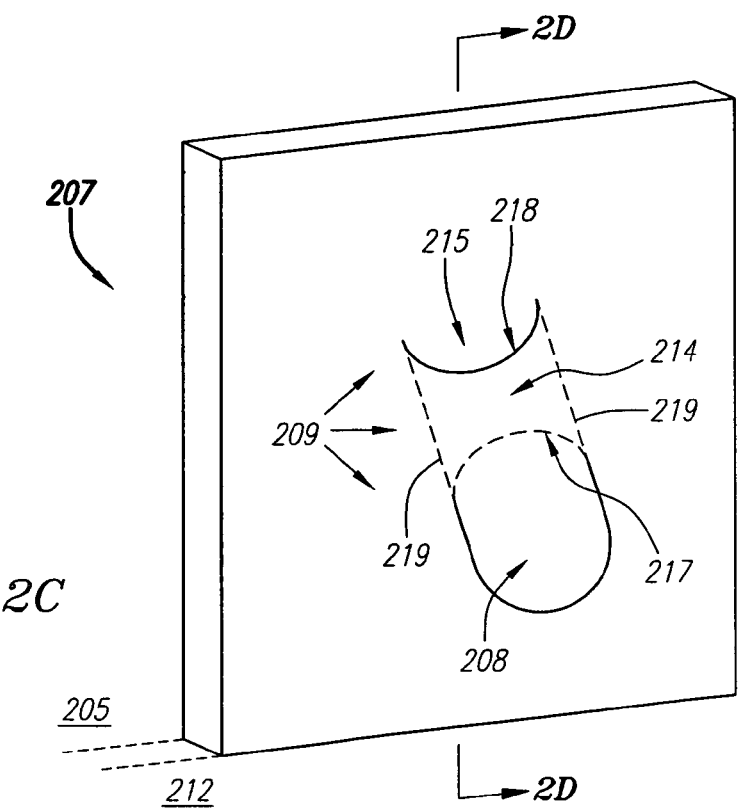

FIG. 2B is an enlarged view of septal wall 207 depicting PFO region 209 in more detail as viewed from right atrium 205. PFO region 209 includes septum secundum 210, which is a first flap-like portion of septal wall 207. The edge of this flap above fossa ovalis 208 is referred to as the limbus 211. FIG. 2C is also an enlarged view of septal wall 207, instead depicting septal wall 207 as viewed from left atrium 212. Here, PFO region 209 is seen to include septum primum 214, which is a second flap-like portion of septal wall 207. Septum primum 214 and septum secundum 210 partially overlap each other and define a tunnel-like opening 215 between sidewalls 219 (indicated as dashed lines in FIGS. 2B-C) that can allow blood to shunt between right atrium 205 and left atrium 212 and is commonly referred to as a PFO.

Figure 2D:
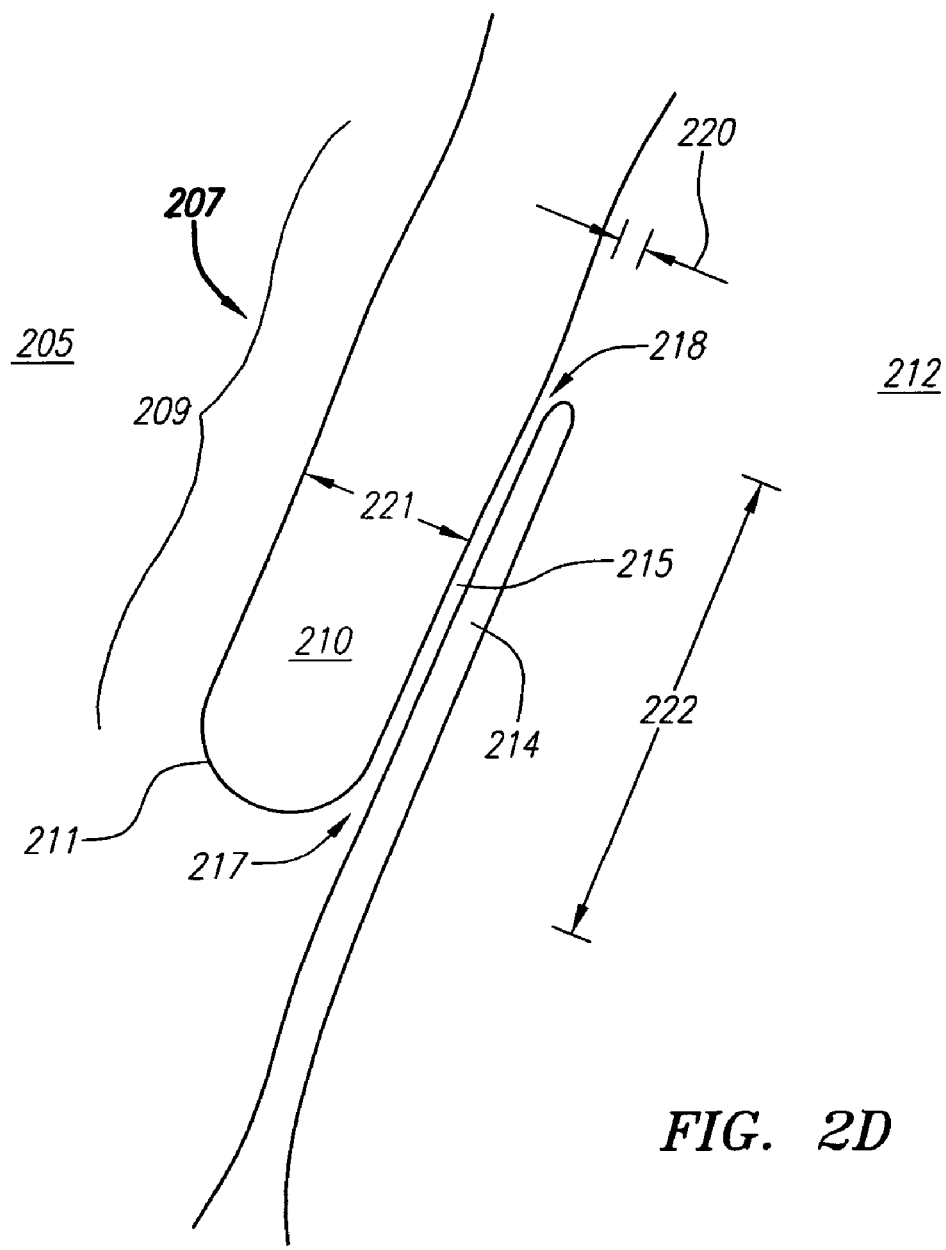
FIG. 2D is a cross-sectional view depicting an example PFO region taken along line 2D-2D of FIGS. 2B-C.

FIG. 2D is a cross-sectional view depicting an example PFO region 209 taken along line 2D-2D of FIGS. 2B-C. Here, it can be seen that septum secundum 210 is thicker than septum primum 214. Typically, the blood pressure within left atrium 212 is higher than that within right atrium 205 and tunnel 215 remains sealed. However, under some circumstances a valsalva condition can occur when the blood pressure within right atrium 205 becomes higher than the blood pressure within left atrium 212 and blood shunts from right atrium 205 to left atrium 212. Because most typical shunts occur in this manner and for purposes of facilitating the discussion herein, region 217 in FIG. 2D will be referred to as PFO entrance 217, and region 218 will be referred to as PFO exit 218.

Many different variations of PFO's can occur. For instance, thickness 220 of septum primum 214, thickness 221 of septum secundum 210, overlap distance 222 and the flexibility and distensibility of both septum primum 214 and septum secundum 210 can all vary. In FIGS. 2B-C, PFO entrance 217 and PFO exit 218 are depicted as being relatively the same size with the width of tunnel 215, or the distance between sidewalls 219, remaining relatively constant. However, in some cases PFO entrance 217 can be larger than PFO exit 218, resulting in an tunnel 215 that converges as blood passes through. Conversely, PFO entrance 217 can be smaller than PFO exit 218, resulting in an opening that diverges as blood passes through. Furthermore, multiple PFO exits 218 can be present, with one or more individual tunnels 215 therebetween. Also, in FIGS. 2B-D, both septum primum 214 and septum secundum 210 are depicted as relatively planar tissue flaps, but in some cases one or both of septum primum 214 and septum secundum 210 can have folded, non-planar, highly irregular shapes.

As will be described in more detail below, treatment of a PFO preferably includes inserting treatment system 100 into the vasculature of a patient and advancing body member 101 through the vasculature to inferior vena cava 202, from which access to right atrium 205 can be obtained. Once properly positioned within right atrium 205, delivery device 104 can be used to deliver one or more suture devices 103 to PFO region 209, preferably by inserting each suture device 103 through septum secundum 210 and primum 214 such that it lies transverse to tunnel 215 to at least partially close tunnel 215. Thus, the use of suture-based systems and methods for treating PFO's allows direct closure of PFO tunnel 215, as opposed to occlusive-type devices that merely block PFO entrance 217 and exit 218 without closing tunnel 215.

Suture device 103 can be configured in numerous variations. FIGS. 3A-J are partial cross-sectional and schematic views depicting exemplary embodiments of suture device 103. Generally, the various embodiments of suture device 103 can be classified as either "looped" or "non-looped." Preferably, looped suture devices 103 include at least a suture body 301 and a lock device 302, while non-looped suture devices 103 include at least a suture body 301 and either multiple anchor devices 303 or a combination of a lock device 302 and one or more anchor devices 303.

FIGS. 3A-B are partial cross-sectional views depicting exemplary embodiments of a non-looped suture device 103 and a looped suture device 103, respectively, implanted within a surgically created, or manmade, opening 206 in septal wall 207. In FIG. 3A, a first end portion 304 of suture body 301 has anchor device 303 located thereon and a second end portion 305 of suture body 301 has lock device 302 located thereon. In this embodiment, first end portion 304 is located adjacent to surface 213 of septum primum 214 in left atrium 212 and second end portion 305 is located adjacent surface 216 of septum secundum 210 in right atrium 205, while a central portion 306 is located between the two end portions 304-305 within septal wall 207. In the looped embodiment of FIG. 3B, both first end portion 304 and second end portion 305 are located in right atrium 205 while central portion 306 is looped through septal wall 207 and left atrium 212. Here, both first and second end portions 304-305 are coupled together with the same lock device 302 and no additional lock devices 302 or anchor devices 303 are necessary.

FIG. 3C is another partial cross-sectional view depicting a non-looped exemplary embodiment of suture device 103 implanted within septal wall 207. Here, the first end portions 304 of two suture bodies 301 are coupled together with a lock device 302 located between septum primum 214 and septum secundum 210 in tunnel 215. The second end portions 305 of each suture body 301 are located near right atrium 205 and left atrium 212, respectively.

Any of the embodiments depicted in FIGS. 3A-C can be implemented with additional suture bodies 301 as desired. For instance, FIG. 3D is a schematic view depicting an exemplary embodiment of a looped suture device 103 having multiple looped suture bodies 301 coupled together in lock device 302. In addition, any combination of looped and non-looped suture bodies 301 can be implemented. For instance, FIG. 3E depicts an embodiment where a looped suture body 301 and two non-looped suture bodies 301 are coupled with lock device 302.

Figure 3F:
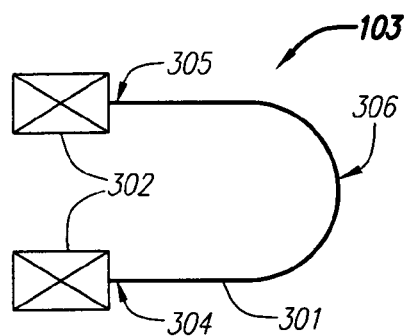
Figure 3G:
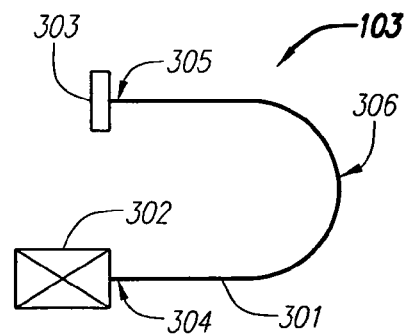
Figure 3H:
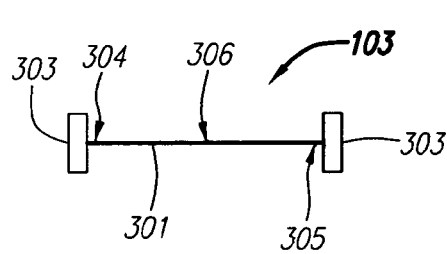
Figure 3I:
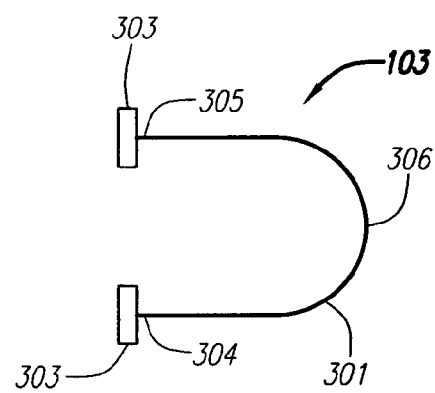
Figure 3J:
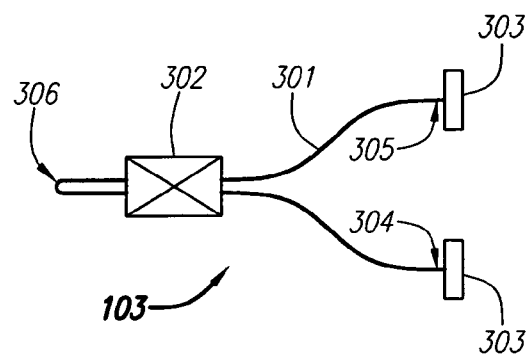

Furthermore, looped suture devices 103 can be implemented with multiple lock devices 302, as depicted in FIG. 3F, or with combinations of lock devices 302 and anchor devices 303, as depicted in FIG. 3G. The position of lock device 302 on suture body 301 is preferably adjustable in order to allow adjustment of the tension on suture body 301. However, if lock device 302 is not used to couple multiple suture bodies 301 together or multiple portions 304-306 of the same suture body together, lock device 302 can be optionally replaced with anchor device 303. FIGS. 3H-I depict non-looped and looped embodiments, respectively, of suture device 103 having only anchor devices 303. Due to the omission of lock device 302, however, these embodiments of suture device 103 are not adjustable and must be sized correctly to apply the proper closing force between septum primum 214 and septum secundum 210. FIG. 3J depicts a looped embodiment where lock device 302 is placed over the looped end to allow further tightening of suture 103. The suture device may exhibit elastic behavior (spring or elastomer, such as silicone, polyurethane and the like) to accommodate variable thickness tissue.

It should be noted that lock device 302 and anchor device 303 are depicted with generic blocks in FIGS. 3A-5F. Lock device 302 and anchor device 303 can be configured in many different ways, as will become evident in the foregoing description. It should also be noted that a lock device 302 can be used in place of anchor device 303 as desired.

Suture 103 can be delivered in any desired manner and with any delivery system. FIGS. 4A-H are partial cross-sectional views depicting exemplary embodiments of delivery device 104 configured for delivery of suture 103 to PFO region 209. The configuration of delivery device 104 and the method of delivery can vary based on whether a looped or non-looped suture 103 is used.

Figure 4A:
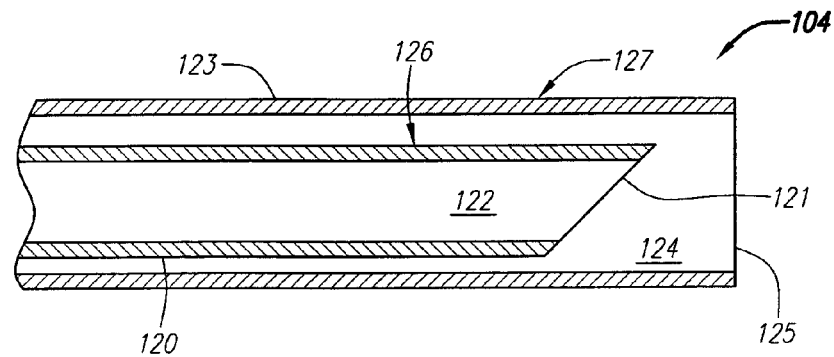
FIGS. 4A-H are partial cross-sectional views depicting exemplary embodiments of a delivery device.

FIG. 4A depicts an exemplary embodiment of delivery device 104 configured to deliver a non-looped suture 103. Here, delivery device 104 includes an elongate inner member 120 having a substantially sharp distal end 121. Inner member 120 can be solid or can have an inner lumen 122 as depicted here. To facilitate the description herein, inner member 120 will be referred to as needle 120, although inner member 120 is not limited to such. Needle 120 is preferably configured to puncture or penetrate at least a portion of septal wall 207, either the part of septal wall 207 adjacent to tunnel 215 or septum primum 214 and/or septum secundum 210. It should be noted that in some of the accompanying figures, needle 120 is depicted in less detail without a structure corresponding to substantially sharp distal end 121, in order to facilitate illustration of the embodiments.

Delivery device 104 also includes an elongate outer tubular member 123 having an inner lumen 124 with an open distal end 125. Inner lumen 124 is preferably configured to slidably receive needle 120. Outer member 123 can be configured to pass through septal wall 207 with needle 120 if desired. As described in co-pending U.S. patent application Ser. No. 11/175,814, proper orientation of treatment system 100 can be difficult, especially if treatment system 100 is routed to PFO region 209 through the superior vena cava 203 or inferior vena cava 202. Preferably, treatment system 100 is configured to properly orient delivery device 104 to enable delivery of suture 103 through septal wall 207, such as through use of any of the off-axis delivery configurations of treatment system 100 and delivery device 104 described in co-pending U.S. patent application Ser. No. 11/175,814.

Suture 103 can be delivered in numerous different ways. For instance, suture 103 can be housed and delivered from within inner lumen 122 of needle 120 (as depicted here), or from within inner lumen 124 of outer member 123, for instance, after needle 120 is proximally withdrawn. Suture 103 can be carried and delivered over outer surface 126 of needle 120 or outer surface 127 of outer member 123. Suture 103 can also be delivered from an additional delivery member inserted through inner lumens 122 or 124 or over outer member 123. Furthermore, suture 103 can be integrated with needle 120 such that a portion of needle 120 is detached or separated to form a portion of suture 103 (e.g., the embodiments described with respect to FIGS. 30A-F below).

Figure 4B:
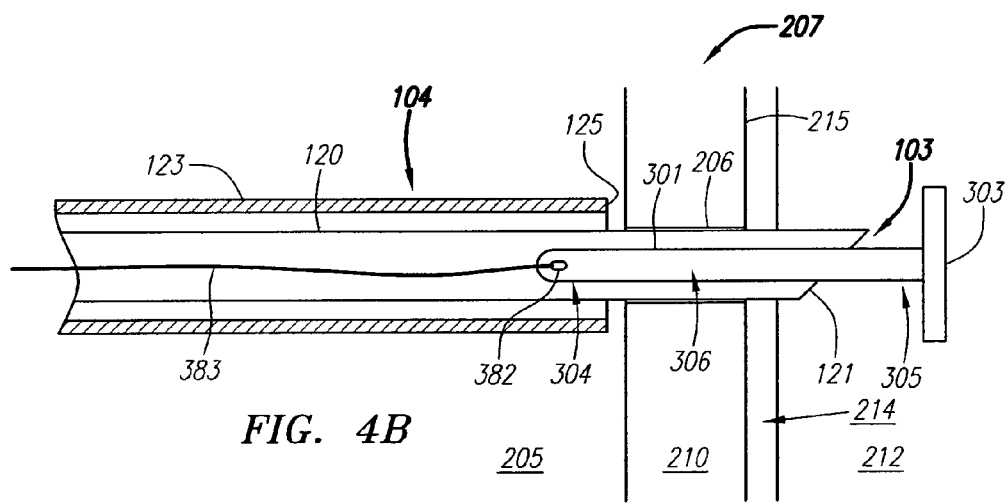

FIG. 4B depicts this embodiment of delivery device 104 after insertion of needle 120 through septum primum 214 and septum secundum 210. Once through septum primum 214, anchor device 303 can be deployed from distal end 121, preferably by advancing suture 103 in a distal direction. Suture 103 is preferably coupled with delivery device 104 to prevent premature deployment, allow for removal of suture 103 during or after deployment (i.e., as a "bail-out" option)

and/or to allow proper positioning and tensioning. In this embodiment, proximal end 304 includes an aperture 382 through which a tether 383 is coupled, which in turn, can be coupled to delivery device 104 or directly accessible by the user. In other embodiments, an elongate hook device can be hooked through aperture 382 or an elongate clamping device can clamp proximal end 304, in which case aperture 382 can be omitted.

Figure 4C:
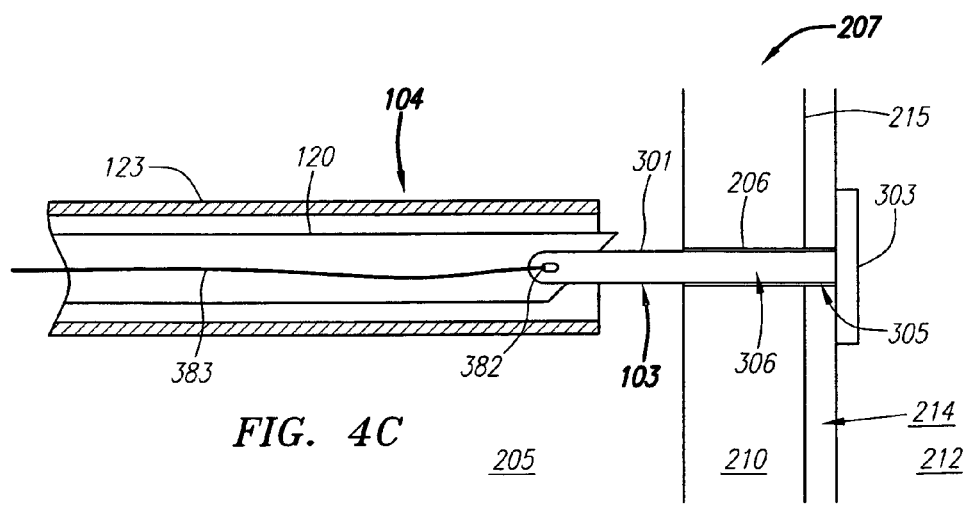

FIG. 4C depicts this embodiment after needle 120 has been proximally retracted through septal wall 207. Here, anchor device 303 is in the deployed position anchoring distal end 305 of suture 103 against septum primum 214 and tether 383 is pulled taut to apply tension to suture body 301 in order to reach the desired degree of closure of tunnel 215.

Figure 4D:
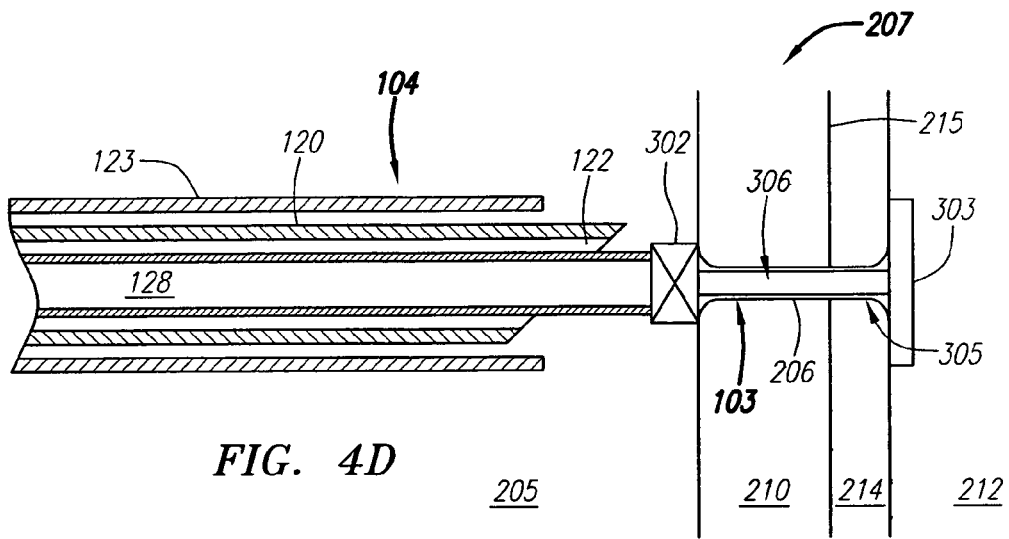
Figure 4E:
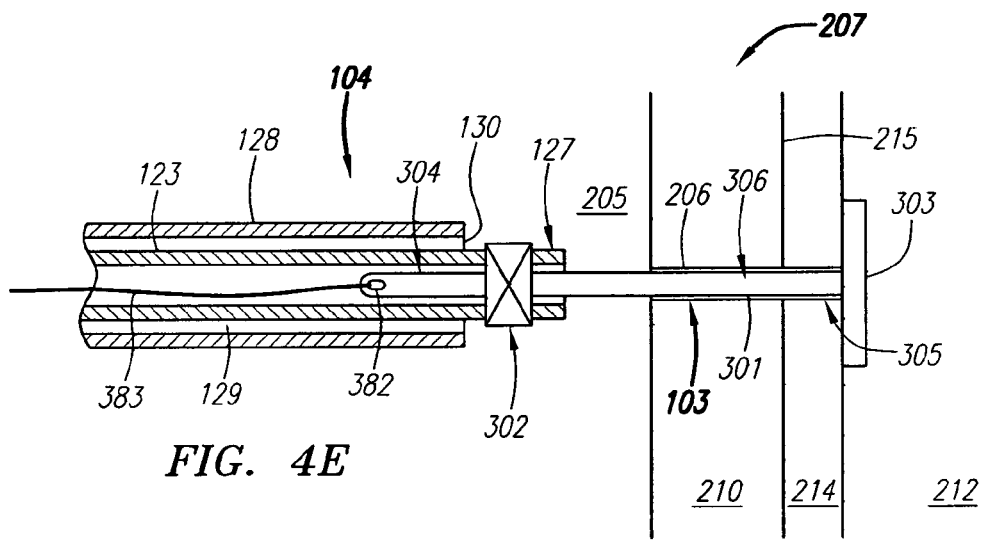

Once the desired degree of closure or tension is reached, lock device 302 can be deployed and advanced distally into proximity or contact with septum secundum 210, as depicted in FIG. 4D. Here, delivery device 104 includes an inner pusher member 128 located within inner lumen 122 of needle 120 for advancing lock device 302 into the desired position. FIG. 4E depicts another exemplary embodiment of delivery device 104 where lock device 302 is carried on outer surface 127 of outer member 123. In this embodiment, pusher member 128 is tubular with inner lumen 129 configured to slidably receive outer member 123. Distal end 130 of pusher member 128 is preferably configured to abut lock device 302 and push lock device 302 off of outer member 123 and onto suture body 301. Once on suture body 301, lock device 302 preferably locks the position of suture body 301 with respect to lock device 302 and also locks, or anchors, the position of suture 103 against septum secundum 210. Any portion of proximal end 304 extending proximally past lock device 302 can then be trimmed as desired.

Figure 4F:
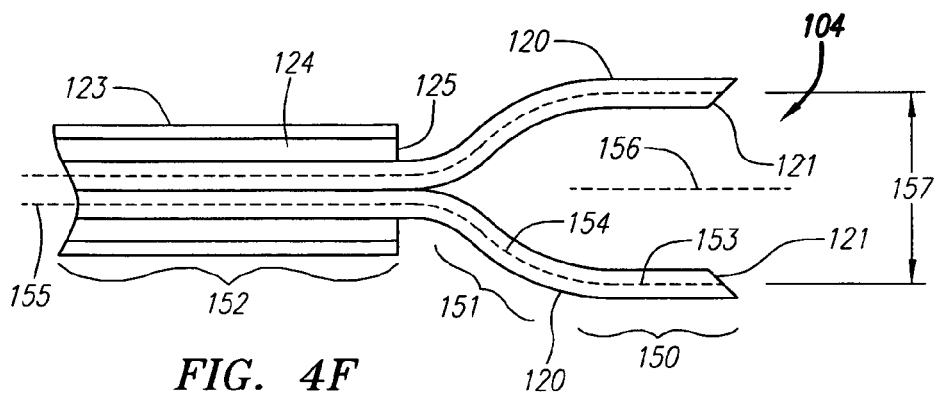
Figure 4G:
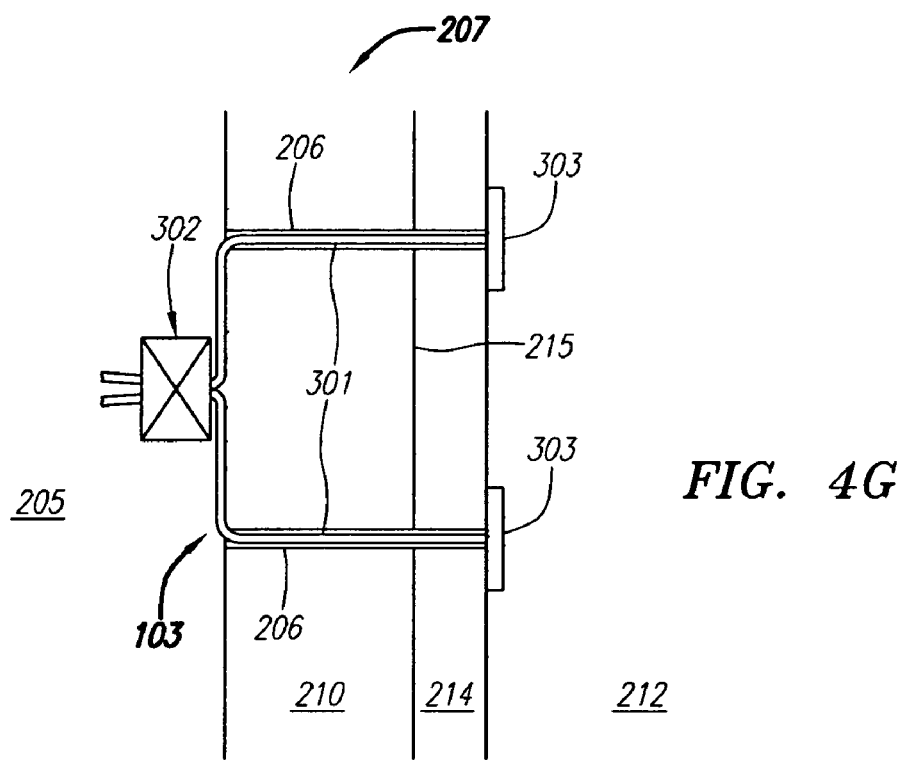

FIG. 4F depicts another exemplary embodiment of delivery device 104 having two needles 120. Here, each needle 120 is preferably formed from NITINOL or another elastic, deformable, shape memory material and heat treated in the deployed configuration depicted here. Each needle 120 has a deflected distal end 121 preferably oriented away from each other in order to deploy suture 103 in a configuration similar to that depicted in FIG. 4G.

In the embodiment depicted in FIG. 4F, each needle 120 has a substantially straight distal portion 150 having a longitudinal axis 153, a substantially straight proximal portion 152 having a longitudinal axis 155, and a curved intermediate portion 151 having a longitudinal axis 154. Outer tubular member 123 also has a longitudinal axis 156. The longitudinal axes 153 and 152 are substantially parallel to longitudinal axis 156, while longitudinal axis 154 of curved intermediate portion 151 is plainly transverse to the other longitudinal axes 153, 155 and 156. Curved intermediate portion 151 is configured to offset distal portions 150 a predetermined distance 008 from each other, thereby allowing needles 120 to create to openings 206 in septal wall at distance 157 apart. Preferably, proximal portions 152 of each needle 120 are coupled together to maintain the desired orientation. Needles 120 can be advanced through septal wall 207 and used to deploy suture 103 in a manner similar to that described above.

Figure 4H:
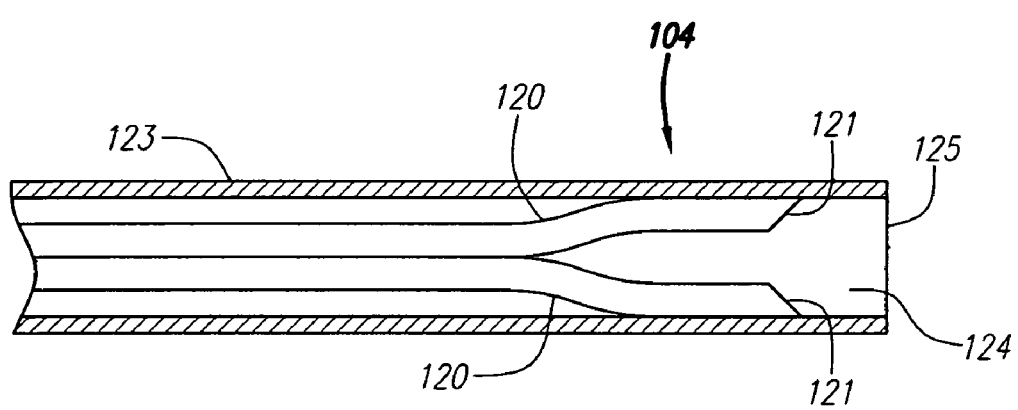

FIG. 4H depicts this embodiment with needles 120 in a deflected configuration for housing within inner lumen 124 of outer member 123 prior to deployment of sutures 103. In this housed configuration, all longitudinal axes 153, 155, 154 and 156 are substantially parallel. It should be noted that this embodiment is not limited to the configurations depicted in FIGS. 4F-H. For instance, distal portions 150 and intermediate portions 152 can be one continuous curved portion.

Figure 5A:
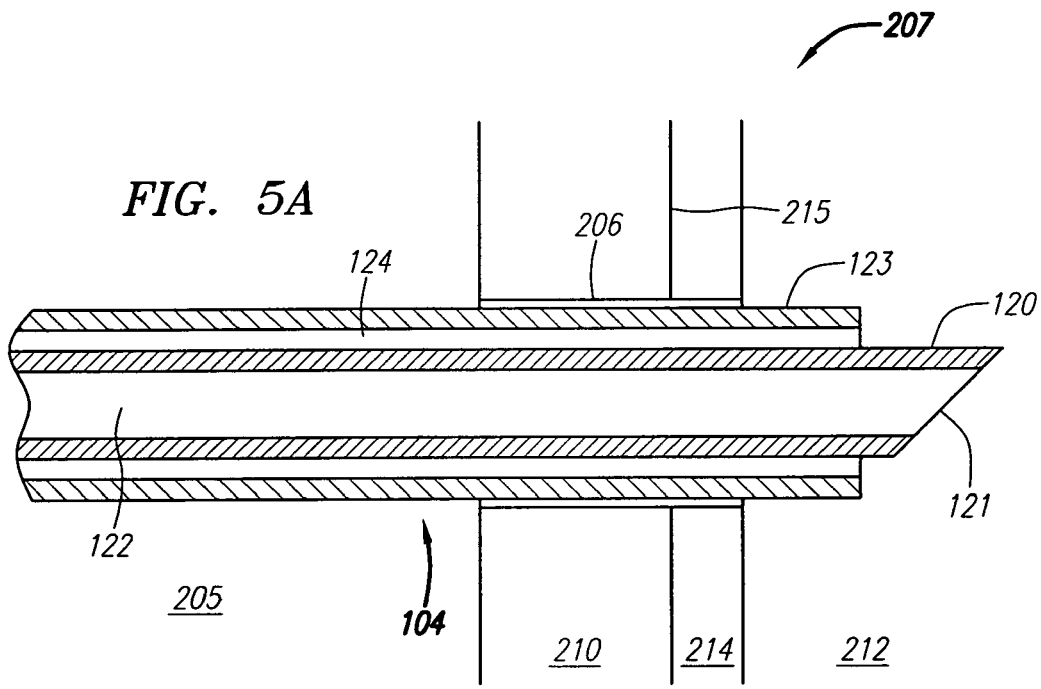
Figure 5B:
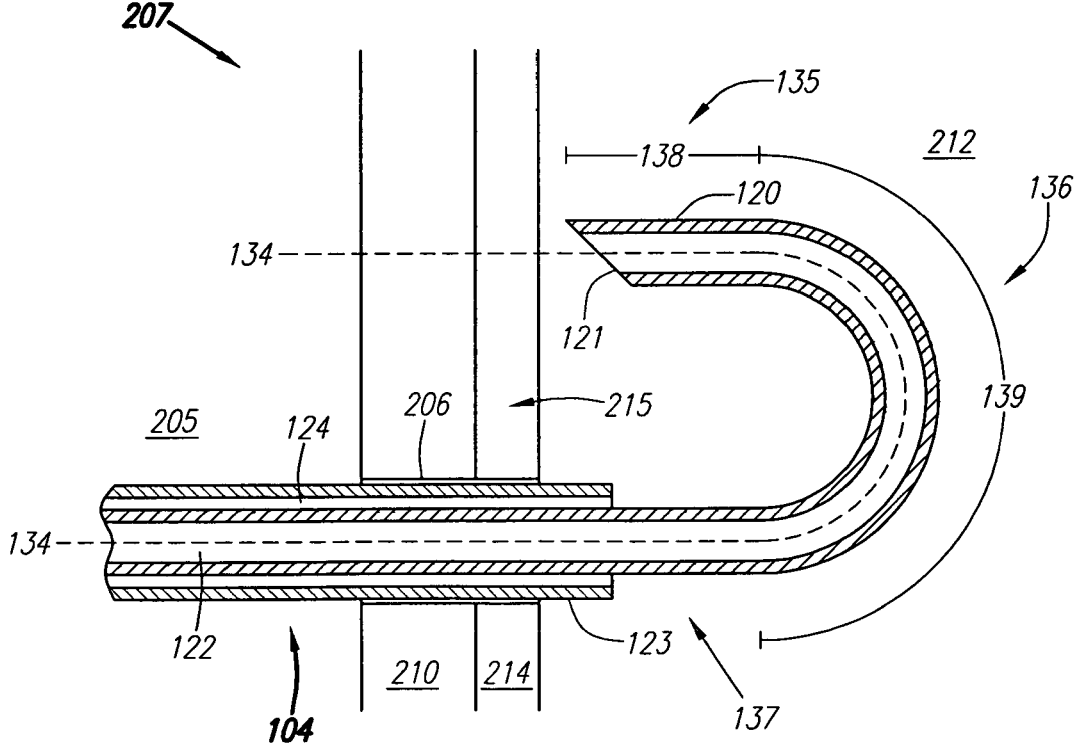

FIGS. 5A-G are partial cross-sectional views depicting additional exemplary embodiments of delivery device 104 where needle 120 can be advanced through septal wall 207 in a relatively, substantially straight configuration and a relatively, substantially curved configuration. FIG. 5A depicts this embodiment after advancement through septal wall 207. Once through septal wall 207, needle 120 is preferably advanced distally from within outer member 123 at which point needle 120 can deflect or deform to a curved state as depicted in FIG. 5B.

In this curved state, distal end 121 is preferably directed back towards septal wall 207, i.e., the longitudinal axis 134 of needle 120 is curved 180 degrees, to allow needle 120 to be advanced through septal wall 207 a second time. In the curved state, needle 120 can be described as having three regions: a first, distal region 135; a second, intermediate region 136; and a third, proximal region 137. Distal region 135 is preferably substantially straight and has a length 138 that is preferably as great or greater than the thickness of septal wall 207, or the portion of septal wall 207 through which needle 120 is intended to be advanced. Intermediate region 136, which is located between distal region 135 and proximal region 137, is preferably curved and has a length 139 that is predetermined based on the size of the loop that is desired to be placed through septal wall 207 (i.e., the distance between separate manmade openings 206). The proximal region 137 extends back to the proximal end of needle 120 following the path of the vasculature of the patient.

The portion of needle longitudinal axis 134 extending through distal region 135 is preferably parallel to the portion of needle longitudinal axis 134 extending through proximal region 137. However, these two portions of longitudinal axis 134 can be non-parallel if desired, so long as there is a sufficient degree of deflection between distal end 121 and proximal region 137 to allow needle 120 to be advanced through septal wall 207 a second time. The portion of needle longitudinal axis 134 extending through intermediate region 136 is curved.

Figure 5C:
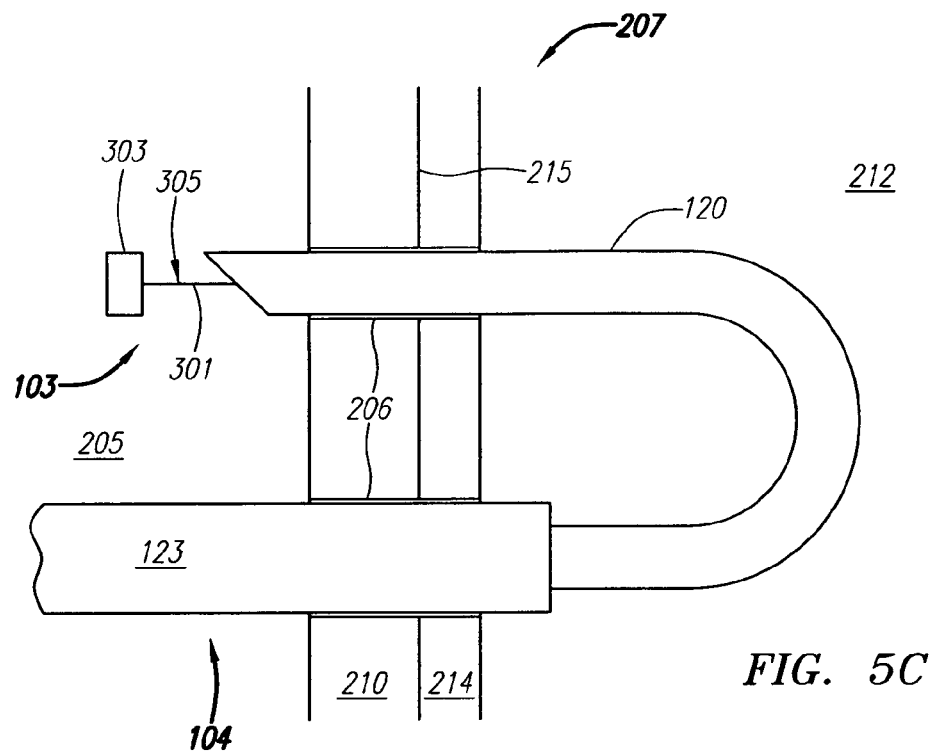
Figure 5D:
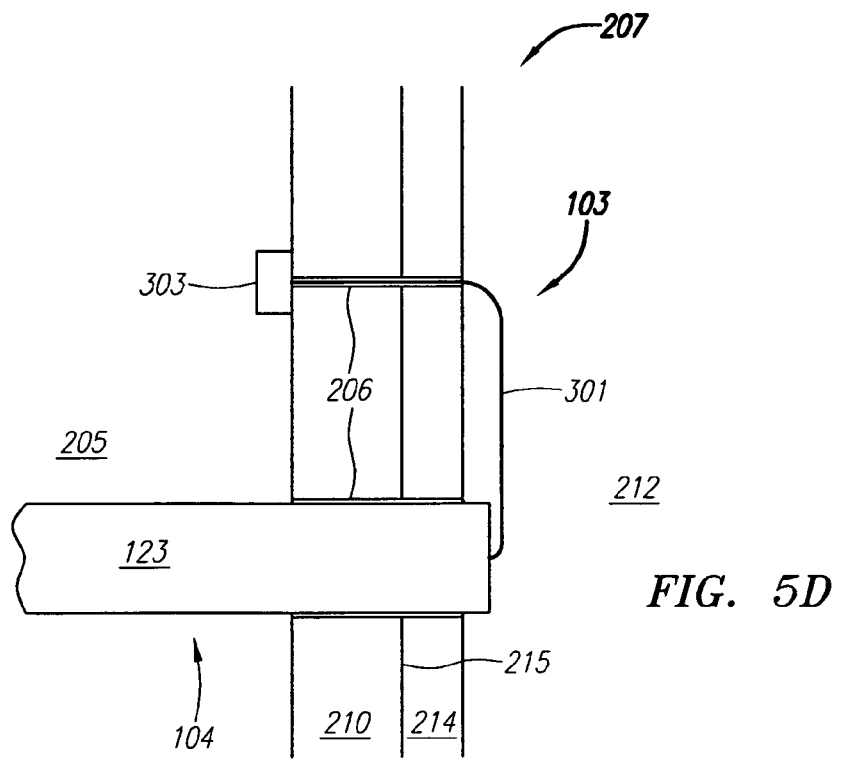
Figure 5F:
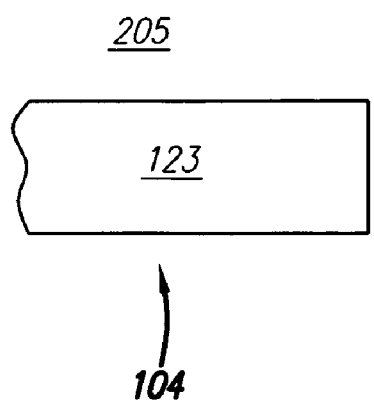
Figure 5F:
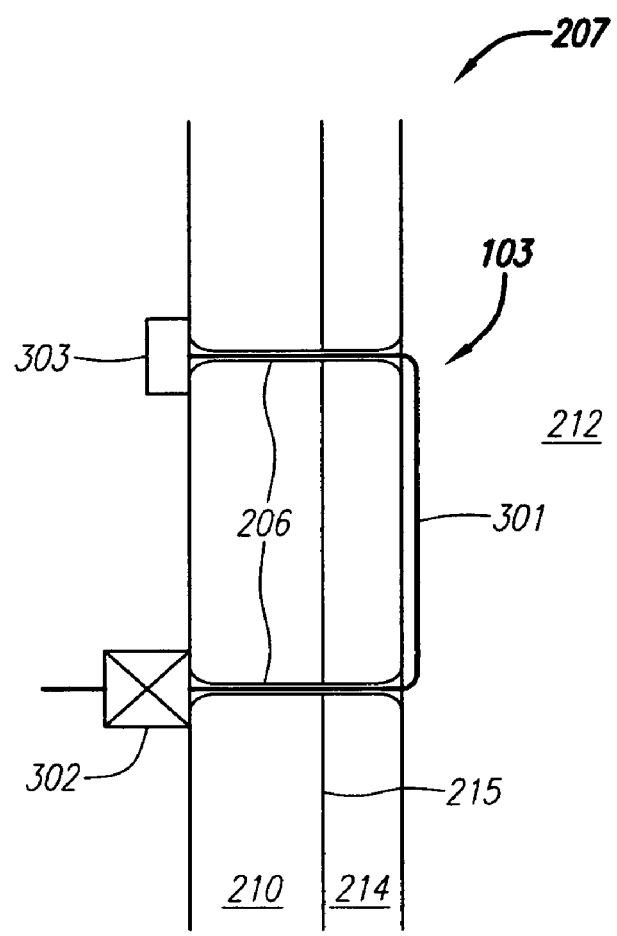

Needle 120 can then be retracted proximally to pull distal end 121 through septal wall 207 a second time. Once through, distal end 305 of suture 103 can be deployed, which in this embodiment includes anchor device 303, as depicted in FIG. 5C. Needle 120 can then be advanced distally back through septal wall 207 and retracted into outer member 123 (and into the substantially straight state) as depicted in FIG. 5D. Then, outer member 123 can be retracted proximally through septal wall 207 to deploy suture body 301 in a non-looped, configuration as depicted in FIG. 5E. Once the desired positioning and/or tensioning of suture body 301 is reached, lock device 302 can be deployed to complete deployment of suture 103 as depicted in FIG. 5F.

Needle 120 can be configured to deflect into the curved state in any desired manner. For instance, in the embodiments described above, needle 120 is fabricated from an elastic or superelastic shape memory material such as NITINOL and heat-treated to memorize the curved configuration described with respect to FIG. 5B. Needle 120 can then be deformed or deflected to the substantially straight configuration by placing needle 120 within outer tubular member 123, which is preferably configured with an adequate degree of rigidity to maintain needle 120 in the straight configuration.

Figure 5G:
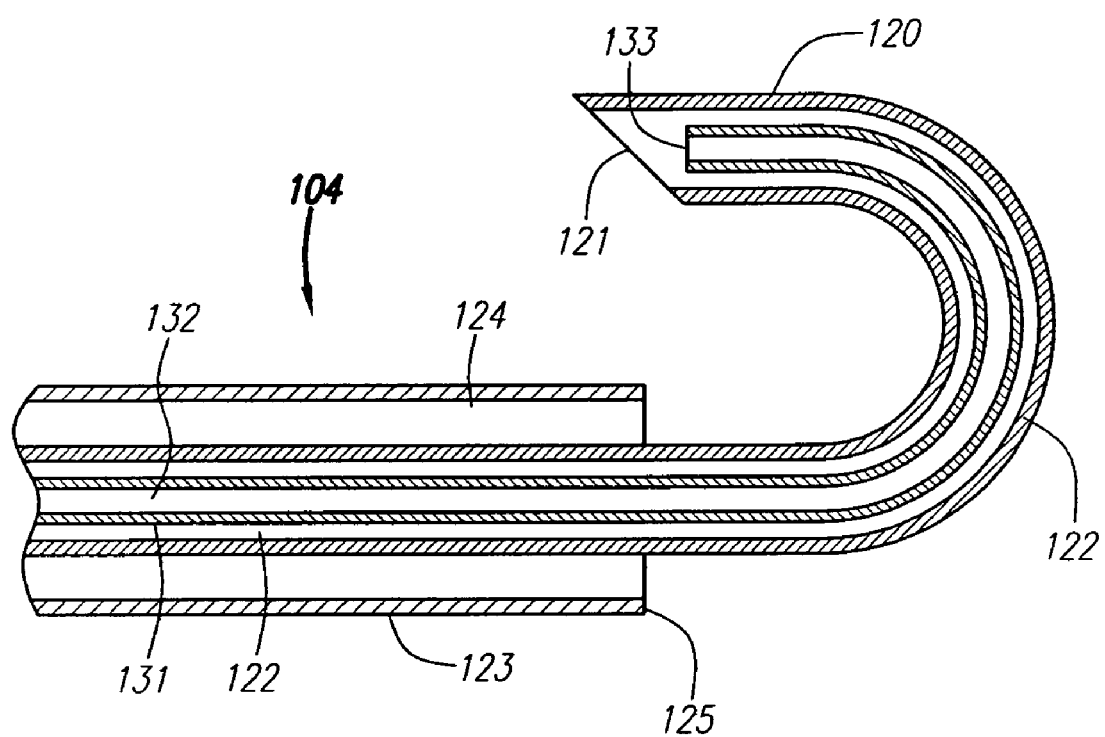

In another embodiment, needle 120 can again be fabricated from an elastic or superelastic material and heat treated to memorize a curved state. A curved stylet 131 can be inserted into needle inner lumen 122 in order to cause needle 120 to curve in the desired manner. FIG. 5G is a cross-sectional view of an exemplary embodiment of delivery device 104 with a curved stylet 131 located therein. Stylet 131 can be tubular with inner lumen 132 and open distal end 133 to allow suture 103 to be deployed from within. In another exemplary embodiment, stylet 131 can be a tubular member configured to be placed outside needle 120.

In addition, any of sutures 103 can be deployed using detachable needle systems, techniques and methods. For instance, the embodiments described herein can be implemented with the systems and methods described in U.S. Pat. No. 6,136,010, which is fully incorporated by reference herein.

It should be noted that the embodiments of delivery device 104 described above can be used to deliver suture-like implantable devices and other implantable devices, such as those described in U.S. patent application Ser. No. 11/175, 814.

Figure 6A:
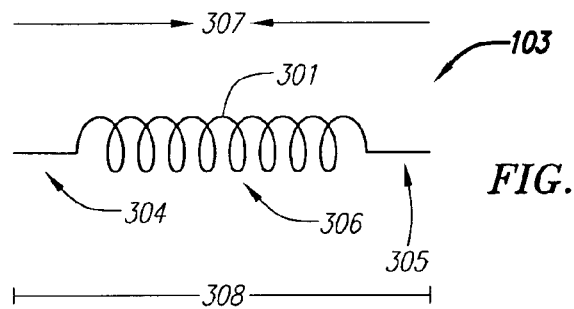
FIGS. 6A-E are schematic views depicting additional exemplary embodiments of a suture device.
Figure 6B:
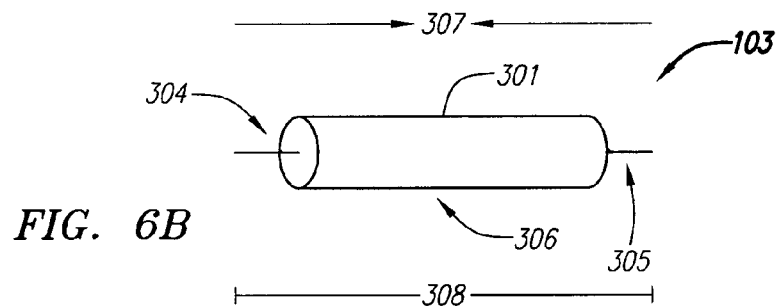

Referring back to suture 103, suture body 301 can be a flexible body configured to resist expansion in response to outward forces applied to end portions 304 and 305, so as to maintain septum primum 214 and septum secundum 210 in an at least partially closed position. For non-looped embodiments of suture device 103, suture body 301 can be configured to apply a compressive force between end portions 304 and 305 to aid in closing tunnel 215. FIGS. 6A-B are schematic views depicting additional exemplary embodiments of non-looped suture devices 103 where suture body 301 is configured to apply a compressive force 307 between end portions 304 and 305.

Figure 6C:
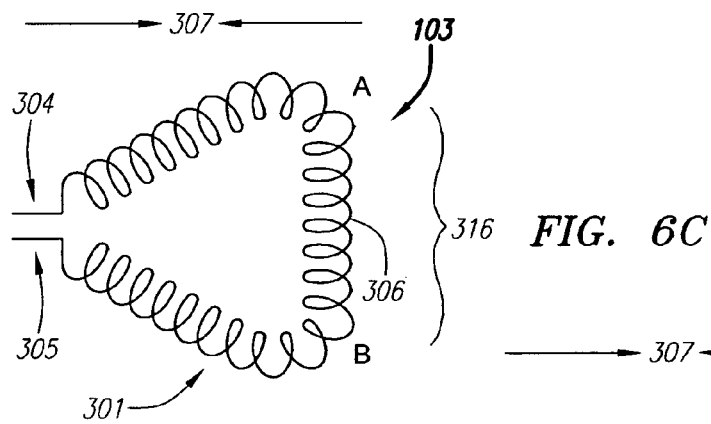
Figure 6D:
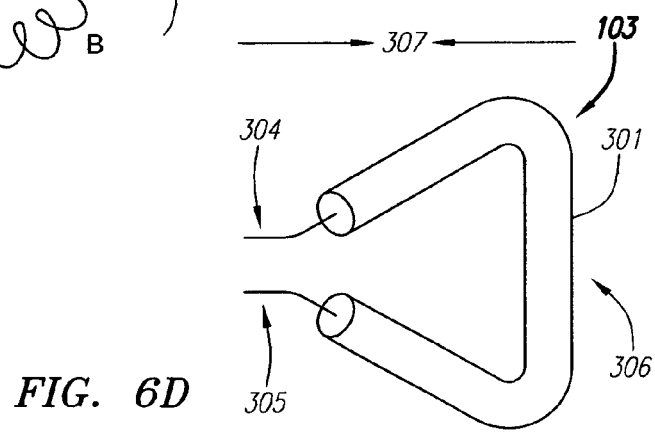

In FIG. 6A, suture body 301 is configured as a spring-like coil having a length 308 and in FIG. 6B, suture body 301 is configured as a stretchable elastomeric body also having length 308. Length 308 is preferably less than the distance between septal surfaces 213 and 216, such that, for both embodiments, suture body 301 applies a compressive force 307 between ends 304 and 305 when implanted in septal wall 207. FIGS. 6C-D is a schematic view depicting an exemplary embodiment of a looped suture device 103 having a coiled suture body 301 and a stretchable elastomeric suture body 301, respectively. In these embodiments, suture body 301 is configured to apply a compressive force 307 between end portions 304-305 and central portion 306. Suture body length 308 (not shown) is preferably small enough to exert compressive force 307 when implanted (e.g., on the order of twice the distance between septal surfaces 213 and 216). In FIG. 6C, the portion of body 316 between points A and B can be non-coiled if desired, since that portion is not exerting as direct a compressive force between portions 306 and 304-305.

Figure 6E:
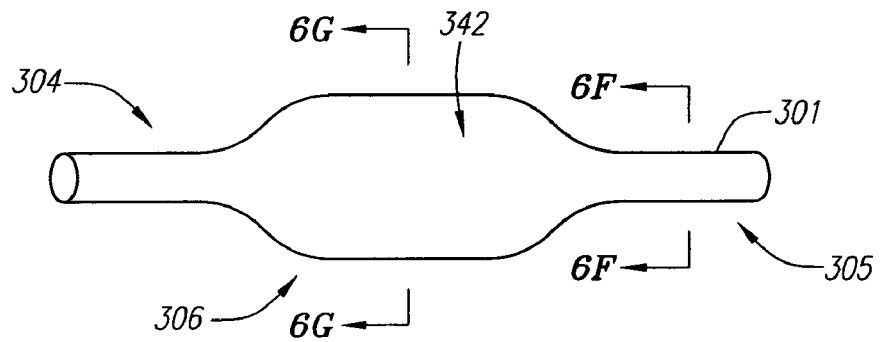
Figure 6F:
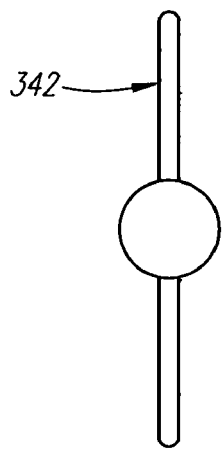
FIGS. 6F-G are cross-sectional views of the embodiment of FIG. 6E taken along lines 6F-6F and 6G-6G, respectively.
Figure 6G:
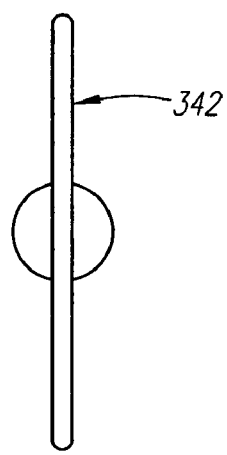
Figure 6H:
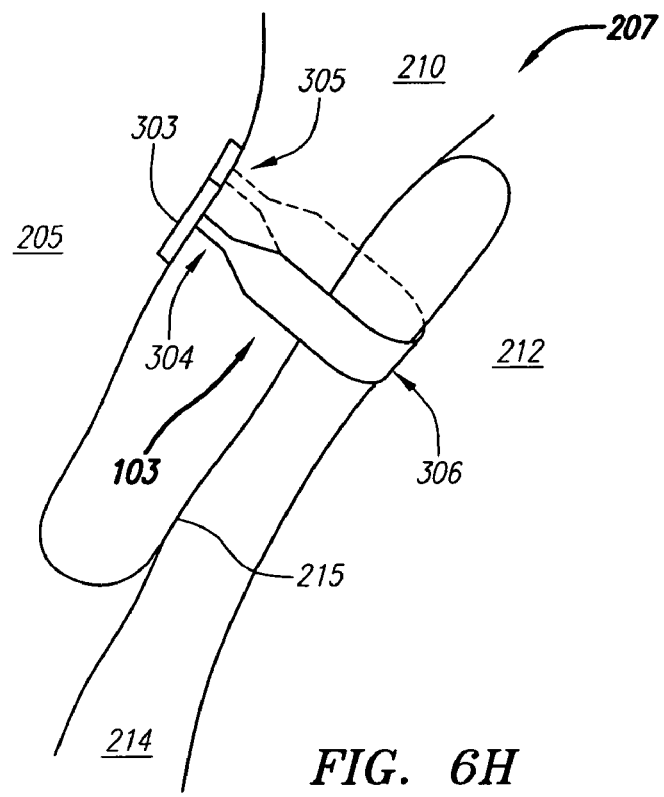
FIG. 6H is a partial cross-sectional view depicting the embodiment of FIG. 6E.

FIG. 6E depicts another exemplary embodiment of suture body 301 configured for use as a looped suture 103. Here, central portion 306 has a relatively wider, flap-like portion 342 configured to abut septal wall 207 and reduce the risk that suture body 301 cuts into the septal wall tissue. FIGS. 6F-G are cross-sectional views of this embodiment taken along lines 6F-6F and 6G-6G, respectively. FIG. 6H is a partial cross-sectional view depicting this embodiment deployed with anchor devices 303 on both ends 304 and 305.

Certain criteria should be considered (but are not required) in the design and implementation of suture 103. With regards to the suture body material, any desired material can be used, including, but not limited to, metallic materials such as NITINOL, stainless steel and the like, polymeric materials such as polypropylene, polyester, silicone, polyurethane, degradable materials and the like, and any combination thereof. Suture body 301 can also be braided if desired. The selection of an appropriate material preferably takes into account: manufacturability, cost, visibility to external and/or internal imaging devices (e.g., radio-opacity, etc.), MRI compatibility, biodegradability, the use of FDA-predicate materials (known in long-term implantable, blood-contacting devices), and robust temperature performance (i.e., the ability to handle any expected manufacturing, sterilization, shipment or storage temperatures). For a suture body 301 containing polymeric materials, creeping issues, ESCR issues, and sterilization issues (e.g., gamma rays/E-beam can impact mechanical properties) can also be taken into account. For a suture body 301 containing metallic materials, the degree of non-abrasiveness with suture body 301 during and after deployment (to prevent severing or weakening suture body 301), resistance to fatigue or fracture, and resistance to corrosion can also be taken into account. Furthermore, any portion of suture 103 can be coated with any desired material as desired and any portion of suture 103 or treatment system 100 can be imagable by an internal or external imaging device (e.g., radio-opaque, etc).

Suture body 301 can also be configured with the desired degree of biocompatibility. Criteria that can be taken into account with regards to biocompatibility include the effect of the material/design on the healing response, the potential of a material or design to cause thrombus formation or an embolic event, and the speed of the healing response (e.g., distance new tissue must migrate across to encapsulate an implant).

Criteria that can be taken into account with regard to the design of suture device 103 include the ability to generate adequate suture retention (i.e., the ability to lock onto suture body 301), easy and reliable actuation, level of complexity, reversibility (i.e., the ability to both tighten and loosen as needed), the number of distinct separate pieces, retrievability (i.e., the ability to "bail-out" and remove the device at any stage of deployment, including post-implantation), and low surface friction between lock device 302 and suture body 301 during deployment and before locking. The design of lock device 302 can also take into account whether incremental locking is desired, for instance, whether lock device 302 is configured to lock at any point on suture body 301 or whether lock device 302 is only lockable at one of multiple discreet positions, which can introduce an additional risk that lock device 302 does not lock completely.

The following section describes various portions of treatment system 100, mainly embodiments of lock device 302 and anchor device 303. Because both lock device 302 and anchor device 303 can be used with multiple suture bodies 301 as well as multiple portions of the same suture body 301, description of these embodiments is done so in relation to one or more generic suture body portions 309. Each generic suture body portion 309 can be a separate suture body 301 or a portion of the same suture body 301.

FIGS. 7A-22B depict various exemplary embodiments of lock device 302. Lock device 302 is preferably configured to lock onto one or more suture bodies 301 and prevent any substantial movement of those suture bodies 301 in relation thereto. For each exemplary embodiment described herein, lock device 302 can be used with both looped and non-looped suture devices 103, unless noted otherwise. Generally, lock device 302 can be configured to provide an anchor function or solely a lock function as desired. With regards to non-looped suture devices 103, lock device 302 is preferably configured to anchor the suture device 103 against septal wall 207 in order to prevent lock device 302 from being pulled through septal wall 207.

In some cases, the embodiments of lock device 302 described below are done so with reference to portions of delivery device 104, for instance, a description of deployment with needle 120. It should be noted that description of an embodiment of lock device 302 with reference to a specific portion of delivery device 104 does not limit use of that lock device 302 to only that portion of delivery device 104. In fact, lock device 302 can be used with any portion of delivery device 104 and any other portion of treatment system 100, whether or not described herein.

Lock device 302 can use any type of locking technique, force or physical mechanism to lock onto suture body 301. The embodiments described with respect to FIGS. 7A-9B each apply a constrictive-type or clamp-type force to the one or more suture bodies 301 to lock them in place with relation to each other and to lock the lock device 302 in place in relation to the one or more suture bodies 301.

Figure 7A:
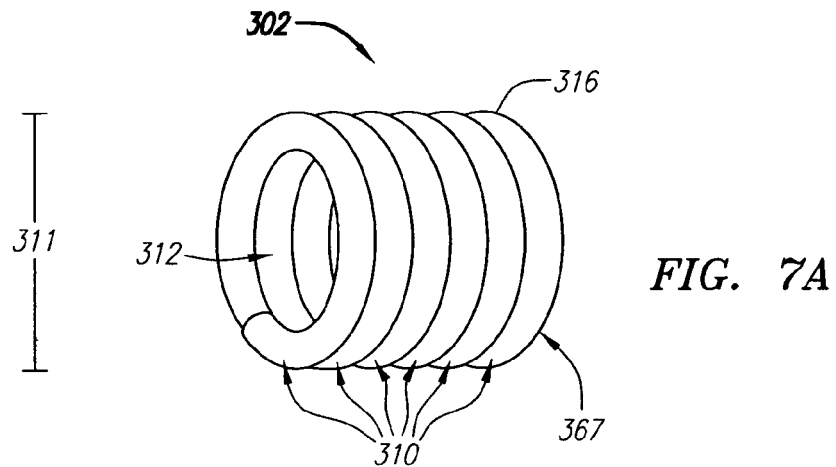
FIG. 7A is a perspective view depicting one exemplary embodiment of a lock device.

FIG. 7A is a perspective view depicting one exemplary embodiment where lock device 302 has a body 316 configured as a coil and fabricated from an elastic or superelastic shape-memory material, such as NITINOL, stainless steel and the like. Lock device 302 is preferably heat-treated in the coiled configuration at a first width 311. Heat treatment can instill a shape memory to body 316 so that lock device 302 will be biased to return to this "memorized" at-rest state when expanded or otherwise deformed.

Figure 7B:
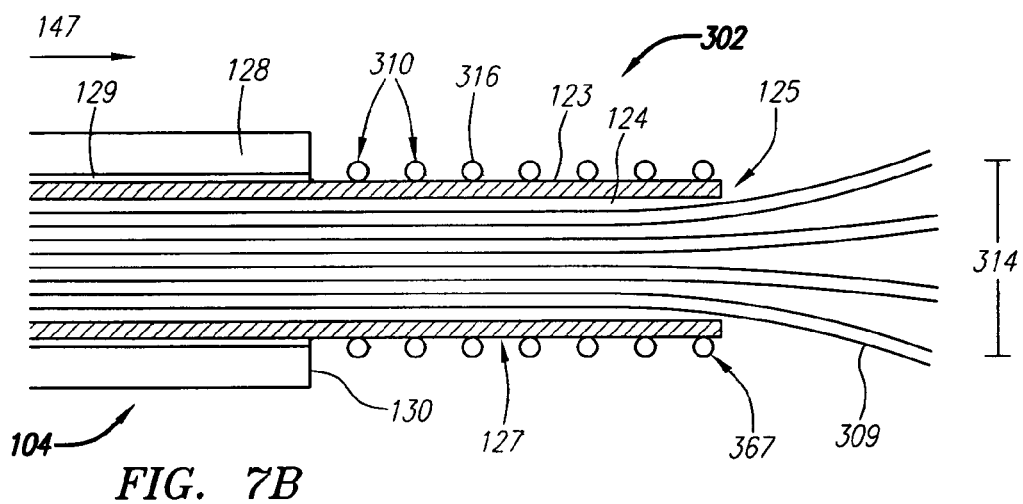
FIG. 7B is a cross-sectional view depicting this embodiment of the lock device.

FIG. 7B is a cross-sectional view depicting this embodiment of lock device 302 prior to deployment. Here, lock device 302 is in an expanded state with a larger width 314 that allows suture body portions 309 to move substantially unimpeded through open central portion 312. Lock device 302 is depicted with an exemplary embodiment of deployment device 104 having outer tubular member 123 and pusher member 128. Outer tubular member 123 is slidably disposed at least partially within inner lumen 129 and open distal end 130 of pusher member 128. Suture body portions 309 are deployed through open distal end 125 of lumen 124 of outer tubular member 123. Needle 120 (not shown) is retracted fully within lumen 124 so that lock device 302 is not damaged by passing over substantially sharp distal end 121.

In this embodiment, coiled lock device 302 is held in the expanded state around outer surface 127 of outer tubular member 123. After deployment of suture body portions 309, pusher member 128 can be advanced distally (direction 147) with respect to outer member 123 to bring pusher distal end 130 into contact with coiled lock device 302. Further advancement of pusher member 128 slides coiled lock device 302 off of distal end 125 of outer member 123, at which point coiled lock device 302 is free to engage and constrict suture body portions 309.

Figure 7C:
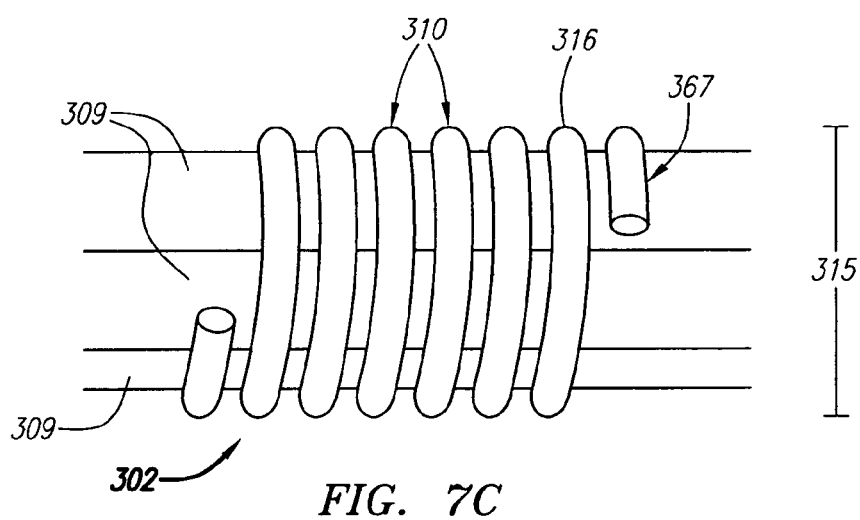
FIG. 7C is another perspective view depicting this exemplary embodiment of the lock device.

FIG. 7C is a perspective view depicting this exemplary embodiment of lock device 302 in a locked state around suture body portions 309. In this state, lock device 302 is preferably configured to constrict suture body portions 309 with sufficient force to lock suture body portions 309 in place with relation to each other and also to lock the lock device 302 in position on suture body portions 309. Also, lock device 302 is preferably configured such that memorized width 311 is less than the width 315 of lock device 302 when in the locked state in order to provide sufficient constrictive force. Provision of sufficient force can also be accomplished by varying the number of coiled segments 310, increasing the cross-sectional size of each coiled segment 310, or decreasing the memorized width 311 of coiled lock device 302, to name a few.

In another exemplary embodiment, an elastomeric tube can be placed between suture body portions 309 and coiled body 316 such that coiled body 316 compresses the elastomeric tube around suture body portions 309. This can provide even greater friction between lock device 302 and portions 309. Yet another way to increase the clamping force or friction between suture body portions 309 and lock device 302 is by adding a coating to one or the other or both. The coating may be elastomeric (silicone, polyurethane and the like) and applied directly via dip coating or by bonding the elastomer to the suture or lock (such as a tube or sheet of silicone). This is applicable to any suture body portion 309 and lock device 302 discussed herein.

Because lock device 302 preferably performs an anchoring function against septal wall 207, outer surface 367 of body 316 can be configured to more readily engage septal wall 207. This can be accomplished by modifying the surface roughness in any manner desired, including, but not limited to texturing, etching, cutting, and the addition of abrasive coatings. Surface 367 can also be configured with one or more barbs or other grabbing structures for this same purpose. It should be noted that each embodiment of lock device 302 described herein, regardless of the configuration, has an outer surface 367 that contacts septal wall 207. This outer surface 367 will be referenced in each applicable figure but not described in the interest of brevity, with the understanding that surface 367, in each embodiment, can be configured to more readily engage septal wall 207 as described above.

Also, in general, for each embodiment of lock device 302 described herein, the surface that contacts any suture body portion 309 can be configured to increase the surface friction with that suture body portion 309. Again, this can be accomplished in any manner desired, including, but not limited to texturing, etching, cutting, and the addition of abrasive coatings. It should be noted that because lock device 302 remains in contact with each suture body portion 309 for what can be a significant period of time, the surface of lock device 302 that contacts any suture body portion 309 should not introduce a significant risk of abrading or severing the suture body portion 309. The NITINOL wire can be configured with a roughened surface at the contact interface (ID) to increase friction and better grip and lock the suture.

Figure 7D:
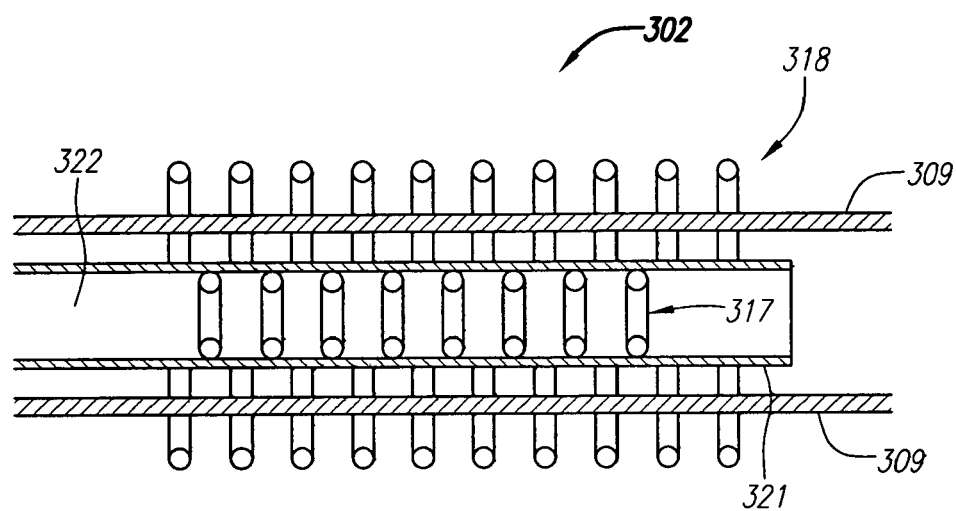
FIGS. 7D-E are cross-sectional views depicting another exemplary embodiment of the lock device.
Figure 7E:
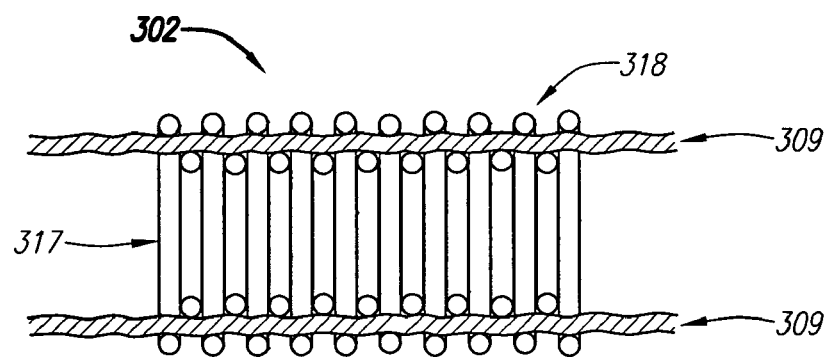

FIG. 7D is a cross-sectional view depicting another embodiment of lock device 302 in the unlocked state. Here, lock device 302 includes an inner coil 317 and an outer coil 318. Inner coil 317 is shown held in a compressed configuration within inner lumen 322 of tubular restraining member 321. Two suture body portions 309 are shown routed between restraining member 321 and outer coil 318. Removal of restraining member 321 allows inner coil 317 to expand and compress suture body portions 309 between inner coil 317 and outer coil 318 as depicted in FIG. 7E.

In another exemplary embodiment, the outer coil 318 is held in an expanded configuration by restraining member 321, removal of which allows outer coil 318 to compress suture body portion 309 against inner coil 317. It should be noted that any expandable or compressible structure(s) can be substituted for coils 317 and 318 including, but not limited to a stent-like body, a deformable elastic tube and the like.

Figure 8A:
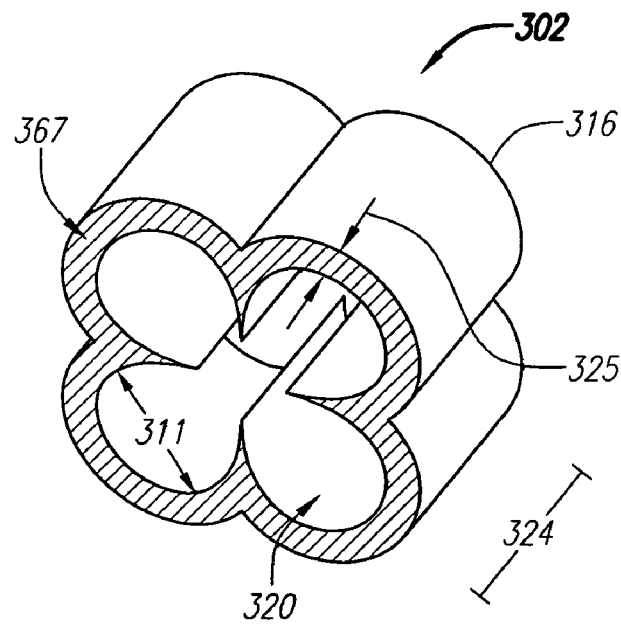
FIG. 8A is a perspective view depicting another exemplary embodiment of the lock device.
Figure 8B:
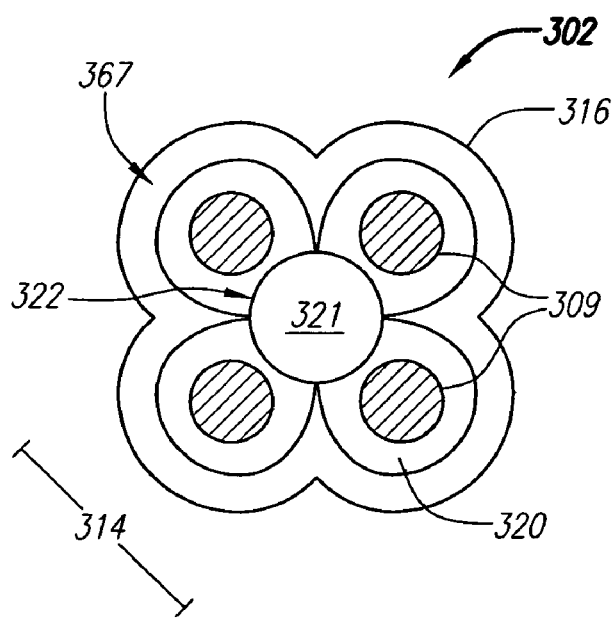
FIGS. 8B-C are front views depicting this exemplary embodiment of the lock device.
Figure 8C:
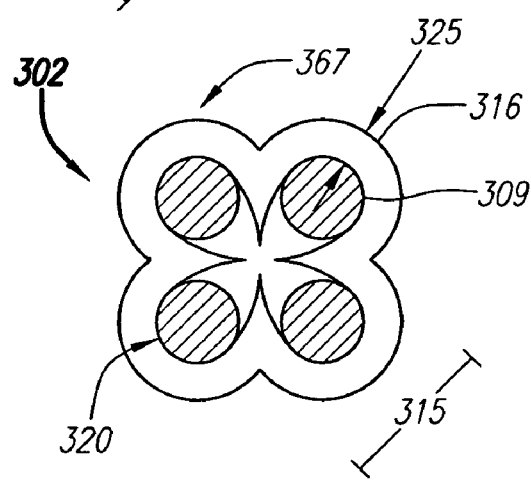

FIGS. 8A-C depict another exemplary embodiment of lock device 302 configured to apply a constrictive force to lock one or more suture body portions 309. In this embodiment, lock device body 316 has a symmetrical, cloverleaf-like shape, with multiple suture lumens 320 for housing suture body portions 309. Like the embodiment described with respect to FIGS. 7A-C, this embodiment of lock device 302 is also preferably fabricated from an elastic or superelastic shape memory material. For instance, in one exemplary embodiment, lock device body 316 is manufactured from a NITINOL tube and crimped or otherwise manipulated to form lumens 320, while in another exemplary embodiment, lock device body 316 is manufactured by laser cutting or photo-etching the desired shape from a NITINOL sheet. FIG. 8A is a perspective view depicting lock device 302 in an at-rest state. Lock device 302 is preferably heat treated with suture lumens 320 at width 311 to instill a bias that attempts to return lock device 302 to the memorized shape and width 311 after expansion or deformation therefrom.

FIG. 8B is a front view depicting this exemplary embodiment of lock device 302 in an expanded state. Here, lock device 302 has a central open portion or slot 322 configured to slidably receive a restraining member 321. Restraining member 321 is inserted through slot 322 to resist the shape memory bias and maintain lock device 302 in the expanded state. In the expanded state, each suture lumen 320 has an expanded width 314 to allow suture body portions 309 to pass substantially unimpeded through lumens 320. When suture body portions 309 are fully deployed, restraining member 321 can be withdrawn from slot 322 to allow lock device 302 to constrict each suture body portion 309 within the respective suture lumen 320.

FIG. 8C is another front view depicting this exemplary embodiment of lock device 302 in the locked state locked over suture body portions 309. Again, similar to the coiled embodiment described above with respect to FIGS. 7A-C, the width 315 in the locked state is preferably greater than the memorized width 311 in order to provide sufficient locking force for each suture body portion 309. Provision of sufficient force can also be accomplished by varying the length 324 of body 316, increasing the thickness 325 of body 316, or decreasing the memorized width 311 of each suture lumen 320, to name a few.

Figure 8D:
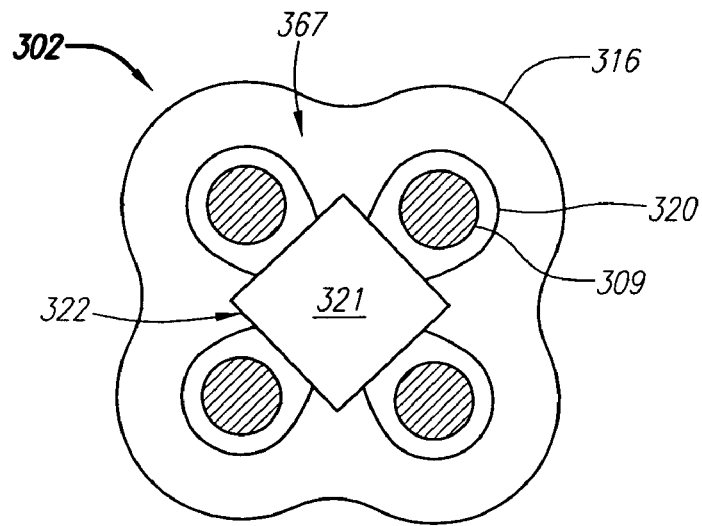
FIGS. 8D-F are front views depicting additional exemplary embodiments of the lock device.
Figure 8E:
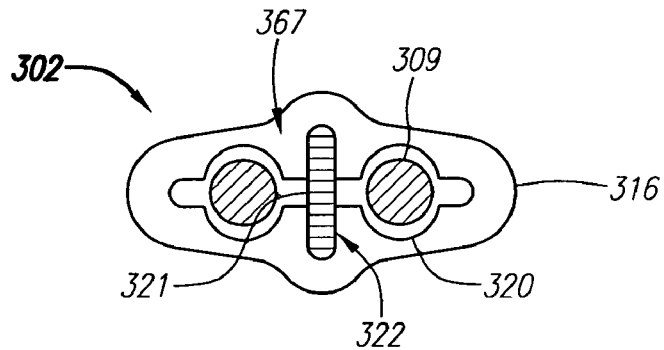
Figure 8F:
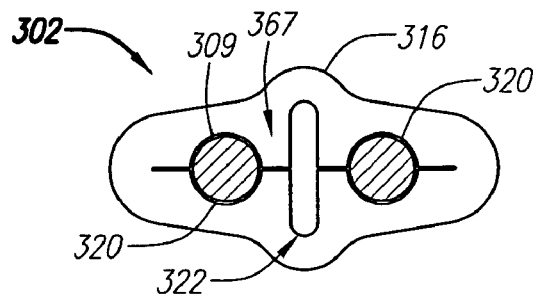

It should be noted that restraining member 321 can be shaped in any manner desired, and is not limited to the cylindrical configuration depicted in FIG. 8B. For instance, FIG. 8D is a front view depicting another exemplary embodiment of lock device 302 where restraining member 321 is polygonal. It should also be noted that these cloverleaf embodiments of lock device 302 can be used with any number of one or more suture body portions 309. For instance, FIGS. 8E-F are front views depicting another exemplary embodiment of lock device 302 in the expanded and locked states, respectively. Here, lock device 302 is configured to lock two suture body portions 309. (It should be noted that the term "cloverleaf" is used since the presence of the four suture lumens 320 resembles a cloverleaf in the embodiments described with respect to FIGS. 8A-D. This term will be used to facilitate the description herein and should not be construed to limit the embodiments to only those having four suture lumens 320.)

Figure 9A:
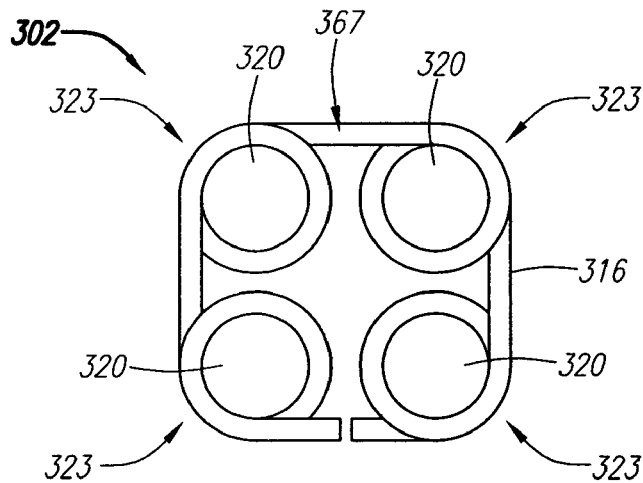
FIGS. 9A-C are front views depicting additional exemplary embodiments of the lock device.
Figure 9B:
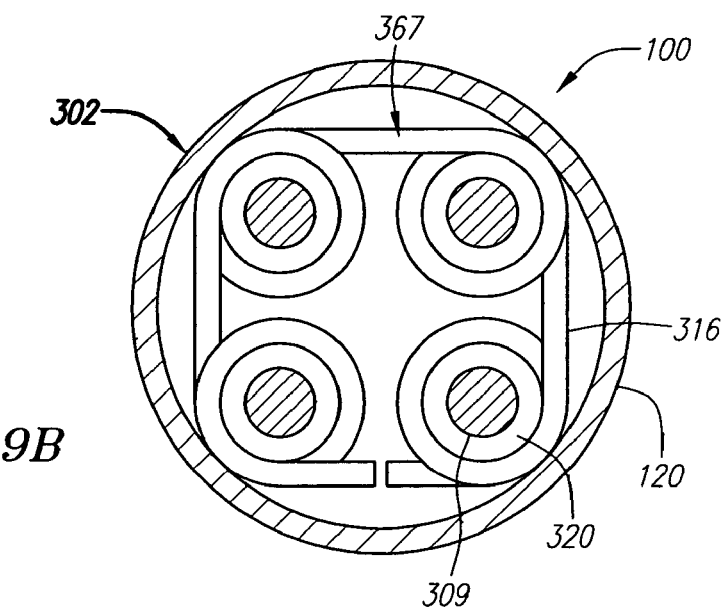
Figure 9C:
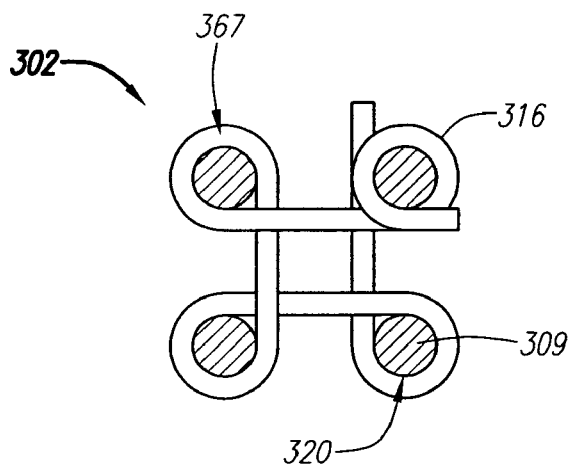

FIGS. 9A-C are front views depicting additional exemplary embodiments of cloverleaf-like lock devices 302. FIG. 9A depicts an exemplary embodiment of lock device 302 in the at-rest state. Here, lock device 302 has a wire-like or ribbon-like body 316 coiled inwards to form any number of two or more (in this case four) suture lumens 320. Coiling of body 316 in this manner allows each suture lumen 320 to be expanded when body 316 is compressed in directions 323. Body 316 is preferably fabricated from an elastic or superelastic shape memory material, such as NITINOL, stainless steel and the like, and preferably heat treated to memorize the configuration of the at-rest state depicted here.

FIG. 9B depicts an exemplary embodiment where lock device 302 is compressed within needle 120 such that each suture lumen 320 is held in an expanded state that allows suture body portions 309 to pass through substantially unimpeded. To lock onto suture body portions 309, lock device 302 can be deployed from within needle 120. This removes the compressive force applied to lock device 302 and allows lock device 302 to return towards the memorized shape. FIG. 9C depicts another exemplary embodiment of lock device 302 in the at-rest state similar to that described with respect to FIGS. 9A-B, except here body 316 is coiled outwards, away from the center of device 302, in order to form suture lumens 320. In another exemplary embodiment, multiple lock devices 302 can be stacked one on top of the other with a common body 316 to provide even greater locking force to each suture body portion 309.

The locking force can be increased by decreasing the width of each suture lumen 320 in the at-rest state, and/or increasing the cross-sectional thickness of body 316, to name a few.

Figure 10A:
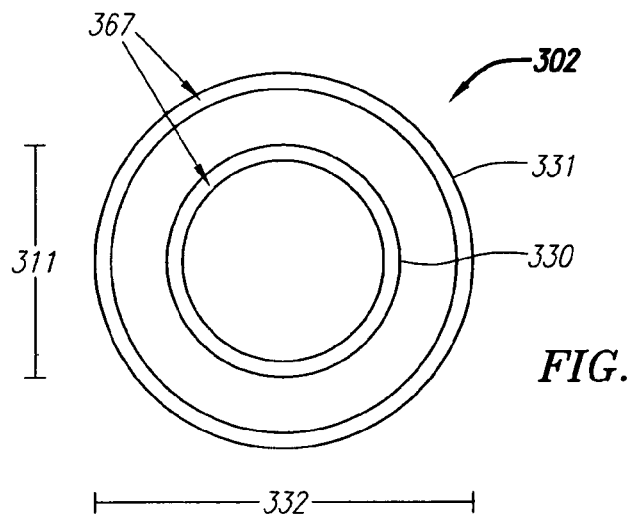
FIGS. 10A-B are front views depicting another exemplary embodiment of the lock device.

The embodiments described with respect to FIGS. 10A-13C each rely on clamping or pinching action to lock the one or more suture body portions 309. FIG. 10A is a front view of an exemplary embodiment of lock device 302 in an at-rest state. Here, lock device 302 has two annular, or ring-like members 330 and 331. Inner annular member 330 is preferably fabricated from an elastic or superelastic shape memory material and heat treated in the annular configuration depicted here with a width 311. Outer annular member 331 has a width 332 and is preferably fabricated from a rigid or semi-rigid material that will not substantially deform when stressed by inner annular member 330.

Figure 10B:
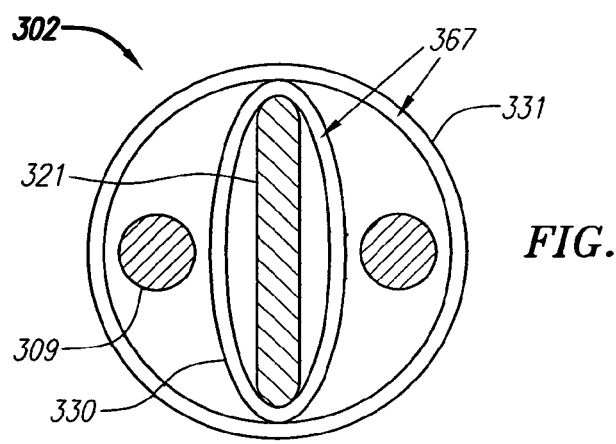
Figure 10C:
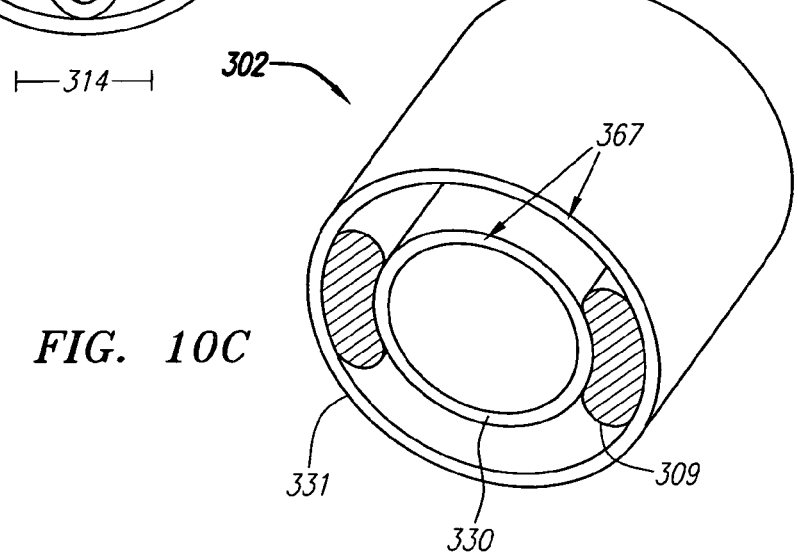
FIG. 10C is a perspective view depicting this exemplary embodiment of the lock device.

FIG. 10B is a front view depicting this embodiment of lock device 302 in an unlocked state. Inner annular member 330 is deformed by restraining member 321 to reduce the width 311 to a smaller width 314, sufficient to allow suture body portions 309 to pass substantially unimpeded on either side. To lock suture body portions 309, restraining member 321 is removed to allow inner annular member 330 to attempt return to the original at-rest state. In doing so, suture body portions 309 are pinched between inner annular member 330 and outer annular member 331, as depicted in the perspective view of FIG. 10C. This embodiment of lock device 302 can be configured for use with any number of one or more suture body portions 309. In order to generate adequate locking force, the difference between widths 311 and 332 is preferably small enough so that the one or more suture body portions 309 are locked before inner annular member 330 returns to the at-rest width 311. Also, the inner surface of outer member 331 and the outer surface of inner member 330 can each be coated with an elastomer or other material to increase the surface friction with suture body portions 309.

In these embodiments, inner and outer annular members 330-331 are depicted as having a circular cross-section in the at-rest state. It should be noted that lock device 302 is not limited to only circular shapes and can have any shape, including, but not limited to, polygonal, oval, elliptical, asymmetric, symmetric, irregular and any combination thereof.

Figure 10D:
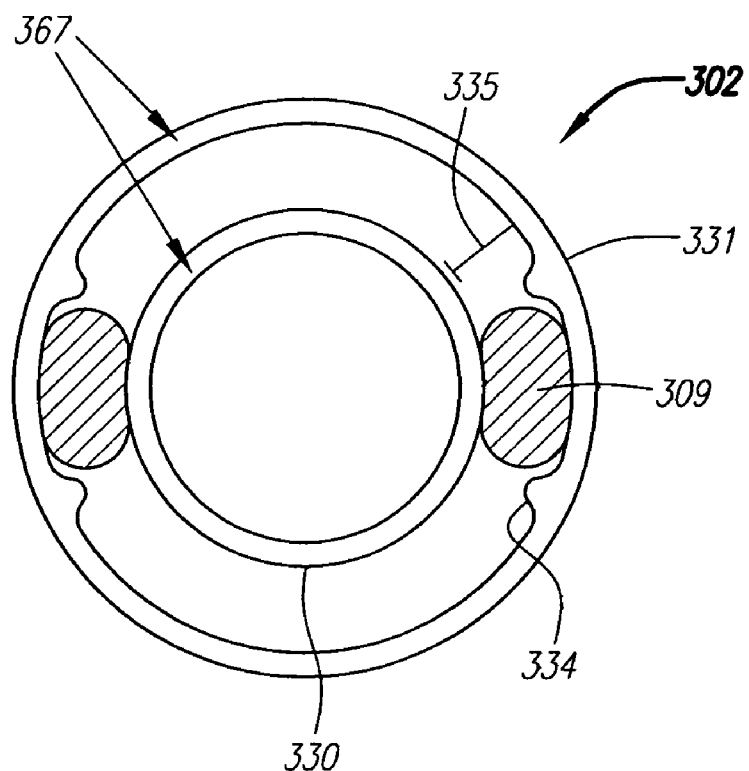
FIGS. 10D-G are front views depicting additional exemplary embodiments of the lock device.

During deployment of suture 103, it is possible that suture body portions 309 shift position so that they are adjacent to each other on one side of inner annular member 330. This can result in less than ideal locking force. Preferably, treatment system 100 is configured to maintain the proper position of suture body portions 309 within lock device 302 during deployment. FIGS. 10D-G are front views depicting additional exemplary embodiments of lock device 302 configured to maintain suture body portions 309 in the proper position. In FIG. 10D, lock device 302 is similar to the embodiment described with respect to FIGS. 10A-C, except outer annular member 331 has multiple abutments 334 for guiding and positioning of suture body portions 309. The length 335 of abutments 334 is preferably long enough to guide suture body portion 309 while also being short enough to allow inner annular member 330 to apply an adequate pinching force.

Figure 10E:
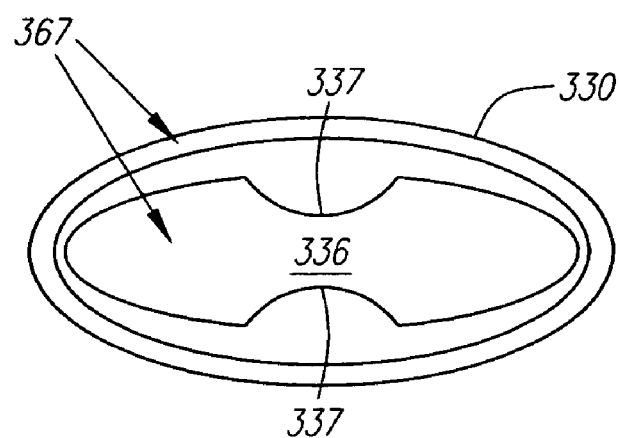
Figure 10F:
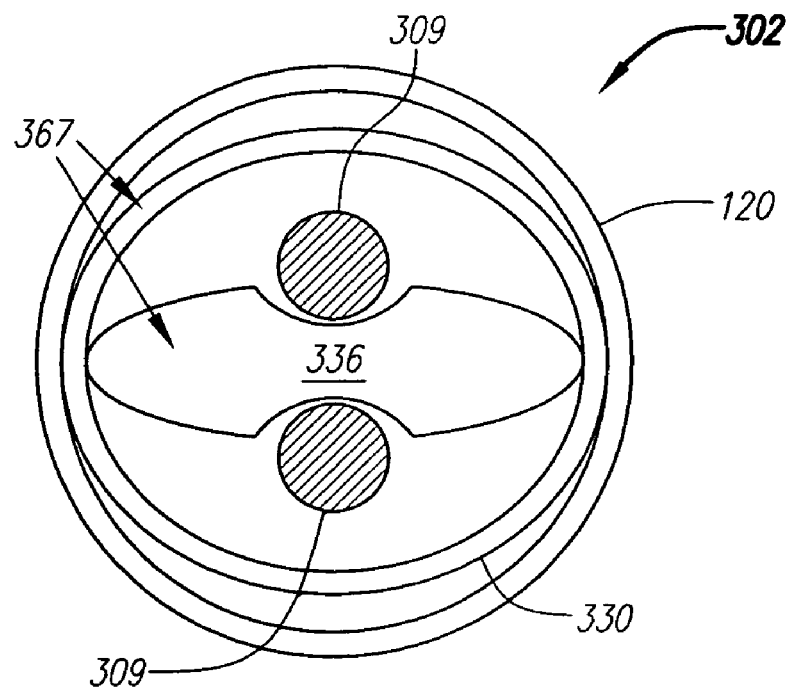
Figure 10G:
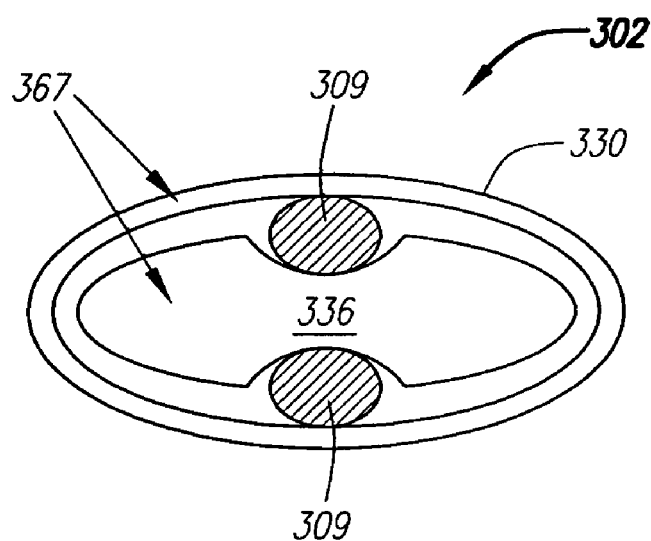

FIG. 10E depicts another exemplary embodiment of lock device 302 in the at-rest state. Here, annular member 330 is heat treated in a flattened configuration. Lock device 302 includes a central member 336 having a cross-sectional shape corresponding to annular member 330. Central member 336 includes multiple guides 337 for guiding the position of suture body portions 309. FIG. 10F depicts this embodiment of lock device 302 in the unlocked state. Here, needle 120 is used to deform inner annular member 330 to a less flattened configuration that allows deployment of suture body portions 309. To place lock device 302 in the locked state, inner annular member 330 is advanced from within needle 120 (such as with pusher member 128) so that inner member 330 is free to pinch and lock suture body portions 309 against central member 336, as depicted in FIG. 10G.

In the embodiments described with respect to FIGS. 10A-G, the locking force provided by any one configuration can be varied by varying the thickness of inner annular member 330 and the length of inner annular member 330, the length of outer annular member 331 (for embodiments that use outer annular member 331 in a locking capacity) and/or the length and/or cross-sectional width of central member 336, to name a few.

Figure 11A:
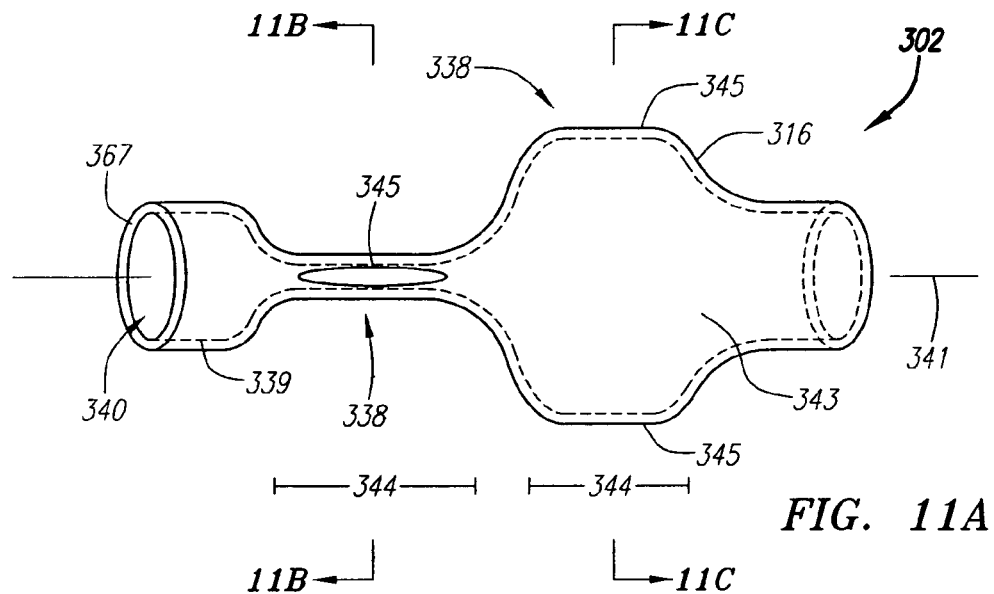
FIG. 11A is a perspective view depicting another exemplary embodiment of the lock device.

FIGS. 11A-G depict additional exemplary embodiments of lock device 302 configured to lock suture body portions 309 with a pinching or clamping type action. FIG. 11A is a perspective view depicting lock device 302 in an at-rest state having a tubular body 316 with two flattened portions 338 and a central axis 341. Dashed line 339 depicts the location of the inner surface 340 of lock device 302. Each flattened portion 338 has a length 344 measured along central axis 341.

Figure 11B:
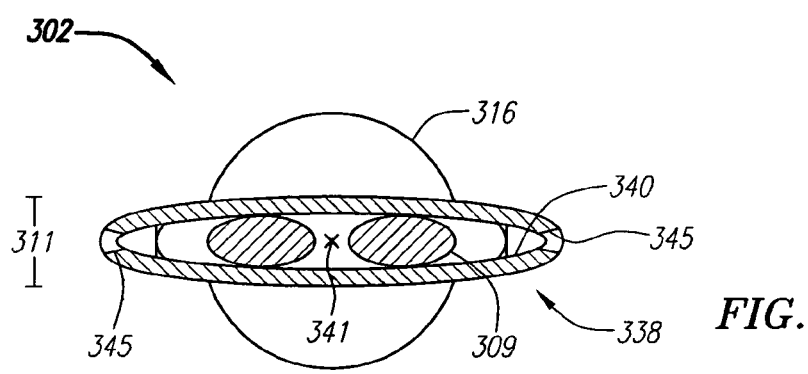
FIGS. 11B-C are cross-sectional views of the lock device taken along lines 11B-11B and 11C-11C, respectively, of FIG. 11A.
Figure 11C:
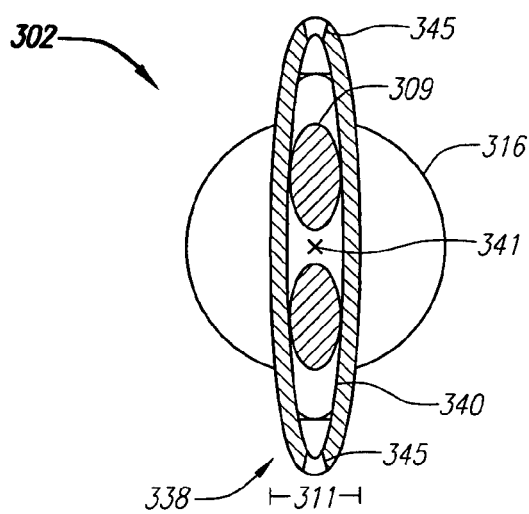

FIGS. 11B-C are cross-sectional views of lock device 302 taken along lines 11B-11B and 11C-11C, respectively, which are coincidental with each flattened portion 338. Flattened portions 338 are used to lock on to suture body portions 309. Although two flattened portions 338 are shown, lock device 302 can have any number of one or more flattened portions 338, having any length 344, width 311, size, shape or configuration. To prevent cracking and allow the sidewalls to be placed closer together, longitudinal slots 345 can be formed in each flattened portion 338.

When multiple flattened portions 338 are present, each flattened portion 338 is preferably oriented differently with respect to one or more of the others in order to provide additional locking force. Here, the orientation of each flattened portion is offset by 90 degrees about central axis 341 of tubular body 316. Lock device 302 is preferably fabricated from an elastic or superelastic shape memory material, such as NITINOL, stainless steel and the like, and preferably heat treated to memorize the configuration of the at-rest state depicted in FIGS. 11A-C. Lock device 302 can fabricated in any manner desired, including, but not limited to forming from a tube or other member having an inner lumen, or cutting or separating from a sheet.

Figure 11D:
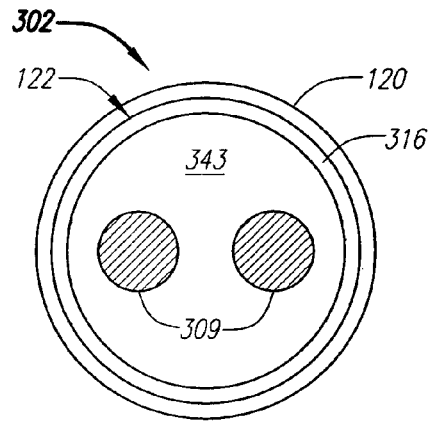
FIGS. 11D-F are front views depicting additional exemplary embodiments of the lock device.
Figure 11E:
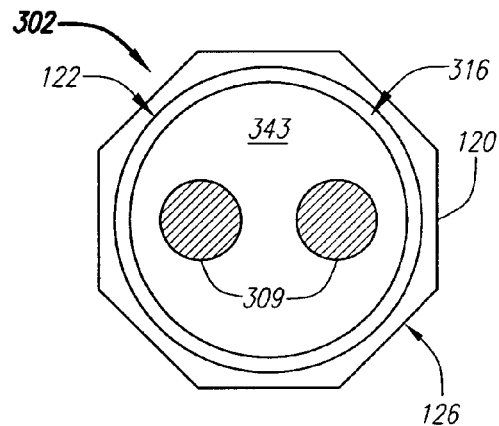

FIGS. 11D-G depict additional exemplary embodiments of lock device 302 in the unlocked state. FIG. 11D is a front view depicting an exemplary embodiment of lock device 302 placed within inner lumen 122 of needle 120. Needle 120 is preferably configured to maintain tubular body 316 in a relatively tubular state where flattened portions 338 (not shown) are deformed to a relatively unflattened state. This allows suture body portions 309 to be deployed through inner lumen 343 of tubular body 316. Once suture body portions 309 are placed in the desired position with the desired tension, lock device 302 can be locked by removing needle 120. This allows flattened portions 338 (not shown) to move towards the at-rest state and lock onto suture body portions 309.

Figure 11F:
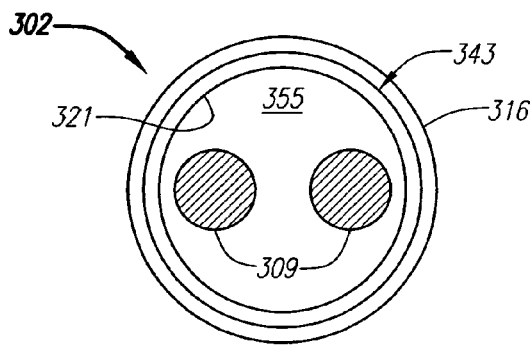

Needle 120 is not limited to circular cross-sectional configurations. For instance, in the embodiment depicted in the front view of FIG. 11E, the cross-sectional profile of outer surface 126 of needle 120 is polygonal to provide added strength. Also, any portion of delivery device 104 can be used instead of needle 120. FIG. 11F depicts another exemplary embodiment of lock device 302 in the unlocked state. Here, instead of using needle 120, tubular restraining member 321 is placed within inner lumen 343 to maintain flattened portions 338 in the deformed, unlocked state. Suture body portions 309 are then routed through inner lumen 355 of restraining member 321. Removal of restraining member 321 allows lock device 302 to lock onto suture body portions 309.

Figure 11G:
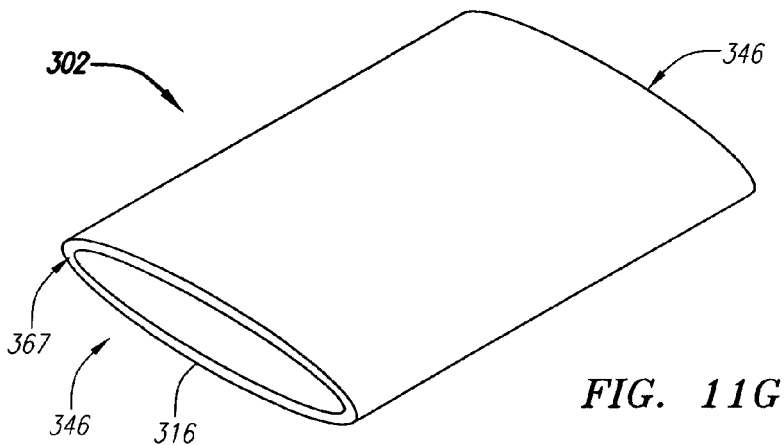
FIG. 11G is a perspective view depicting another exemplary embodiment of the lock device.

It should be noted that the entire length of tubular body 316 can be flattened if desired. FIG. 11G is a perspective view depicting an exemplary embodiment of lock device 302 having a flattened body 316. However, the end portions 346 of tubular body 316 in such a configuration are preferably configured so as to not significantly abrade suture body portions 309. Also, if lock device 302 is intended to act as an anchor against septal wall 207, the septal wall area contacted and encompassed by any end portion 346 is preferably large enough to resist being pulled through septal wall 207.

In the embodiments described with respect to FIGS. 11A-G, the locking force provided can be increased by increasing the number of flattened portions 338, increasing length 344 of any flattened portion 338, increasing the thickness of tubular body 316, and decreasing the width 311 of any flattened portion in the at-rest configuration.

Figures 12A, 12B:
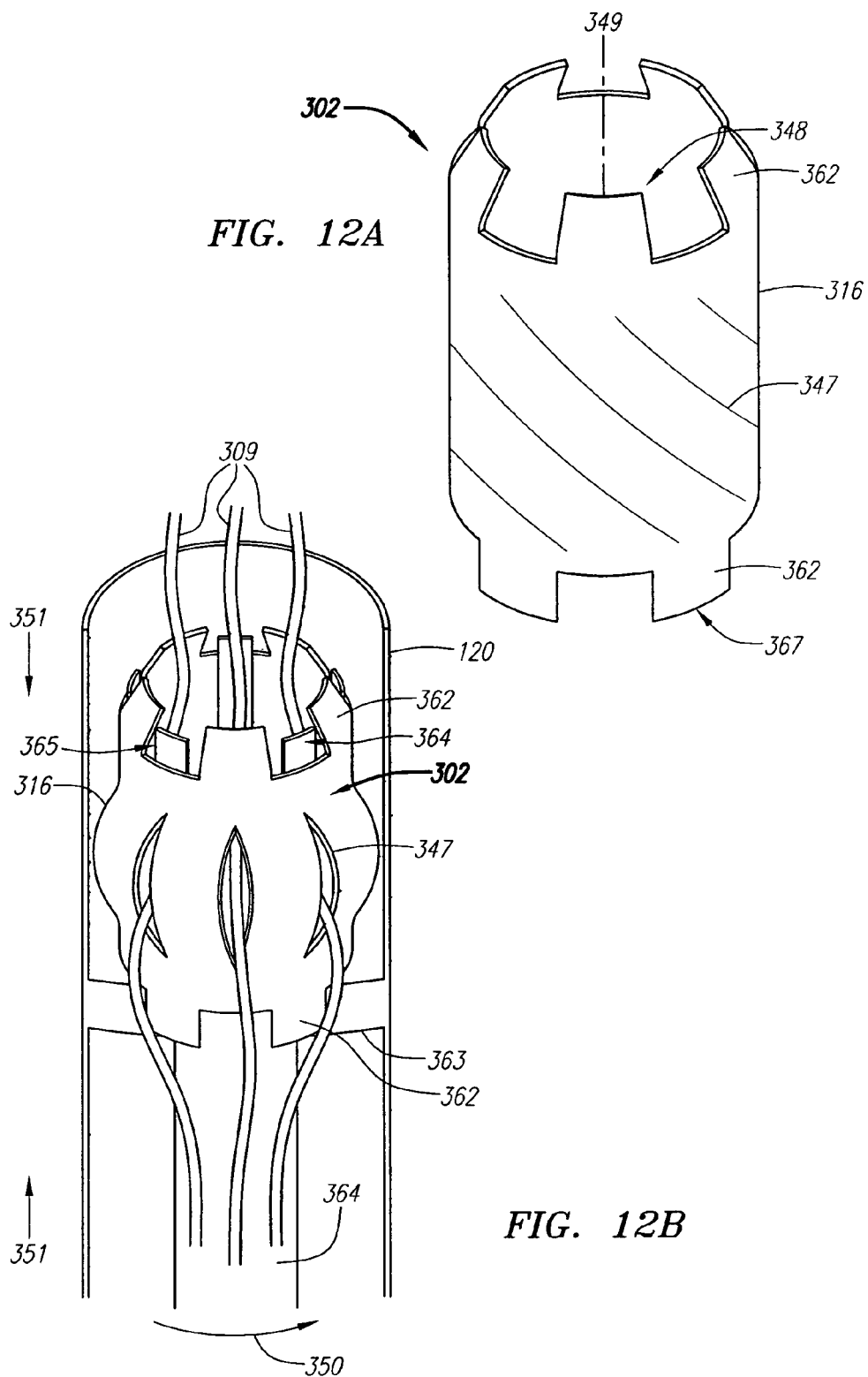
FIG. 12A is a perspective view depicting another exemplary embodiment of the lock device.
FIG. 12B is a partial cross-sectional view depicting this exemplary embodiment of the lock device.

FIGS. 12A-F depict additional exemplary embodiments of lock device 302 configured to lock suture body portions 309 with a pinching or clamping type action. FIG. 12A is a perspective view depicting lock device 302 in an at-rest state. Here, lock device 302 has a tubular body 316 with an inner lumen 348 and a central axis 349. Tubular body 316 includes a plurality of slots 347, which, in this embodiment, are oriented non-parallel to central axis 349. Slots 347 are substantially straight in this embodiment, but it should be noted that any shaped slot can be used. Lock device 302 is preferably fabricated from an elastic or superelastic shape memory material, such as NITINOL, stainless steel and the like, and preferably heat treated to memorize the configuration of the at-rest state depicted in FIG. 12A. Slots 347 can be fabricated in any manner, including, but not limited to laser cutting.

FIG. 12B is a partial cross-sectional view depicting lock device 302 in an unlocked state. Here, tubular body 316 has been rotated in direction 350 and compressed in directions 351 so as to open slots 347 by an amount sufficient to allow suture body portions 309 to pass through substantially unimpeded. Other embodiments can be configured so that only one of rotation in direction 350 or compression in direction 351 are needed to expand slots 347. For instance, if slots 347 are formed parallel to central axis 349, compression in direction 351 alone will expand slots 347 as needed.

Body 316 includes one or more castellations 362 on each end to facilitate rotation thereof. Here, castellations 362 on the proximal end of body 316 contact corresponding abutments 363 on needle 120 of delivery device 104. A tubular rotation member 364 having abutments 365 is placed through inner lumen 348 such that abutments 365 are in contact with castellations 362 on the distal end of body 316. These distal castellations 362 are deflected inwards to allow easier contact with rotation member 364. Rotation member 364 can the be rotated as indicated to rotate body 316 and open slots 347 to accommodate suture body portions 309. It should be noted that the use of castellations 362, abutments 363 and rotation member 364 is just one example of a method for opening slots 347. One of skill in the art will readily recognize that other methods can also be used.

Figure 12C:
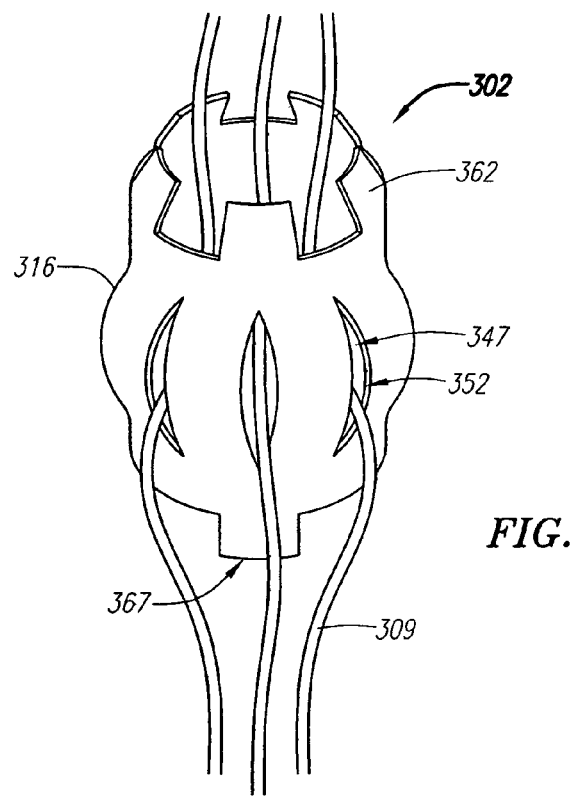
FIG. 12C is a perspective view depicting this exemplary embodiment of the lock device.

When suture body portions 309 are in the desired position with the desired tension, lock device 302 can be locked as shown in the perspective view of FIG. 12C. The inner sidewall surfaces 352 of slots 347 are preferably configured to be substantially unabrasive (such as an electropolished mirror-like surface) to lessen the risk of suture body portions 309 being inadvertently severed during or after deployment.

Figure 12D:
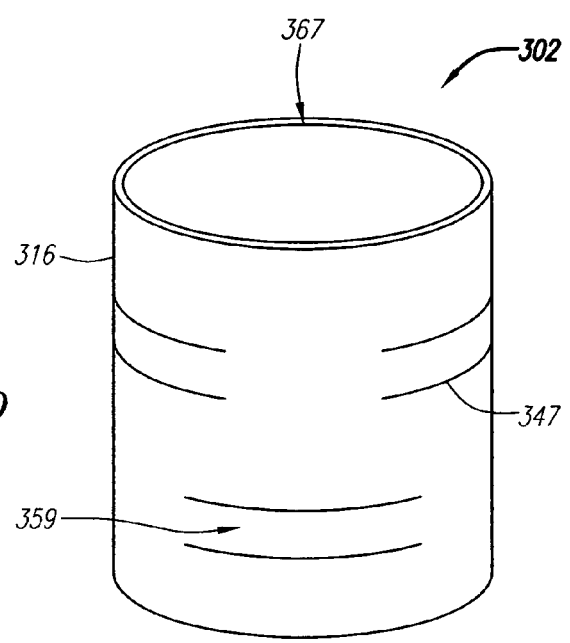
FIG. 12D is a perspective view depicting another exemplary embodiment of the lock device.
Figure 12E:
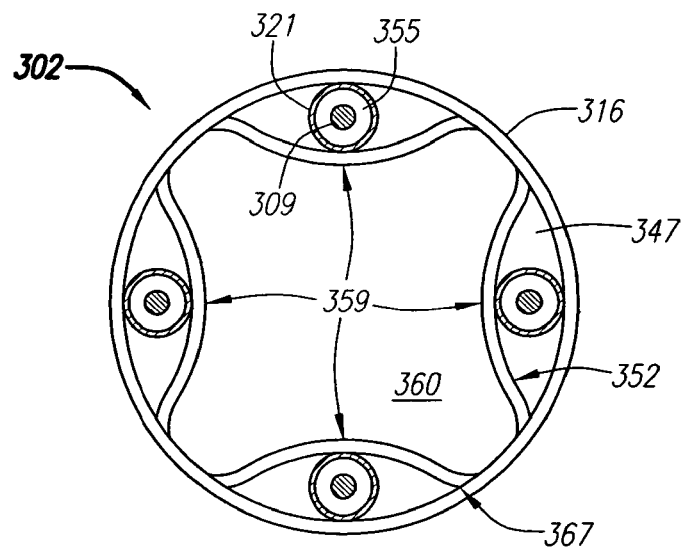
FIG. 12E is a top down view of this embodiment of the lock device.
Figure 12F:
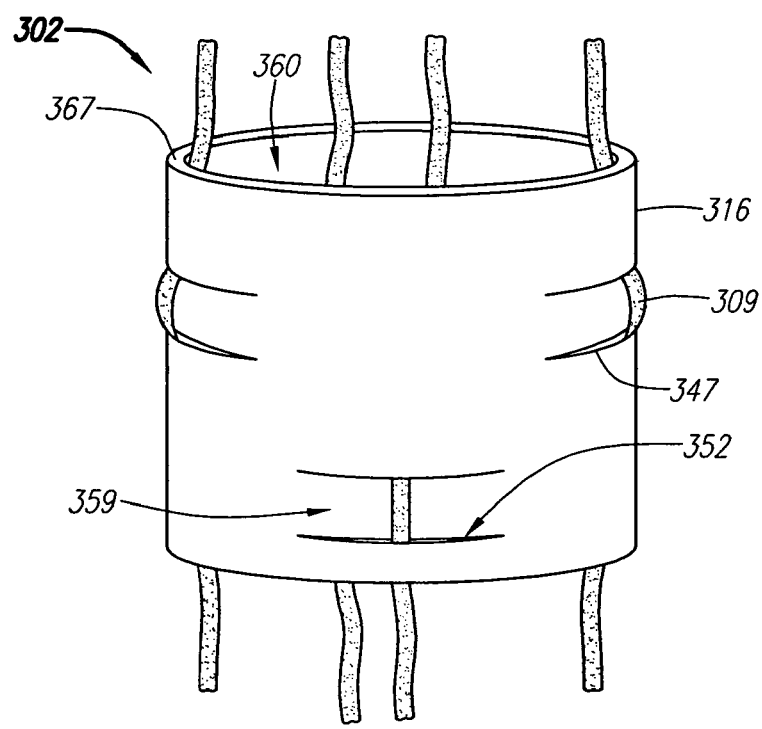
FIG. 12F is a perspective view depicting this exemplary embodiment of the lock device.

FIGS. 12D-F depict another exemplary embodiment of lock device 302 configured to lock one or more suture body portions 309 with a pinching or clamping type action. FIG. 12D is a perspective view depicting an embodiment of lock device 302 in the at-rest state where body 316 has a tubular configuration with multiple elongate slots 347 formed therein. Here, slots 347 are arranged in pairs to form a deflectable strut 359 therebetween.

FIG. 12E is a top down view of this embodiment of lock device 302 in the unlocked state with struts 359 deflected inwards into inner lumen 360. Here, multiple tubular restraining members 321 are used to maintain each strut 359 in the deflected state. Restraining member 321 has an inner lumen 355 through which one or more suture body portions 309 can pass. Restraining member 321 can be removed to free struts 359 and allow struts 359 to lock suture body portions 309 as depicted in the perspective view of FIG. 12F.

In the embodiments described with respect to FIGS. 12A-F, the locking force can be increased by increasing the thickness of body 316 and by texturing inner sidewall surfaces 352, to name a few.

Figure 13A:
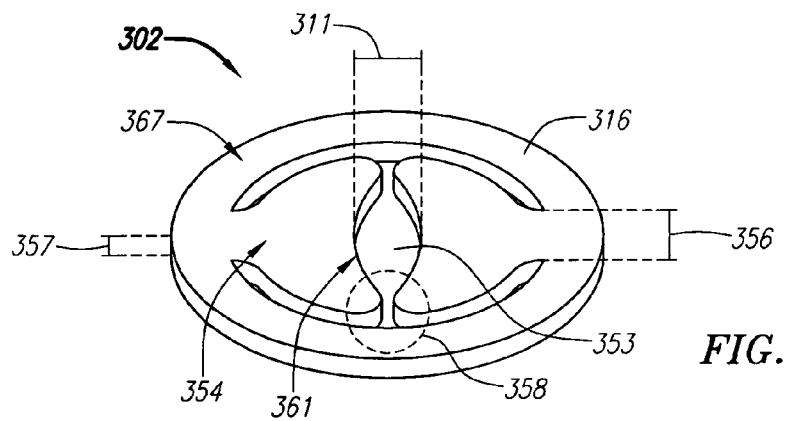
FIGS. 13A-B are perspective views depicting another exemplary embodiment of the lock device.
Figure 13B:
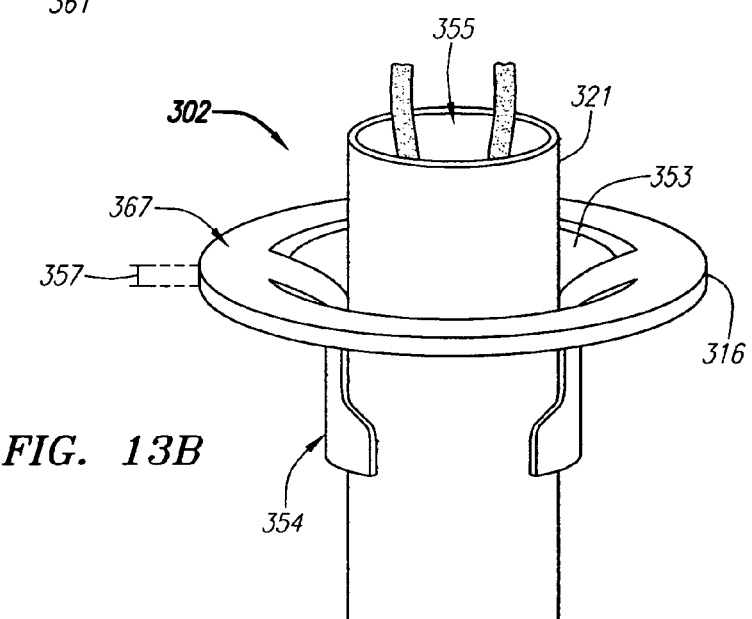
Figure 13C:
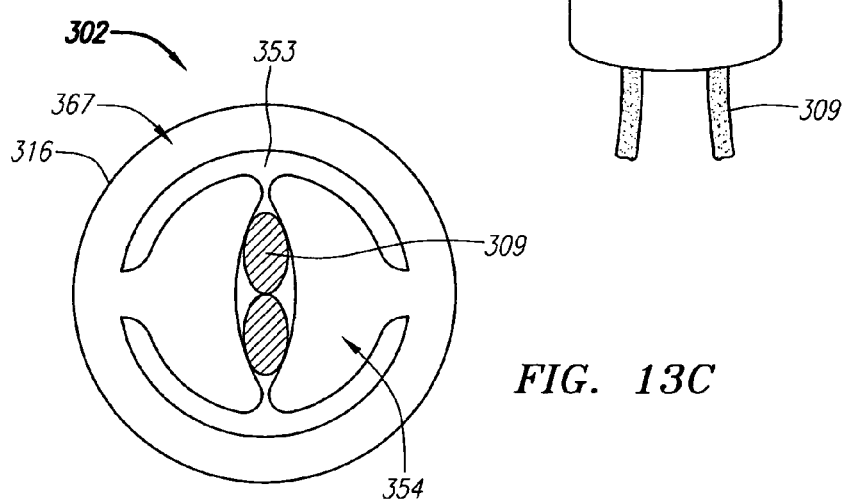
FIG. 13C is a top-down view depicting this exemplary embodiment of the lock device.

FIGS. 13A-C depict additional exemplary embodiments of lock device 302 configured to lock suture body portions 309 with a pinching or clamping type action. FIG. 13A is a perspective view depicting lock device 302 in an at-rest state. Here, lock device 302 has a plate-like body 316 with an open inner portion 353 defining two arm members 354. Arm members 354 are configured to grasp and lock one or more suture body portions 309 extending through open inner portion 353. Lock device 302 is preferably fabricated from an elastic or superelastic shape memory material, such as NITINOL, stainless steel and the like, and preferably heat treated to memorize the configuration of the at-rest state depicted in FIG. 13A. Here, arm members 354 lie substantially within a major plane of the body, i.e., the entire plate-like body lies substantially within the same plane. Open portion 353 can be created in any manner, including, but not limited to laser cutting and chemical etching. In one exemplary embodiment, plate-like body 316 is fabricated by laser cutting the desired shape from a sheet of NITINOL.

FIG. 13B is a perspective view depicting lock device 302 in the unlocked state. Here, restraining member 321 is inserted through open inner portion 353 to maintain arms 354 in a deflected state where the arms 354 lie substantially outside of the major plane of the body. Restraining member 321 is tubular member with an inner lumen 355 configured to allow suture body portions 309 to pass substantially unimpeded. When suture body portions 309 are in the desired position with the desired tension, restraining member 321 can be removed to allow lock device 302 to enter the locked state as shown in the top-down view of FIG. 13C.

Side surfaces 361 of arm members 354 are preferably configured to adequately contact suture body portions 309 without introducing a significant risk of severing suture body portions 309. Side surfaces 361 can be indented as shown to increase the surface area that contacts suture body portions 309. The width 356 of the base of each arm member 354 and the thickness 357 of each arm member 354 can be varied to effect the locking force applied to the one or more suture bodies 309, where a greater width 356 or thickness 357 would result in a greater locking force. Also, the at-rest width 311 between arm members 354 is preferably less than the width of suture body portion 309 in order to provide adequate locking force. Plate-like body 316 is preferably disc-shaped to match the inner diameter of the portion of delivery device 104 from which lock device 302 is preferably delivered. It should also be noted that the region of open portion 353 denoted by reference line 358 should be smaller than the cross-sectional size of suture body portion 309 so that arm members 354 can still lock suture body portion 309 if it migrates into this region during delivery.

Although, the embodiment described with respect to FIGS. 13A-C has two arm members 354, it should be noted that this embodiment of lock device 302 can have any number of one or more arm members 354. Also, this embodiment of lock device 302 can be used with any number of one or more suture body portions 309.

The embodiments described with respect to FIGS. 14A-K each rely on introducing a tortuous path for each suture body portion 309 to follow in order to lock the one or more suture body portions 309 in place. It should be noted that the routing of suture body portion 309 necessary to create a tortuous path will vary according to the actual implementation. Factors that should be considered include surface friction between suture body portion 309 and lock device 302, the number and frequency of turns suture body portion 309 makes, the tightness of each turn, and contact of suture body portion 309 with any surface edges of lock device 302.

Figure 14A:
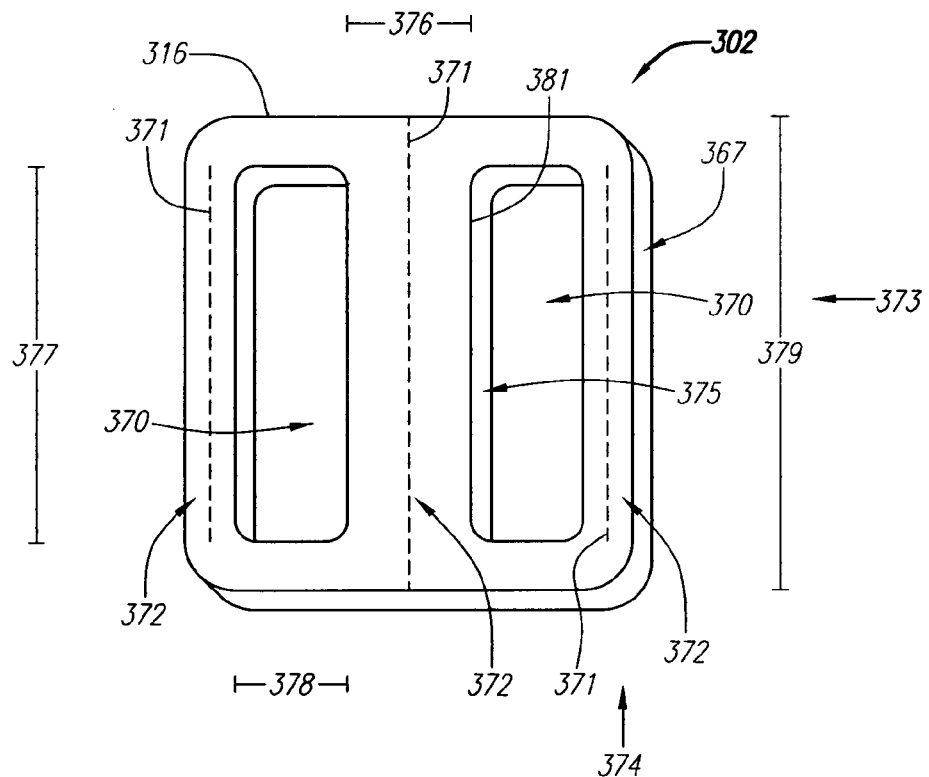
FIG. 14A is a perspective view depicting another exemplary embodiment of the lock device.

FIG. 14A is a perspective view depicting an exemplary embodiment of lock device 302 in an at-rest state where body 316 includes two elongate slots 370. Body 316 also includes deflectable struts 372 extending on each side of slots 370 and having longitudinal axes 371. Lock device 302 is preferably fabricated from an elastic or superelastic shape memory material, such as NITINOL, stainless steel and the like, and preferably heat treated to memorize the configuration of this at-rest state. In one exemplary embodiment, lock device 302 is laser cut or otherwise separated or formed from a NITINOL sheet.

Figure 14B:
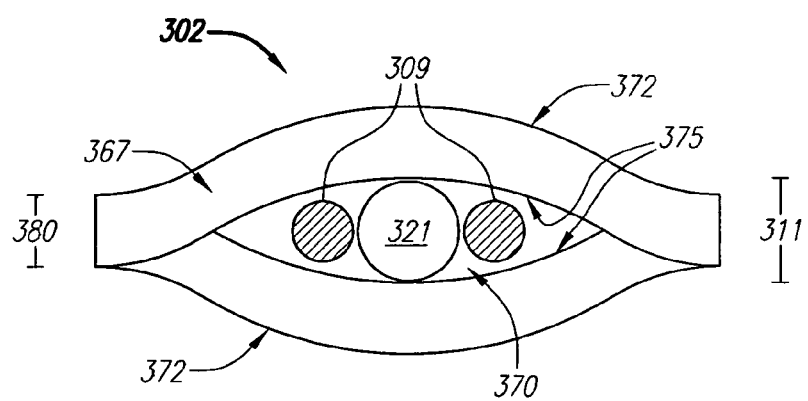
FIGS. 14B-D are side views depicting this embodiment of the lock device.

Elongate slots 370 are preferably configured to slidably receive one or more suture body portions 309 when struts 372 are deflected outwards from the at-rest state. FIG. 14B is a side view of this embodiment of lock device 302 taken from direction 373 of FIG. 14A. Here, lock device 302 is shown in the unlocked state with two suture body portions 309 and restraining member 321 extending through slots 370. Restraining member 321 is preferably configured to maintain struts 372 in the deflected position as shown, such that the width 311 between the inner surface 375 of each strut 372 is sufficient to allow suture body portions 309 to slide substantially unimpeded. Restraining member 321 is depicted here as being cylindrical or wire-like in shape. It should be understood that any shape or configuration of restraining member 321 can be used and, also, any number of desired restraining members 321 can be used.

Figure 14C:
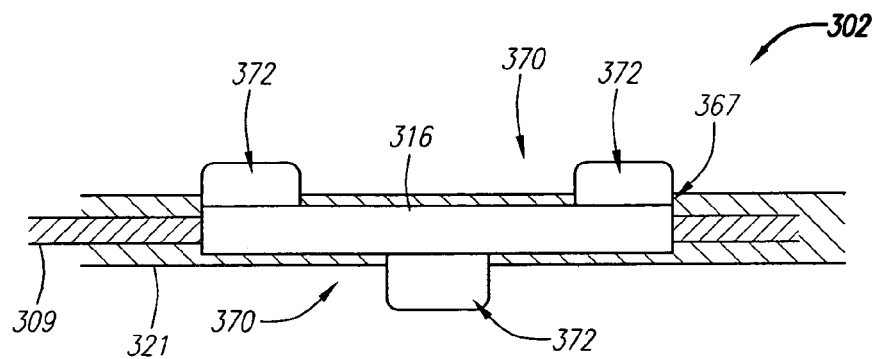
Figure 14D:
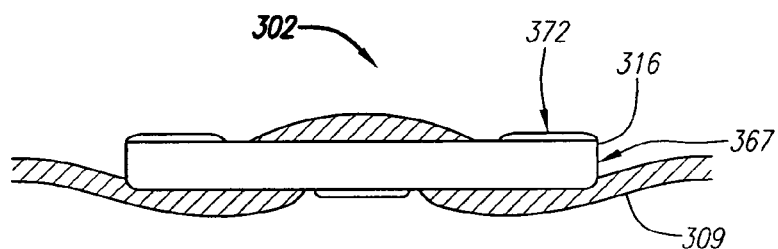

FIG. 14C is a side view of lock device 302 taken from direction 374 of FIG. 14A. Lock device 302 is shown here again in the unlocked state with suture body portions 309 and restraining member 321 extending through slots 370. It can be seen here that suture body portions 309 are routed through slots 370 in a relatively, or substantially straight path. Once suture body portions 309 are positioned as desired with the desired tension, restraining member 321 can be removed to allow struts 372 to move inwards and lock suture body portions 309 in place. FIG. 14D is another side view depicting this embodiment of lock device 302 in the locked state. Here, it can be seen that suture body portions 309 are now routed through a relatively non-straight, tortuous path that applies adequate surface friction and surface tension to lock suture body portions 309 in place.

Referring back to FIG. 14A, struts 372 each have a width 376 and a length 377 that can be varied to apply the desired locking force. Each strut 372 can have a different width 376 and/or length 377 if desired. Elongate slots 370 can each have a width 378 that is approximately equal to or greater than the width of a suture body portion 309. If slots 370 have a width 378 that is on the order of or less than that of suture body portion 309, body 316 can be apply a clamping-type force in addition to a tortuous path. Body 316 has a height 379 that can be varied to accommodate any number of one or more suture body portions 309 and any number of desired restraining members 321.

The locking force applied by this embodiment of lock device 302 can be varied by increasing the thickness 380 of body 316, decreasing the length of struts 372, increasing the width 376 of struts 372 and decreasing the width 378 of slots 370, to name a few. Also, strut inner surfaces 375 can be textured to increase surface friction. Furthermore, strut edges 381 can also be configured to increase the locking force. In FIG. 14A, strut edges 381 are generally square to increase the surface tension and surface friction applied to suture body portions 309. Strut edges 381 and strut inner surfaces 375 are preferably not configured such that they introduce an significant risk that suture body portions 309 are inadvertently severed.

Figure 14E:
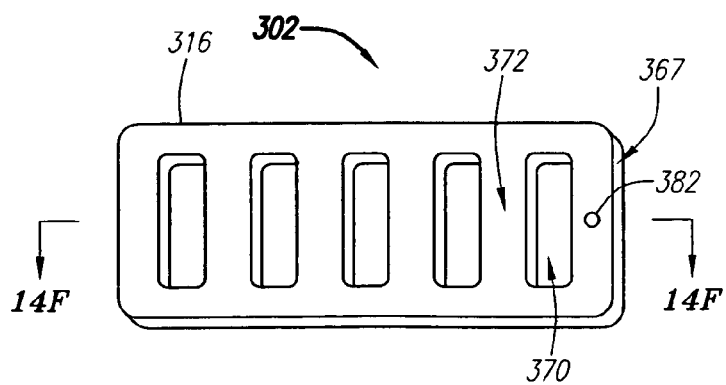
FIG. 14E is a perspective view of another exemplary embodiment of the lock device.
Figure 14F:
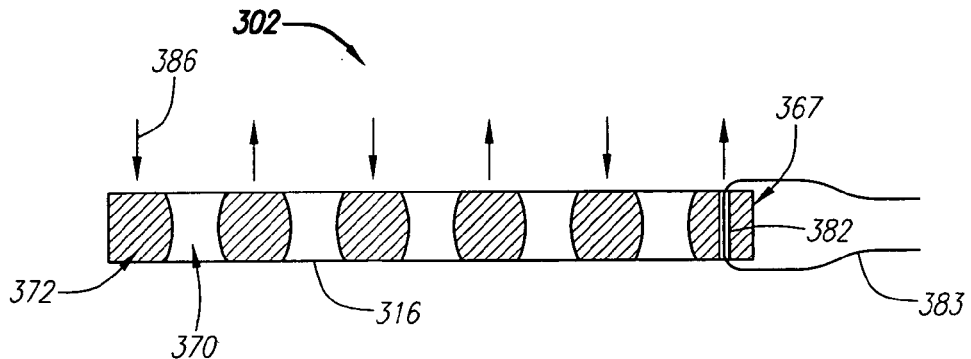
FIG. 14F is a cross-sectional view of this embodiment taken along line 14F-14F of FIG. 14E.

The locking force can also be adjusted through the number of struts 372 used. FIG. 14E is a perspective view of another exemplary embodiment of lock device 302 in the unlocked state. Here, lock device 302 includes six struts 372, five slots 370 and an aperture 382 configured for use in a "bail-out" procedure. Generally, the more slots 370 and struts 372 implemented in lock device, the more tortuous a path suture body portions 309 will need to follow and, accordingly, the more locking force that will be exerted. FIG. 14F is a cross-sectional view of this embodiment taken along line 14F-14F of FIG. 14E. Arrows 386 show the direction in which each strut 372 is deflected. In this embodiment, each strut 372 is deflected in a direction opposite that of the immediately adjacent struts 372, although struts 372 can be deflected in any manner desired. Here, tether 383 is shown extending through aperture 382. As mentioned above, tether 383 can be used if retrieval of lock device 302 and suture 103 becomes necessary during or after deployment.

Figure 14G:
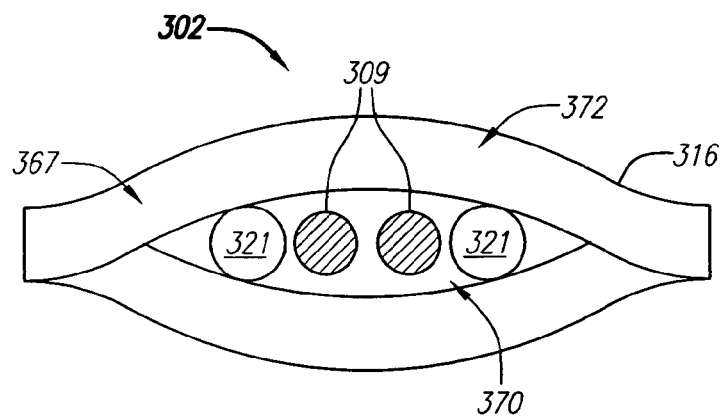
FIGS. 14G-H are side views depicting additional exemplary embodiment of the lock device.

As mentioned above, any number of restraining members 321 can be used with lock device 302. FIG. 14G is a side view depicting an exemplary embodiment of lock device 302 where two restraining members 321 are used to maintain struts 372 in the deflected state. Here, because restraining members 321 are placed on either side of suture body portions 309, restraining members 321 have a relatively smaller cross-sectional size than the embodiment described with respect to FIG. 14B. Also, placement of suture body portions 309 between restraining members 321 in the center of lock device 302 provides relatively more space for movement of suture body portions 309.

Figure 14H:
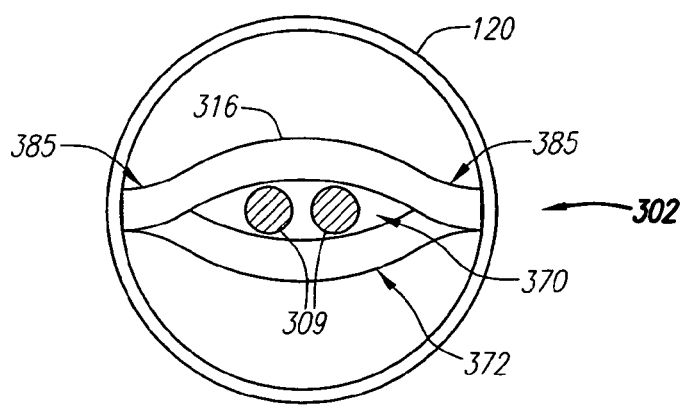

Other techniques can also be used to maintain lock device 302 in the deflected, unlocked state. For instance, FIG. 14H is a side view depicting another exemplary embodiment of lock device 302. Here, needle 120 is used to exert force on the side portions 385 of lock device 302 and maintain configuration in the unlocked state.

Figure 14I:
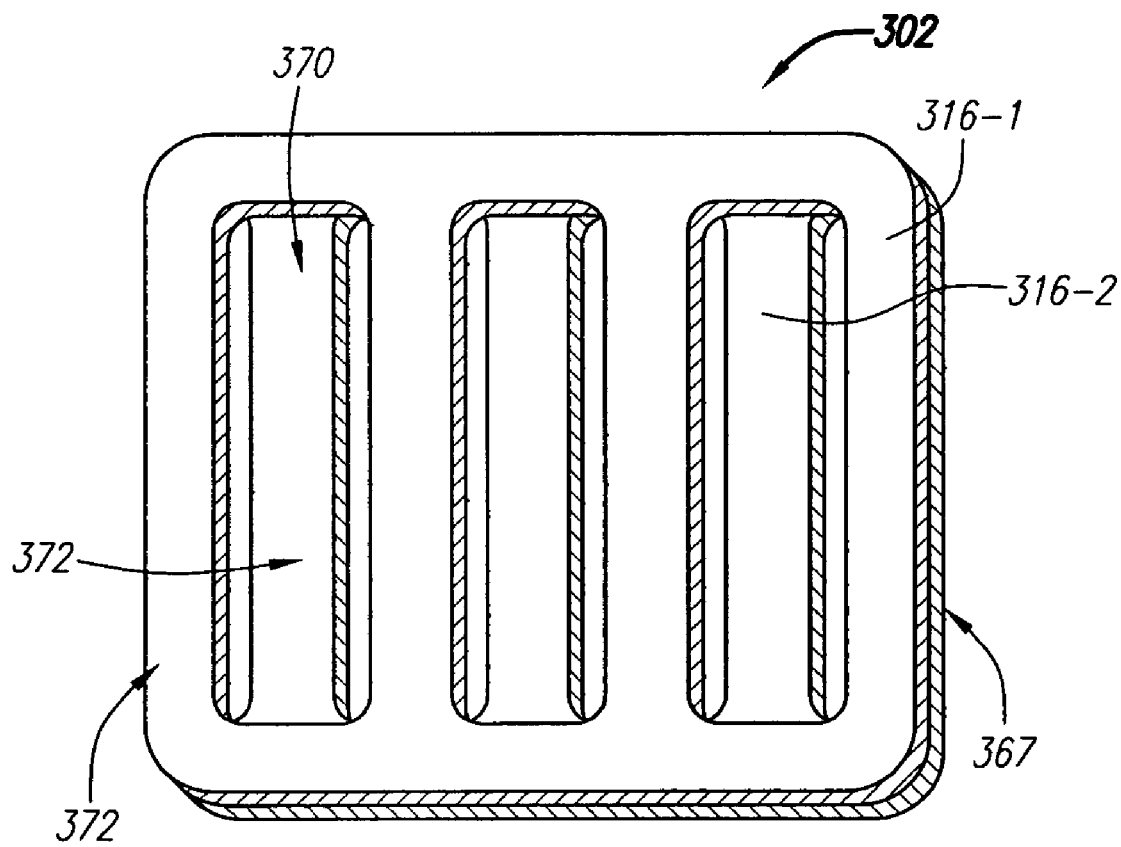
FIG. 14I is a perspective view depicting another exemplary embodiment of the lock device.

FIG. 14I is a perspective view depicting another exemplary embodiment of lock device 302 in the at-rest state. Here, lock device 302 includes two interlocking bodies 316-1 and 316-2. Struts 372 on body 316-1 are deflectable through slots 370 on body 316-2 and vice versa. The use of interlocking bodies 316-1 and 316-2 allows a denser placement of the struts 372 that each suture body portion 309 is routed over. Bodies 316-1 and 316-2 can be coupled together in any manner desired, including, but not limited to soldering, mechanical interlocking, welding, and adhesives. However, because bodies 316-1 and 316-2 are interlocking, it is not necessary to couple them together. In an alternative embodiment, the configuration depicted in FIG. 14I can be formed from one body 316.

Figure 14J:
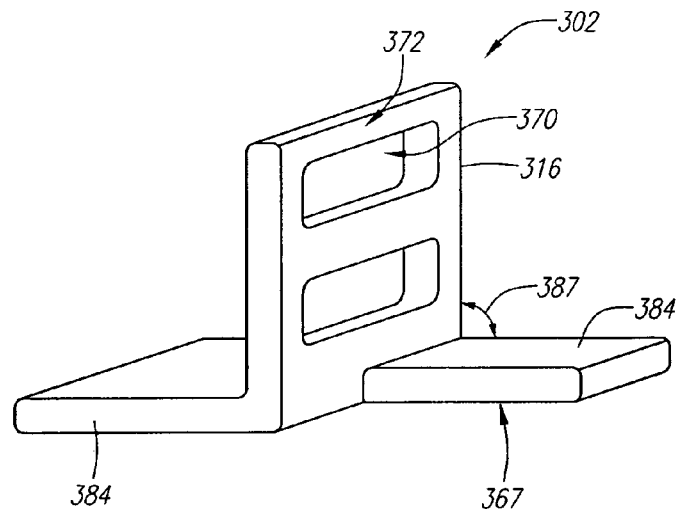
FIG. 14J is a perspective view depicting another exemplary embodiment of the lock device.
Figure 14K:
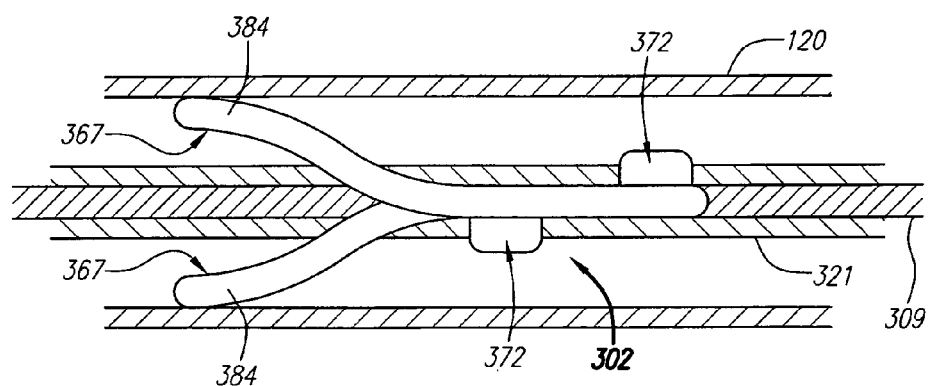

As mentioned above, lock device 302 preferably performs an anchoring function as well as a locking function. FIG. 14J is a perspective view depicting an exemplary embodiment of lock device 302 having two deflectable legs 384 at the base of the portion of body 316 containing struts 372. Here, lock device 302 is shown in the at-rest state with legs 384 configured to abut septal wall 207 and anchor lock device 302. Legs 384 can be deflected at any angle 387 from the remainder of body 316, preferably ninety degrees. FIG. 14K is a partial cross-sectional view of lock device 302 in the unlocked state within needle 120. Needle 120 is preferably configured to restrain legs 384 and prevent them from deflecting fully into the at-rest state shown in FIG. 14J. Once deployed from needle 120, legs 384 are free to return to the at-rest state. One of skill in the art will readily recognize that other techniques for restraining legs 384 can also be used.

Here, legs 384 are generally flat and rectangular-like in shape. It should be noted that legs 384 can be configured in any manner desired, with any shape, size, coating, surface texture and the like. Also, although only two legs 384 are shown, it should be noted that any number of one or more legs 384 can be used in any given embodiment.

In the embodiments described with respect to FIGS. 14A-K, each longitudinal axis 371 of strut 372 is generally parallel with each other when in the at-rest state. It should be noted that struts 372 can be configured in any manner desired, with any shape, size or orientation. Struts 372 can be oriented differently such that each longitudinal axis in not parallel, in order to provide a more irregular and tortuous path for suture body portions 309.

Figure 15A:
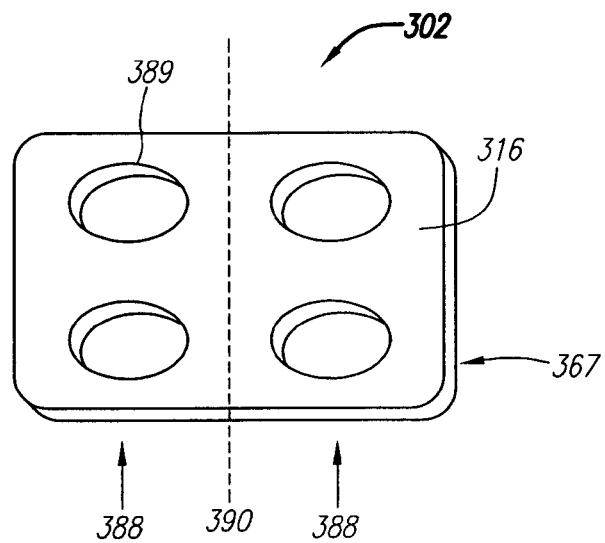
FIG. 15A is a perspective view depicting another exemplary embodiment of the lock device.

FIGS. 15A-G depict additional exemplary embodiments of lock device 302 configured to lock one or more suture body portions 309 with a tortuous path. FIG. 15A is a perspective view depicting an exemplary embodiment of lock device 302 in the at-rest state. Lock device 302 includes two rows 388 of apertures 389 each configured to slidably receive a suture body portion 309. Lock device 302 is preferably fabricated from an elastic or superelastic shape memory material, such as NITINOL, stainless steel and the like, and preferably heat treated to memorize the configuration of this at-rest state. In one exemplary embodiment, lock device 302 is laser cut or otherwise separated or formed from a NITINOL sheet.

Figure 15B:
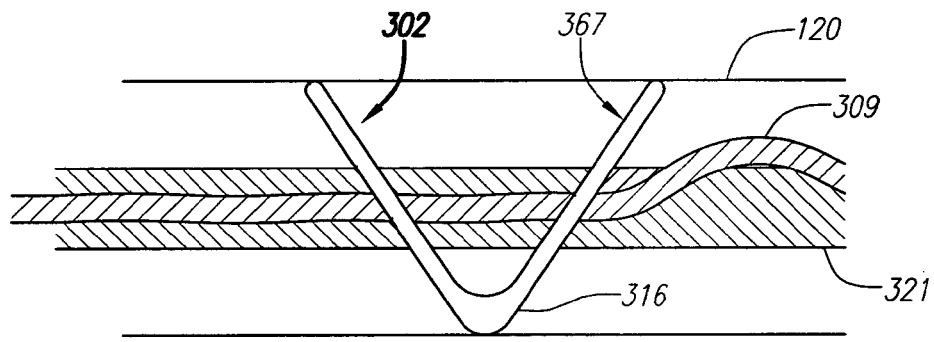
FIG. 15B is a partial cross-sectional view of this embodiment of the lock device.
Figure 15C:
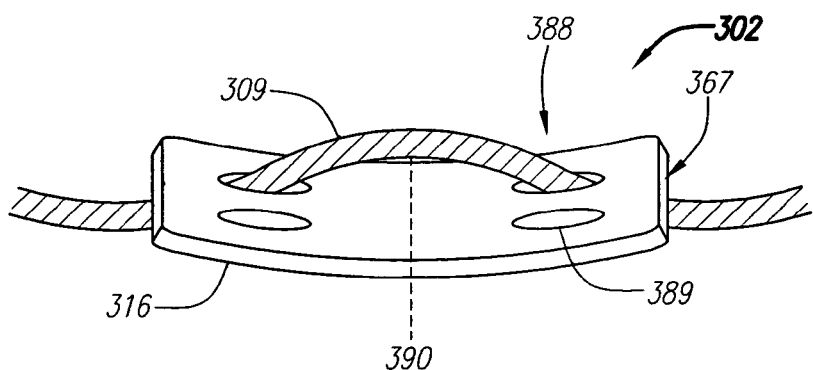
FIG. 15C is a perspective view depicting this embodiment of the lock device.

Body 316 is preferably bendable about axis 390 in order to transition between the locked and unlocked states. FIG. 15B is a partial cross-sectional view of this embodiment of lock device 302 in the unlocked state within needle 120. Here, lock device 302 is restrained in the bent, unlocked state by restraining member 321 routed through an aperture 389 in each row 388. Suture body portions 309 are free to pass through the other aperture 389 in each row 388 substantially unimpeded. FIG. 15C is a perspective view depicting lock device 302 in the relatively straightened and locked state with restraining member 321 removed. Apertures 389 are preferably on the order of or slightly larger than suture body portions 309 in order to allow adjustment of suture body portions 309 as desired while at the same time restricting movement of suture body portions 309 when lock device 302 is in the locked state.

Figure 15D:
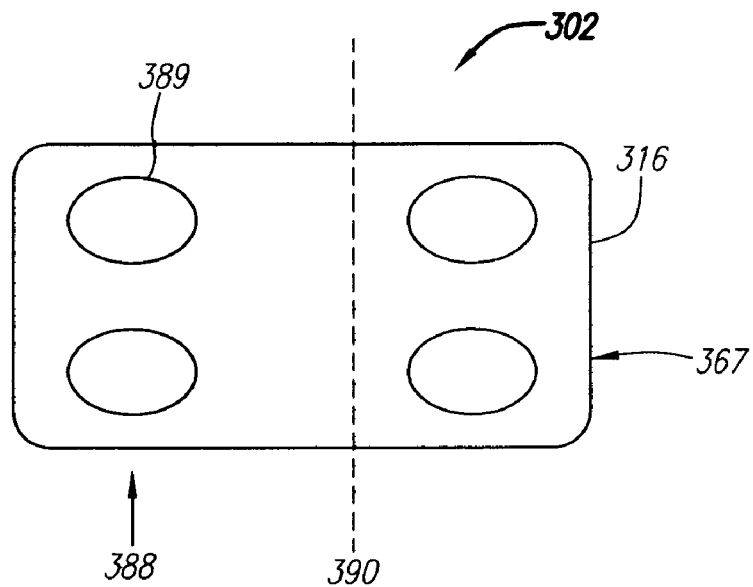
FIG. 15D is a top down view depicting another exemplary embodiment of the lock device.

Body 316 can be configured to aid bending about axis 390. For instance, body 316 can be made relatively thinner along axis 316 or can include indentations that are located along axis 390 and create an area of body 316 that is more prone to bend when placed under pressure. In FIG. 15A, axis 390 is shown placed symmetrically, approximately in the center of body 316. FIG. 15D is a top down view depicting another exemplary embodiment where axis 390 is placed asymmetrically, closer to one side of body 316.

Figure 15E:
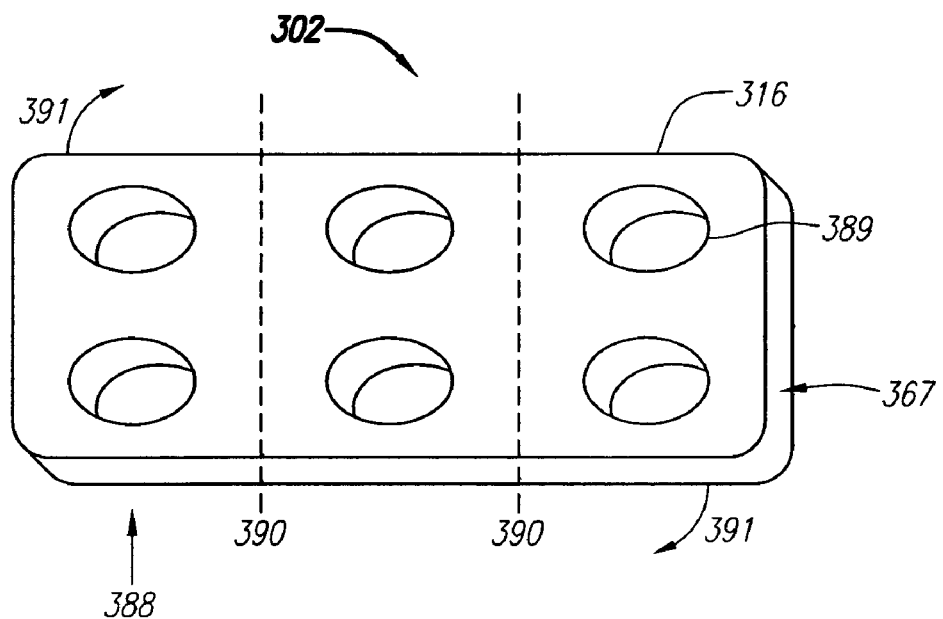
FIG. 15E is a perspective view depicting another exemplary embodiment of the lock device.
Figure 15F:
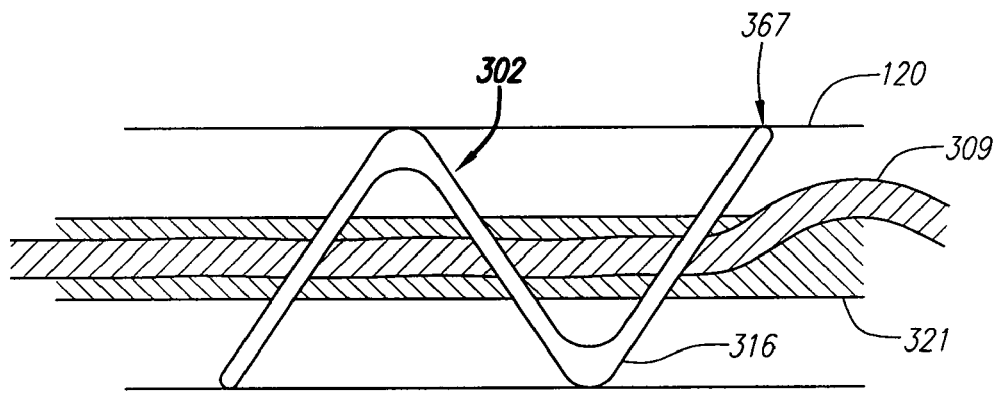
FIG. 15F is a partial cross-sectional view of this embodiment of the lock device.
Figure 15G:
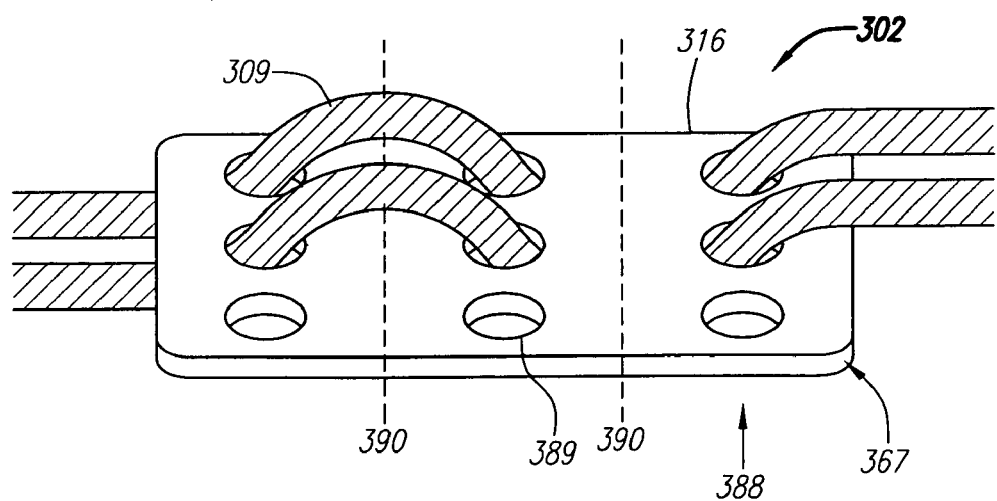
FIG. 15G is a perspective view depicting another exemplary embodiment of the lock device.

FIG. 15E is a perspective view of another exemplary embodiment of lock device 302 in the at-rest state. In this embodiment, body 316 includes three rows 388 of three apertures 389 and is bendable in opposite directions 391 about two axes 390. FIG. 15F is a partial cross-sectional view of this embodiment in the unlocked state within needle 120. Similar to the embodiment described with respect to FIGS. 15A-D, restraining member 321 is used to restrain lock device 302 until suture body portions 309 are positioned as desired, at which point lock device 302 can be deployed to lock suture body portions 309 in place, as depicted in the perspective view of FIG. 15G.

Although apertures 389 are depicted in FIGS. 15A-G as being generally circular, it should be noted that apertures 389 can be configured in any shape, including, but not limited to elliptical, oval, polygonal, irregular and any combination thereof.

The locking force applied by lock device 302 can be increased by increasing thickness 380 of body 316, decreasing the size of apertures 389 or by increasing the number of bend axes 390 and corresponding rows 388, to name a few.

Figure 16A:
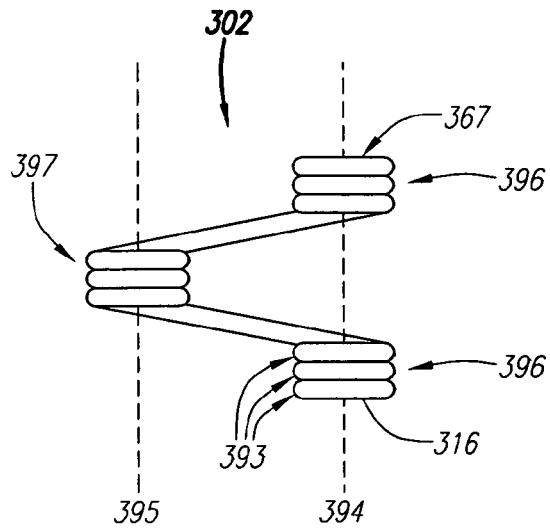
FIG. 16A is a front view depicting another exemplary embodiment of the lock device.

FIGS. 16A-F depict additional exemplary embodiments of lock device 302 configured to lock suture body portions 309 with a tortuous path. In these embodiments, body 316 is wire-like or ribbon-like and coiled to form multiple coiled segments 393. FIG. 16A is a front view of one exemplary embodiment of lock device 302 in the at-rest state. Lock device 302 preferably has a main axis 394 and an off axis 395, with portions of coiled segments 393 oriented around each. Here, body 316 includes two portions 396 oriented about main axis 394 and one portion 397, located between main axis portions 396, oriented about off-axis 395. Lock device 302 is preferably fabricated from an elastic or superelastic shape memory material, such as NITINOL, stainless steel and the like, and preferably heat treated to memorize the configuration of this at-rest state.

Figure 16B:
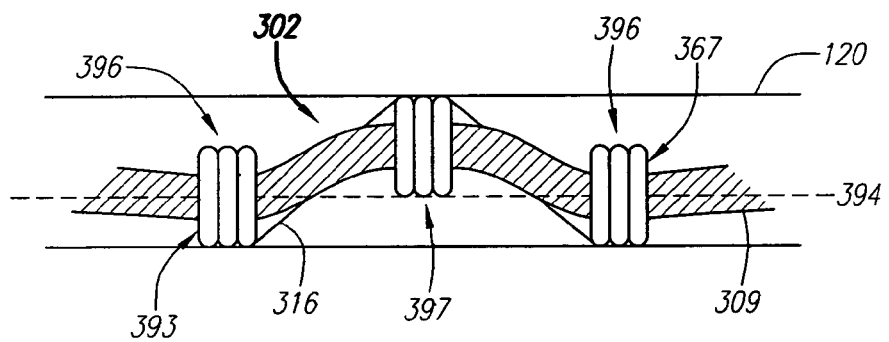
FIGS. 16B-C are partial cross-sectional views depicting this embodiment of the lock device.
Figure 16C:
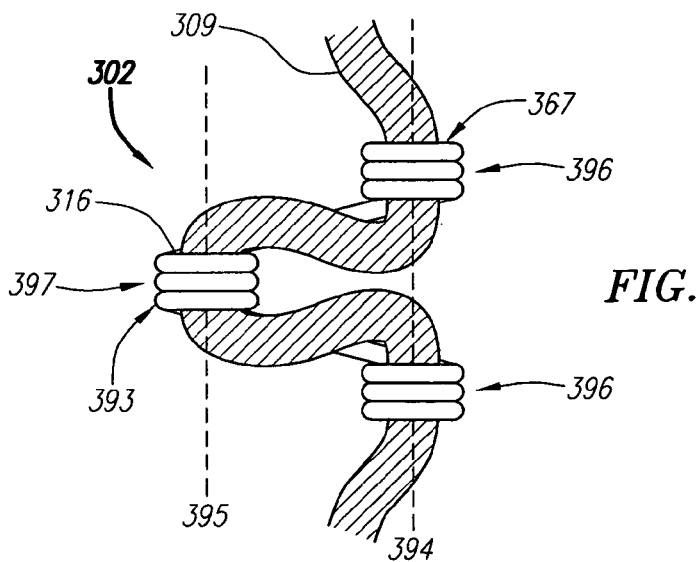

FIG. 16B is a partial cross-sectional view depicting this embodiment of lock device 302 in the unlocked state with suture body portions 309 routed through each coiled segment 393. Here, off axis body portion 397 is deflected so that it is oriented substantially about main axis 394. Needle 120 is preferably configured to restrain off axis body portion 397 from returning to the at-rest state. In this unlocked state, each portion 396-397 is oriented in a similar manner and suture body portions 309 can be routed along a substantially straight path that allows substantially unimpeded movement. When suture body portions 309 are in the desired position with the desired tension, lock device 302 can be deployed from within needle 120 and allowed to enter the locked state depicted in FIG. 16C. Other techniques of restraining off axis portion 397 can be used, including, but not limited to, insertion/withdrawal of a rigid restraining member 321 through the center of each coiled segment 393.

Figure 16D:
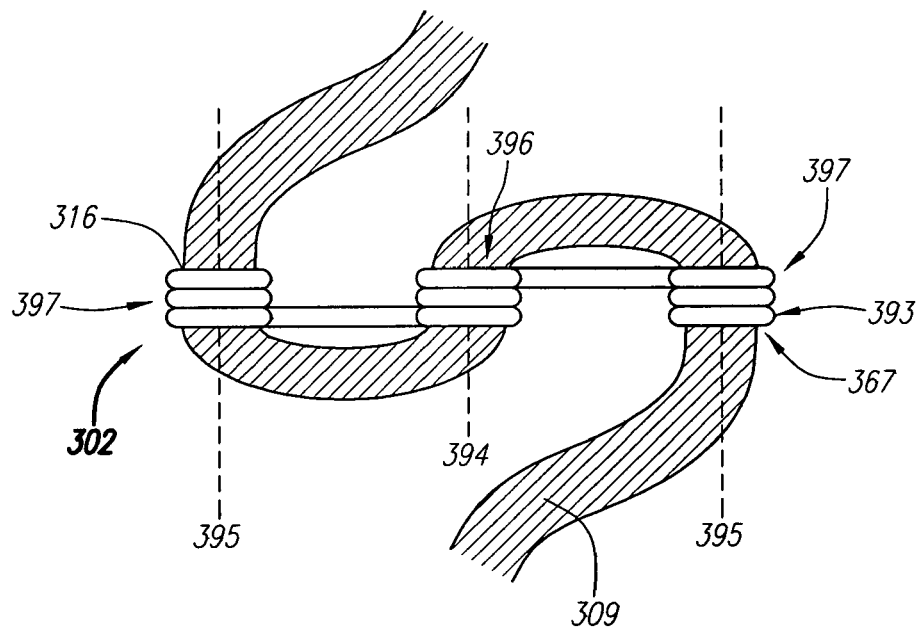
FIGS. 16D-E are front views depicting additional exemplary embodiments of the lock device.

Each portion 396-397 of body 316 can include any number of one or more coiled segments 393 each having any configuration desired. For instance, the size and shape of each coiled segment 393 can be varied as can the distance between adjacent coiled segments 393. Furthermore, any number of main axis portions 396 and off axis portions 397 can be included and, these portions 396-397 can be arranged and deflected in any manner desired, not limited to the alternating arrangement depicted in FIGS. 16A-C. For instance, FIG. 16D is a front view depicting another exemplary embodiment of lock device 302 in the unlocked state. Here, lock device 302 includes one main axis portion 396 and two off axis portions 397, each oriented about a separate off axis 395.

Figure 16E:
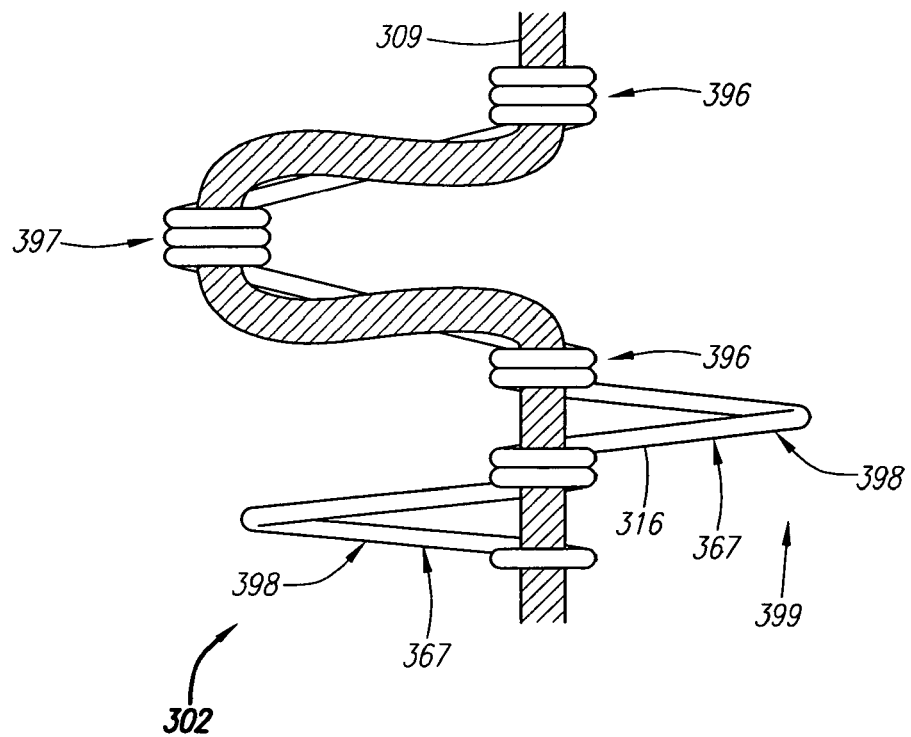
Figure 16F:
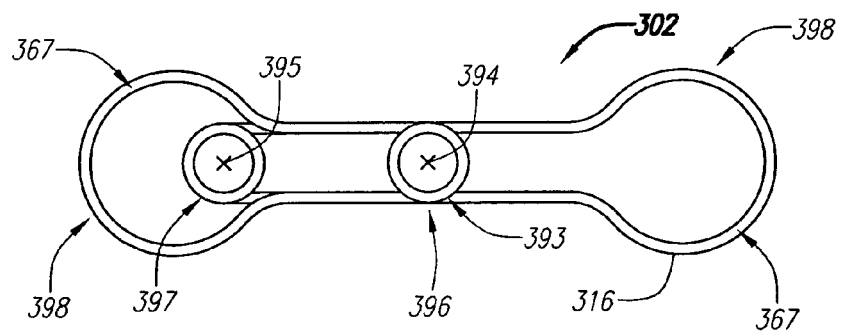
FIG. 16F is a bottom up view depicting the embodiment of FIG. 16E.

FIG. 16E is a front view depicting another exemplary embodiment of lock device 302, which, in order to increase the anchoring ability, is configured to include two wing members 398. Here, wing members 398 are formed by extending wire-like body 316 outwards from main axis 394 to form a wire loop. FIG. 16F is a bottom up view depicting this embodiment from direction 399 of FIG. 16E, showing wing members 398 in greater detail without suture body portion 309. Wing members 398 are configured to abut septal wall 207 and prevent lock device 302 from being pulled through. Any number of one or more wing members 398 can be implemented as desired. Wing members 398 can be formed from a wire loop as shown here, or can be single-ended extensions of body 316 or even separate members coupled to body 316.

Figure 17A:
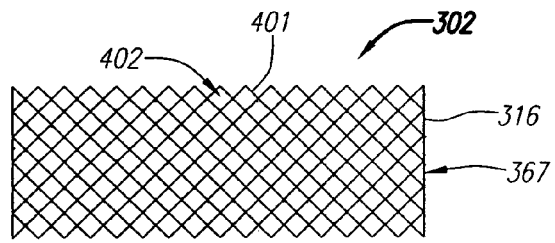
FIG. 17A is a front view depicting another exemplary embodiment of the lock device.
Figure 17B:
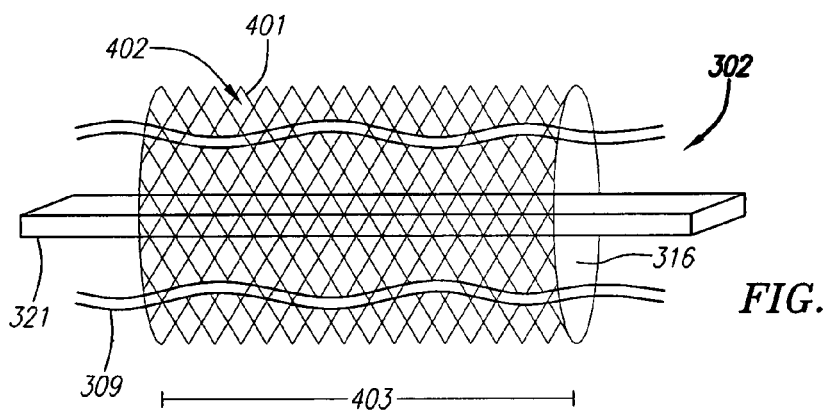
FIGS. 17B-C are perspective views depicting this exemplary embodiment of the lock device.
Figure 17C:
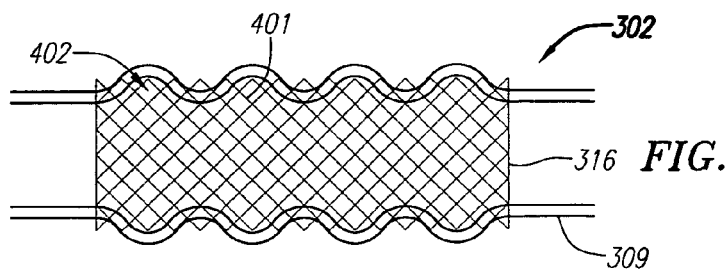

FIGS. 17A-C depict another exemplary embodiment of lock device 302 configured to lock one or more suture body portions 309 by introducing a tortuous path. FIG. 17A is a front view depicting lock device 302 with a stent-like configuration. Body 316 includes multiple, intertwined wire-like or ribbon-like portions 401 with apertures 402 located therebetween. Lock device 302 is preferably fabricated from an elastic or superelastic shape memory material, such as NITINOL, stainless steel and the like, and preferably heat treated to memorize the configuration of this at-rest state.

Lock device 302 is preferably expandable from this at-rest state to an expanded state as depicted in the perspective view of FIG. 17B. In the expanded state, suture body portions 309 can pass through apertures 402 substantially unimpeded, allowing adjustment by the user. Here, a flat restraining member 321 is used to maintain lock device 302 in the expanded state, while not interfering with the movement of suture body portions 309. In this embodiment, the length 403 of lock device 302 is less in the expanded state than in the at-rest state. When suture body portions 309 are positioned as desired with the desired tension, restraining member 321 can be removed to allow body 316 to retract into the locked state depicted in FIG. 17C, where suture body portions 309 are routed through a relatively more tortuous path. In this embodiment, variation of the locking force can be accomplished by altering the implementation to have smaller apertures 402, thicker body portions 401, and a greater number of apertures 402 in the device length 403, to name a few.

Figure 18A:
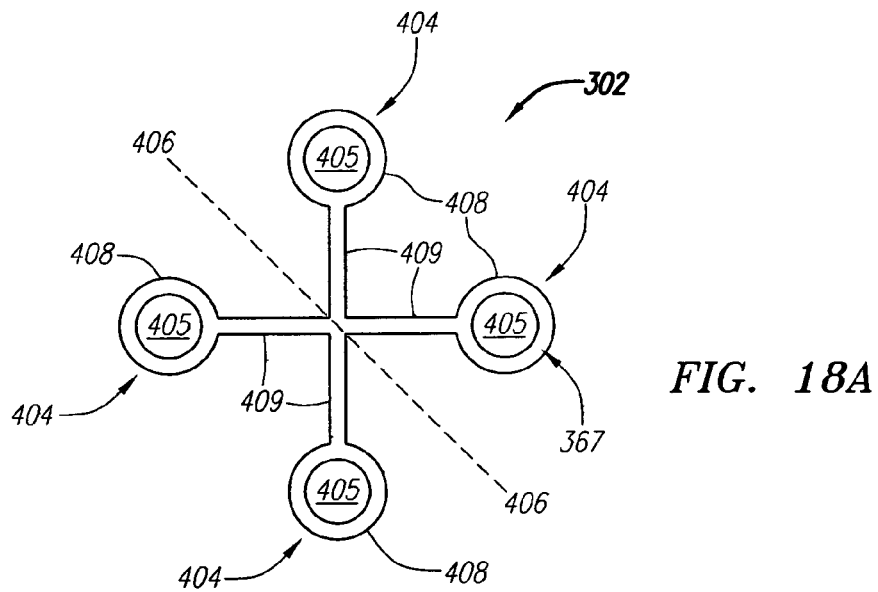
FIGS. 18A-D are front views depicting additional exemplary embodiments of the lock device.

FIGS. 18A-F depict additional exemplary embodiments of lock device 302 configured to lock one or more suture body portions 309 by introducing a tortuous path. FIG. 18A is a front view depicting lock device 302 with four petal-like members 404 in the at-rest state. Each petal-like member 404 has an aperture 405 configured to slidably receive one or more suture body portions 309. Aperture 405 is located within an annular, or ring-like portion 408, which is placed on the end of an arm 409. Lock device 302 is preferably fabricated from an elastic or superelastic shape memory material, such as NITINOL, stainless steel and the like, and preferably heat treated to memorize the configuration of this at-rest state. Lock device 302 is preferably deformable, or bendable, along axis 406, so that each petal-like member 404 is adjacent to another petal-like member 404, with apertures 405 generally concentric.

Figure 18B:
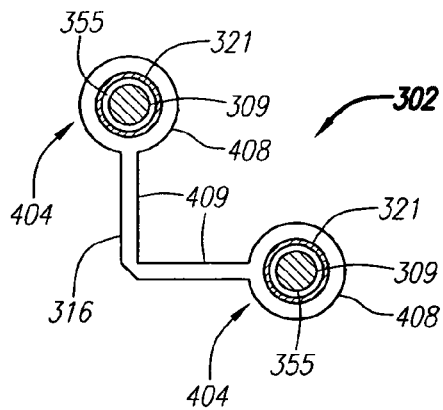
Figure 18C:
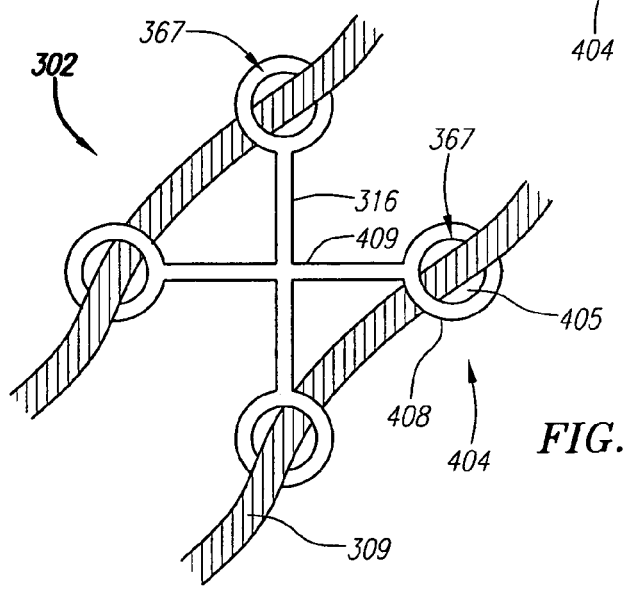

FIG. 18B depicts this embodiment of lock device 302 deformed into the unlocked state (i.e., folded about axis 406). Here, tubular restraining members 321 are placed through the pairs of concentric apertures 405 to maintain body 316 in the deformed state. One or more suture body portions 309 are routed through inner lumen 355, which is large enough to allow substantially unimpeded movement. When suture body portions 309 are position as desired with the desired tension, restraining members 321 can be removed to allow body 316 to move towards the at-rest state and introduce a tortuous path that can lock suture body portions 309 as depicted in FIG. 18C. It should be noted that only one restraining member 321 can be used if body 316 is configured with sufficient rigidity. As one can see, this embodiment is configured for use with at least two or more suture body portions 309; however it should be noted that lock device 302 can be configured to lock any number of one or more suture body portions 309. For instance, in one exemplary embodiment, lock device 302 includes only two petal-like members 404 and is configured for use with one or more suture body portions 309.

Figure 18D:
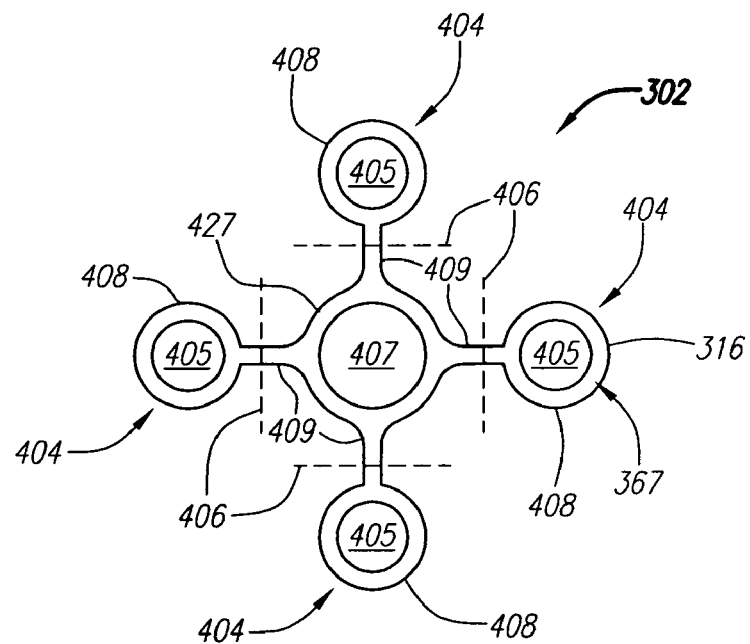

FIG. 18D depicts another exemplary embodiment of lock device 302 in the at-rest state and configured for use with one or more suture body portions 309. The embodiment described with respect to FIG. 18D is configured to introduce a relatively more tortuous path than the embodiment described with respect to FIG. 18C. Here, in addition to the four apertures 405 located on petal-like members 404, body 316 also includes a central aperture 407 within a central annular portion 427. Each petal-like member 404 is preferably bendable along axis 406 so that apertures 405 and 407 become generally concentric.

Figure 18E:
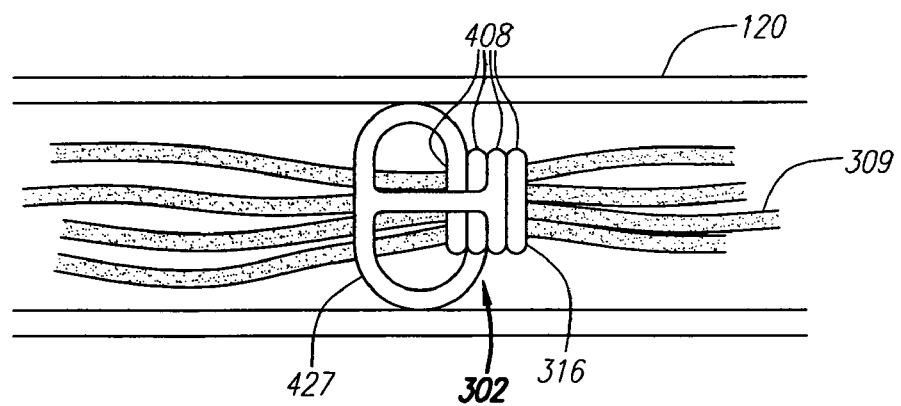
FIGS. 18E-F are partial cross-sectional views depicting the embodiment of FIG. 18D.
Figure 18F:
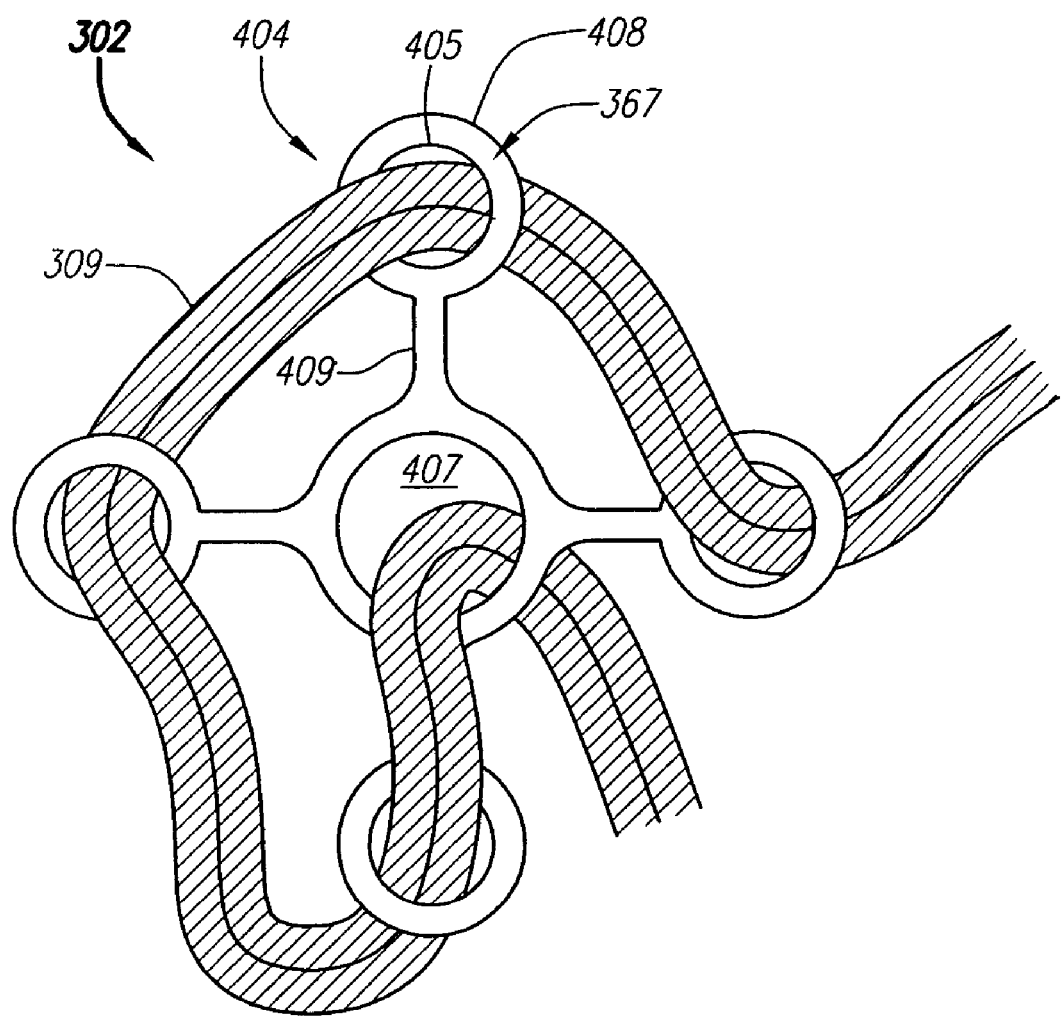

FIG. 18E is a partial cross-sectional view depicting this embodiment of lock device 302 in the unlocked state within needle 120, which can be configured to restrain body 316. Tubular restraining member 321 can also be used to restrain body 316. Here, four suture body portions 309 are routed through concentric apertures 405 and 407, which are preferably large enough to allow suture body portions 309 to pass substantially unimpeded. To lock suture body portions 309, lock device 302 can be deployed from within needle 120 where it can move towards the at-rest state and lock suture body portions 309, as depicted in FIG. 18F. Different routings of suture body portions 309 through apertures 405 and 407 can be used, depending on the order in which each petal-like member 404 is bent over central aperture 407, as well as the side to which each member 404 is bent.

In the embodiments described with respect to FIGS. 18A-F, the locking force can be increased by altering the implementation to have smaller apertures 405 and 407, a thicker body 316, and longer arms 409, to name a few.

Figure 19A:
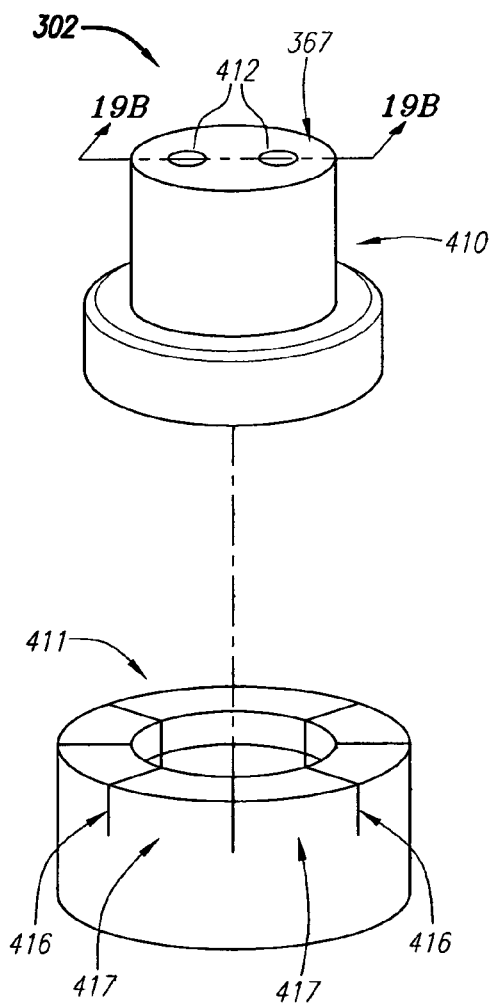
FIG. 19A is a perspective view depicting another exemplary embodiment of the lock device.
Figure 19B:
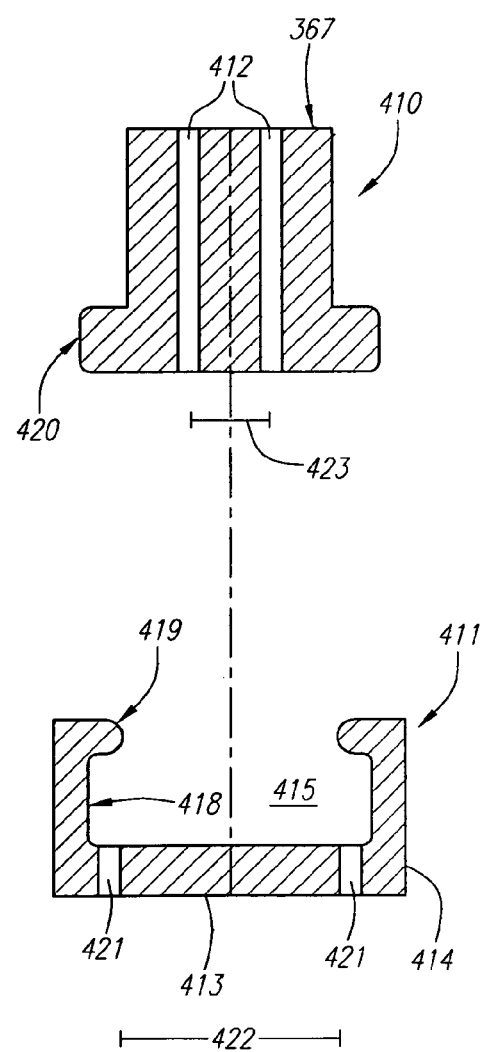
FIG. 19B is a cross-sectional view of this embodiment taken along line 19B-19B of FIG. 19A.
Figure 19C:
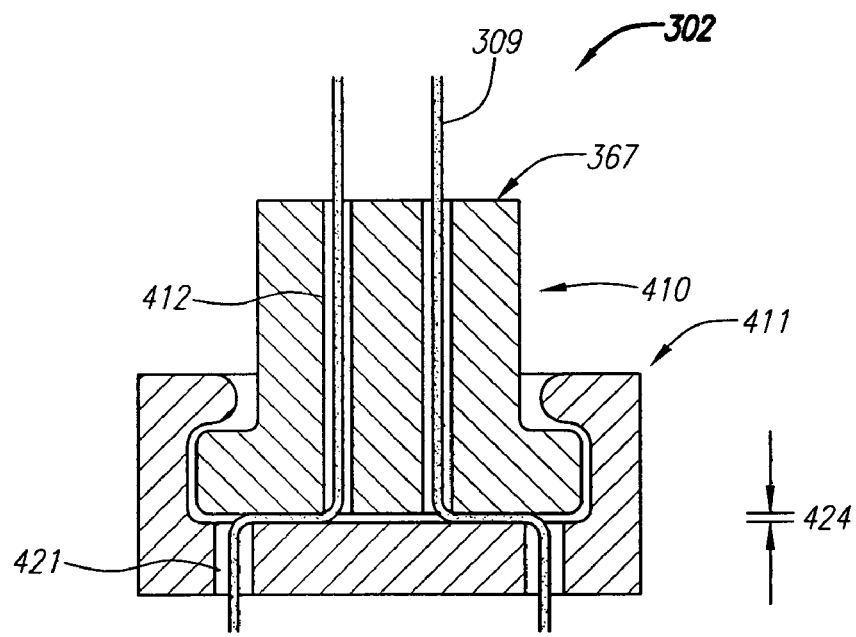
FIG. 19C is a cross-sectional view of this embodiment of the lock device.

FIGS. 19A-C depict another exemplary embodiment of lock device 302 configured to lock one or more suture body portions 309 by introducing a tortuous path. FIG. 19A is a perspective view depicting lock device 302 with a plug portion 410 and a cap portion 411. FIG. 19B is a cross-sectional view of this embodiment taken along line 19B-19B of FIG. 19A. In this embodiment, the unlocked and at-rest states are preferably the same. Lock device 302 is preferably fabricated from an elastic or superelastic shape memory material, such as NITINOL, stainless steel and the like, and preferably heat treated to memorize the configuration of the at-rest/unlocked state depicted here.

Here, plug portion 410 is generally cylindrical and includes two open-ended inner lumens 412, each configured to slidably receive suture body portion 309. Cap portion 411 includes a base 413, sidewall 414 and an open inner portion 415. Open inner portion 415 is configured to slidably receive plug portion 410. Sidewall 414 includes multiple slots 416, which form deflectable arms 417 therebetween. Inner surface 418 of each arm 417 includes a detent 419 configured to abut a corresponding detent 420 located on plug portion 410. Base 413 includes two open-ended lumens 421 spaced apart at a distance 422 that is preferably different than distance 423 between lumens 412 of plug portion 410. In this embodiment, distance 422 is larger than distance 423.

FIG. 19C is a cross-sectional view of this embodiment of lock device 302 in the locked state. Here, cap portion 411 has been slid over plug portion 410 and detents 419 and 420 are now on the opposite sides of each other in a locked position. Because lumens 412 and 421 are preferably offset (i.e., distances 422 and 423 are not equal), a tortuous path is created for suture body portions 309. It should be noted that offsetting lumens 412 and 421 is not necessary to lock suture body portions 309. For instance, in another embodiment, suture body portions 309 can be locked by changing the orientation, e.g., rotating, cap portion 411 with respect to plug portion 410. It should be noted that offsetting lumens 412 and 421 allows the user to ignore the orientations of each portion 410-411.

In this embodiment, the distance 424 between cap portion 411 and plug portion 410 in the locked state can be selected to be on the order of or less than the diameter of suture body portions 309. This will apply a clamping force to suture body portions 309 and increase the locking force.

It should be noted that any number of one or more lumens 412 can be used with any number of one or more lumens 421, i.e., the number of lumens 412 does not have to equal the number of lumens 421. Accordingly, each lumen 412 and 421 can be configured to slidably receive any number of one or more suture body portions 309.

Figure 19D:
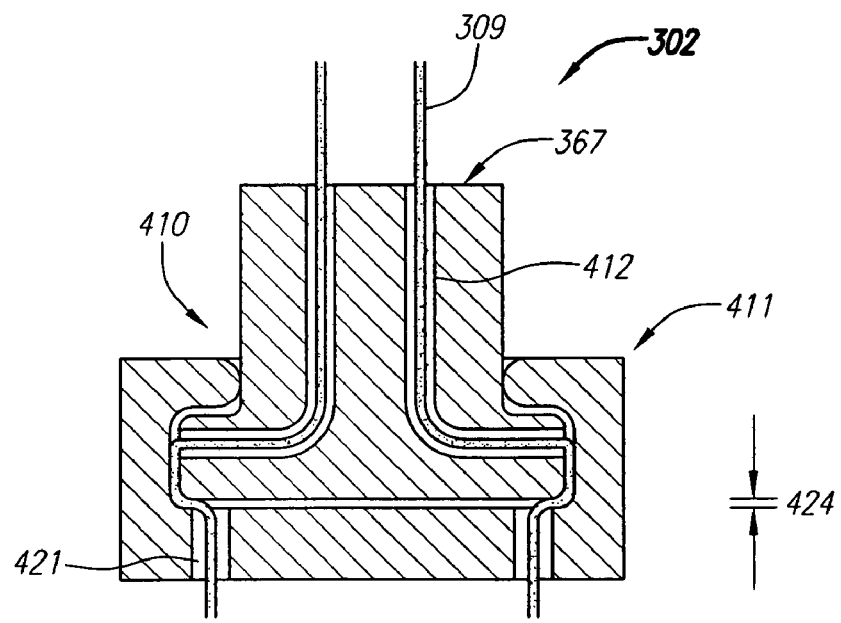
FIG. 19D is a cross-sectional view depicting another exemplary embodiment of the lock device.

In the embodiments described with respect to FIGS. 19A-C, the locking force can be increased by altering the implementation to have smaller lumens 412 and 421, a smaller distance 424 (preferably smaller than the width of suture body portions 309), and a greater difference between distances 422 and 423, to name a few. In addition, lumens 412 and/or 421 can be misaligned to an even greater degree to create a more tortuous path for suture body portions 309. For instance, FIG. 19D depicts another exemplary embodiment where lumens 412 exit the side of plug portion 410, making suture body portions 309 pass around relatively more of the outer surface of plug portion 410.

Figure 20A:
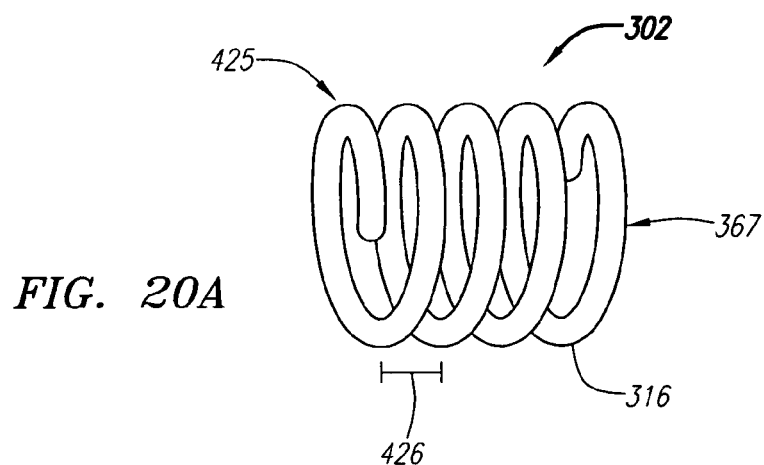
FIGS. 20A-D are perspective views depicting additional exemplary embodiments of the lock device.
Figure 20B:
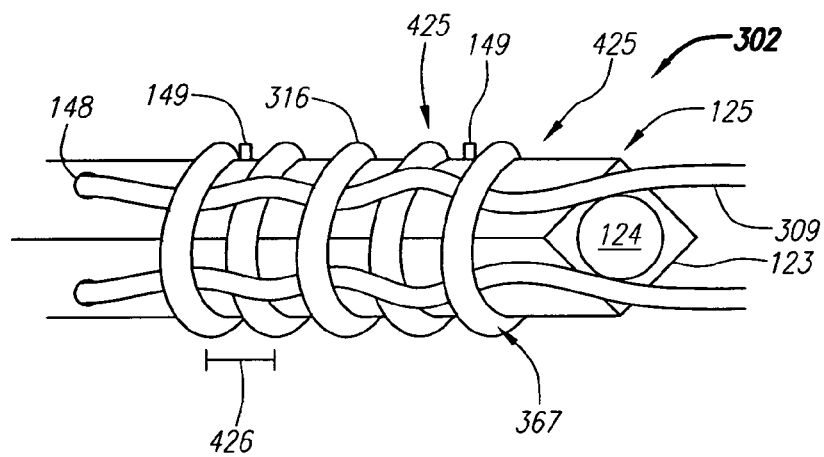
Figure 20C:
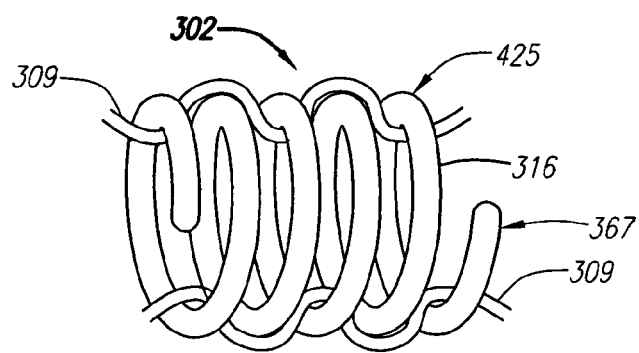

FIGS. 20A-C depict another exemplary embodiment of lock device 302 configured to lock one or more suture body portions 309 by introducing a tortuous path. FIG. 20A is a perspective view of lock device 302 in the at-rest state. Here, body 316 is wire-like or ribbon-like and configured as a coil having multiple coiled segments 425. Lock device 302 is preferably fabricated from an elastic or superelastic shape memory material, such as NITINOL, stainless steel and the like, and preferably heat treated to memorize the at-rest/unlocked configuration depicted here.

Figure 20D:
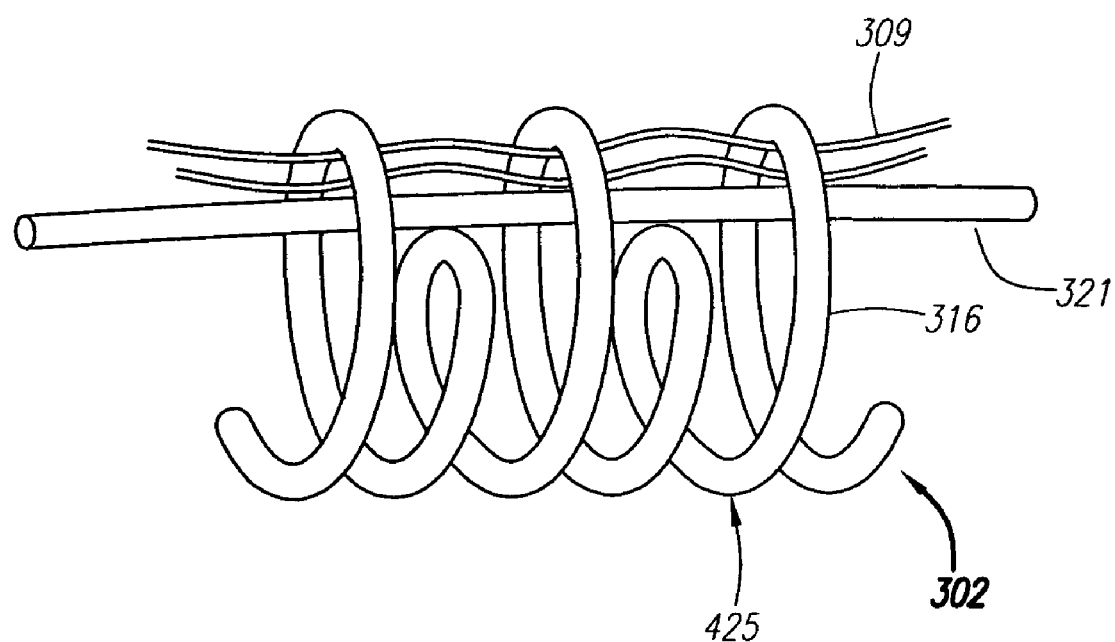

FIG. 20B is a perspective view depicting lock device 302 in the unlocked state with multiple suture body portions 309 routed between coiled segments 425. Here, body 316 is expanded (via primarily an axial stretch) from the at-rest state to enlarge the gaps 426 between coiled segments 425 by an amount sufficient to allow suture body portions 309 to pass through substantially unimpeded. To lock suture body portions 309, body 316 is preferably placed over outer member 123. Outer member 123 can be configured to have a polygonal outer surface (as depicted here) or any other outer surface with gaps sufficient to allow suture body portions 309 to pass. The proximal portion of each suture body portion 309 is preferably routed through an aperture 148 into lumen 124. Outer member 123 can also have deflectable pins 149 for holding each end of body 316 in place. Pusher member 128 can then be advanced to push lock device 302 off distal end 125 of outer member 123, to allow body 316 to move towards the at-rest configuration as depicted in FIG. 20C. This creates a more tortuous path for suture body portions 309 and, also, pinches or clamps suture body portions 309 between adjacent coiled segments 425. FIG. 20D depicts another manner of maintaining lock device 302 in the unlocked state. Here, restraining member 321 is a rigid, rod-like member routed through every other coiled segment 425. The locked configuration for this embodiment is similar to that depicted in FIG. 20C.

The locking force can be increased by increasing the number of coiled segments 425, decreasing the gap between adjacent coiled segments 425 in the at-rest state, increasing the cross-sectional thickness of body 316, and/or increasing the width of body 316, to name a few.

Figure 20E:
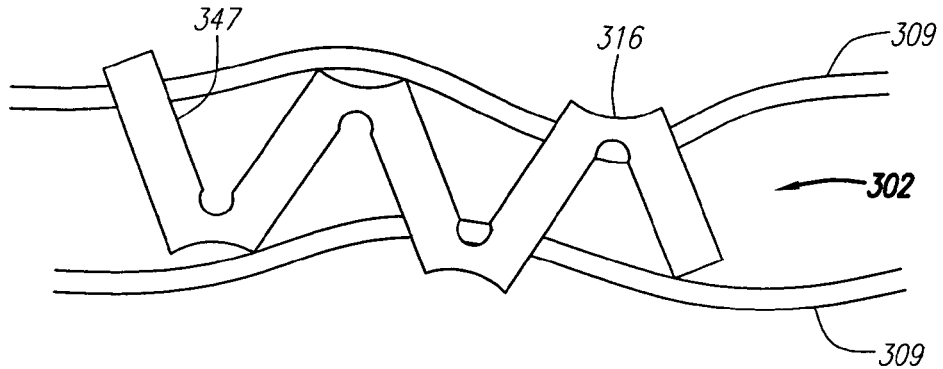
FIGS. 20E-H are front views depicting additional exemplary embodiments of the lock device.
Figure 20F:
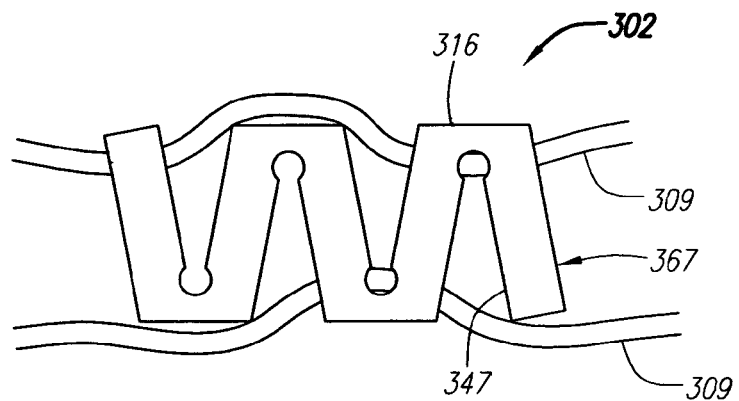
Figure 20G:
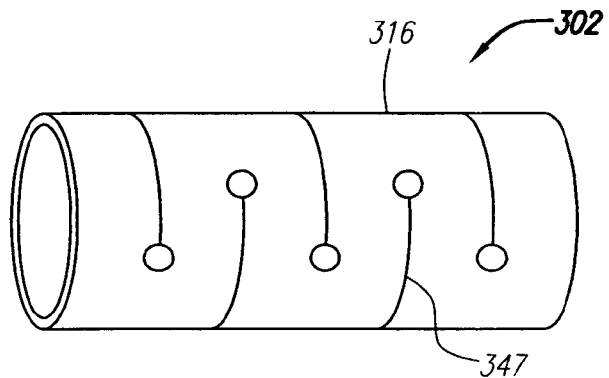
Figure 20H:
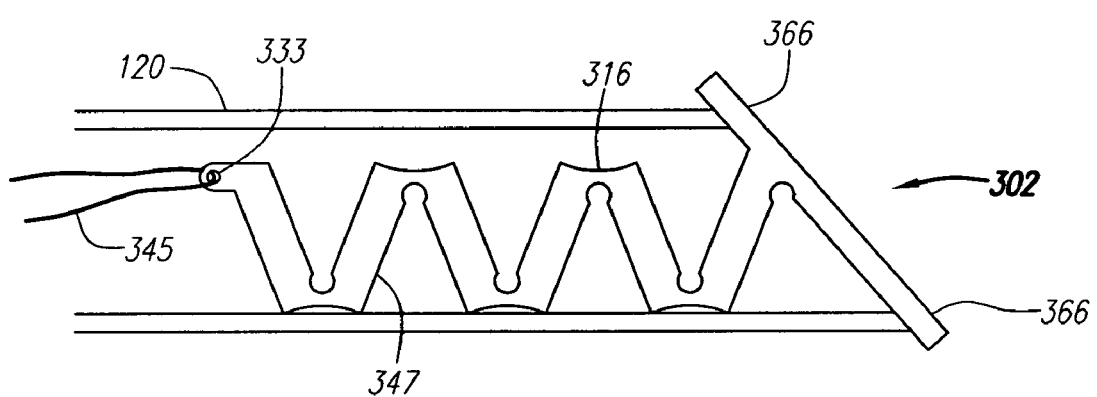

FIGS. 20E-H are front views depicting an additional exemplary embodiment of lock device 302, similar to that described with respect to FIGS. 20A-D, except body 316 is formed from a NITINOL tube. Body 316 includes a plurality of slots 347, which can be formed by laser cutting for instance, that allow body 316 to expand and compress in a manner similar to a coil. FIG. 20E depicts lock device 302 in the unlocked state (restraining member 321 is not shown) and FIG. 20F depicts lock device 302 in the locked state. FIG. 20G depicts lock device 302 in the at-rest state prior to routing of suture body portions 309. FIG. 20H is a partial cross-sectional view depicting another embodiment of lock device 302 within needle 120. This embodiment is configured for deployment without restraining member 321. Here, lock device 302 is held in the unlocked state through the use of tether 383 and distal leg abutments 366. Pull wire 345 is placed through an eyelet 333 in the proximal portion of body 316. It should be noted that slots 347 depicted in FIGS. 20E-H as well as those used in any embodiment described herein, may be configured in any manner desired, such as various orientations and shapes, such as curved, jagged, irregular, any combination thereof and the like.

Figure 21A:
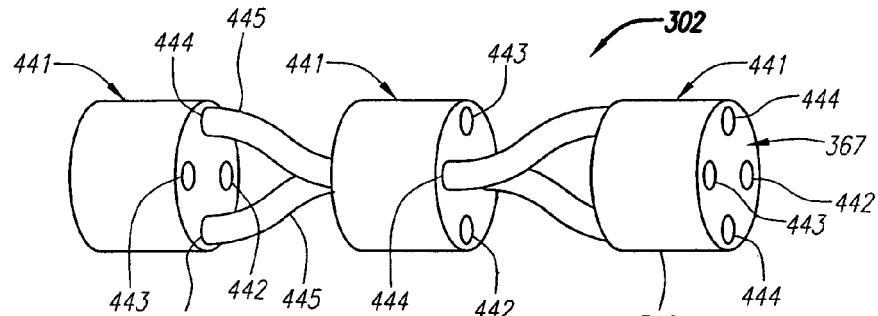
FIGS. 21A-D are perspective views depicting additional exemplary embodiments of the lock device.

FIGS. 21A-D are perspective views depicting another exemplary embodiment of lock device 302 configured to lock one or more suture body portions 309 by introducing a tortuous path. FIG. 21A depicts an exemplary embodiment of lock device 302 in the at-rest state. Here, body 316 includes three deflectable portions 441, each having a restraining member lumen 442, a suture lumen 443 and two deflection wire lumens 444. Body 316 also includes two deflection wires 445 routed through and coupled to the two deflection wire lumens 444, respectively, of each portion 441. Deflection wires 445 are preferably fabricated from an elastic or superelastic shape memory material, such as NITINOL, stainless steel and the like, and preferably heat treated to memorize the configuration of the at-rest state depicted here.

Figure 21B:
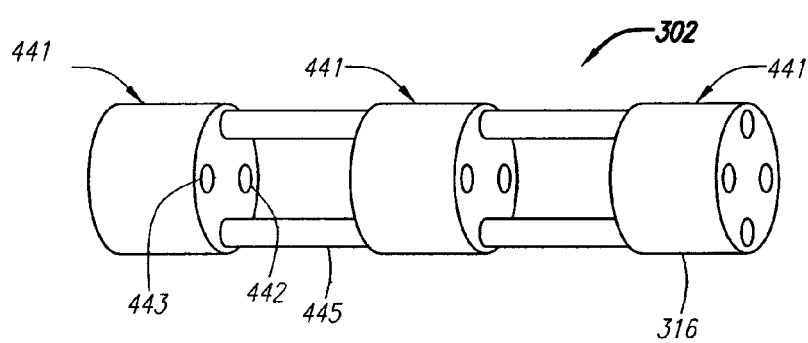

FIG. 21B depicts this embodiment prior to heat treatment. Here, each portion 441 is generally aligned. Before heat treating body 316, at least one portion 441 of body 316 is preferably rotated with respect to at least one other portion 441. In this embodiment, the centermost portion 441 is rotated ninety degrees with respect to the non-central portions 441. Heat treatment of body 316 instills the at-rest configuration depicted in FIG. 21A. In the at-rest configuration, each suture body portion 309 follows a tortuous path through suture lumen 443 of each portion 441.

Figure 21C:
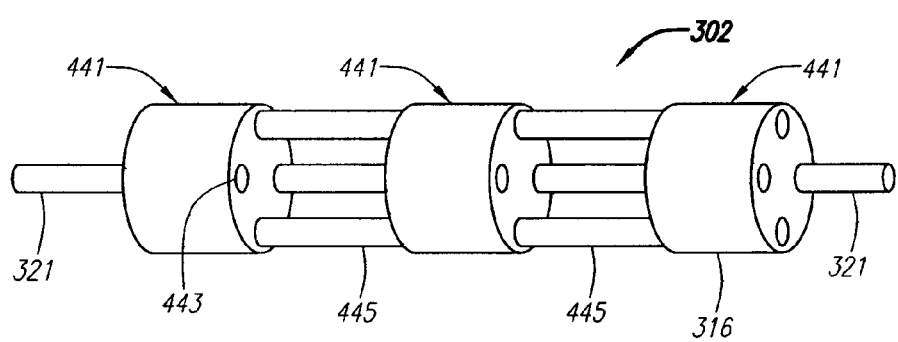
Figure 21D:
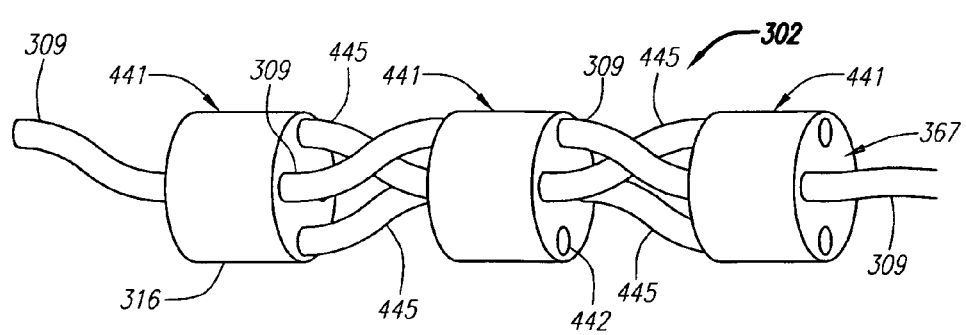

FIG. 21C depicts this embodiment of lock device 302 in the unlocked state. Here, restraining member 321 has been inserted through the restraining member lumen 442 of each portion 441. Restraining member 321 is preferably configured to be substantially rigid and capable of restraining body 316 from the at-rest state. To lock suture body portions 309, restraining member 321 can be removed from restraining member lumens 442, allowing body 316 to return to the at-rest configuration and introduce the tortuous path to each suture body portion 309, as depicted in FIG. 21D.

In the embodiment described with respect to FIGS. 21A-D, three portions 441 are described with the centermost portion 441 being rotated with respect to the non-center portions. It should be noted that any number of two or more portions 441 can be used, with any degree of rotation between them sufficient to create a tortuous path. Also, any number of restraining members 321 can be used and any number of suture lumens 443 can be used, each configured to carry any number of suture body portions 309.

The locking force in this embodiment can be increased by increasing the number of non-aligned portions 421, increasing the amount of non-alignment between portions 441, decreasing the spacing between portions 441, increasing the cross-sectional thickness of deflection wires 445, and/or decreasing the width of suture lumen 443, to name a few.

Figure 22A:
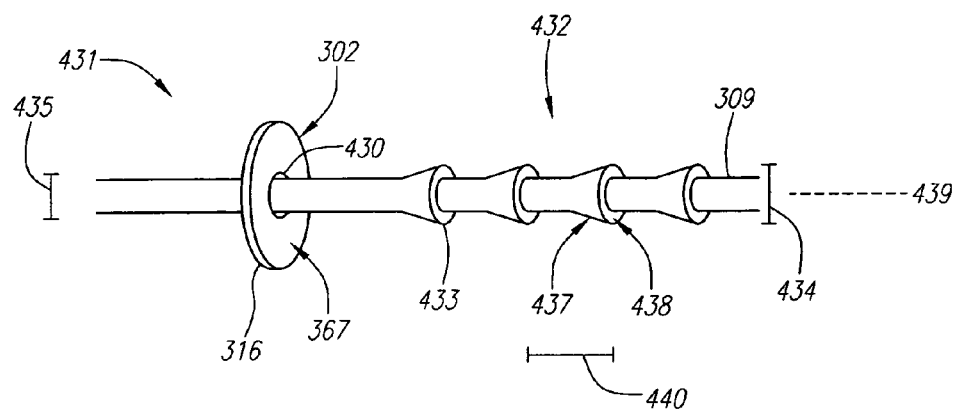
FIGS. 22A-B are perspective views depicting another exemplary embodiment of the lock device.
Figure 22B:
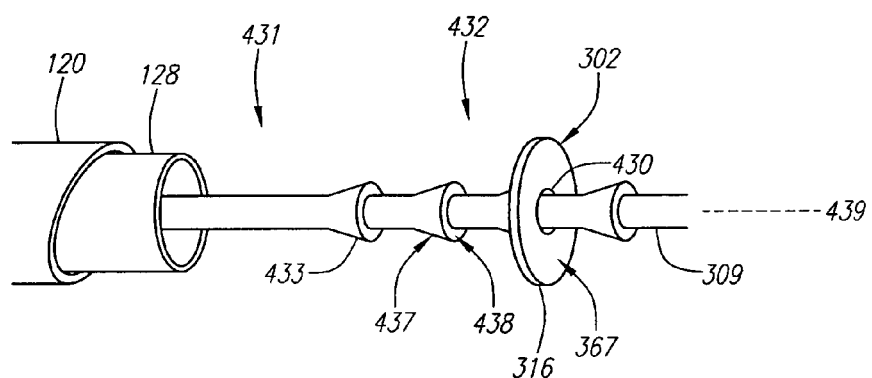

The embodiments described with respect to FIGS. 22A-B each rely on the use of abutments on suture body 301 to interact with lock device 302 and lock suture body portions 309. These embodiments are configured for use with non-looped sutures 103. FIG. 22A is a perspective view depicting an exemplary embodiment of lock device 302 in an unlocked state. Here, body 316 is disc-shaped and includes an inner aperture 430. Lock device 302 is positioned within delivery device 104 and a proximal region 431 of suture body portion 309 is slidably disposed within aperture 430. Distal region 432 of suture body portion 309 can include one or more abutments 433, preferably extending around the circumference of suture body portion 309. Each abutment 433 preferably has a width 434 that is greater than the diameter 435 of aperture 430. To lock suture body portion 309, lock device 302 can be advanced distally over one or more abutments 433 by a pusher member 128 within needle 120, as depicted in FIG. 22B. In this embodiment, pusher member 128 is a tubular member.

Abutments 433 are preferably configured to resist any proximal push back of lock device 302. Here, abutments 433 are generally conical with a tapered proximal surface 437 and a distal surface 438 preferably oriented perpendicular to a longitudinal axis 439 of suture body portion 309. By decreasing the distance 440 between adjacent abutments 433, a larger number of incremental locking positions per unit space can be provided.

Turning now to anchoring, FIGS. 23A-32E depict exemplary embodiments of anchor device 303 configured for use with any of the abovementioned embodiments of lock device 302. In general, each exemplary embodiment of anchor device 303 is deformable, meaning that anchor device 303 can have one configuration prior to or during deployment and another configuration after deployment.

In some cases, the embodiments of anchor device 303 described below are done so with reference to portions of delivery device 104, for instance, a description of deployment with needle 120. It should be noted that description of an embodiment of anchor device 303 with reference to a specific portion of delivery device 104 does not limit use of that anchor device 303 to only that portion of delivery device 104. In fact, anchor device 303 can be used with any portion of delivery device 104 and any other portion of treatment system 100, whether or not described herein.

Figure 23A:
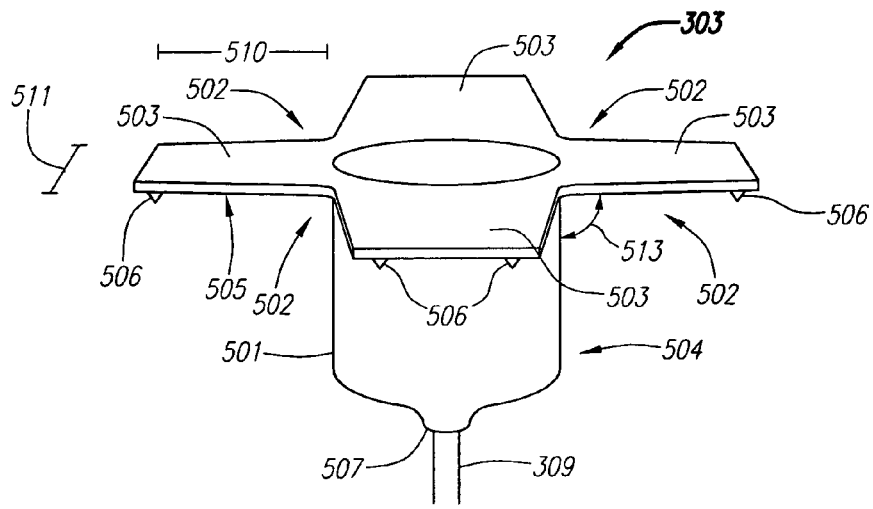
FIG. 23A is a perspective view depicting an exemplary embodiment of the anchor device.

FIG. 23A is a perspective view depicting an exemplary embodiment of a deformable anchor device 303. Here, anchor device 303 has a tubular body 501 with multiple slots 502 formed therein. Deflectable leg members 503 are formed between adjacent slots 502. FIG. 23A depicts body 501 in the at-rest state, where leg members 503 are deflected outwards from proximal tubular portion 504 by an angle 513, which is preferably at a ninety degree angle or less, in order to apply sufficient locking force. An angle 513 less than ninety degrees can cause leg members 503 to embed within the septal wall tissue, preventing any protrusions in the blood flow path, which can promote healing. It should be noted that, although four leg members 503 are depicted here, any number of one or more leg members 503 can be used. Anchor device 303 is preferably fabricated from an elastic or superelastic shape memory material, such as NITINOL, stainless steel and the like, and preferably heat treated to memorize the configuration of this at-rest state.

Outer surface 505 of a portion of body 316, in this case located on each leg member 503, can be configured to more readily engage septal wall 207 by modifying the surface roughness in any manner desired, including, but not limited to texturing, etching, cutting, and the addition of abrasive coatings. Leg members 503 can also be configured with one or more barbs 506 or other grabbing structures for this same purpose. It should be noted that each embodiment of anchor device 303 described herein, regardless of the configuration, has an outer surface 505 that contacts septal wall 207. This outer surface 505 will be referenced in each applicable figure but not described in the interest of brevity, with the understanding that surface 505, in each embodiment, can be configured to more readily engage septal wall 207 as described above.

Figure 23B:
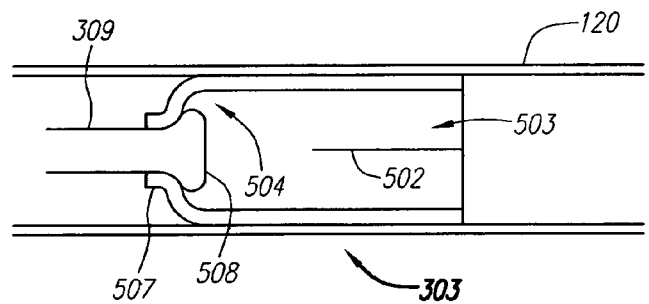
FIG. 23B is a cross-sectional view depicting this embodiment of the anchor device.

FIG. 23B is a cross-sectional view depicting the embodiment described with respect to FIG. 23A in an undeployed state within needle 120. Here, leg members 503 are deflected inwards such that body 501 has a generally tubular configuration along it's entire length. Leg members 503 are restrained in the deflected state by needle 120, until the time for deployment, at which point anchor device is advanced distally from within needle 120 and allowed to return to the at-rest state.

Proximal end 507 of proximal tubular portion 504 is enclosed around suture body portion 309 in order to couple anchor device 303 with suture body portion 309. Proximal end 507 can be enclosed in any manner desired, such as by crimping and the like. Suture body portion 309 can have a relatively larger distal end tip 508 in order to facilitate the coupling with anchor device 303. In one exemplary embodiment, suture body portion 309 and anchor device 303 are formed from the same material and integrated together in one continuous structure. To facilitate the description herein, this and other embodiments of anchor device 303 will be described with respect to one suture body portion 309. However, it should be noted that anchor device 303 can be used and coupled with any number of suture body portions 309, as desired.

Figure 23C:
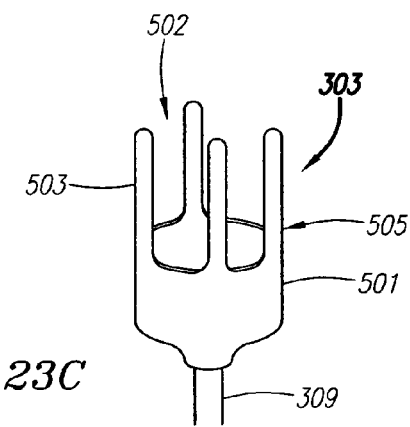
FIG. 23C is a perspective view depicting another exemplary embodiment of the anchor device.

FIG. 23C is a perspective view depicting another exemplary embodiment of anchor device 303 in the undeployed state. In this embodiment, leg members 503 are relatively more narrow, giving anchor device 303 a prong-like appearance. Leg members 503 can be configured or shaped in any manner desired. The anchoring capability of the embodiments described with respect to FIGS. 23A-C can be increased by increasing the length 510 and width 511 of leg members 503 and by increasing the thickness of body 501, to name a few.

Figure 24A:
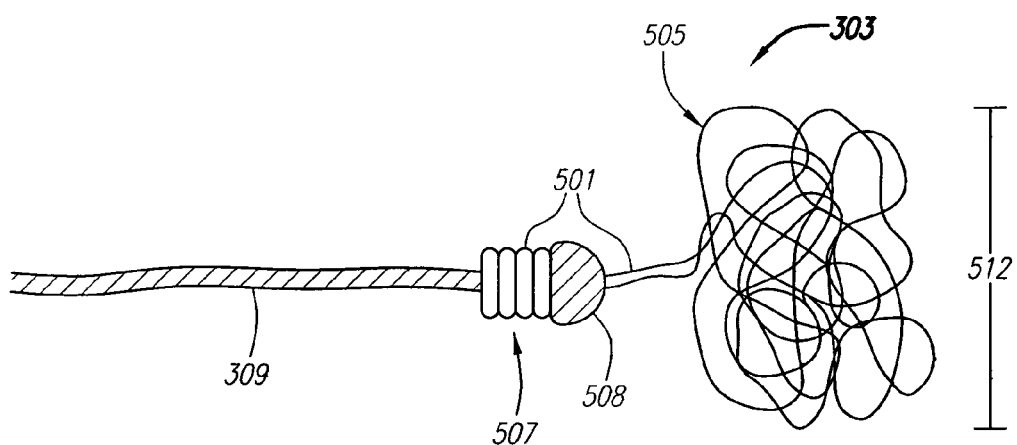
FIGS. 24A-B are front and partial cross-sectional views, respectively, depicting another exemplary embodiment of the anchor device.
Figure 24B:
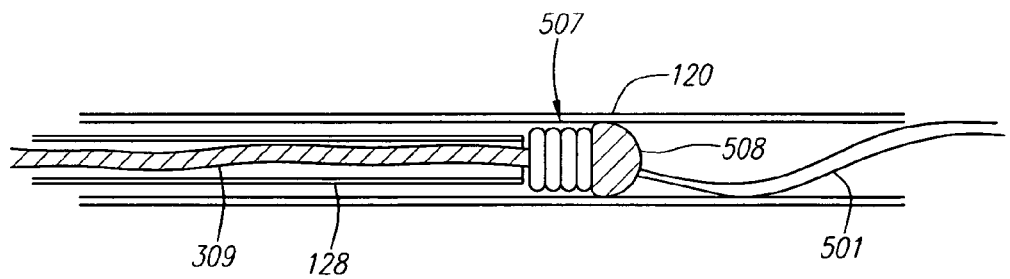

FIGS. 24A-B are front and partial cross-sectional views, respectively, depicting another exemplary embodiment of anchor device 303 in the at-rest state. Here, body 501 is a wire-like or ribbon-like highly wound and intertwined structure. The highly wound and intertwined structure preferably has a tendency to bunch together and become entangled in itself giving anchor device 303 a width 512 larger than the cross-sectional width of body 501. This allows anchor device 303 to sufficiently anchor suture body portion 309. Anchor device 303 is preferably fabricated from an elastic or superelastic shape memory material, such as NITINOL, stainless steel and the like, and preferably heat treated to memorize the configuration of this at-rest state.

FIG. 24B depicts this embodiment of anchor device 303 in the undeployed state within delivery device 104. Here, body 501 is held in a relatively straightened state by needle 120. To deploy anchor device 303, the user can advance anchor device from within delivery device 104 using pusher member 128, at which point anchor device 303 is free to move towards the at-rest state. In this embodiment, pusher member 128 is a tubular member configured to slidably receive suture body portion 309 and abut body 501. However, pusher member 128 can be configured in any desired manner. It should be noted that the pusher member 128 used to deploy anchor device 303 can be the same as, or different from, the pusher member 128 used to deploy lock device 302.

Proximal end 507 of body 501 can be coupled with suture body portion 309 in any manner desired. Here, proximal end 507 is coiled around suture body portion 309. In another exemplary embodiment, anchor device 303 and suture body portion 309 are formed from the same material and integrated together as one continuous structure.

The anchoring capability of the embodiments described with respect to FIGS. 24A-B can be increased by increasing the width 512 of anchor device 303 in the at-rest state, by increasing the degree to which body 501 is wound and intertwined in the at-rest state, and by increasing the thickness of body 501 itself, to name a few.

Figure 25A:
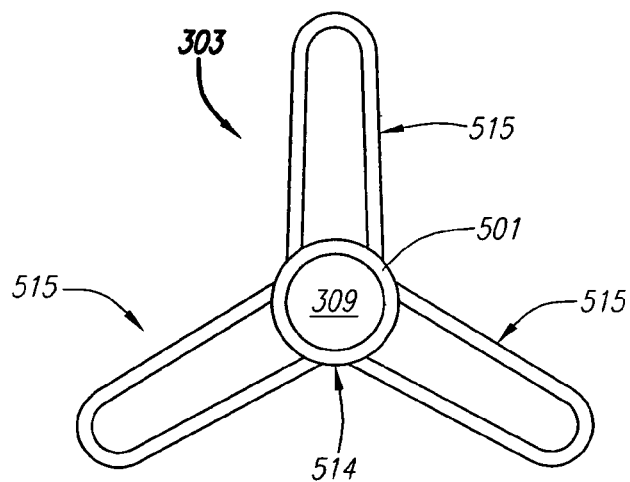
FIG. 25A is a bottom up view depicting another exemplary embodiment of the anchor device.

FIGS. 25A-I depict additional exemplary embodiments of deformable anchor device 303. In these embodiments, anchor device 303 has a wire-like or ribbon-like body 501 configured with a suture coupling portion 514 for coupling with suture body portion 309 and leg portions 515 for anchoring suture 103 against septal wall 207. FIG. 25A is a bottom up view depicting an exemplary embodiment of anchor device 303 in the at-rest state. Anchor device 303 is preferably fabricated from an elastic or superelastic shape memory material, such as NITINOL, stainless steel and the like, and preferably heat treated to memorize the configuration of this at-rest state.

Here, anchor device 303 includes three leg portions 515 arranged symmetrically around suture coupling portion 514. Each leg portion 515 can be formed by configuring body 501 in a loop-like manner as depicted here. Any number of one or more leg portions 515 can be implemented as desired, in any desired arrangement, symmetrical or otherwise.

Figure 25B:
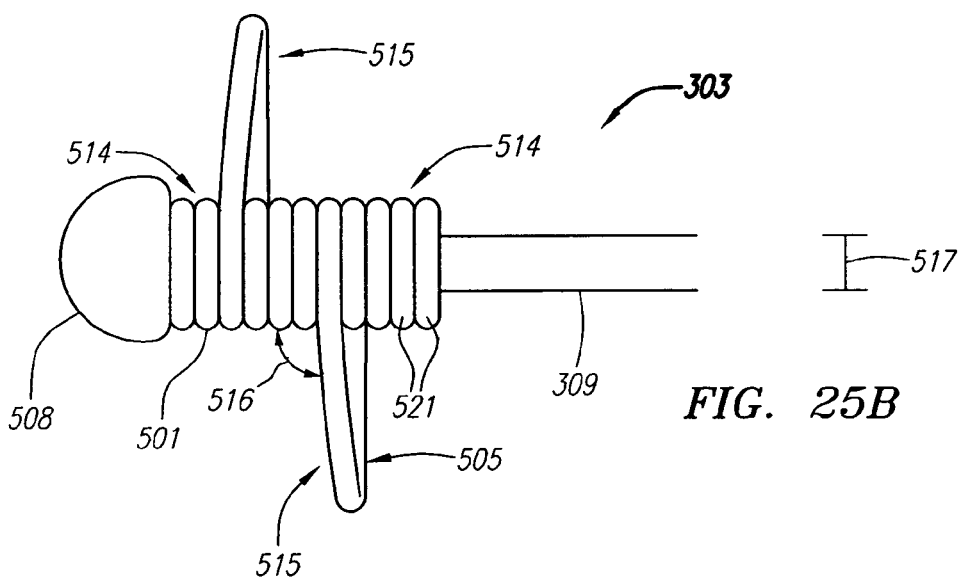
FIG. 25B is a side view depicting this embodiment of the anchor device.

FIG. 25B depicts a side view of this embodiment of anchor device 303. In this embodiment, suture coupling portion 514 is a coiled portion of body 501 having multiple coiled segments 521 each having a diameter 517 that is preferably on the order of the diameter of suture body portion 309 in order to fixably engage with suture body portion 309 and minimize slippage. Suture coupling portion 514 preferably abuts enlarged distal end 508 of suture body portion 309. In another exemplary embodiment, anchor device 303 and suture body portion 309 are formed from the same material and integrated together as one continuous structure.

Here, leg portions 515 are oriented at an angle 516 from suture coupling portion 514. Angle 516 can be any angle desired, preferably less than or equal to ninety degrees. Similar to the embodiment described with respect to FIG. 23A, use of this size angle 516 can increase the anchoring capability and promote healing.

Figure 25C:
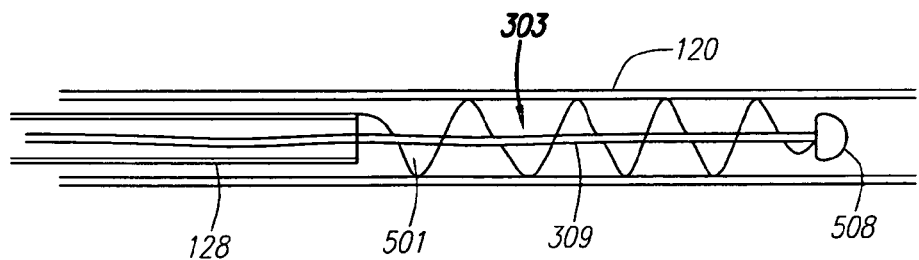
FIG. 25C is a partial cross-sectional view depicting this embodiment of the anchor device.

FIG. 25C is a partial cross-sectional view depicting this embodiment in the undeployed state within a portion of delivery device 104, preferably needle 120. Here, body 501 is restrained in a relatively straightened configuration around suture body portion 309. To deploy anchor device 303, pusher member 128 is advanced distally against body 501 to push body 501 from within needle 120. As body 501 leaves needle 120, it is free to return to the at-rest state depicted in FIGS. 25A-B.

Figure 25D:
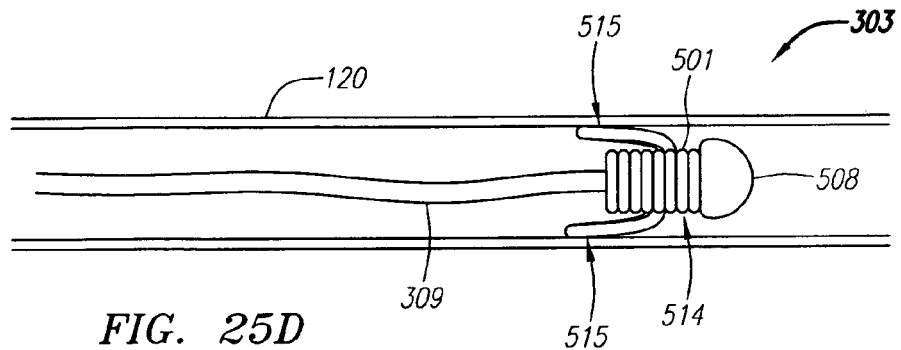
FIG. 25D is a partial cross-sectional view depicting another exemplary embodiment of the anchor device.

FIG. 25D is a partial cross-sectional view depicting another exemplary embodiment of anchor device 303 in the undeployed state within delivery device 104. Here, each leg portion 515 is deflected towards suture coupling portion 514 for housing within needle 120. Deployment can be achieved by advancing pusher member 128 (not shown) distally against body 501.

Figure 25E:
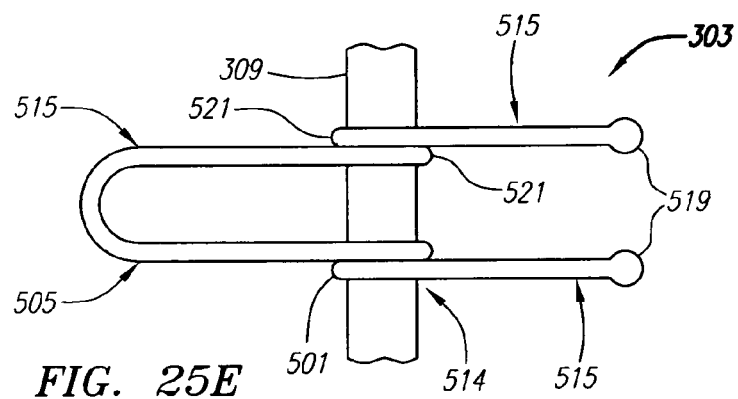
FIG. 25E is a side view depicting another exemplary embodiment of the anchor device.

FIG. 25E is a side view of another exemplary embodiment of anchor device 303 having three leg portions 515. Here, one leg portion 515 is a wire loop and the remaining two leg portions are the un-looped ends 519 of body 501. Each end 519 can be configured to be substantially atraumatic, for instance, by configuring each to be relatively larger than the cross-sectional width of body 501 as depicted here. Examples of end 519 can include, but are not limited to a weld ball, a floppy spring-like tip, and any non-piercing or non-abrading tip. Furthermore, end 519 can be configured to be radio-opaque or otherwise visually imagable. Also, each coiled segment 521 in suture coupling portion 514 is oriented generally perpendicular to looped leg portion 515.

Figures 25F, 25G:
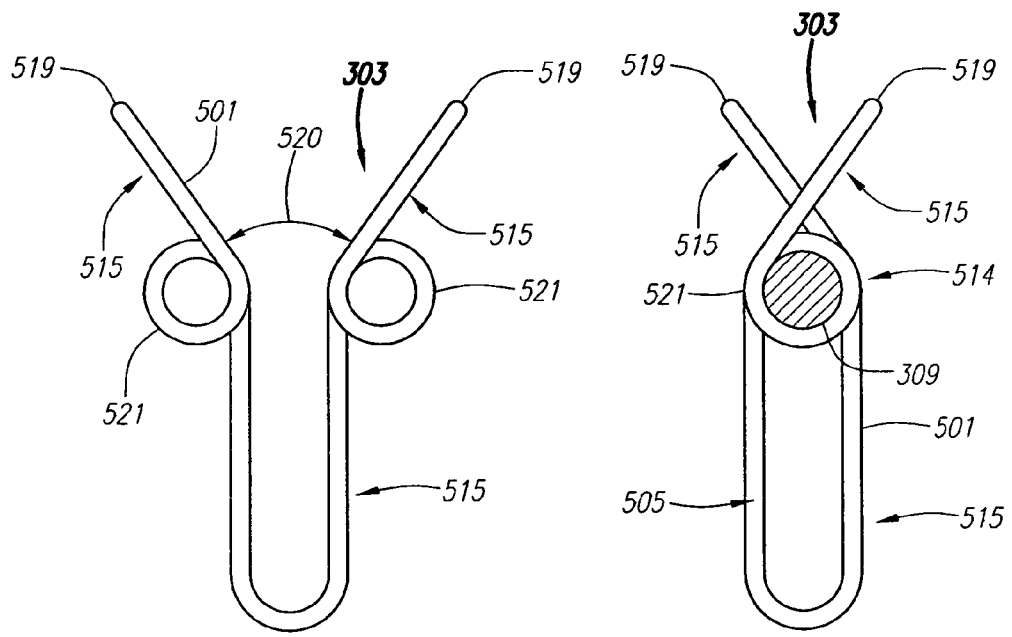
FIGS. 25F-G are bottom up views depicting another exemplary embodiment of the anchor device.

FIGS. 25F-G are bottom up views depicting another exemplary embodiment of anchor device 303 having three leg portions 515. FIG. 25F depicts anchor device 303 prior to coupling with suture body portion 309. Again, one leg portion 515 is a wire loop and the remaining two leg portions are the un-looped ends 519 of body 501, although in this embodiment, each un-looped leg portion 515 is offset at an angle 520 from each other. FIG. 25G depicts this embodiment in the at-rest state after coupling with suture body portion 309. Each coiled segment 521 is now generally concentric. Each coiled segment 521 is generally parallel, or generally in-plane, with the looped leg portion 515, allowing substantially the entire looped leg portion 515 to contact septal wall 207.

Figure 25H:
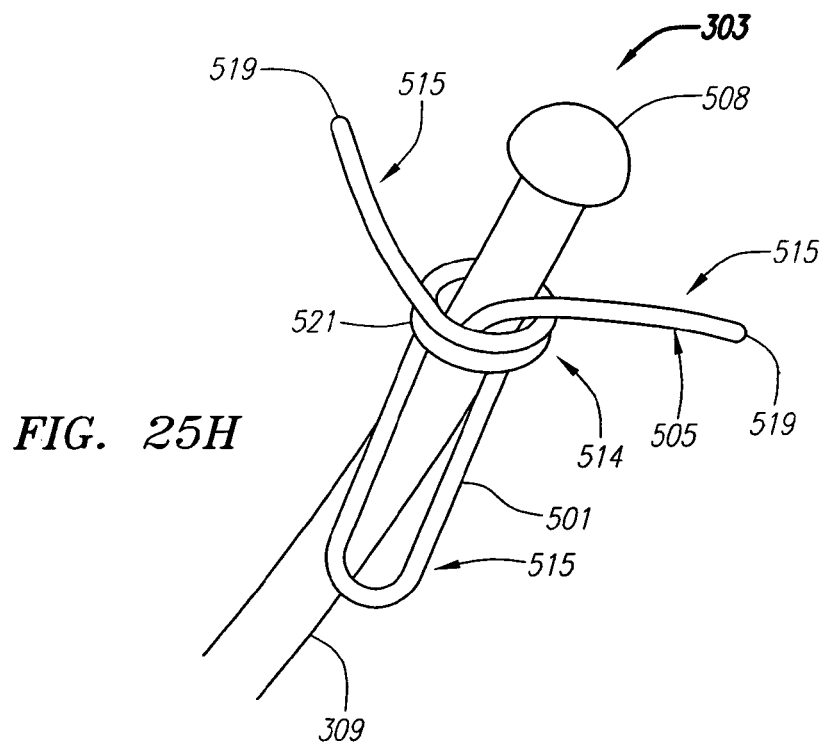
FIG. 25H is a perspective view depicting another exemplary embodiment of the anchor device.
Figure 25I:
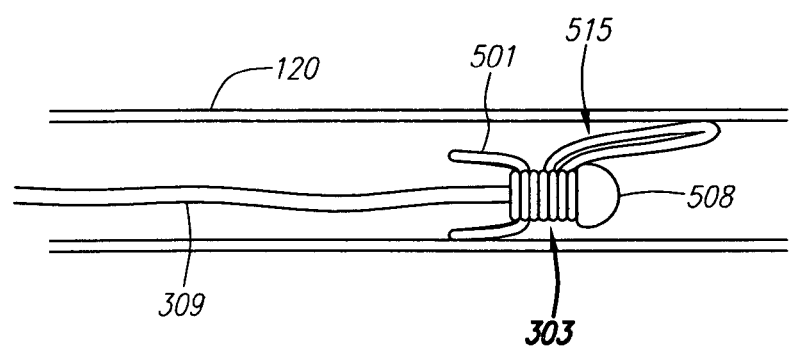

FIG. 25H is a perspective view depicting another exemplary embodiment of anchor device 303 having three leg portions 515. Here, leg portions 515 are interlocked with each other through suture coupling portion 514. This can provide greater stability to anchor device 303. FIG. 25I is a partial cross-sectional view of this embodiment in the undeployed state within needle 120.

Figure 26A:
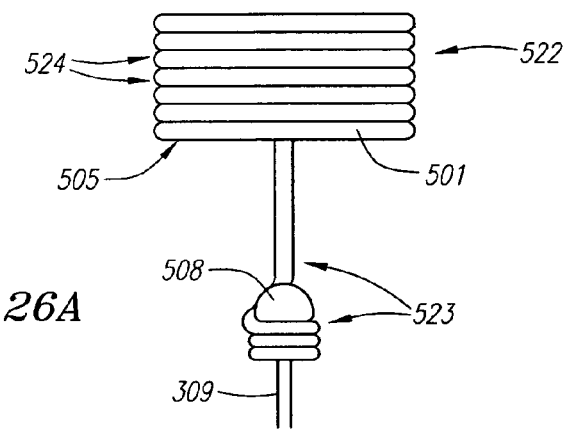
FIG. 26A is a front view depicting another exemplary embodiment of the anchor device.

FIGS. 26A-G depict additional exemplary embodiments of deformable anchor device 303. In these embodiments, anchor device 303 has a wire-like or ribbon-like coiled body 501. FIG. 26A is a front view depicting an exemplary embodiment of anchor device 303 in the at-rest state. Here, body 501 includes a coiled, anchoring portion 522, having multiple concentric coiled segments 524, and a suture coupling portion 523. Anchor device 303 is preferably fabricated from an elastic or superelastic shape memory material, such as NITINOL, stainless steel and the like, and preferably heat treated to memorize the configuration of this at-rest state.

Figure 26B:
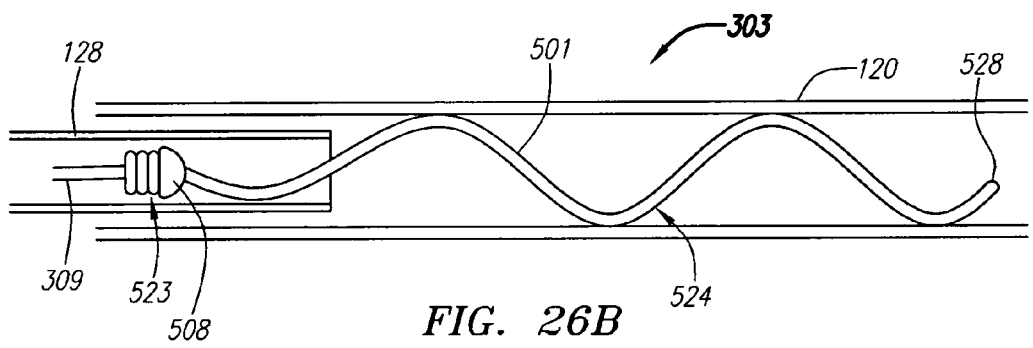
FIGS. 26B-C are partial cross-sectional views depicting additional exemplary embodiments of the anchor device.
Figure 26C:
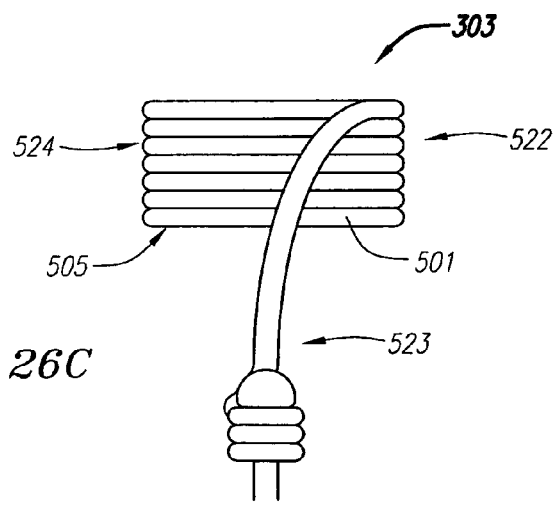

FIG. 26B is a partial cross-sectional view depicting an exemplary embodiment of anchor device 303 within needle 120. Here, body 501 is restrained in a relatively straightened, undeployed state. Deployment of anchor device 303 can be accomplished with pusher member 128, which is preferably tubular. Distal tip 528 of body 501 is preferably configured to be atraumatic, so as to minimize any injury to the septal wall tissue during deployment.

Coiled portion 522 can include any number of one or more coiled segments 524. In this embodiment, each coiled segment has a similar width 525, although width 525 can vary between segments 524. Also, although each coiled segment 524 is depicted as being rounded, or circular, any shape or configuration of coiled segment 524 can be implemented, including, but not limited to, circular, oval, elliptical, rounded, polygonal, symmetric, asymmetric, irregular and any combination thereof. Body 501 and each coiled segment 524 is also depicted as having a rounded cross-section, although any shape, size or configuration of cross-section can be used, and that shape, size or configuration can vary across body 501.

In addition, in this embodiment, suture coupling portion 523 is coupled with the coiled segment 524 configured for deployment immediately adjacent to septal wall 207. Suture coupling portion 523 can be coupled with any desired coiled segment 524, such as the coiled segment 524 configured for deployment at the farthest location from septal wall 207 as depicted in the cross-sectional view of FIG. 26C. Coupling in this fashion can increase the amount of pull force that anchor device 303 can withstand before being pulled through septal wall 207.

Figure 26D:
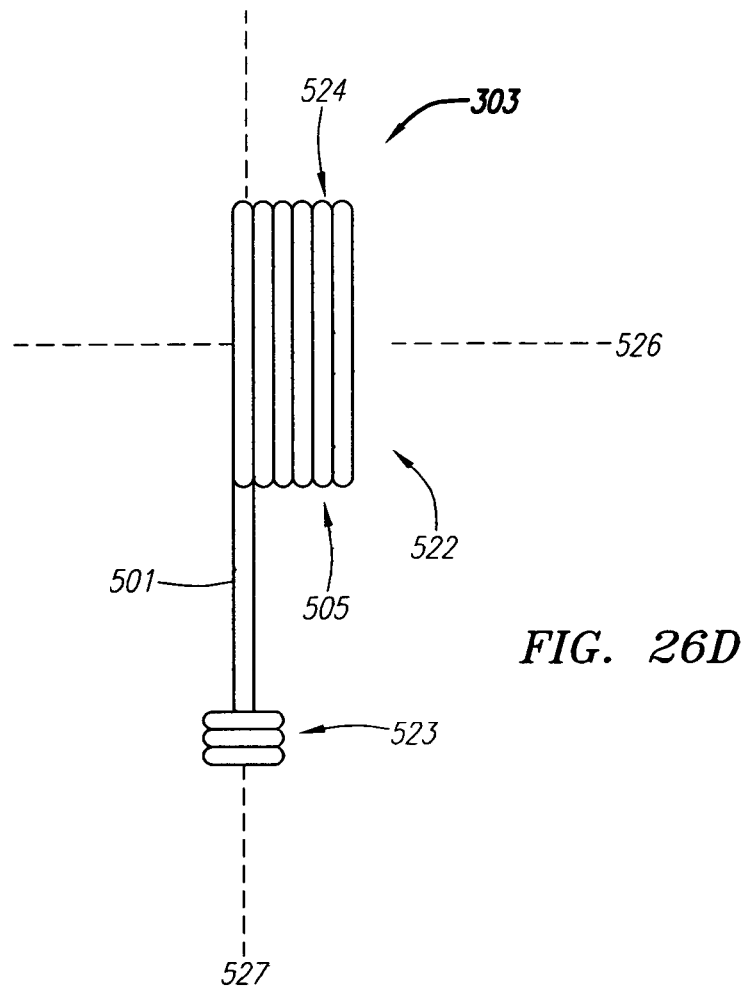
FIG. 26D is a front view depicting another exemplary embodiment of the anchor device.

Coiled segments 524 can also be oriented as desired. For instance, FIG. 26D is a front view depicting an exemplary embodiment where coiled segments 524 are oriented around a central axis 526 that is perpendicular to a longitudinal axis 527 of suture coupling portion 523.

Figure 26E:
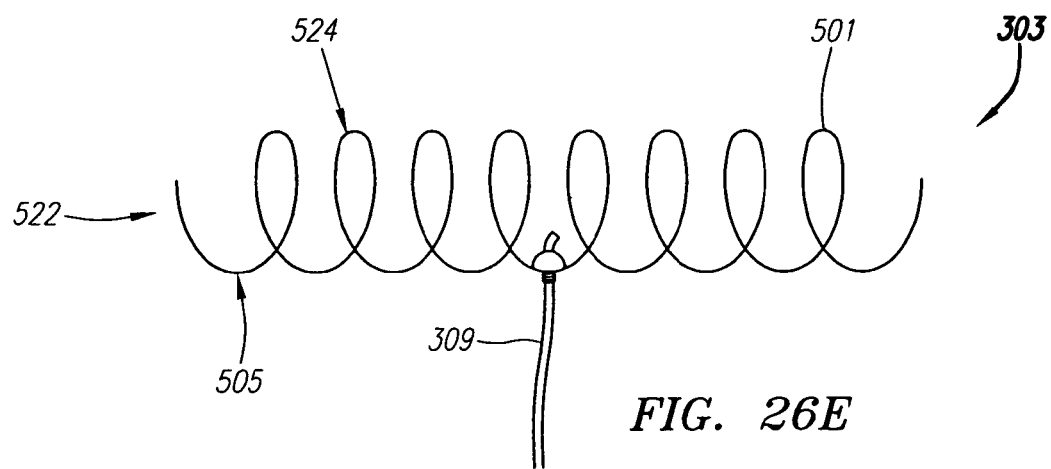
FIG. 26E is a front view depicting another exemplary embodiment of the anchor device.

Preferably, suture body portion 309 and anchor device 303 are formed from the same material and integrated together in one continuous structure, in which case suture coupling portion 523 is not necessary. If suture body portion 309 and anchor device 303 are coupled together, they can be done in any manner desired. In the embodiments described with respect to FIGS. 26A-D, suture coupling portion 523 is formed by coiling body 501 around suture body portion 309. FIG. 26E is a front view depicting an exemplary embodiment where suture body portion 309 and body 501 are formed of different materials yet suture body portion 309 is coupled with the centermost coiled segment 524 of coiled portion 522. Portions 309 and 522 can be coupled together in any desired manner. Here, suture body portion 309 is knotted around coiled portion 522.

Figure 26F:
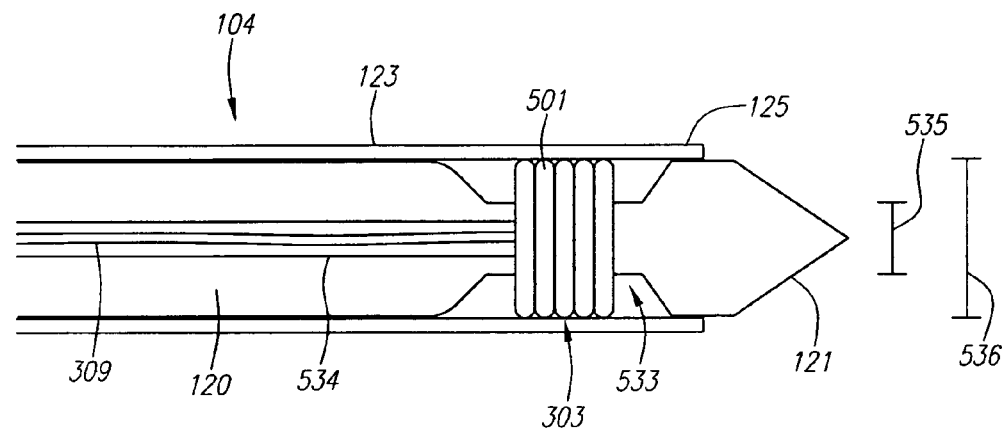
FIGS. 26F-G are partial cross-sectional views depicting another exemplary embodiment of the anchor device.

FIG. 26F is a partial cross-sectional view depicting another exemplary embodiment of anchor device 303 in the undeployed state. Here, delivery device 104 is depicted with needle 120 and outer tubular member 123. Needle 120 has a first recessed portion 533 with a reduced width 535 for carrying anchor device 303 in a compressed state having a smaller width than the width 525 of the at-rest state. Needle 120 also has a second recessed, canal-like portion 534 for housing one or more suture body portions 309.

Figure 26G:
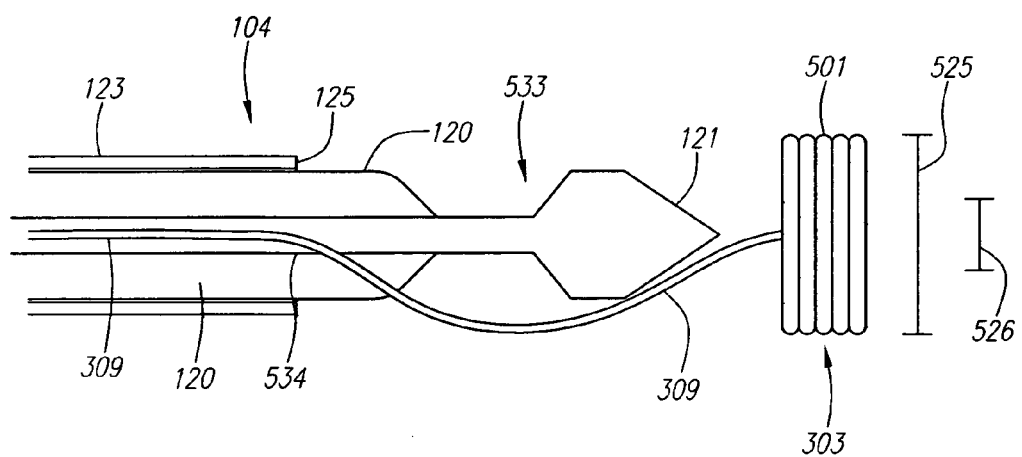

To deploy anchor device 303, needle 120 and outer member 123 are inserted through septal wall 207 (e.g., septum primum 214 and septum secundum 210) in the configuration depicted in FIG. 26F. Once through septal wall 207, outer member 123 can be withdrawn proximally with relation to needle 120 to expose anchor device 303. Once exposed, anchor device 303 is free to return to the at-rest state, where width 525 of coiled segments 524 is preferably larger than the width 526 of needle 120. This allows distal end 121 to be withdrawn through anchor device 303, as depicted in FIG. 26G.

Figure 27A:
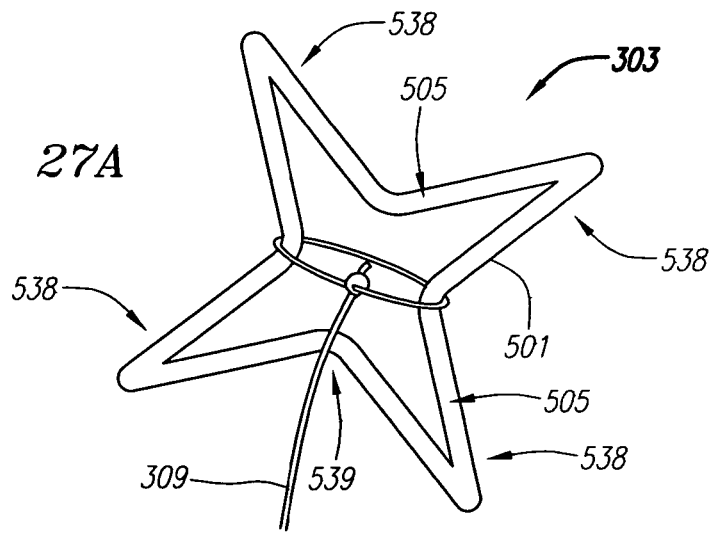
FIG. 27A is a perspective view depicting another exemplary embodiment of the anchor device.

FIGS. 27A-D depict additional exemplary embodiments of deformable anchor device 303. In these embodiments, anchor device 303 has a wire-like or ribbon-like body 501. FIG. 27A is a perspective view depicting an exemplary embodiment of anchor device 303 in the at-rest state. Here, body 501 is cross-shaped with four leg portions 538 extending outwards from a central portion 539, which is preferably coupled with suture body portion 309 in any desired manner. Anchor device 303 is preferably fabricated from an elastic or superelastic shape memory material, such as NITINOL, stainless steel and the like, and preferably heat treated to memorize the configuration of this at-rest state.

Figure 27B:
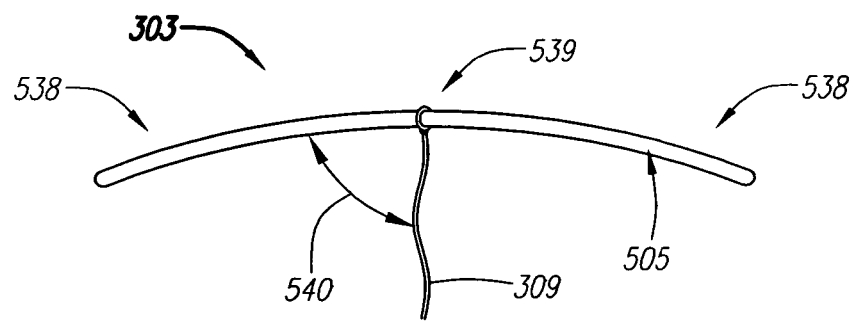
FIG. 27B is a side view depicting this embodiment of the anchor device.

FIG. 27B is a side view depicting this embodiment of anchor device 303 where each leg portion 538 is oriented at an angle 540 from suture body portion 309. Angle 540 is preferably less than or equal to ninety degrees.

Figure 27C:
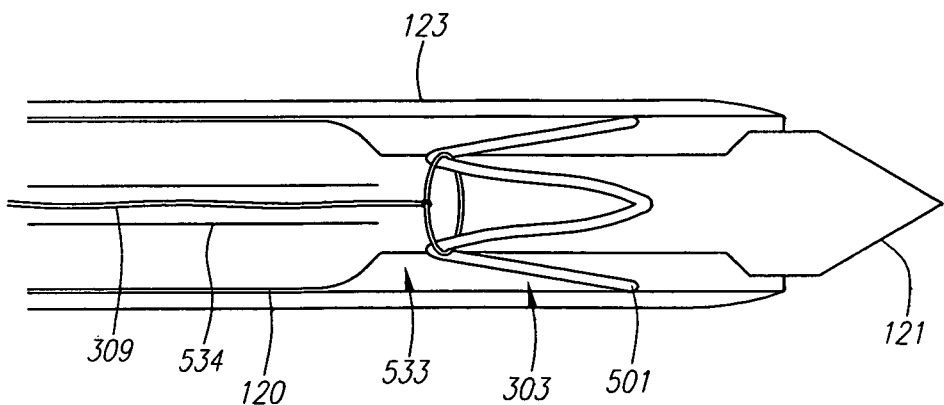
FIG. 27C is a partial cross-sectional view depicting this embodiment of the anchor device.

FIG. 27C is a partial cross-sectional view depicting this exemplary embodiment of anchor device 303 in the undeployed state. Here, body 501 is deformed and seated in recessed portion 533 of needle 120. Outer tubular member 123 restrains body 501 and maintains body 501 the undeployed state. Anchor device 303 can be deployed by exposing body 501 from within outer tubular member 123 in a manner similar to that described with respect to FIGS. 26F-G above. In these embodiments, suture body portion 309 is depicted wrapped around body 316. However, any manner of coupling suture body portion 309 can be used. For instance, in another exemplary embodiment, body 316 includes an eyelet through which suture body portion 309 can be coupled. Formation of the eyelet can occur in any manner desired, for instance, all of body 316 including the eyelet can be laser cut from a NITINOL sheet.

Figure 27D:
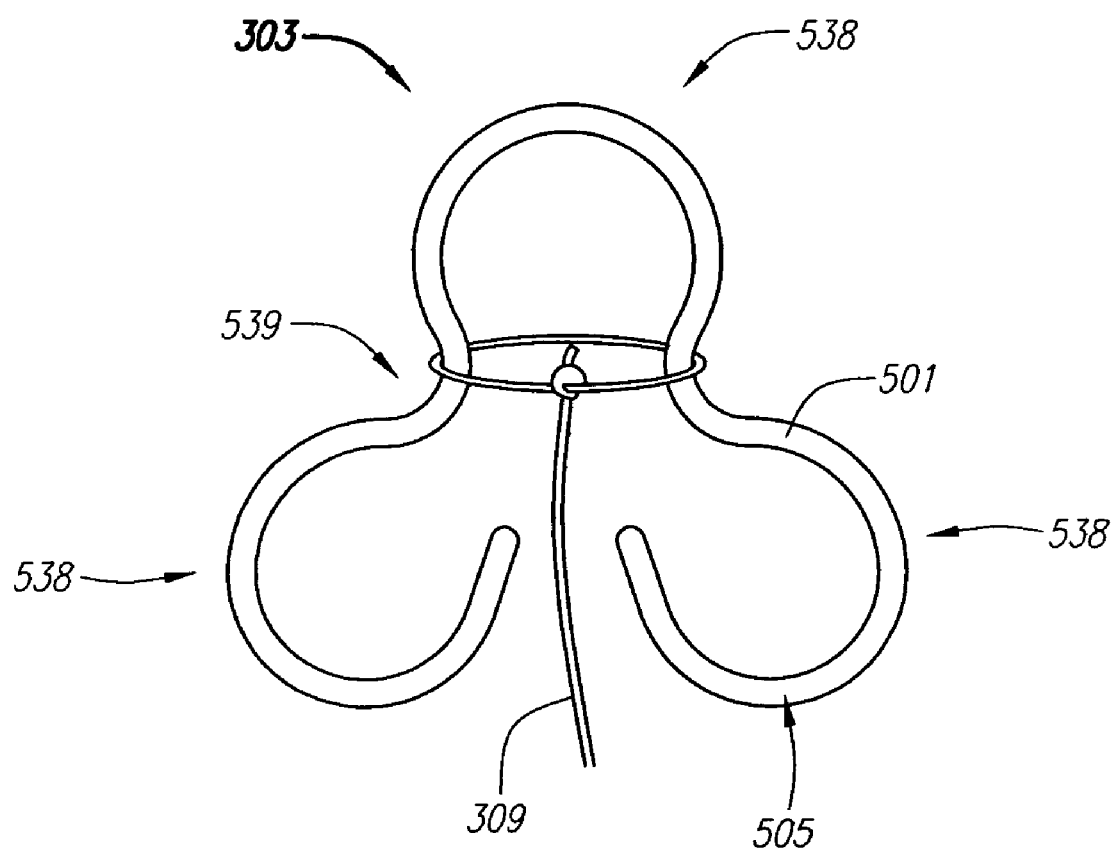
FIG. 27D is a front view depicting another exemplary embodiment of the anchor device.

It should be noted that leg portions 538 can be configured in any manner desired. For instance, FIG. 27D is a front view depicting another exemplary embodiment of anchor device 303 where leg portions 538 are generally circular. It should also be noted that body 501 can be configured with any number of one or more leg portions 538. Also, the anchoring capability of anchor device 303 can be increased by increasing the thickness of body 501, increasing the surface area covered by each leg portion 538 and/or decreasing angle 540, to name a few.

Figure 28A:
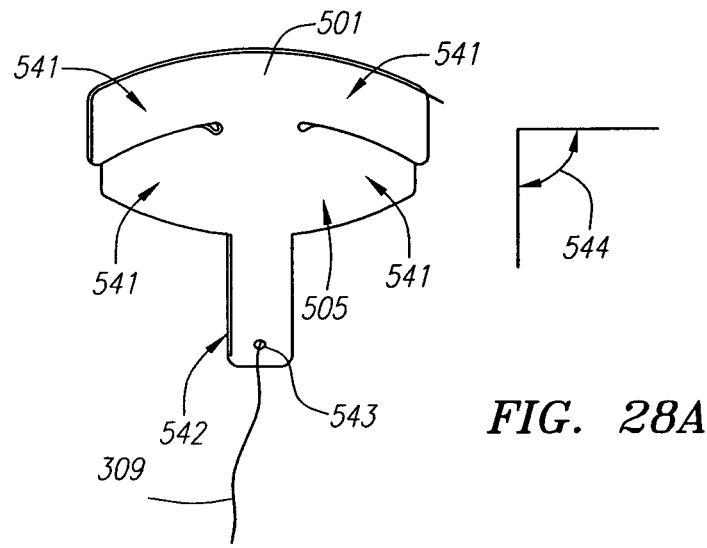
FIG. 28A is a perspective view depicting another exemplary embodiment of the anchor device.
Figure 28B:
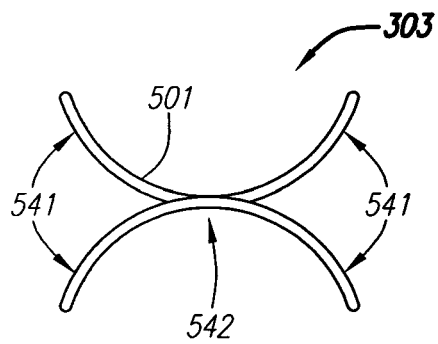
FIG. 28B is a top down view depicting this embodiment of the anchor device.

FIGS. 28A-B depict another exemplary embodiment of deformable anchor device 303. FIG. 28A is a perspective view depicting an exemplary embodiment of anchor device 303 in the at-rest state and configured for anchoring against septal wall 207. FIG. 28B is a top down view depicting this same embodiment. In this embodiment, anchor device 303 has a generally planar body 501 having four leg portions 541 extending outwards from a central portion 542, which is preferably coupled with suture body portion 309 in any desired manner. Here, aperture 543 is included through which suture body portion 309 can be coupled.

In this embodiment, central portion 542 optionally extends away from leg portions 541 giving body 501 a "T" shape. Leg portions 541 are oriented with respect to suture body portion 309 at an angle 544. Anchor device 303 is preferably fabricated from an elastic or superelastic shape memory material, such as NITINOL, stainless steel and the like, and preferably heat treated to memorize the configuration of this at-rest state. In one exemplary embodiment, body 501 is laser cut or otherwise formed from a NITINOL tube or sheet.

Figure 28C:
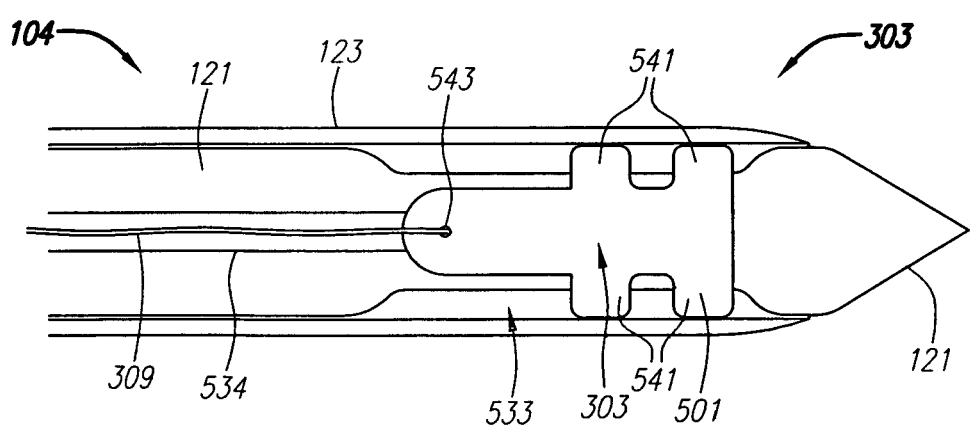
FIG. 28C is a partial cross-sectional view depicting this embodiment of the anchor device.
Figure 28D:
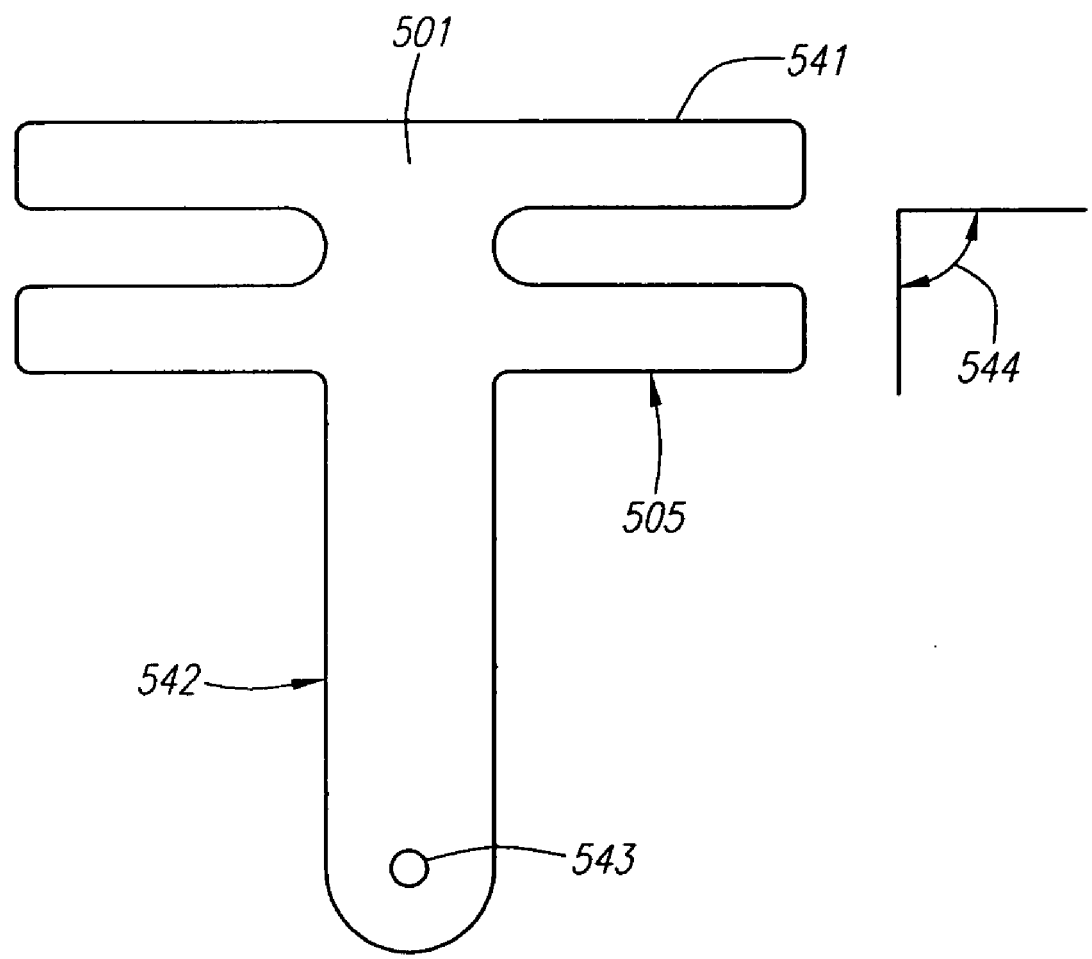
FIG. 28D is a front view depicting this embodiment of the anchor device.

FIG. 28C is a partial cross-sectional view depicting this embodiment in the undeployed state within delivery device 104. Specifically, body 501 is deformed and seated within recess 533, with each leg portion 541 wrapped partially around the circumference of needle 120. Outer tubular member 123 restrains body 501 and maintains the undeployed state. Anchor device 303 can then be deployed by exposing body 501 from within outer tubular member 123. FIG. 28D depicts an embodiment of body 501 cut from a NITINOL sheet prior to heat treatment.

It should also be noted that body 501 can be configured with any number of one or more leg portions 541 having any shape or size. Also, the anchoring capability of anchor device 303 can be increased by increasing the thickness of body 501, increasing the surface area covered by each leg portion 541 and/or decreasing angle 544, to name a few.

Figure 29A:
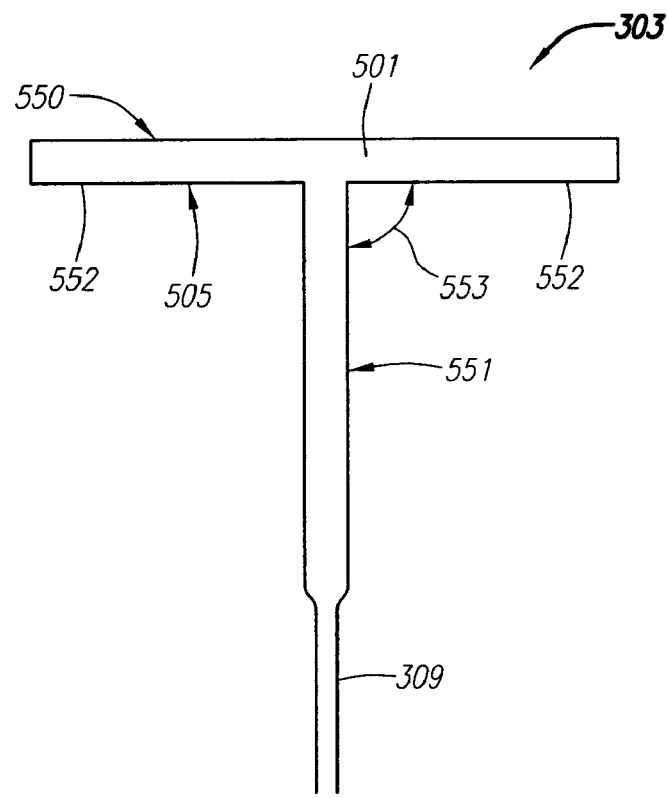
FIG. 29A is a side view depicting another exemplary embodiment of the anchor device.
Figure 29B:
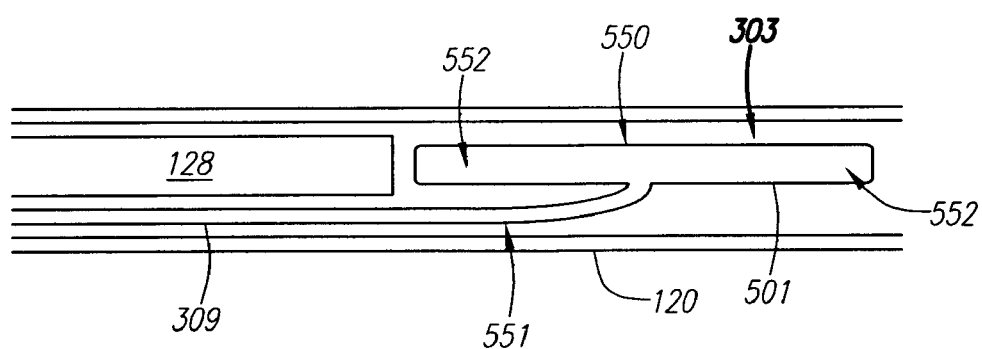
FIG. 29B is a cross-sectional view depicting this embodiment of the anchor device.
Figure 29C:
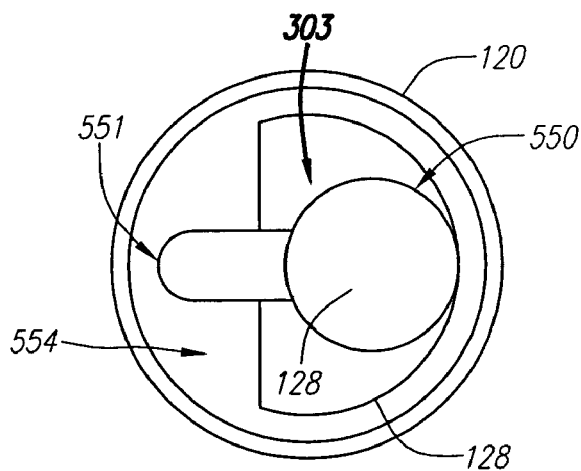
FIG. 29C is an end on view depicting this embodiment of the anchor device.
Figure 29D:
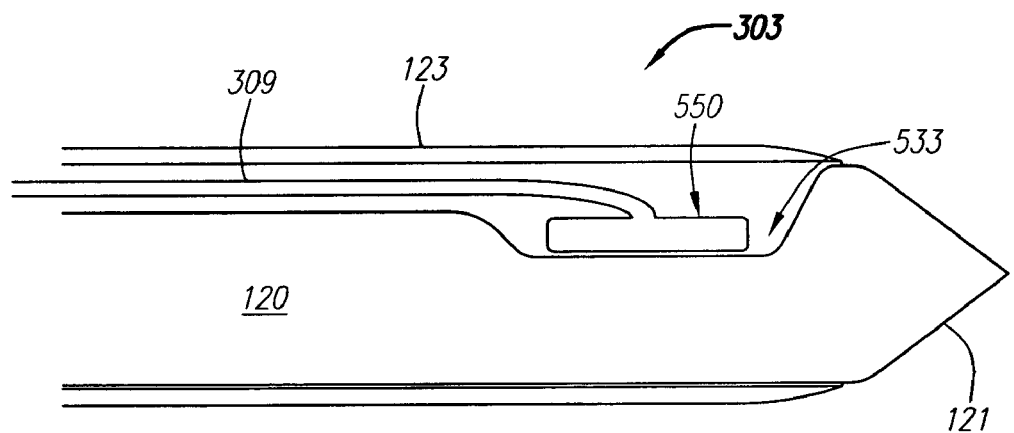
FIGS. 29D-E are cross-sectional views depicting additional exemplary embodiments of the anchor device.
Figure 29E:
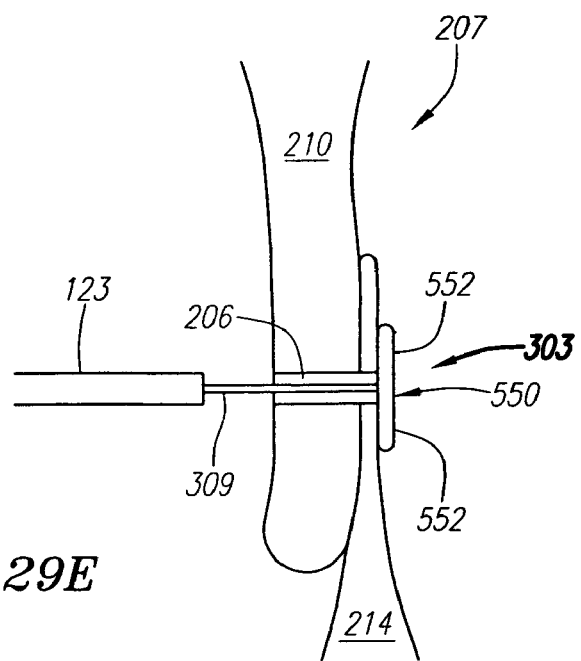
Figure 29F:
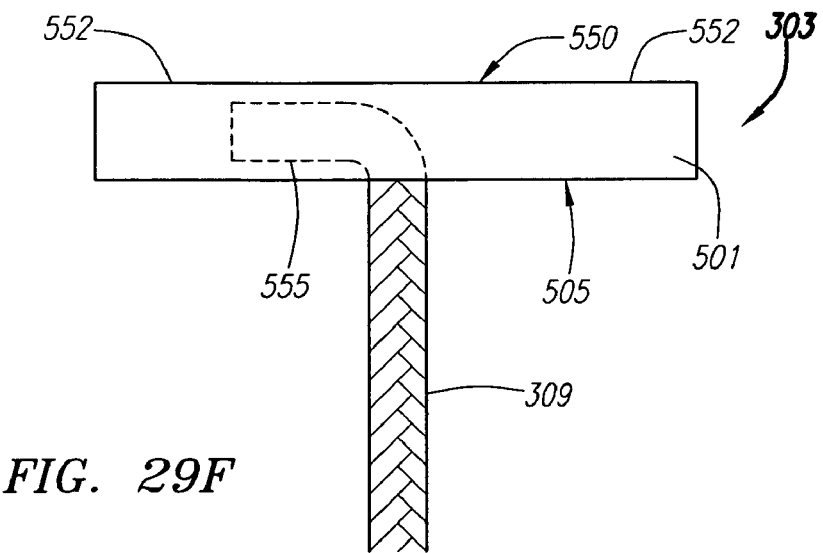
FIGS. 29F-G are schematic views depicting additional exemplary embodiments of the anchor device.
Figure 29G:
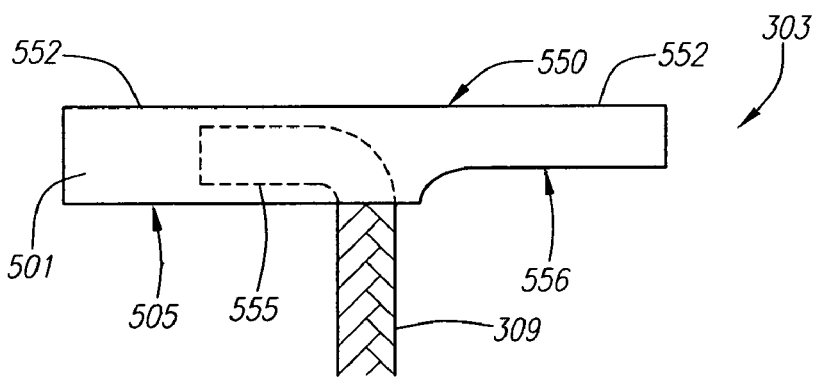
Figure 29H:
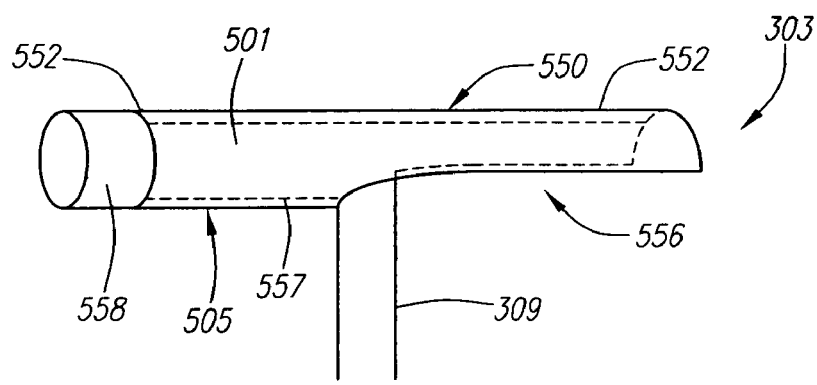
FIG. 29H is a perspective view depicting another exemplary embodiment of the anchor device.
Figure 29I:
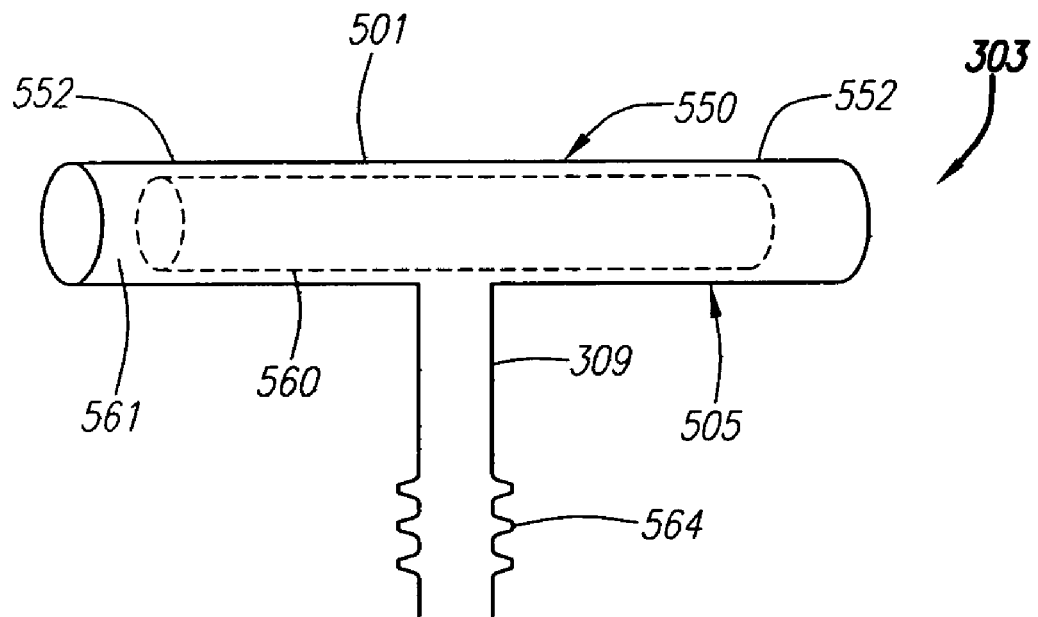
FIG. 29I is a perspective view depicting another exemplary embodiment of the anchor device.
Figure 29J:
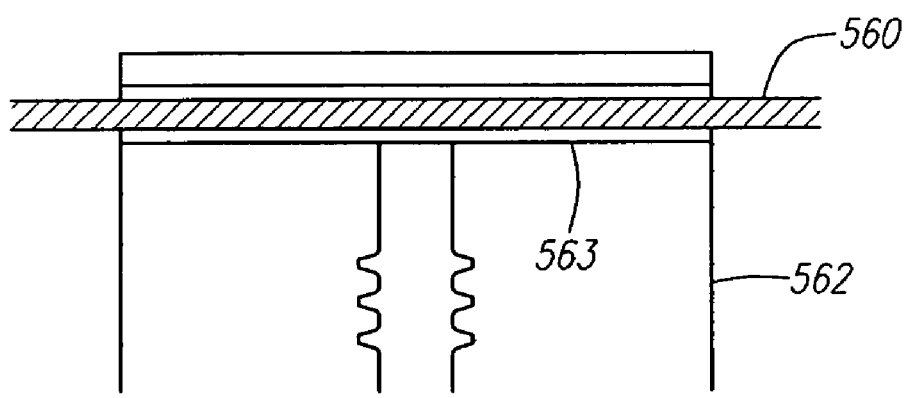
FIG. 29J is a cross-sectional view of a mold usable in the formation of an exemplary embodiment of the anchor device.
Figure 29K:
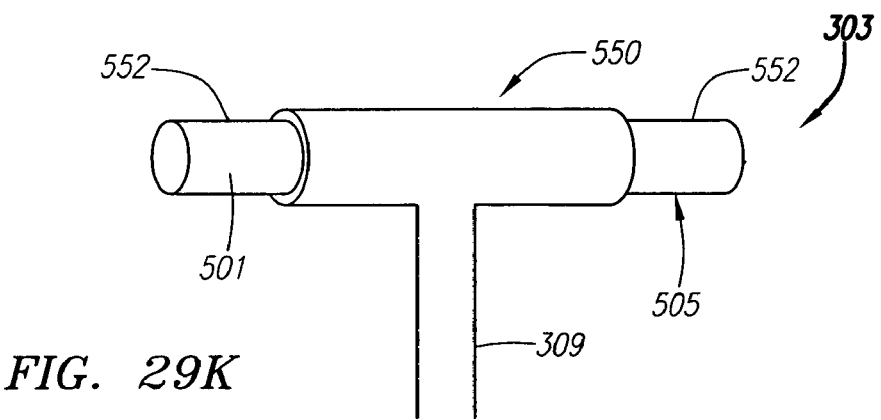
FIGS. 29K-L are perspective views depicting another exemplary embodiment of the anchor device.
Figure 29L:
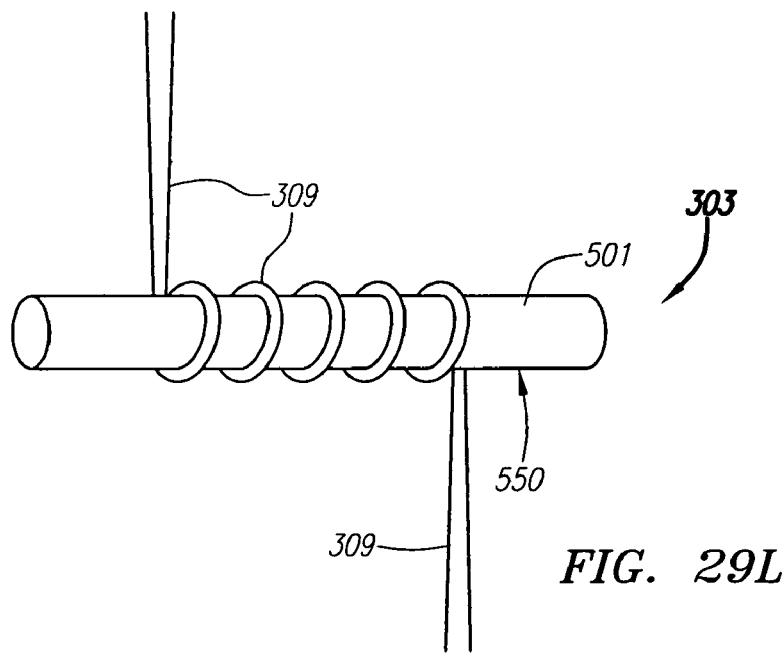
Figure 29M:
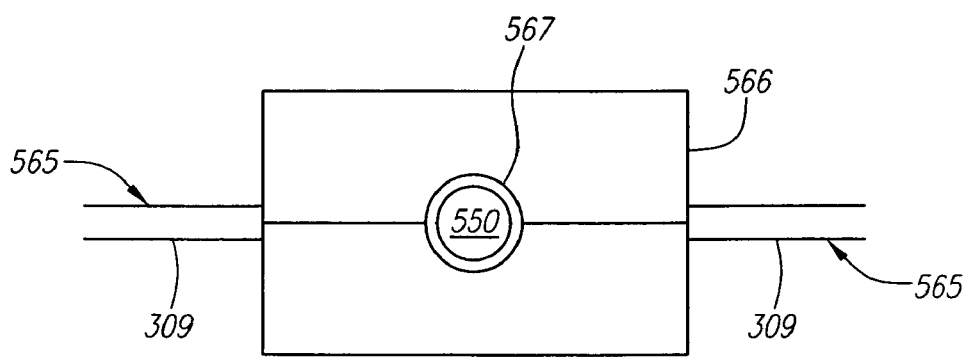
FIG. 29M is a schematic view depicting this embodiment of the anchor device during a subsequent stage of fabrication.
Figure 29N:
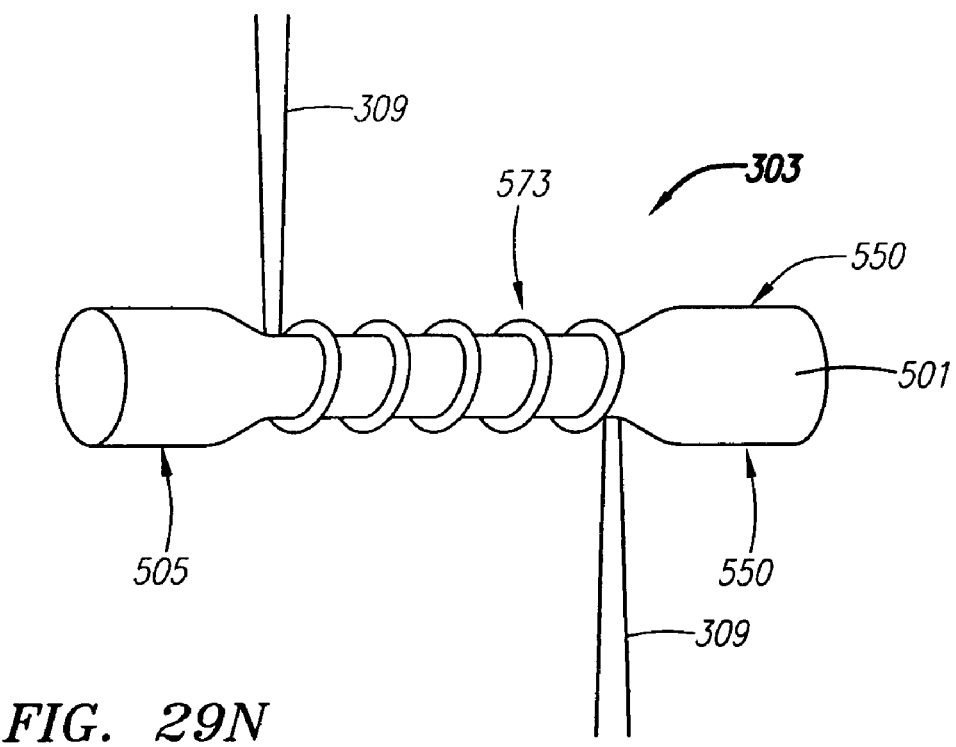
FIGS. 29-N-O are perspective views depicting additional exemplary embodiments of the anchor device.
FIG. 29P is a front view depicting another exemplary embodiment of the anchor device.
FIGS. 29Q-R are front views depicting additional exemplary embodiments of the anchor device.
Figure 29O:
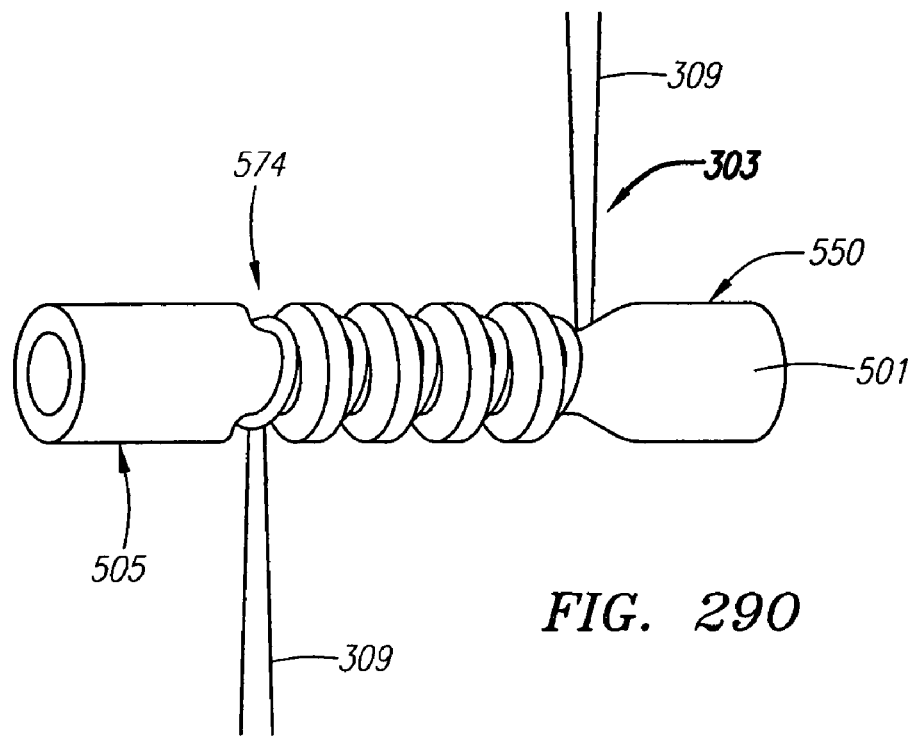
Figure 29P:
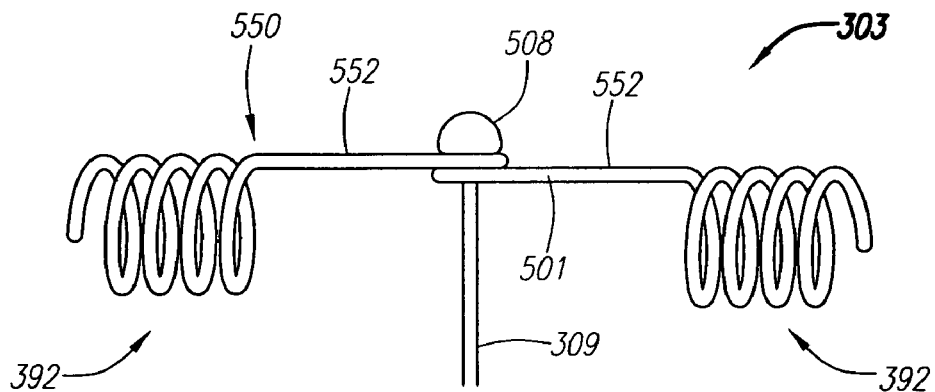
Figure 29Q:
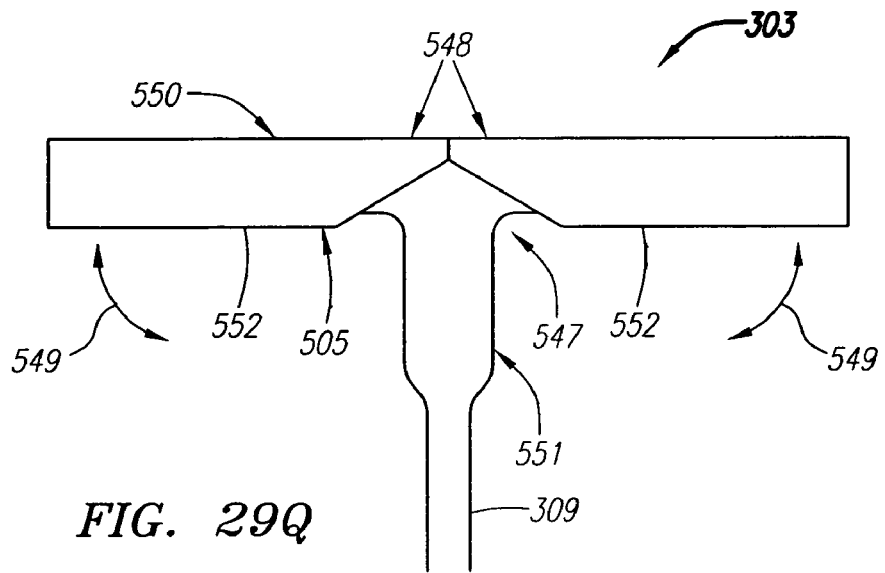
Figure 29R:
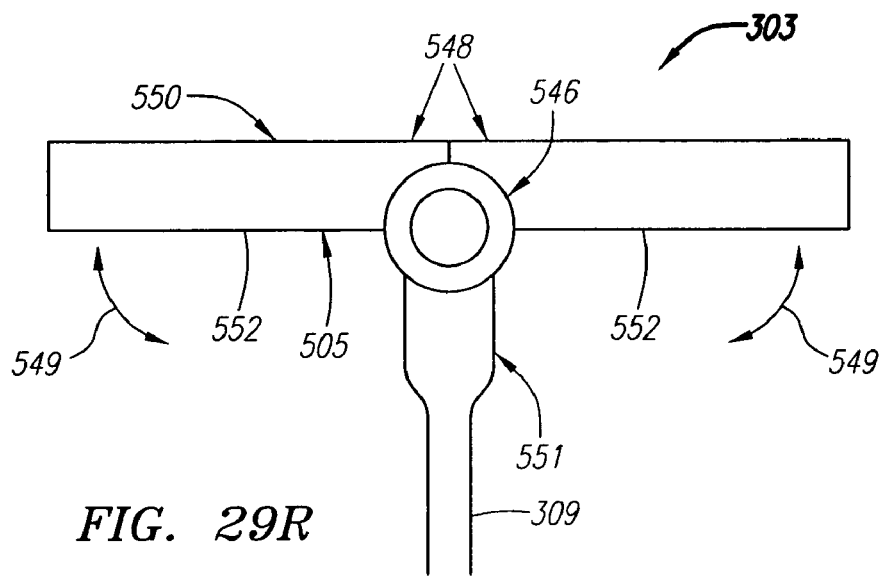

FIGS. 29A-R depict exemplary embodiments of anchor device 303, where body 501 is generally described as having a "T" configuration. FIG. 29A is a side view of one exemplary embodiment of anchor device 303. Depending on the configuration, body 501 can include a deflectable head portion 550 and a suture coupling portion 551, as depicted here, or body 501 can include only head portion 550. In this embodiment, head portion 550 and suture coupling portion 551 are both formed from the same material and integrated together as one continuous structure. Head portion 550 and suture coupling portion 551 can be fabricated from an elastic or superelastic shape memory material, such as NITINOL, stainless steel and the like, and heat treated to memorize the configuration depicted here, which can then be referred to as the at-rest state. In one exemplary embodiment, head portion 550 and suture coupling portion 551 are laser cut or otherwise formed from a NITINOL sheet.

Alternatively, head portion 550 and a suture coupling portion 551 can be fabricated from an elastic or deformable material having relatively less shape-memory characteristics, such as polypropylene and other polymeric materials and the like. In one exemplary embodiment, head portion 550 and suture coupling portion 551 are formed by injection molded polypropylene.

Head portion 550 preferably includes two opposing legs 552 and is configured to abut septal wall 207 and perform the anchoring function of anchor device 303. Legs 552 can be oriented at any angle 553 with respect to suture coupling portion 551 (or suture body portion 309), preferably less than or equal to ninety degrees. In the embodiments of anchor device 303 described or depicted herein as having a "T" configuration, it should be understood that head portion 550 can have any number of one or more legs 552 oriented in any manner with respect to each other (not necessarily opposing or symmetric).

Suture coupling portion 551, if included, is preferably configured to couple head portion 550 with suture body portion 309. Any manner of coupling can be used including, but not limited to, crimping suture coupling portion 551 around suture body portion 309 and coiling suture coupling portion 551 around suture body portion 309. If suture coupling portion 551 is not included, suture body portion 309 can be coupled directly to head portion 550.

FIG. 29B is a cross-sectional view depicting this embodiment of anchor device 303 within a cross-section of an exemplary embodiment of delivery device 104. Here, head portion 550 is deflected so that one leg 552 is adjacent suture coupling portion 551. Head portion 550 is restrained in this configuration by needle 120. Also shown is pusher member 128, which is preferably configured to accommodate suture body portion 309 and suture coupling portion 551.

FIG. 29C is an end on view depicting this embodiment of anchor device 303 within delivery device 104. It can be seen here that pusher member 128 has a recessed portion 554 for accommodating suture body portion 309 and suture coupling portion 551, giving pusher member 128 a "D" shaped profile from this perspective. Pusher member 128 can be configured in any manner for accommodating suture body portion 309 and suture coupling portion 551 including, but not limited to, the use of a canal-like recessed portion for suture body portion 309 or by reducing the overall width of pusher member 128.

FIG. 29D is a cross-sectional view depicting this embodiment of anchor device 303 within a cross-section of another exemplary embodiment of delivery device 104. Here, delivery device 104 includes needle 120 and outer tubular member 123. Needle 120 can include recessed portion 533 for housing head portion 550. In this embodiment, anchor device 303 can be deployed as needle 120 is advanced distally from within outer tubular member 123 and, accordingly, pusher member 128 can be omitted.

To deploy anchor device 303, pusher member 128 can advanced distally against any portion of suture 103 until head portion 550 is exposed entirely from within delivery device 104. Upon exposure, leg 552 of head portion 550 located adjacent to suture coupling portion 551 preferably deflects away from suture coupling portion 551. When suture 103 is retracted proximally, legs 552 can abut septal wall 207 and anchor suture 103, as depicted in the partial cross-sectional view of FIG. 29E.

As mentioned above, suture coupling portion 551 can be omitted if desired, in which case suture body portion 309 can be coupled directly with head portion 550. FIGS. 29F-P depict additional exemplary embodiments of anchor device 303 with suture coupling portion 551 omitted, and methods for manufacturing the same. FIG. 29F is a schematic view depicting an exemplary embodiment of anchor device 303 having a polymeric head portion 550 coupled with a braided polyester suture body portion 309. In this embodiment, head portion 550 has been bonded, cast, or injection molded over suture body portion 309, the presence of which within head portion 550 is indicated by dashed reference line 555. By molding head portion 550 over braided suture body portion 309 allows the polymeric material to fill the interstitial spaces of suture body portion 309. This can increase the strength of the bond between the two portions 550 and 551. FIG. 29G depicts another exemplary embodiment of anchor device 303 similar to the embodiment described with respect to FIG. 29F, except having a recessed portion 556 for allowing easier deflection of head portion 550 into the undeployed state.

FIG. 29H is a perspective view of another embodiment of anchor device 303 having recessed portion 556. Here, head portion 550 can be formed from a NITINOL or stainless steel tube and the like. Recessed portion 556 can be formed during tube fabrication or can be removed after tube fabrication, such as by laser cutting and the like. Suture body portion 309 can be a polymeric material, such as polypropylene and the like. Suture body portion 309 can be coupled with head portion 550 by injection molding the polymeric material through inner lumen 557 of head portion 550 (the presence of inner lumen 557 within head portion 550 is indicated by a dashed line) and forming an enlarged cap 558 over the end of head portion 550 to abut head portion 550 and couple portions 550 and 309 together. Injection molding of suture body portion 309 can be controlled by plugging the leg 552 having recessed portion 556.

FIG. 29I is a perspective view depicting another exemplary embodiment of anchor device 303. Here, head portion 550 can include a core member 560 formed from a metallic material such as NITINOL, stainless steel and the like. Core member 560 is encapsulated by covering 561, which is preferably formed from the same material as suture body portion 309, such as a polymeric material and the like. Core member 560 is referenced by a dashed line to indicate encapsulation within covering 561. It should be noted that core member 560 can be only partially encapsulated if desired. Also, suture body portion 309 can include one or more serrations 564, configured to mate with a right atrial anchor device 303, and can also include a metallic core encapsulated by a polymeric covering if desired. FIG. 29J is a cross-sectional view of mold 562, which can be used in the formation of this embodiment of anchor device 303. Mold 562 has inner lumen 563 into which the polymeric material for suture body portion 309 and covering 561 can be introduced over core member 560. Here, core member 560 is depicted as a wire, which can be trimmed to the desired length.

FIG. 29K is a perspective view depicting another exemplary embodiment of anchor device 303. Here, head portion 550 can be formed from a NITINOL or stainless steel tube and the like and suture body portion 309 can be a polymeric material, such as polypropylene and the like. In this embodiment, suture body portion 309 relatively thinly encapsulates a part of head portion 550 to create a relatively lower profile anchor device 303.

FIG. 29L depicts this embodiment of anchor device 303 described with respect to FIG. 29K during one exemplary stage of fabrication. Here, suture body portion 309 is shown wrapped around head portion 550 prior to encapsulation. FIG. 29M is a schematic view depicting this embodiment during a subsequent stage of fabrication where tension is applied to both ends 565 of suture body portion 309 while anchor device 303 is placed within a heat mold 566, which reforms the wrapped portion of suture body portion 309 as a relatively thin encapsulation layer around head portion 309. Head portion 550 is preferably suspended within lumen 567 to ensure adequate encapsulation. One end 565 of suture body portion 309 can then be trimmed as desired. FIG. 29N is a perspective view depicting another exemplary embodiment where both head portion 550 and suture body portion 309 have been narrowed in region 573 to further reduce the profile prior to placement within mold 566. Head portion 550 can alternatively be configured with grooves 574 around which suture body portion 309 can be wrapped as depicted in FIG. 29O.

FIG. 29P is a front view depicting yet another exemplary embodiment of anchor device 303 having a T configuration. Here, head portion 550 can be formed from a metallic material coiled around suture body portion 309, which can be formed from any desired material. Each end of legs 552 includes an atraumatic microcoil having a smaller diameter than the non-coiled portion of each leg 552.

FIGS. 29Q-R are front views depicting yet another exemplary embodiment of anchor device 303 having a T configuration. Here, legs 552 are deflectable (in direction 549) in relation to suture coupling portion 551 to allow anchor device 303 to have a lower profile for housing within delivery device 104. In one embodiment, head portion 550 is formed from an elastic shape memory material such as NITINOL, stainless steel and the like to allow deflection of legs 552. In another embodiment, legs 552 are coupled with a flexible portion 547 as depicted in FIG. 29Q. The flexible portion 547 can be composed of a flexible material such as polypropylene, other polymers, flexible metals and the like. Legs 552 can include restraining abutments 548 to prevent deflection too far from suture coupling portion 551. In yet another embodiment, legs 552 are coupled with a hinge-type device 546 as depicted in FIG. 29R.

Figure 30A:
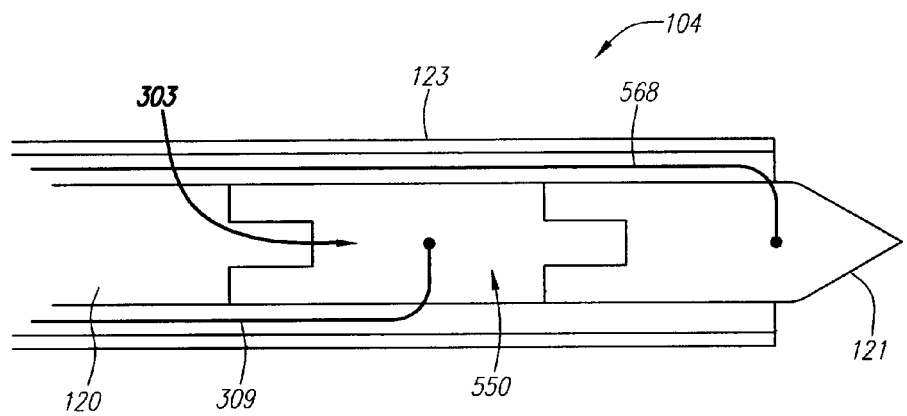
FIGS. 30A-30G are partial cross-sectional views depicting additional exemplary embodiments of the anchor device within additional embodiments of the treatment system.

FIGS. 30A-F depict additional exemplary embodiments of anchor device 303 having a T configuration. In these embodiments, anchor device 303 is integrated with delivery device 104. FIG. 30A is a partial cross-sectional view depicting an exemplary embodiment of anchor device 303 and delivery device 104. In this embodiment, head portion 550 forms a detachable mid-portion of needle 120. The distal end portion of needle 120 having distal end 121 is also detachable.

Figure 30B:
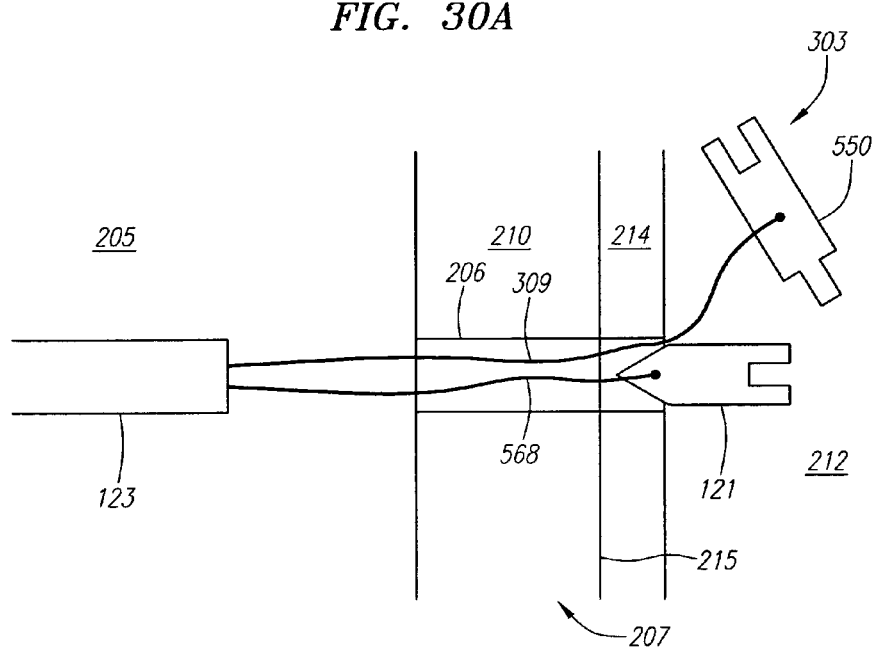
Figure 30C:
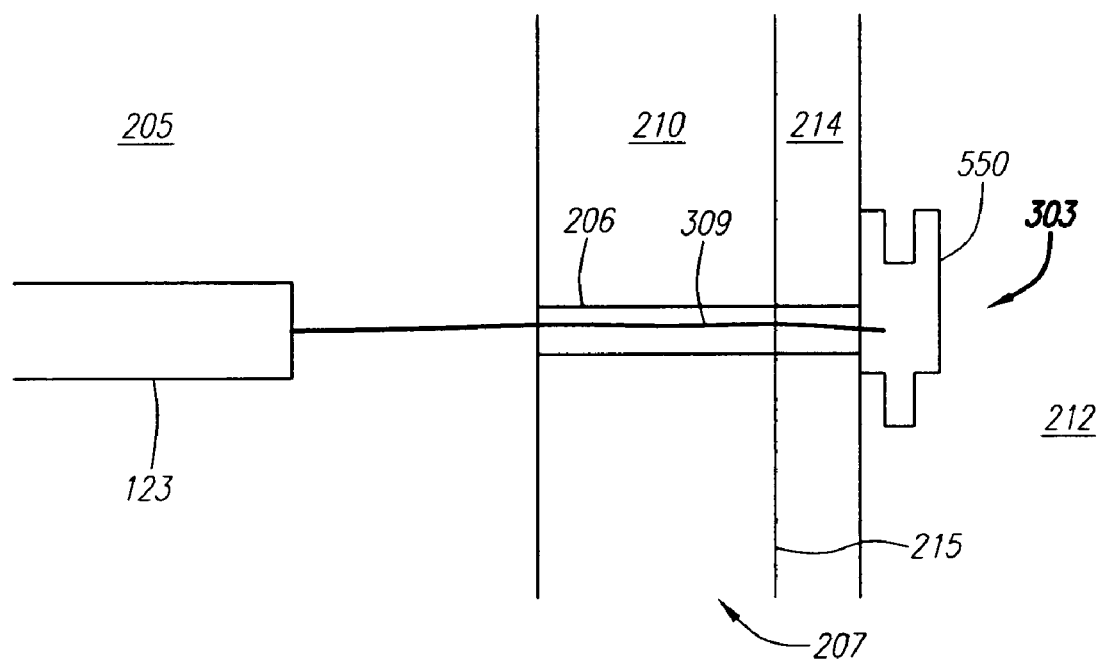

Once passed through septal wall 207, head portion 550 and distal end 121 can be detached by pulling proximally on suture body portion 309, or in any other desired manner. Distal end 121 is preferably coupled with a pull wire 568, which can be used to retrieve distal end 121 after detachment by pulling distal end 121 back through opening 206 as depicted in FIG. 30B. After retrieval, anchor device 303 is preferably positioned to anchor suture 103, as depicted in FIG. 30C.

Figure 30D:
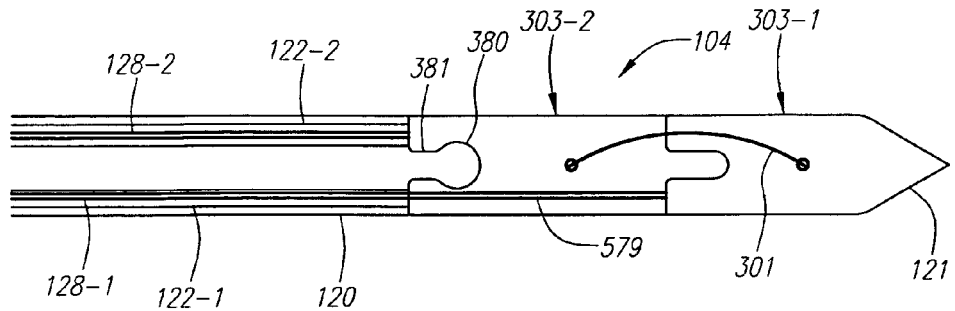
Figure 30E:
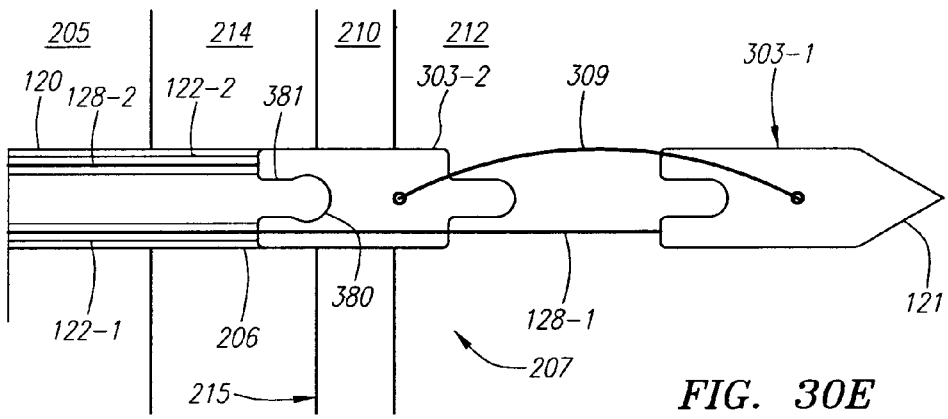

FIG. 30D is a partial cross-sectional view of another exemplary embodiment where first and second anchor devices 303-1 and 303-2 are integrated with an embodiment of delivery device 104. Here, substantially sharp distal end 121 of needle 120, is detachable and forms first anchor device 303-1. Needle 120 also includes a second detachable mid-portion which forms second anchor device 303-2. Anchor device 303-1 is preferably configured for deployment on the left atrial side of septal wall 207, while anchor device 303-2 is preferably configured for deployment on the right atrial side of septal wall 207. Anchor devices 303-1 and 303-2 are coupled together with suture body 301. Needle 120 can include two lumens 122-1 and 122-2 for housing pusher members 128-1 and 128-2 respectively. Anchor device 303-2 includes an inner lumen 579 for housing the distal portion of pusher member 128-1.

Figure 30F:
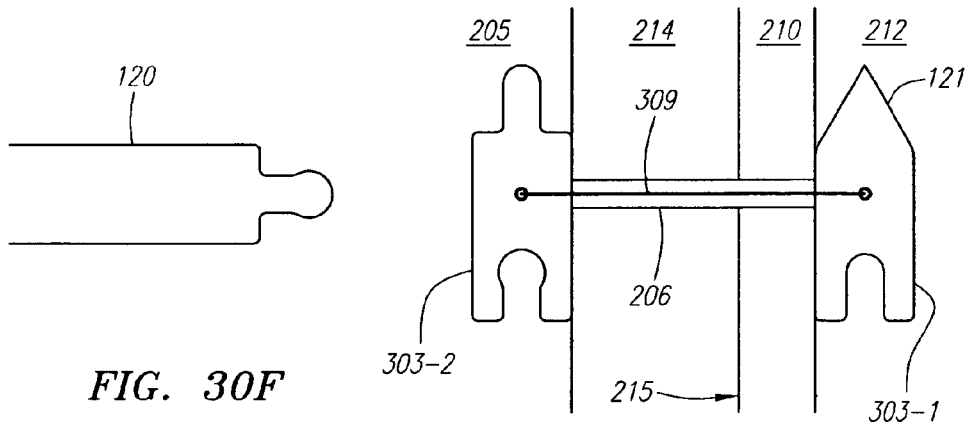

To deploy anchor device 303-1, needle 120 is first advanced distally through septal wall 207. Distal force can then be applied to pusher member 128-1, which abuts the proximal end of anchor device 303-1, to separate and deploy anchor device 303-1, as depicted in the partial cross-sectional view of FIG. 30E. Needle 120 can then be withdrawn from opening 206, at which point pusher member 128-2 can be used to separate and deploy anchor device 303-2, at which point anchor devices 303-1 and 303-2 are in position to at least partially close tunnel 206 as depicted in FIG. 30F. In this embodiment, needle 120 and anchor device 303-2 include opposing detents 380 and 381 to keep anchor device 303-2 from deploying during withdrawal of needle 120 through tunnel 215. Suture body 301 is preferably configured to apply a compressive force between anchor devices 303-1 and 303-2 to provide adequate closing force to tunnel 206.

Figure 30G:
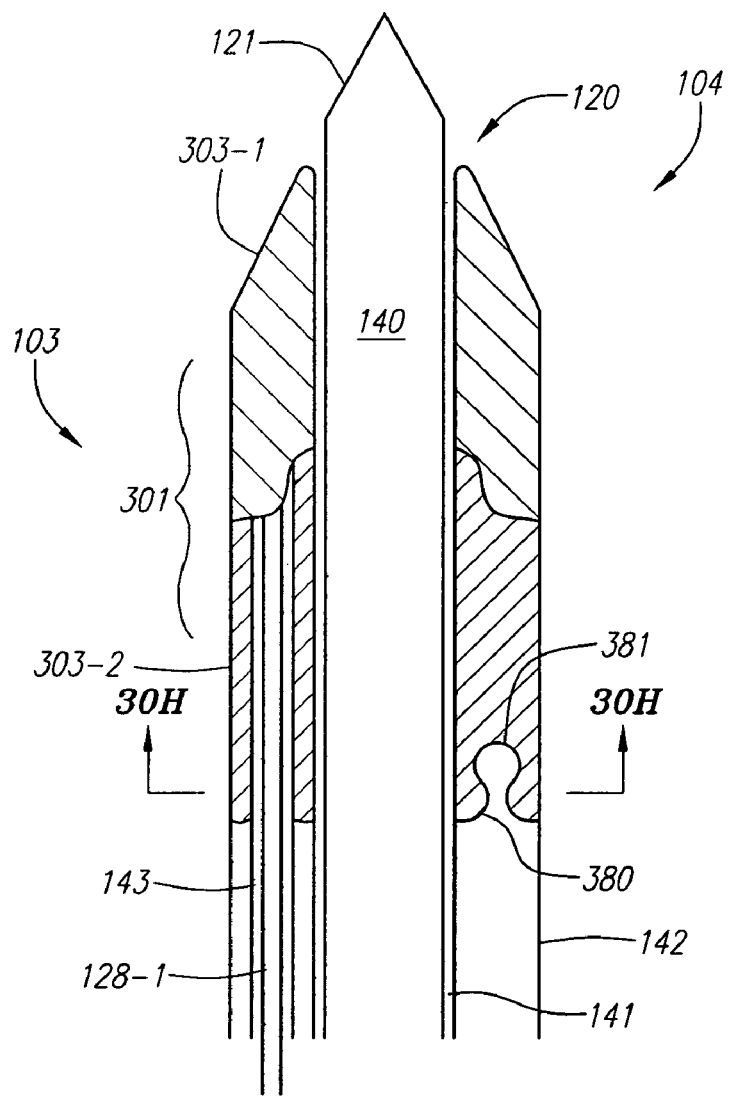
Figure 30H:
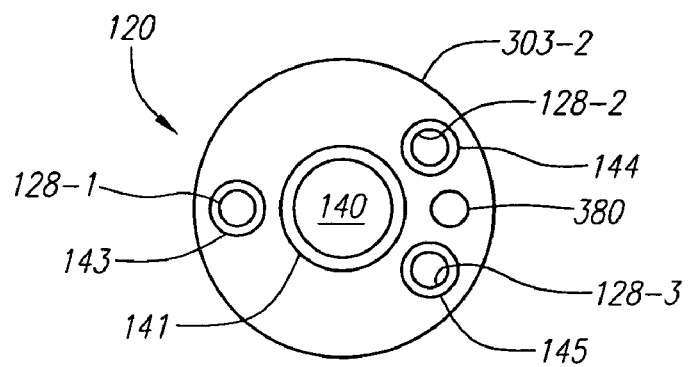
FIG. 30H is a cross-sectional view of this embodiment taken along line 30H-30H of FIG. 30G.

FIG. 30G is a cross-sectional view of yet another exemplary embodiment where first and second anchor devices 303-1 and 303-2 are integrated with an embodiment of delivery device 104. Here, needle 120 includes a retractable piercing member 140 configured to slide within an inner lumen 141 of a sheath 142. Anchor devices 303-1 and 303-2 are integrated with sheath 142 as depicted here and are independently detachable therefrom. Like the previous embodiment, anchor devices 303-1 and 303-2 are coupled together with suture body 301 and are preferably configured for deployment on the left and right atrial sides of septal wall 207, respectively. Sheath 142 includes a second inner lumen 143, third inner lumen 144 and fourth inner lumen 145 for slidably receiving pusher members 128-1, 128-2 and 128-3, respectively, as depicted in the cross-sectional view of FIG. 30H, which is taken along line 30H-30H of FIG. 30G.

Before deploying anchor device 303-1, needle 120 is first advanced distally through septal wall 207, at which point piercing member 140 can be retracted from within inner lumen 141. Deployment of anchor devices 303-1 and 303-2 can then proceed in a manner similar to that described with respect to FIGS. 30E-F, with pusher member 128-1 being used to deploy anchor device 303-1 and pusher members 128-2 and 128-3 being used to deploy anchor device 303-2.

In this embodiment, sheath 142 and anchor device 303-2 include opposing detents 380 and 381, respectively, to keep anchor device 303-2 from deploying during withdrawal of sheath 142 through tunnel 206. Suture body 301 is preferably configured to apply a compressive force between anchor devices 303-1 and 303-2 to provide adequate closing force to tunnel 206.

Figure 30I:
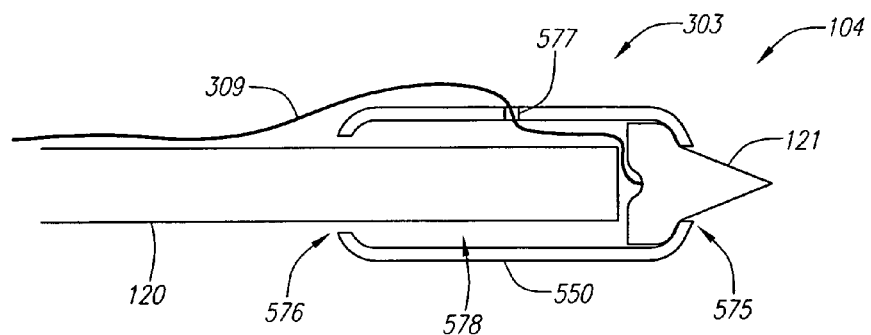
FIGS. 30I-30K are partial cross-sectional views depicting additional exemplary embodiments of the anchor device within additional embodiments of the treatment system.
Figure 30J:
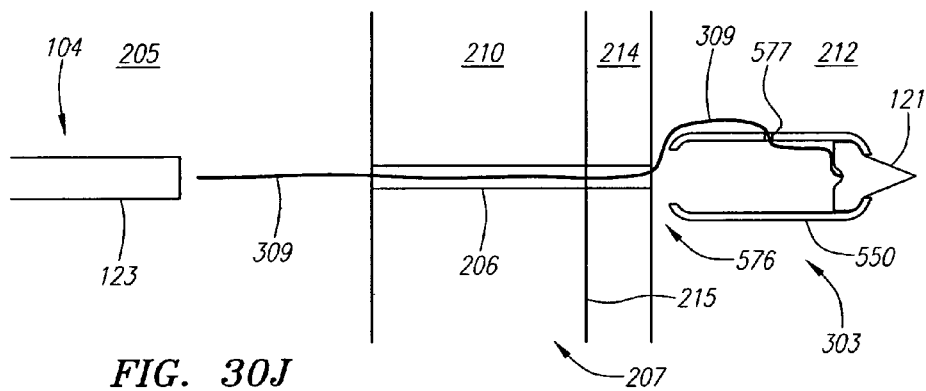
Figure 30K:
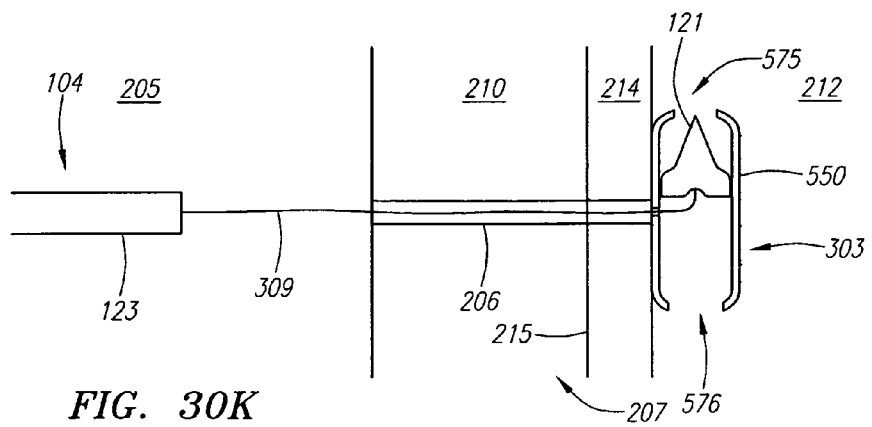

FIGS. 30I-K are partial cross-sectional views depicting another exemplary embodiment where anchor device 303 is integrated with delivery device 104. In this embodiment, substantially sharp distal end 121 of needle 120 is detachable and housed within inner lumen 578 of head portion 550, which includes an open distal end 575 and open proximal end 576. Distal end 121 of needle 126 is preferably configured to partially pass through open distal end 575 and needle 120 is preferably configured to pass through open proximal end 576. Head portion 550 includes a centrally located aperture 577 through which suture body portion 309 can pass.

To deploy anchor device 303, needle 120 is first advanced through septal wall 207 until head portion 550 is completely exposed on the opposite side. Needle 120 can then be proximally retracted so that proximal end 576 of head portion 550 abuts septal wall 207 and causes head portion 550 to separate and deploy, as depicted in FIG. 30J. Proximal force is then preferably applied to suture body portion 309 in order to properly position head portion 550, as well as to retract distal end 121 into head portion inner lumen 578, where it is no longer exposed to internal body tissue, as depicted in FIG. 30K.

In another embodiment, instead of configuring distal end 121 to be retractable into anchor device 303, the sharp distal end 121 of needle 120 has a sharp tip that is made of a material (such as a water soluble polymer) that in time dissolves. As a result, the sharp portion of the anchor goes away, leaving a blunt portion that is less likely to perforate the septa.

Figure 31A:
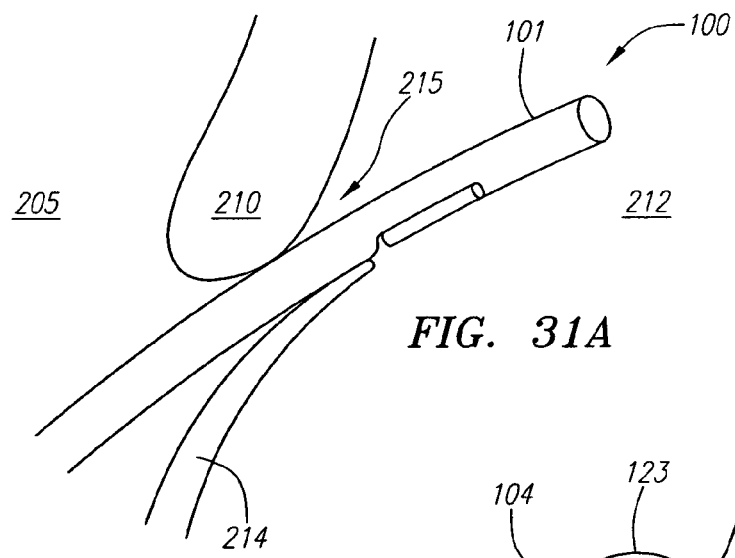
FIGS. 31A-31D are partial cross-sectional views depicting additional exemplary embodiments of the anchor device within additional embodiments of the treatment system.
Figure 31B:
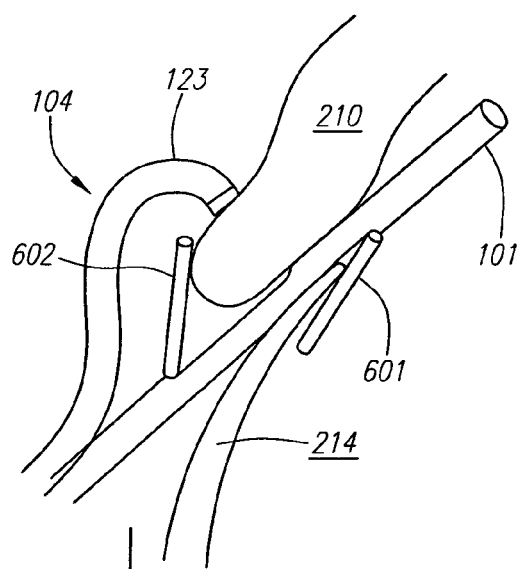

FIGS. 31A-D depict additional exemplary embodiments of treatment system 100 where anchor device 303 is connected to suture body portion 309 after advancing needle 120 through septal wall 207. FIG. 31A is a partial cross-sectional view depicting an embodiment of body member 101 located within PFO tunnel 215. In this embodiment, body member 101 includes a retractable foot 601 configured to house anchor device 303. Foot 601 can be retracted in a proximal direction, by way of a pull wire (not shown) or the like, so that it overlaps septum primum 210 in the manner depicted in FIG. 31B. (It should be noted that the functionality described in foot 601 can also be incorporated in the embodiments of the grasping device 502 described in U.S. patent application Ser. No. 11/175,814.) Also shown is delivery device 104 configured for off-axis delivery with arm member 602 (which is similar to arm member 409 described in U.S. patent application Ser. No. 11/175,814.)

Figure 31C:
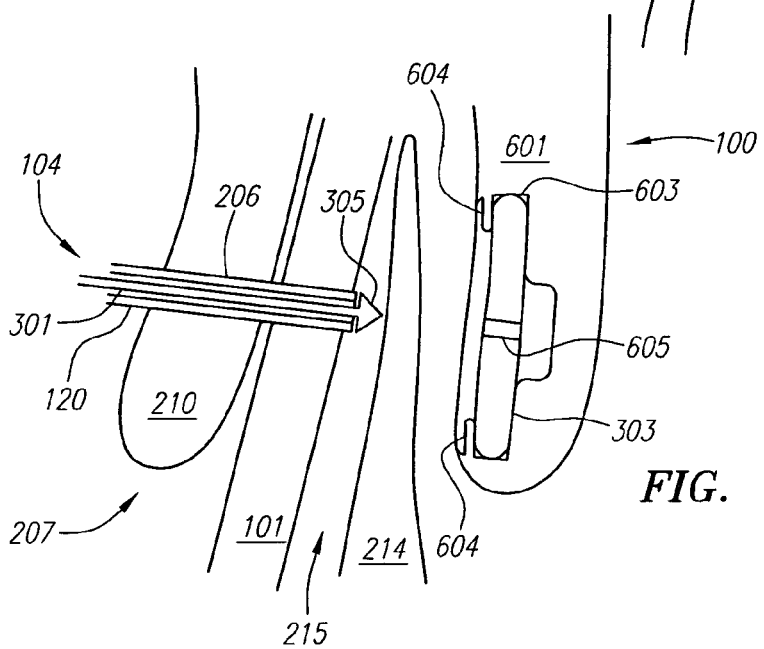
Figure 31D:
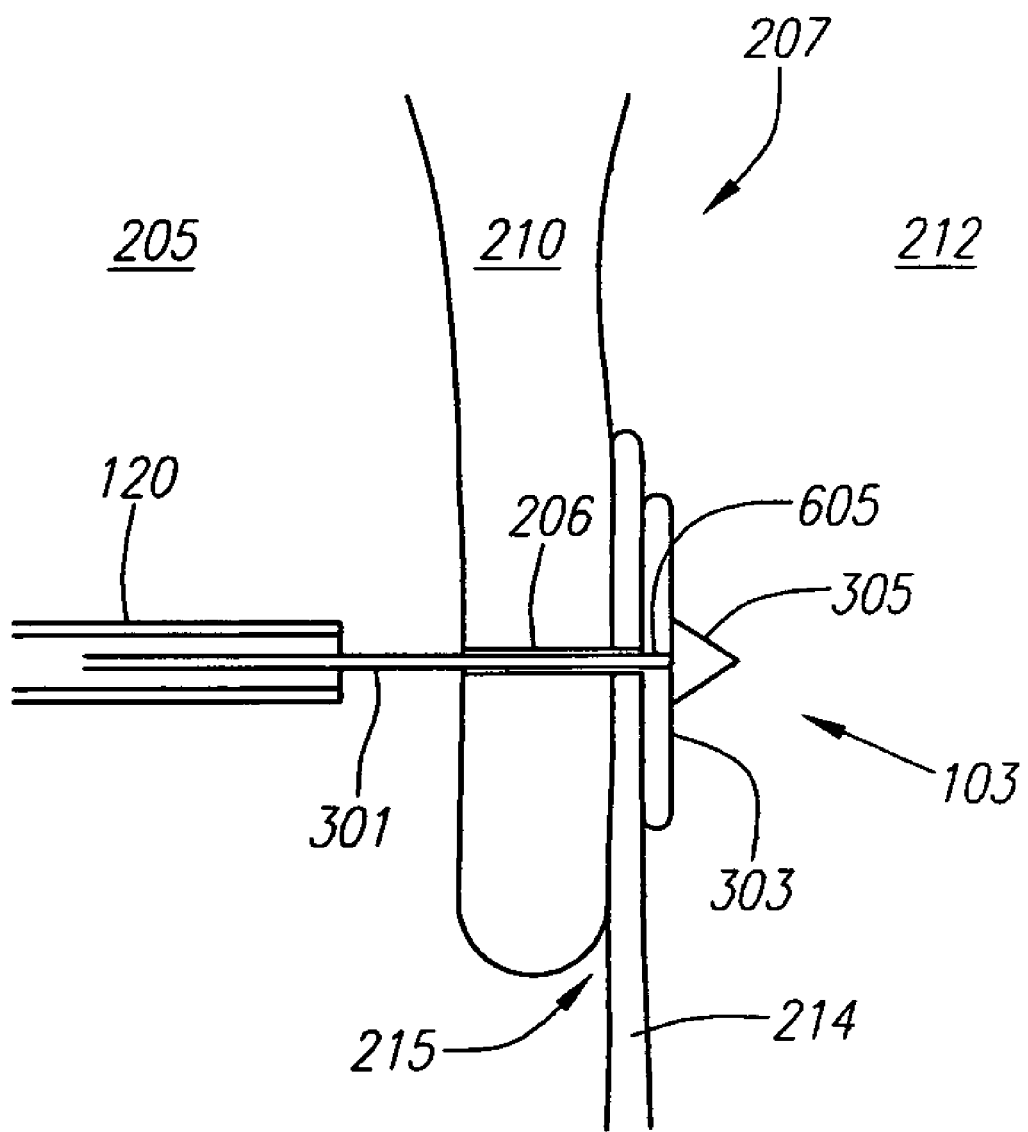

FIG. 31C is an enlarged view of septal wall 207 after needle 120 has been advanced from within outer member 123 through septum secundum 210. Distal end 121 of needle 120 is formed by substantially sharp distal end 305 of suture 103. Distal end 305 is configured to couple with anchor device 303, which is preferably housed within a Foot 601 a recess 603 of foot 601. Abutments 604 within recess 603 maintain anchor device 303 within recess 603. Anchor device 303 preferably includes an aperture 605 configured to receive distal end 305 of suture 103. Preferably, delivery device 104 and foot 601 are aligned and offset from body member 101 such that distal end 305 automatically enters aperture 605 upon advancement of needle 120. In order to aid alignment, both distal end 305 and aperture 605 can be coated with or fabricated from a magnetic material (or one can be coated with or composed of a metallic material) in order to provide an attractive force that guides the alignment. Once advanced far enough, distal end 305 couples with anchor device 303, forming suture 103. Needle 120 and suture body 301 can then be retracted to separate anchor device 303 from foot 601 and body member 101 can be withdrawn as depicted in FIG. 31D.

Figure 32A:
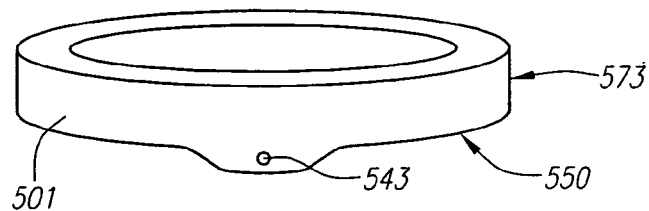
FIGS. 32A-E are perspective views depicting additional exemplary embodiments of the anchor device.
Figure 32B:
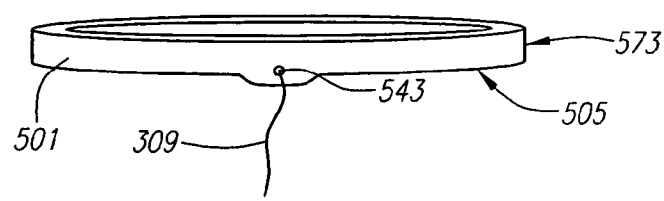
Figure 32C:
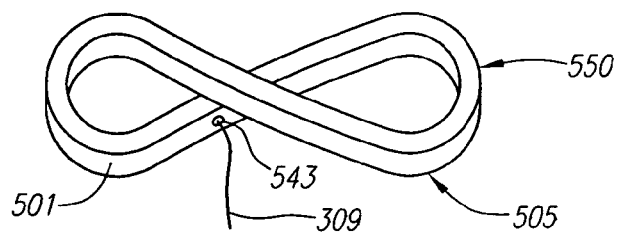
Figure 32D:
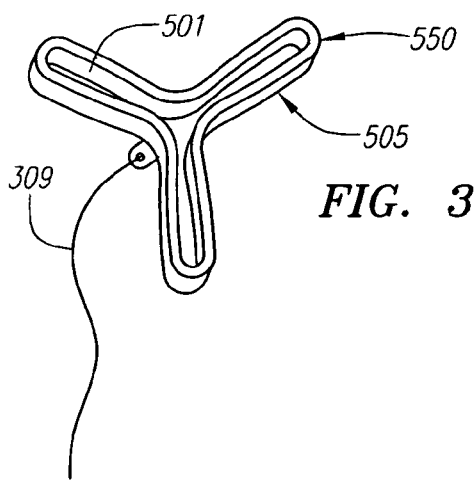
Figure 32E:
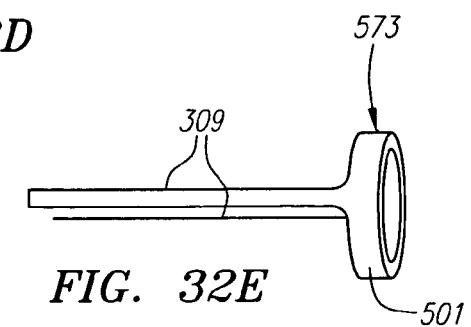

FIGS. 32A-E are perspective views depicting additional exemplary embodiments of anchor device 303 having a T configuration, where body 501 can be formed from a NITINOL tube. FIG. 32A depicts a circular NITINOL tube section 573 prior to shaping. Tube section 573 can be bent, twisted, compressed or otherwise altered to form any desired anchoring configuration. FIG. 32B depicts section 573 after having been flattened to form head portion 550. Here, head portion 550 is coupled directly to suture body portion 309, although head portion 550 and suture body portion 309 can be integrated as one continuous NITINOL structure. FIG. 32C depicts section 573 after having been twisted to form a figure 8-type shape head portion 550. FIG. 32D depicts section 573 after having been compressed, or indented, to form an Y-type shape head portion 550. These embodiments formed from section 573 are just a few examples of the numerous configurations possible. To integrate suture body portion 309 with head portion 550, section 573 can be cut with one or more suture body portions 309 included (here two), as depicted in FIG. 32E.

It should be noted that any feature, function, method or component of any embodiment described with respect to FIGS. 1-32E can be used in combination with any other embodiment, whether or not described herein. As one of skill in the art will readily recognize, treatment system 100 and the methods for treating a septal defect can be configured or altered in an almost limitless number of ways, the many combinations and variations of which cannot be practically described herein.

The devices and methods herein may be used in any part of the body, in order to treat a variety of disease states. Of particular interest are applications within hollow organs including but not limited to the heart and blood vessels (arterial and venous), lungs and air passageways, digestive organs (esophagus, stomach, intestines, biliary tree, etc.). The devices and methods will also find use within the genitourinary tract in such areas as the bladder, urethra, ureters, and other areas.

Other locations in which and around which the subject devices and methods find use include the liver, spleen, pancreas and kidney. Any thoracic, abdominal, pelvic, or intravascular location falls within the scope of this description.

The devices and methods may also be used in any region of the body in which it is desirable to appose tissues. This may be useful for causing apposition of the skin or its layers (dermis, epidermis, etc), fascia, muscle, peritoneum, and the like. For example, the subject devices may be used after laparoscopic and/or thoracoscopic procedures to close trocar defects, thus minimizing the likelihood of subsequent hernias. Alternatively, devices that can be used to tighten or lock sutures may find use in various laparoscopic or thoracoscopic procedures where knot tying is required, such as bariatric procedures (gastric bypass and the like) and Nissen fundoplication. The subject devices and methods may also be used to close vascular access sites (either percutaneous, or cut-down). These examples are not meant to be limiting.

The devices and methods can also be used to apply various patch-like or non-patchlike implants (including but not limited to Dacron, Marlex, surgical meshes, and other synthetic and non-synthetic materials) to desired locations. For example, the subject devices may be used to apply mesh to facilitate closure of hernias during open, minimally invasive, laparoscopic, and preperitoneal surgical hernia repairs.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit of the disclosure.

What is claimed is:

1. In a method of closing a patent foramen ovale in a septal wall of the heart, the improvement comprising:
    advancing an elongate flexible outer tubular member having an inner lumen through the vasculature of a patient and into proximity with the patient's heart;
    advancing the outer tubular member into the patient's heart and into proximity with the septum secundum of a patent foramen ovale, the outer tubular member housing in its inner lumen a first and a second inner elongate tubular member in a first constrained configuration, each inner elongate tubular member having a lumen and a substantially sharp distal end and each inner tubular member having, respectively, a first and second suture body in its lumen each inner elongate tubular member further having a distal portion, a proximal portion, and a non-linear intermediate portion located therebetween, wherein a longitudinal axis of each distal portion is substantially parallel to a longitudinal axis of each proximal portion;
    advancing the first and second inner elongate tubular members distally out of the inner lumen of the outer tubular member such that the first and second inner elongate tubular members deflect from the first constrained configuration to a second expanded configuration wherein the distal portion of each of the inner elongate tubular members is spaced away from the other and the distal portions and sharp distal ends extend in a distal direction and transverse to the septum secundum prior to penetrating the septum secundum;
    advancing said first and second tubular members distally so that each of them penetrates the septum secundum and the septum primum; and
    deploying said first and second suture bodies from within the first and second inner elongate tubular members respectively.

2. The method of claim 1, further comprising simultaneously penetrating at least a portion of the septal wall in different locations with the first and second inner elongate tubular members.

3. The method of claim 2, wherein the each have a distal portion, a proximal portion and a curved intermediate portions are each curved.

4. The method of claim 3, wherein the distal and proximal portions of each inner elongate member are substantially straight.

5. The method of claim 1, wherein the first and second inner elongate members are coupled together.

6. The method of claim 1, further comprising penetrating through the septal wall comprising the septum secundum and the septum primum simultaneously with the first and second inner elongate members.

7. The method of claim 6, wherein the first portion of the first and second suture bodies each comprises an anchor device.

8. The method of claim 1, further comprising deploying a first portion of a first suture body having an anchor device thereon from an inner lumen of the first inner elongate tubular member on a first side of the septal wall and deploying a first portion of a second suture body having an anchor device thereon from an inner lumen of the second inner elongate tubular member on the first side of the septal wall.

9. The method of claim 8, further comprising retracting the first and second inner elongate tubular members from the septal wall to deploy a second portion of the first and second suture bodies on a second side of the septal wall.

10. The method of claim 9, further comprising deploying a lock device on the second portion of the first suture body.

11. The method of claim 10, wherein the lock device comprises a coil-like body.

12. The method of claim 11, wherein the coil-like body is configured to compress the first and second suture bodies.

13. The method of claim 11, wherein deploying the lock device comprises pushing the coil-like body off of a distal end of the outer tubular member.

14. The method of claim 11, wherein the coil-like body comprises two or more coiled segments and is deflectable between a first configuration where each coiled segment is substantially oriented about a main axis of the body and a second configuration where at least one coiled segment is deflected to be oriented about an off axis of the body offset from the main axis.

15. The method of claim 11, wherein the coil-like body comprises a plurality of coil-like segments, the first suture body being routed between at least two coil-like segments.

16. The method of claim 15, further comprising inserting a restraining member into the coil-like body prior to delivering the lock device, wherein the restraining member increases the spacing between the at least two coil-like segments through which the first suture body is routed.

17. The method of claim 15, wherein deploying the lock device comprises removing a restraining member from the coil-like body to allow the coil-like body to introduce a relatively more tortuous path to the first suture body.

18. The method of claim 17, wherein the coil-like body is configured to compress the first suture body between the at least two coil-like segments upon removal of the restraining member.

19. The method of claim 10, wherein the lock device comprises an outer body having an inner lumen and an inner body configured to fit within the inner lumen of the outer body.

20. The method of claim 19, wherein the inner body is deformable between an expanded and a compressed configuration and biased towards the expanded configuration.

21. The method of claim 20, wherein deploying the lock device comprises removing a tubular restraining member from between the outer body and the inner body such that the inner body is free to expand and compress the first suture body against the outer body.

22. The method of claim 21, wherein the inner body is a coil-like body.

23. The method of claim 21, wherein the inner body is a stent-like body.

24. The method of claim 21, wherein deploying the lock device comprises advancing the lock device from within the inner lumen of the first elongate tubular member to allow the coil-like body to deflect from the first configuration to the second configuration.

25. The method of claim 21, wherein deploying the lock device further comprises deploying a wing member from the coil-like body, wherein the wing member is configured to anchor the first suture body.

26. The method of claim 19, wherein the outer body is deformable between an expanded and a compressed configuration and biased towards the compressed configuration.

27. The method of claim 26, wherein deploying the lock device comprises:
removing a tubular restraining member from between the outer body and the inner body such that the outer body is free to compress the first suture body against the inner body.

28. The method of claim 10, wherein the lock device comprises an inner body and an outer tubular body, the inner body being located within an inner lumen of the outer tubular body.

29. The method of claim 28, wherein deploying the lock device comprises compressing the first suture body between the inner body and the outer tubular body.

30. The method of claim 29, wherein the inner body is a deformable tubular body having an inner lumen, the inner tubular body being deformable between a first relatively flattened configuration and a second relatively unflattened configuration, the inner tubular body being biased towards the second configuration.

31. The method of claim 30, further comprising:
inserting a restraining member into the inner lumen of the inner tubular body to deform the body into the first configuration prior to deploying the lock device; and
placing the first suture body between the inner tubular body and the outer tubular body.

32. The method of claim 31, wherein deploying the lock device further comprises removing the restraining member to allow the inner body to deform to the second configuration.

33. The method of claim 31, wherein at least one of the inner tubular body and outer tubular body comprises a guide configured to maintain the first suture body in a predetermined location within the outer tubular body.

34. The method of claim 29, wherein the outer body is deformable between a first relatively flattened configuration and a second relatively unflattened configuration, the outer body being biased towards the first configuration.

35. The method of claim 34, wherein the outer tubular body is a first outer tubular body, the method further comprising:
inserting the lock device into an inner lumen of a second outer tubular body configured to maintain the first outer tubular body in the second configuration prior to deploying the lock device; and
placing the first suture body between the inner body and the first outer tubular body.

36. The method of claim 35, wherein deploying the lock device further comprises removing the second outer tubular body to allow the first outer tubular body to deform to the first configuration.

37. The method of claim 35, wherein at least one of the inner body and the first outer tubular body comprises a guide configured to maintain the first suture body in a predetermined location within the first outer tubular body.

38. The method of claim 10, wherein the lock device comprises a slotted tubular body being deformable between a first configuration where a slot is open an amount sufficient to allow passage of the first suture body therethrough and a second configuration where the slot is configured to compress the first suture body, the slotted tubular body being biased towards the second configuration.

39. The method of claim 38, further comprising compressing the tubular body to place the slot in the first configuration prior to deploying the lock device.

40. The method of claim 39, wherein the slot is oriented in a direction substantially parallel with a central axis of the tubular body.

41. The method of claim 38, wherein deploying the lock device comprises allowing the lock device to deform from the first configuration to the second configuration.

42. The method of claim 38, further comprising rotating a first end of the tubular body with respect to a second end of the tubular body to place the slot in the first configuration prior to deploying the lock device.

43. The method of claim 42, wherein the slot is oriented in a direction non-parallel to a central axis of the tubular body.

44. The method of claim 43, wherein the tubular body comprises a castellation and wherein rotating a first end of the tubular body comprises:
   placing a tubular rotation member into contact with the castellation; and
   rotating the tubular rotation member while in contact with the castellation.

45. The method of claim 38, wherein the slotted tubular body comprises a plurality of slots, each slot having the same orientation with respect to the tubular body.

46. The method of claim 38, wherein the slotted tubular body comprises a plurality of slots, at least two slots having different orientations with respect to the tubular body.

47. The method of claim 38, wherein the slot is oriented substantially parallel to a central axis of the tubular body.

48. The method of claim 47, wherein the slot is deflected into an inner lumen of the tubular body in the first configuration.

49. The method of claim 48, wherein deploying the lock device comprises removing a restraining member from within the slot to allow the slot to deflect from the first configuration to the second configuration.

50. The method of claim 10, wherein the lock device comprises a slotted tubular body being deformable between a first configuration where the slot is open an amount sufficient to allow the first suture body to pass therethrough relatively unimpeded and a second configuration where the slot is relatively more closed than the first configuration such that the first suture body passes through a relatively more tortuous path than in the first configuration, the deformable body being biased towards the second configuration.

51. The method of claim 50, further comprising axially stretching the lock device to place the slotted tubular body in the first configuration prior to deploying the lock device.

52. The method of claim 51, wherein deploying the lock device comprises allowing the slotted tubular body to deform to the second configuration.

53. The method of claim 10, wherein the lock device comprises a plate-like body having a deflectable arm member and an open inner portion, the arm member being configured to compress the first suture body within the open inner portion.

54. The method of claim 53, wherein the arm member is deflectable between a first configuration where the arm member lies outside a major plane of the body and the open portion is large enough to allow the first suture body to pass therethrough and a second configuration where the arm member lies substantially within the major plane of the body, the body being biased towards the second configuration.

55. The method of claim 54, wherein deploying the lock device comprises removing a restraining member from within the open portion to allow the arm member to deflect towards the second configuration.

56. The method of claim 10, wherein the lock device comprises a deformable body comprising two slots and a strut located therebetween.

57. The method of claim 56, further comprising:
   routing the first suture body through each slot prior to deploying the lock device; and
   deforming the deformable body to a first configuration so that the first suture body can pass through the slots.

58. The method of claim 57, wherein the deformable body is deformable between the first configuration and a second configuration where the first suture body is routed through a relatively more tortuous path, the deformable body being biased towards the second configuration.

59. The method of claim 58, wherein the deformable body is deformable between the first configuration and a second configuration where the first suture body is compressed by at least one slot.

60. The method of claim 58, wherein deploying the lock device comprises allowing the deformable body to deform from the first configuration to the second configuration.

61. The method of claim 60, further comprising removing a restraining member from within the slots to allow the deformable body to deform from the first configuration to the second configuration.

62. The method of claim 60, wherein the first inner elongate tubular member is configured to maintain the deformable body in the first configuration when the deformable body is located within the inner lumen of the first inner elongate tubular member.

63. The method of claim 60, wherein the deformable body comprises a plurality of struts, each strut being located between two slots.

64. The method of claim 63, wherein the first suture body is routed through each slot.

65. The method of claim 64, wherein the first suture body is routed on opposite sides of adjacent struts.

66. The method of claim 9, further comprising deploying the lock device on both the second portion of the first suture body and the second portion of the second suture body.

67. In a medical system for closing a patent foramen ovale, the improvement comprising:
   an elongate flexible outer tubular member having a proximal and a distal end and having an inner lumen and configured for advancement through the vasculature of a patient; and
   a first and a second inner elongate tubular member housed in said outer tubular member, each inner elongate tubular member having a substantially sharp extending in a distal direction and configured to pierce septal tissue in a septal wall of the heart;
   wherein the first and second inner elongate tubular members are configured to be slidably housed within the inner lumen of the outer tubular member in a configuration such that the distal ends of the first and second inner elongate tubular members are in relative proximity to each other, and wherein the first and second inner elongate tubular members are configured to deflect, upon advancement from within the inner lumen, such that the distal ends of the first and second inner elongate tubular members are spaced a relatively greater distance from each other than when housed within the inner lumen, and wherein each inner elongate tubular member further has a distal portion, a proximal portion, and a non-linear intermediate portion located therebetween, wherein a longitudinal axis of each distal portion is substantially parallel to a longitudinal axis of each proximal portion.

68. The system of claim 67, wherein the first and second coupled together.

69. The system of claim 68, wherein the inner elongate members each have a distal portion, a proximal portion and a curved intermediate portions are each curved.

70. The system of claim 69, wherein the distal and proximal portions of each inner elongate member are substantially straight.

71. The system of claim 68, further comprising implantable closure devices housed within an inner lumen of the first inner elongate member and an inner lumen of the second inner elongate member, wherein the closure devices comprise a suture having an anchor device at its distal end.

72. The system of claim 71, further comprising a lock device coupled with the first and second inner elongate members, wherein the lock device is configured to be deployed over a proximal portion of the suture of implantable closure device.

73. The system of claim 72, wherein the lock device comprises a coil-like body.

74. The system of claim 67, wherein
said intermediate portion is at an angle to said proximal and distal portions.

* * * * *